United States Patent
Zhu et al.

(10) Patent No.: US 9,623,028 B2
(45) Date of Patent: Apr. 18, 2017

(54) METHODS OF TREATING A CANCER USING SUBSTITUTED PYRROLOPYRIMIDINE COMPOUNDS, COMPOSITIONS THEREOF

(71) Applicant: Signal Pharmaceuticals, LLC, San Diego, CA (US)

(72) Inventors: Dan Zhu, San Diego, CA (US); John Boylan, Bedminster, NJ (US); Shuichan Xu, San Diego, CA (US); Jennifer Riggs, Cardiff, CA (US); Tao Shi, San Diego, CA (US); Andrew Wurmser, San Diego, CA (US); David Mikolon, San Diego, CA (US); Gordafaried Deyanat-Yazdi, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 14/797,548

(22) Filed: Jul. 13, 2015

(65) Prior Publication Data
US 2016/0008365 A1    Jan. 14, 2016

Related U.S. Application Data

(60) Provisional application No. 62/024,158, filed on Jul. 14, 2014.

(51) Int. Cl.
*A61K 31/519* (2006.01)
*A61K 31/437* (2006.01)
(Continued)

(52) U.S. Cl.
CPC ............ *A61K 31/519* (2013.01); *A61K 31/00* (2013.01); *A61K 31/5377* (2013.01); *A61K 31/635* (2013.01)

(58) Field of Classification Search
None
See application file for complete search history.

(56) References Cited

U.S. PATENT DOCUMENTS

| | | | |
|---|---|---|---|
| 3,507,866 A | 4/1970 | Jones et al. | |
| 3,567,725 A | 3/1971 | Grabowki et al. | |

(Continued)

FOREIGN PATENT DOCUMENTS

| | | |
|---|---|---|
| CA | 2 458 699 A1 | 3/2003 |
| DE | 262 026 | 11/1988 |

(Continued)

OTHER PUBLICATIONS

Levin et al. Recent Results Cancer Res., 2007, vol. 174, pp. 205-215 (abstract attached).*

(Continued)

*Primary Examiner* — Anna Pagonakis
(74) *Attorney, Agent, or Firm* — Jones Day

(57) ABSTRACT

Provided herein are methods for treating or preventing a cancer, in particular solid tumors and hematological cancers, comprising administering to a subject in need thereof an effective amount of a compound of formula (I):

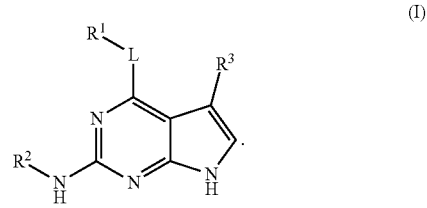

18 Claims, 4 Drawing Sheets

(51) Int. Cl.
    *A61K 31/5377*     (2006.01)
    *A61K 31/635*     (2006.01)
    *A61K 31/00*     (2006.01)

(56) References Cited

U.S. PATENT DOCUMENTS

| | | |
|---|---|---|
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,825,184 B2 | 11/2004 | Cirillo et al. |
| 6,855,723 B2 | 2/2005 | McMahon et al. |
| 7,199,119 B2 | 4/2007 | Burkitt et al. |
| 7,247,621 B2 | 7/2007 | Hong et al. |
| 7,429,572 B2 | 9/2008 | Clark |
| 7,476,665 B2 | 1/2009 | Burgey |
| 7,608,622 B2 | 10/2009 | Liu et al. |
| 7,902,187 B2 | 3/2011 | Neagu et al. |
| 7,919,490 B2 | 4/2011 | Neagu et al. |
| 7,968,556 B2 | 6/2011 | Mortensen et al. |
| 7,981,893 B2 | 7/2011 | Mortensen et al. |
| 8,110,578 B2 | 2/2012 | Perrin-Ninkovic et al. |
| 8,268,809 B2 | 9/2012 | Kalman |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 8,507,492 B2 | 8/2013 | Perrin-Ninkovic et al. |
| 8,569,494 B2 | 10/2013 | Harris et al. |
| 8,642,660 B2 | 2/2014 | Goldfard |
| 9,040,547 B2 | 5/2015 | Cheng et al. |
| 9,155,736 B2 | 10/2015 | Xu et al. |
| 2004/0063658 A1 | 4/2004 | Roberts et al. |
| 2004/0213757 A1 | 10/2004 | Zhu et al. |
| 2006/0004014 A1 | 1/2006 | Hoffmann et al. |
| 2006/0142269 A1 | 6/2006 | Dykes |
| 2009/0281075 A1 | 11/2009 | Roughton et al. |
| 2010/0144738 A1 | 6/2010 | Bornmann et al. |
| 2011/0257167 A1 | 10/2011 | Chopra et al. |
| 2012/0028972 A1 | 2/2012 | Wong |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2013/0245026 A1 | 9/2013 | Xu et al. |
| 2013/0245028 A1 | 9/2013 | Xu et al. |
| 2013/0245029 A1 | 9/2013 | Xu et al. |
| 2014/0113904 A1 | 4/2014 | Mortensen et al. |
| 2014/0200206 A1 | 7/2014 | Calabrese et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2006/050076 | 5/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/065703 | 6/2006 |
| WO | WO 2006/087530 | 8/2006 |
| WO | WO 2006/091737 | 8/2006 |
| WO | WO 2006/108103 | 10/2006 |
| WO | WO 2008/016669 | 2/2008 |
| WO | WO 2008/051493 | 5/2008 |
| WO | WO 2008/051494 | 5/2008 |
| WO | WO 2009/126926 | 10/2009 |
| WO | WO 2009/131687 | 10/2009 |
| WO | WO 2010/062571 | 6/2010 |
| WO | WO 2010/068483 | 6/2010 |
| WO | WO 2011/097333 | 8/2011 |
| WO | WO 2013/042006 | 3/2013 |
| WO | WO 2014/025486 | 2/2014 |
| WO | WO 2014/113429 | * 7/2014 |

OTHER PUBLICATIONS

Barlin, "Purine analogs as amplifiers of phleomycin. VII. Some 1H-inidazo[4,5-b]pyrazines and related compound," Australian Journal of Chemistry, vol. 35, pp. 2299-2306 (1982).
Beresnev et al., "Interaction of 5-methoxy-1,2,4-traizines with uras as a new route to 6-azapurines," Medeleev Commu., vol. 2, pp. 58-59 (2000).
Bergmann et al., "2-Phenylpurines, their chemical and enzumological reactivity," J. Chem Org., pp. 3729-3735 (1963).
Booth et al., "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemistry, vol. pp. 2119-2126 (1992).
Booth et al., "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675 (1995).
Booth et al., "The Reactions of Diaminomaleonitrile with Isocyanates and Either Aldehydes or Ketones Revisited," J. Org Chem, vol. 66, pp. 8436-8441 (2001).
Booth, et al., "Synthesis of 4- and 5-Disubstituted 1-Benzylimidazoles, Important Precursors of Purine Analogs," J. of Heterocyclic of Chemistry, vol. 31(2), pp. 345-350 (1994).
Chupakhin et al., "A simple one pot synthesis of condensed 1,2,4-triazines by using the tandem $A_N$-$S_N ipso$ and $S_N{}^H$—$S_N ipso$ reactions," J. of Heterocyclic Chemistry, vol. 38(4), pp. 901-907 (2001).
Cohen, "The role of protein phosphorylation in human health and disease," Eur. J. Biochem, vol. 268, pp. 5001-5010 (2001).
Cohen, P. "Protein kinases—the major drug targets of the twenty-first century?" Nature Reviews/Drug Discovery, vol. 1, pp. 309-315 (2002).
Coish, et al., "Small molecule inhibitors of IKK kinase activity," Expert Opin. Ther. Patents, vol. 16(1), pp. 1-12 (2006).
Costa et al., "Aspects of mTOR biology and the use of mTOR inhibitors in non-Hodgkin's lymphoma," Cancer Treatment Reviews, Saunders, US, vol. 33(1), pp. 78-84 (2007).
Crofts et al., "Metabolism of 2-amino-1-methyl-6-phenylimidazo[4,5-b]pyridine (PhIP) by human cytochrome P4501B1," Carcinogenesis, vol. 18(9), pp. 1793-1798 (1997).
Dang et al., "Efficient synthesis of purines and purine nucelosides via an inverse electron demand diels—alder reaction," J. Am Chem Soc., vol. 121(24), pp. 5833-5834 (1999).
Database Caplus Online Chemical Abstracts Service, Columbus, Ohio, Database Accession No. 1951:49974 (XP-002472261) (1951).
Database Caplus Online Chemical Abstracts Service, Columbus, Ohio, Database Accession No. 1978:433195 (XP-002472262) (1978).

(56) References Cited

OTHER PUBLICATIONS

Database Caplus Online Chemical Abstracts Service, Columbus, Ohio, Database Accession No. 1966:26849 (XP-002472263) (1965).
Dornow et al., "Synthese von2-Oxy-imidazolo-(5',4':2,3)-pyridinen)," Arch Pharm. vol. 290, pp. 20-31 (1957) (w/English language abstract).
Dorwald F. Zaragoza, "Side Reactions in Organic Synthesis: A Guide to Successful Synthesis Design," Weinheim: Wiley-VCH Verlag GmbH & Co. KgaA, Preface. (2005).
Dzierba et al., "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23), pp. 5783-5790 (2004).
EPO Supplementary European Search Report dated Feb. 8, 2013 issued in connection with PCT/US2010/053678.
Fabbro et al., "Protein kinases as targets for anticancer agents: from inhibitors touseful drugs," Pharmacology & Therapeutics, vol. 93, pp. 79-98 (2002).
Farhadi et al., "The role of protein kinase C isoforms in modulating injury and repair of the intestinal barrier," J. Pharm Exp. Ther., vol. 316(1), pp. 1-7 (2006).
Frandsen et al., "Reaction of the N2-acetoxy derivative of 2-amino-l-methyl-6-phenylimidazo[4,5,b] pyridine . . . ," Carcinogenesis, vol. 13(4), pp. 629-635 (1992).
Frost et al., "AKT activity regulates the ability of mTOR inhibitors to prevent angiogenesis and VEGF expression in multiple myeloma cells," Oncogene, vol. 26(16), pp. 2255-2262 (2007).
Georgakis and Younes, "From rapi nui to rapamycin: targeting PI3K/Akt/mTOR for cancer therapy," Expert Rev. Anticancer Ther., vol. 6(1), 131-140 (2006).
Hamad, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4), pp. 939-944 (2001).
Product specification of "Bis(di-tert-butyl(4-dimethylaminophenyl)phosphine)dichloropalladium(II)" from SIGMA-ALDRICH: http://www.sigmaaldrich.com/catalog/product/ALDRICH/678740?lang=en&region=US, last accessed Nov. 1, 2012.
Product specification of "[1,1'-Bis(di-tert-butylphosphino)ferrocene]dichloropalladium(II)" from SIGMA-ALDRICH: http://www.sigmaaldrich.com/catalog/product/ALDRICH/701602?lang=en&region=US#, last accessed Nov. 1, 2012.
Product specification of "[1,1'-Bis(diphenylphosphino)ferrocene]dichloropalladium(II)" from SIGMA-ALDRICH:http://www.sigmaaldrich.com/catalog/product/aldrich/697230?lang=en&region=US, last accessed Nov. 1, 2012.
"Application Guide for Palladium Catalyzed Cross-Coupling Reactions" http://www.sigmaldrich.com/chemistry/chemical-synthesis/technology-spotlights/catalysisapplicationguide.html, last accessed Nov. 1, 2012.
Irie et al., "Toward the development of new medicinal leads with selectivity for protein kinase C isozymes," The Chemical Record, vol. 5, pp. 185-195 (2005).
Itoh et al., "A novel practical synthesis of C-2-arylpurines," Advanced Synthesis & Catalysis, vol. 346, pp. 1859-1867 (2004).
Gulati et al. "Involvement of mTORC1 and mTORC2 in regulation of glioblastoma multiforme growth and motility," International Journal of Oncology, vol. 35(4) (2009), abstract.
Jones et al., "6-Substituted-5-chloro-1,3-dihydro-2H-imidazo(4,5-b)pyrazin-2-ones with hypotensive activity," J. Med. Chem., vol. 16(5), pp. 537-542 (1973).
Jordan, V.C., Nature Reviews: Drug Discover, vol. 2, p. 205 (2003).
Kazaoka et al., "Synthesis of 6-substituted 9-benzyl-8-hydroxypurines with potential interferon-indcuing activity," Chemical & Pharmaceutical Bulletin, vol. 51(5), pp. 608-611 (2003).
Killday et al., "Microxine, a new cdc2 kinase inhibitor from the Australian marine sponge Microxina species," J. of Natural Products, vol. 64(4), pp. 525-526 (2001).
Minehan et al., "Molecular recognition of DNA by Hoechst Benzimidazoles: Exploring beyond theopyrrole-imidazole-hydroxypyrrole polyamide-pairing code," Helvitica Chima Acta, vol. 83(9), pp. 2197-2213 (2000).
Mortensen et al., "Discovery and SAR exploration of a novel series of imidazo[4,5-] pyrazin-2-ones as potent and selective mTOR kinase inhibitors," Bioorganic & Medicinal Chemistry Letters, Pergamon, Elsevier Science, GB, vol. 21(22), pp. 6793-6799 (2011).
Nagashima et al., "Solution-Phase parallel synthesis of an N-Alkylated dihydropteridinone library from fiuorous amino acids," J of Comb. Chemistry, vol. 6(6), pp. 942-949 (2004).
Park et al., "A novel mechanism of TRAF signaling revealed by structural and functional analyses of the TRADD-TRAF2 interaction," Cell, vol. 101, pp. 777-787 (2000).
Patani et al., "Bioisosterim: A rational approach in drug design," Chemical Reviews, vol. 96, pp. 3147-3176 (1996).
Registry File Document for RN 863501-03-5, 863502-39-0 (Sep. 20, 2005).
Seela et al., "Product Class 17: Purines," Science of Synthesis, vol. 16, pp. 945-1108 (2004).
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-254.
Sridhar et al., "Protein Kinasesas Therapeutic Targets," Pharm. Research, vol. 17(11), pp. 1345-353 (2000).
Office Action mailed Jun. 11, 2009 for U.S. Appl. No. 11/975,652.
Office Action mailed Sep. 2, 2009 for U.S. Appl. No. 11/975,652.
Final Office Action mailed Feb. 2, 2010 for U.S. Appl. No. 11/975,652.
Office Action mailed May 12, 2010 for U.S. Appl. No. 11/975,652.
Final Office Action mailed Sep. 30, 2010 for U.S. Appl. No. 11/975,652.
PCT International Search Report dated Mar. 29, 2010 issued in connection with PCT/US2009/062143.
PCT Written Opinion of the International Searching Authority dated Mar. 29, 2010.
Office Action mailed Nov. 10, 2010 for U.S. Appl. No. 12/605,791.
PCT IPRP with Written Opinion of the International Searching Authority dated May 12, 2011 in connection with PCT/US2009/062143.
Office Action mailed Jan. 19, 2011 for U.S. Appl. No. 12/605,791.
Final Office Action mailed May 10, 2011 for U.S. Appl. No. 12/605,791.
Advisory Action mailed Aug. 17, 2011 for U.S. Appl. No. 12/605,791.
PCT International Search Report dated Dec. 27, 2010 issued in connection with PCT/US2010/053678.
PCT Written Opinion dated Dec. 27, 2010 in connection with PCT/US/10/53678.
Office Action mailed Feb. 28, 2012 for U.S. Appl. No. 12/910,920.
PCT IPRP dated May 10, 2012 issued in connection with PCT/US2010/053678.
Office Action mailed Jun. 28, 2012 for U.S. Appl. No. 12/910,920.
Final Office Action mailed Nov. 6, 2012 for U.S. Appl. No. 12/910,920.
Office Action mailed Apr. 2, 2012 for U.S. Appl. No. 13/295,513.
Office Action mailed Aug. 27, 2012 for U.S. Appl. No. 13/295,513.
PCT Partial International Search dated Feb. 21, 2013 issued in connection with PCT/US2012/060723.
PCT International Search Report dated Feb. 13, 2013 issued in connection with PCT/US2012/067172.
PCT Written Opinion dated Feb. 13, 2013 issued in connection with PCT/US/2012/067172.
Vippagunta et al., Advanced Drug Delivery Reviews, vol. 48, pp. 3-26 (2001) (Cited in Office Action in connection with U.S. Appl. No. 12/605,791).
Wallace, "Palladium-catalyzed synthesis of quinoxaline derivatives," Tetrahedron, vol. 64, pp. 9675-9684 (2008).
Westover et al., "Synthesis and antiviral activity of certain 9-β-D-Riofuranoaylpurine-6-carboxamides," J.Med. Chem., vol. 24(8), pp. 941-946 (1981).

(56) References Cited

OTHER PUBLICATIONS

Wolff, Manfred E., Ed. Burger's Medicinal Chemistry and Drug Discovery—Fifth Edition, New York: John Wiley & Sons, vol. 1, pp. 975-976 (1996).
Yoneda et al., "A transformation of 7-azapteridines into 6-azapurines (Imidazo[4,5-e]—as—triazines)," Heterocycles, vol. 4(9), pp. 1503-1508 (1976).
Yoneda et al., "Synthesis of imadazo[4,5-e]-as-triazine (6-Azapurine) Deriviatives," Chem & Pharm Bulletin, vol. 26(10), pp. 3154-3160 (1978).
Zaki et al., "The synthesis of imidazol[4,5-d]pyridines from a substituted imidazole and acyl or sulfonyl acetonitrile," Tetrahedron, vol. 63(18), pp. 3745-3753 (2007).
PCT Partial International Search dated Nov. 15, 2012 issued in connection with PCT/US2012/049281.
PCT International Search Report dated Jan. 11, 2013 issued in connection with PCT/US2012/049281.
PCT Written Opinion dated Feb. 13, 2013 issued in connection with PCT/US2012/049281.
Yuan et al., "Targeting tumorigenesis: development and use of mTOR inhibitors in cancer therapy," Journal of Hematology & Oncology, vol. 2(1), p. 45 (2009).
Carretero et al., "Integrative Genomic and Proteomic Analyses Identify Targets for Lkb1-Deficient Metastatic Lung Tumors," Cancer Cell, vol. 17( 6), pp. 547-559 (2010).
Gao et al., "LKB1 in lung cancerigenesis: a serine/threonine kinase as tumor suppressor," Protein & Cell, vol. 2(2), pp. 99-107 (2011).
Gao et al., "LKB1 inhibits lung cancer progression through lysyl oxidase and extracellular matrix remodeling," Proceedings of the National Academy of Sciences, vol. 107(44), pp. 18892-18897 (2010).
Inge et al., "Expression of LKB1 tumor suppressor in non-small cell lung cancer determines sensitivity to 2-deoxyglucose," Journal of Thoracic and Cardiovascular Surgery, vol. 137(3), pp. 580-558 (2009).
Wingo et al., "Somatic LKB1 Mutations Promote Cervical Cancer Progression," Plos One, vol. 4(4), pp. 5137-5138 (2009).
Shaw et al., "The LKB1 tumor suppressor negatively regulates mTOR signaling," Cancer Cell, vol. 6(1), pp. 91-99 (2004).
Huang et al., "Genetic and epigenetic silencing of SCARA5 may contribute to human hepatocellular carcinoma by activating FAK signaling," Journal of Clinical Investigation, vol. 120(1), pp. 223-241(2010).
Brenner et al., "Mechanistic Rationale for Inhibition of Poly(ADP-Ribose) Polymerase in ETS Gene Fusion-Positive Prostate Cancer," Cancer Cell, vol. 19, pp. 664-678 (2011).
Brenner et al., "PARP-1 Inhibition as a Targeted Strategy to Treat Ewing's Sarcoma," Cancer Res vol. 72, pp. 1608-1613 (2012).
Dey et al., "Preclinical efficacy of a dual PI3K-mTOR inhibitor, BEZ235 in triple negative breast cancer," European Journal of Cancer, vol. 47, No. Suppl. 4, Oct. 2011 (Oct. 2011), p. 517.
Johnston, "Are we missing the mTOR target in breast cancer?," Breast Cancer Research and Treatment, Kluwer Academic Publishers, Bolivia, vol. 128, No. 3, Oct. 16, 2010 (Oct. 16, 2010), pp. 607-611.
Lehmann et al., "Identification of human triple-negative breast cancer subtypes and preclinical models for selection of targeted therapies," The Journal of Clinical Investigation, Jul. 2011, vol. 121, No. 7, Jul. 2011 (Jul. 2011), pp. 2750-2767.
Liu et al., "Combinatorial Effects of Lapatinib and Rapamycin in Triple-Negative Breast Cancer Cells," Molecular Cancer Therapeutics, vol. 10, No. 8, Aug. 1, 2011 (Aug. 1, 2011), pp. 1460-1469.
Lori Berk et al., "Analysis of the pharmacodynamic activity of the mTOR inhibitor ridaforolimus (AP23573, MK-8669) in a phase 1 clinical trial," Cancer Chemotherapy and Pharmacology, Springer, Berlin, Germany, vol. 69, No. 5, Jan. 10, 2012 (Jan. 10, 2012), pp. 1369-1377.
Macaskill et al., "The mammalian target of rapamycin inhibitor everolimus (RAD001) in early breast cancer: results of a pre-operative study," Breast Cancer Research and Treatment, Kluwer Academic Publishers, Bolivia, vol. 128, No. 3, Oct. 13, 2010 (Oct. 13, 2010), pp. 725-734.
Sanchez et al., "Preclinical modeling of combined phosphatidylinositol-3-kinase inhibition with endocrine therapy for estrogen receptor-positive breast cancer," Breast Cancer Research, Current Science, London, United Kingdom, vol. 13, No. 2, Mar. 1, 2011 (Mar. 1, 2011), p. R21.
Toft et al., "Minireview: Basal-Like Breast Cancer: From Molecular Profiles to Targeted Therapies," Molecular Endocrinology, vol. 25, No. 2, Feb. 1, 2011 (Feb. 1, 2011), pp. 199-211.
Zeng et al., "Treating triple-negative breast cancer by a combination of rapamycin and cyclophosphamide: An in vivo bioluminescence imaging study," European Journal of Cancer, Pergamon Press, Oxford, United Kingdom, vol. 46, No. 6, Apr. 1, 2010 (Apr. 1, 2010), pp. 1132-1143.
Zhao et al., "The effect of mTOR inhibition alone or combined with MEK inhibitors on brain metastasis: an in vivo analysis in triple-negative breast cancer models," Breast Cancer Research and Treatment, Kluwer Academic Publishers, Bolivia, vol. 131, No. 2, Mar. 11, 2011 (Mar. 11, 2011), pp. 425-436.

* cited by examiner

METHODS OF TREATING A CANCER USING SUBSTITUTED PYRROLOPYRIMIDINE COMPOUNDS, COMPOSITIONS THEREOF

This application claims the benefit of U.S. Provisional Application No. 62/024,158, filed Jul. 14, 2014, the entire contents of which are incorporated herein by reference.

FIELD

Provided herein are methods for treating or preventing a cancer, in particular solid tumors and hematological cancers as described herein, comprising administering an effective amount of a pyrrolopyrimidine compounds to a subject in need thereof. Also provided herein are Pyrrolopyrimidine Compounds that can be used in said methods.

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., Immunology, 17.1-17.12 (3rd ed., Mosby, St. Louis, Mo., 1993)).

Cancers figure among the leading causes of death worldwide, accounting for 8.2 million deaths in 2012. It is expected that annual cancer cases will rise from 14 million in 2012 to 22 million within the next two decades (See Cancer Fact sheet No 297, World Health Organization, February 2014, retrieved 10 Jun. 2014 and Globocan 2012, IARC).

The current drugs used in cancer treatment are highly toxic and often non-specific. Current anticancer therapy strategies are typically focused on rapid proliferating cells, which can shrink primary and metastatic tumors, but such effects are usually transient and tumor relapse of most metastatic cancers frequently occur. One possible reason for failure is the existence of cancer stem cells. Unlike most cells within the tumor, cancer stem cells are resistant to well-defined chemotherapy, and after treatment, they can regenerate all the cell types in the tumor through their stem cell-like behavior of largely quiescent nature and their abundant expression of drug transporters.

There is an enormous variety of cancers which are described in detail in the medical literature. The incidence of cancer continues to climb as the general population ages, as new cancers develop, and as susceptible populations (e.g., people infected with AIDS or excessively exposed to sunlight) grow. However, options for the treatment of cancer are limited. A tremendous demand therefore exists for new methods and compositions that can be used to treat patients with cancer.

SUMMARY

Provided herein are Pyrrolopyrimidine Compounds that can be used in the methods provided herein.

Provided herein are methods of treating a cancer, in particular a solid tumor or a hematological cancer. The Pyrrolopyrimidine Compound provided herein can be used in the methods for treating or preventing the cancer, in particular the solid tumor or the hematological cancer. The methods comprise administering to a subject in need thereof an effective amount of Pyrrolopyrimidine Compound. Also provided herein are methods for preventing cancer metastasis, comprising administering to a subject in need thereof an effective amount of a Pyrrolopyrimidine Compound as provided herein. The Pyrrolopyrimidine Compound provided herein can be used in the methods for preventing cancer metastasis. Additionally, provided herein are methods of eradicating cancer stem cells in a subject, comprising administering to a subject in need thereof an effective amount of a Pyrrolopyrimidine Compound as provided herein. The Pyrrolopyrimidine Compound provided herein can be used in the methods of eradicating cancer stem cells in a subject. Also provided are methods of inducing differentiation in cancer stem cells in a subject, comprising administering to a subject in need thereof an effective amount of a Pyrrolopyrimidine Compound as provided herein. The Pyrrolopyrimidine Compound provided herein can be used in the methods of inducing differentiation in cancer stem cells in a subject. In another aspect, provided are methods of inducing cancer stem cell death in a subject, comprising administering to a subject in need thereof an effective amount of a Pyrrolopyrimidine Compound as provided herein. The Pyrrolopyrimidine Compound provided herein can be used in the methods of inducing cancer stem cell death in a subject. In yet another aspect, provided herein are methods for treating or preventing a cancer, in particular a solid tumor or hematological cancer, comprising administering to a subject in need thereof an effective amount of a compound that inhibits TTK, CLK1, and CLK2 kinase activity, and optionally CAMKK2 kinase activity. The compound that inhibits TTK, CLK1, and CLK2 kinase activity, and optionally CAMKK2 kinase activity can be used in the methods for treating or preventing a cancer, in particular a solid tumor or hematological cancer. Also provided are methods for treating or preventing a cancer associated with the pathways involving TTK, CLK1, and CLK2 and mutants or isoforms thereof, comprising administering to a subject in need thereof an effective amount of a compound that inhibits TTK, CLK1, and CLK2 kinase activity, and optionally CAMKK2 kinase activity. The compound that inhibits TTK, CLK1, and CLK2 kinase activity, and optionally CAMKK2 kinase activity can be used in the methods for treating or preventing a cancer associated with the pathways involving TTK, CLK1, and CLK2 and mutants or isoforms thereof.

The compound that inhibits TTK, CLK1, and CLK2 kinase activity, and optionally CAMKK2 kinase activity is a Pyrrolopyrimidine Compound as provided herein.

Compounds useful in the methods disclosed herein are Pyrrolopyrimidine Compounds as described herein, such as, for example, in Table A, or a pharmaceutically acceptable salt, tautomer, stereoisomer, enantiomer, or isotopologue thereof.

The present embodiments can be understood more fully by reference to the detailed description and examples, which are intended to exemplify non-limiting embodiments.

DETAILED DESCRIPTION

Definitions

Figure 1:
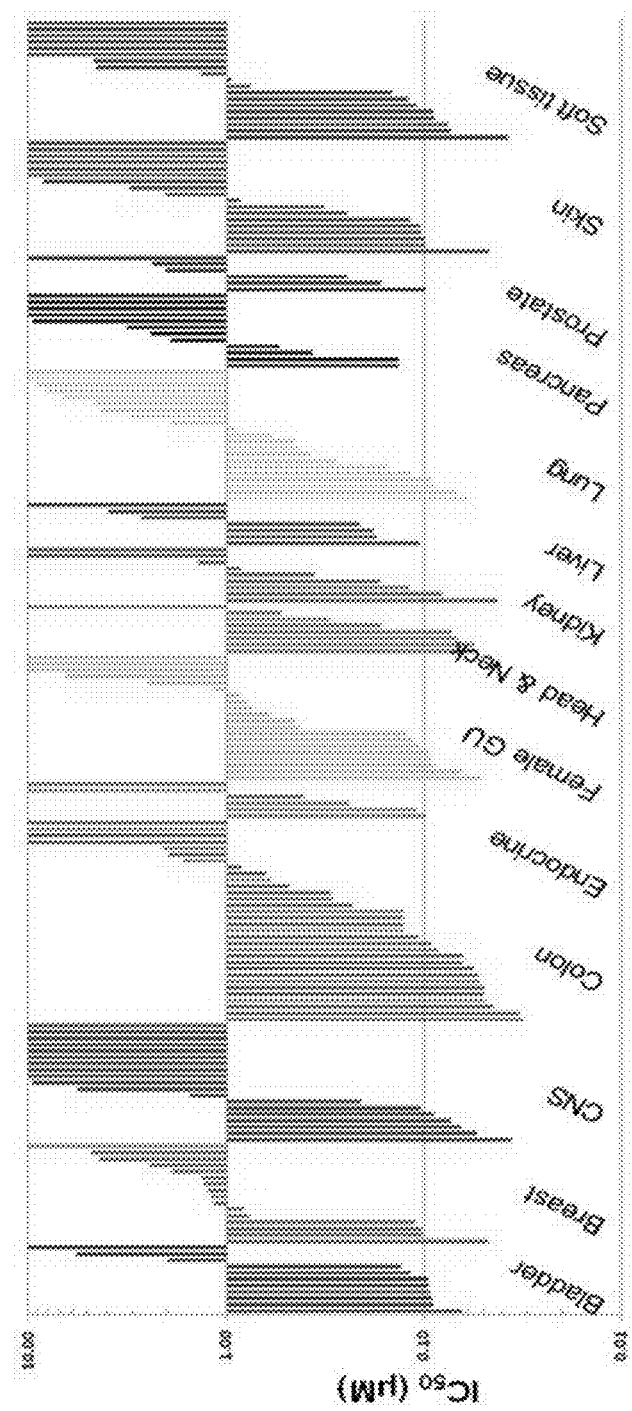
FIG. 1: Pyrrolopyrimidine Compounds showed anti-proliferative activity in a variety of solid tumors, namely, cancers of the bladder, breast, CNS, colon, endocrine, female GU, head and neck, kidney, liver, lung, pancreas, prostate, skin and soft-tissue (exemplified by Cmpd. 38 in FIG. 1).

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or 2 to 4 carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1] pentyl, bicyclo[2.1.1]hexyl, bicyclo[2.2.1]heptyl, bicyclo [2.2.2]octyl, adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d] oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —NH$_2$.

A "hydroxyl amine" group is a radical of the formula: —N(R$^\#$)OH or —NHOH, wherein R$^\#$ is a substituted or unsubstituted alkyl, cycloalkyl, aryl, aralkyl, heterocyclyl or heterocyclyl group as defined herein.

An "alkoxyamine" group is a radical of the formula: —N(R$^\#$)O-alkyl or —NHO-alkyl, wherein R$^\#$ is as defined above.

An "aralkoxyamine" group is a radical of the formula: —N(R$^\#$)O-aryl or —NHO-aryl, wherein R$^\#$ is as defined above.

An "alkylamine" group is a radical of the formula: —NH-alkyl or —N(alkyl)$_2$, wherein each alkyl is independently as defined above.

An "aminocarbonyl" group is a radical of the formula: —C(=O)N(R$^\#$)$_2$, —C(=O)NH(R$^\#$) or —C(=O)NH$_2$, wherein each R$^\#$ is as defined above.

An "acylamino" group is a radical of the formula: —NHC(=O)(R$^\#$) or —N(alkyl)C(=O)(R$^\#$), wherein each alkyl and R$^\#$ are independently as defined above.

An "O(alkyl)aminocarbonyl" group is a radical of the formula: —O(alkyl)C(=O)N(R$^\#$)$_2$, —O(alkyl)C(=O)NH(R$^\#$) or —O(alkyl)C(=O)NH$_2$, wherein each R$^\#$ is independently as defined above.

An "N-oxide" group is a radical of the formula: —N$^+$—O$^-$.

A "carboxy" group is a radical of the formula: —C(=O)OH.

A "ketone" group is a radical of the formula: —C(=O)(R$^\#$), wherein R$^\#$ is as defined above.

An "aldehyde" group is a radical of the formula: —CH(=O).

An "ester" group is a radical of the formula: —C(=O)O(R$^\#$) or —OC(=O)(R$^\#$), wherein R$^\#$ is as defined above.

A "urea" group is a radical of the formula: —N(alkyl)C(=O)N(R$^\#$)$_2$, —N(alkyl)C(=O)NH(R$^\#$), —N(alkyl)C (=O)NH$_2$, —NHC(=O)N(R$^\#$)$_2$, —NHC(=O)NH(R$^\#$), or —NHC(=O)NH$_2$$^\#$, wherein each alkyl and R$^\#$ are independently as defined above.

An "imine" group is a radical of the formula: —N=C(R$^\#$)$_2$ or —C(R$^\#$)=N(R$^\#$), wherein each R$^\#$ is independently as defined above.

An "imide" group is a radical of the formula: —C(=O)N(R#)C(=O)(R$^\#$) or —N((C=O)(R$^\#$)$_2$, wherein each R$^\#$ is independently as defined above.

A "urethane" group is a radical of the formula: —OC(=O)N(R$^\#$)$_2$, —OC(=O)NH(R$^\#$), —N(R$^\#$)C(=O)O(R$^\#$), or —NHC(=O)O(R$^\#$), wherein each R$^\#$ is independently as defined above.

An "amidine" group is a radical of the formula: —C(=N(R$^\#$))N(R$^\#$)$_2$, —C(=N(R$^\#$))NH(R$^\#$), —C(=N(R$^\#$))NH$_2$, —C(=NH)N(R$^\#$)$_2$, —C(=NH)NH(R$^\#$), —C(=NH)NH$_2$, —N=C(R$^\#$)N(R$^\#$)$_2$, —N=C(R$^\#$)NH(R$^\#$), —N=C(R$^\#$)NH$_2$, —N(R$^\#$)C(R$^\#$)=N(R$^\#$), —NHC(R$^\#$)=N(R$^\#$), —N(R$^\#$)C(R$^\#$)=NH, or —NHC(R$^\#$)=NH, wherein each R$^\#$ is independently as defined above.

A "guanidine" group is a radical of the formula: —N(R$^\#$)C(=N(R$^\#$))N(R$^\#$)$_2$, —NHC(=N(R$^\#$))N(R$^\#$)$_2$, —N(R$^\#$)C(=NH)N(R$^\#$)$_2$, —N(R$^\#$)C(=N(R$^\#$))NH(R$^\#$), —N(R$^\#$)C(=N(R$^\#$))NH$_2$, —NHC(=NH)N(R$^\#$)$_2$, —NHC(=N(R$^\#$))NH(R$^\#$), —NHC(=N(R$^\#$))NH$_2$, —NHC(=NH)NH(R$^\#$), —NHC(=NH)NH$_2$, —N=C(N(R$^\#$)$_2$)$_2$, —N=C(NH(R$^\#$))$_2$, or —N=C(NH$_2$)$_2$, wherein each R$^\#$ is independently as defined above.

An "enamine" group is a radical of the formula: —N(R$^\#$)C(R$^\#$)=C(R$^\#$)$_2$, —NHC(R$^\#$)=C(R$^\#$)$_2$, —C(N(R$^\#$)$_2$)=C(R$^\#$)$_2$, —C(NH(R$^\#$))=C(R$^\#$)$_2$, —C(NH$_2$)=C(R$^\#$)$_2$, —C(R$^\#$)=C(R$^\#$)(N(R$^\#$)$_2$), —C(R$^\#$)=C(R$^\#$)(NH(R$^\#$)) or —C(R$^\#$)=C(R$^\#$)(NH$_2$), wherein each R$^\#$ is independently as defined above.

An "oxime" group is a radical of the formula: —C(=NO(R$^\#$))(R$^\#$), —C(=NOH)(R$^\#$), —CH(=NO(R$^\#$)), or —CH(=NOH), wherein each R$^\#$ is independently as defined above.

A "hydrazide" group is a radical of the formula: —C(=O)N(R$^\#$)N(R$^\#$)$_2$, —C(=O)NHN(R$^\#$)$_2$, —C(=O)N(R$^\#$)NH(R$^\#$), —C(=O)N(R$^\#$)NH$_2$, —C(=O)NHNH(R$^\#$)$_2$, or —C(=O)NHNH$_2$, wherein each R$^\#$ is independently as defined above.

A "hydrazine" group is a radical of the formula: —N(R$^\#$)N(R$^\#$)$_2$, —NHN(R$^\#$)$_2$, —N(R$^\#$)NH(R$^\#$), —N(R$^\#$)NH$_2$, —NHNH(R$^\#$)$_2$, or —NHNH$_2$, wherein each R$^\#$ is independently as defined above.

A "hydrazone" group is a radical of the formula: —C(=N—N(R$^\#$)$_2$)(R$^\#$)$_2$, —C(=N—NH(R$^\#$))(R$^\#$)$_2$, —C(=N—NH$_2$)(R$^\#$)$_2$, —N(R$^\#$)(N=C(R$^\#$)$_2$), or —NH(N=C(R$^\#$)$_2$), wherein each R$^\#$ is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S(R$^\#$), wherein R$^\#$ is as defined above.

A "thiocarbonyl" group is a radical of the formula: —C(=S)(R$^\#$), wherein R$^\#$ is as defined above.

A "sulfinyl" group is a radical of the formula: —S(=O)(R$^\#$), wherein R$^\#$ is as defined above.

A "sulfone" group is a radical of the formula: —S(=O)$_2$(R$^\#$), wherein R$^\#$ is as defined above.

A "sulfonylamino" group is a radical of the formula: —NHSO$_2$(R$^\#$) or —N(alkyl)SO$_2$(R$^\#$), wherein each alkyl and R$^\#$ are defined above.

A "sulfonamide" group is a radical of the formula: —S(=O)$_2$N(R$^\#$)$_2$, or —S(=O)$_2$NH(R$^\#$), or —S(=O)$_2$NH$_2$, wherein each R$^\#$ is independently as defined above.

A "phosphonate" group is a radical of the formula: —P(=O)(O(R$^\#$))$_2$, —P(=O)(OH)$_2$, —OP(=O)(O(R$^\#$))(R$^\#$), or —OP(=O)(OH)(R$^\#$), wherein each R$^\#$ is independently as defined above.

A "phosphine" group is a radical of the formula: —P(R$^\#$)$_2$, wherein each R$^\#$ is independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amine; alkylamine; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "Pyrrolopyrimidine Compound" refers to compounds of formula (I), as well as to further embodiments provided herein. In one embodiment, a "Pyrrolopyrimidine Compound" is a compound set forth in Table 1. The term "Pyrrolopyrimidine Compound" includes pharmaceutically acceptable salts, tautomers, stereoisomers, enantiomers and isotopologues of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein and unless otherwise indicated, the term "stereoisomer" or "stereomerically pure" means one stereoisomer of a Pyrrolopyrimidine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Pyrrolopyrimidine Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Pyrrolopyrimidine Compounds, as well as the use of mixtures of those forms, are encompassed by the embodiments disclosed herein. For example, mixtures comprising equal or unequal amounts of the enantiomers of a particular Pyrrolopyrimidine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Pyrrolopyrimidine Compounds can include E and Z isomers, or a mixture thereof, and cis and trans isomers or a mixture thereof. In certain embodiments, the Pyrrolopyrimidine Compounds are isolated as either the E or Z isomer. In other embodiments, the Pyrrolopyrimidine Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

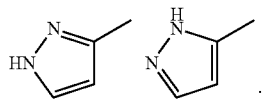

As readily understood by one skilled in the art, a wide variety of functional groups and other stuctures may exhibit tautomerism and all tautomers of compounds of formula (I) are within the scope of the present invention.

It should also be noted the Pyrrolopyrimidine Compounds can contain unnatural proportions of atomic isotopes at one or more of the atoms. For example, the compounds may be radiolabeled with radioactive isotopes, such as for example tritium ($^3$H), iodine-125 ($^{125}$I) sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., breast cancer therapeutic agents, research reagents, e.g., binding assay reagents, and diagnostic agents, e.g., in vivo imaging agents. All isotopic variations of the Pyrrolopyrimidine Compounds as described herein, whether radioactive or not, are intended to be encompassed within the scope of the embodiments provided herein. In some embodiments, there are provided isotopologues of the Pyrrolopyrimidine Compounds, for example, the isotopologues are deuterium, carbon-13, or nitrogen-15 enriched Pyrrolopyrimidine Compounds.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer, in particular, a solid tumor or hematological cancer. In some embodiments, "treating" means an alleviation, in whole or in part, of a cancer, or symptoms associated with a cancer, in particular, a solid tumor or hematological cancer, or a slowing, or halting of further progression or worsening of those symptoms.

"Preventing" as used herein, means a method of delaying and/or precluding the onset, recurrence or spread, in whole or in part, of a cancer, in particular, a solid tumor or hematological cancer; barring a subject from acquiring a cancer, in particular, a solid tumor or hematological cancer; or reducing a subject's risk of acquiring a cancer, in particular, a solid tumor or hematological cancer.

The term "effective amount" in connection with a Pyrrolopyrimidine Compound means an amount capable of treating or preventing cancer, in particular, a solid tumor or hematological cancer, or symptoms thereof, as disclosed herein. The effective amount of Pyrrolopyrimidine Compound, for example in a pharmaceutical composition, may be at a level that will exercise the desired effect; for example, about 0.005 mg/kg of a subject's body weight to about 100 mg/kg of a patient's body weight in unit dosage for parenteral administration. As will be apparent to those skilled in the art, it is to be expected that the effective amount of a Pyrrolopyrimidine Compound disclosed herein may vary depending on the severity of the indication being treated.

The terms "patient" and "subject" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having cancer, in particular, a solid tumor or hematological cancer, or symptoms thereof. In one embodiment, a patient is a human having histologically or cytologically-confirmed solid tumor or hematological cancer, including subjects who have progressed on (or not been able to tolerate) standard anticancer therapy or for whom no standard anticancer therapy exists.

As used herein, and unless otherwise specified, the terms "cancer" refers to or describes the physiological condition in mammals that is typically characterized by unregulated cell growth. Examples of cancer include solid tumors and hematological cancer. In some embodiments, the cancer is a primary cancer, in others, the cancer is metastasized.

As used herein "solid tumors" includes, but is not limited to, bladder cancer (including, but not limited to, superficial bladder cancer), breast cancer (including, but not limited to, luminal B type, ER+, PR+ and Her2+ breast cancer), central nervous system cancer (including, but no tlimited to, glioblastoma multiforme (GBM), glioma, medulloblastoma, and astrocytoma), colorectal cancer, gastrointestinal cancer (including, but not limited to, stomach cancer, oesophagus cancer, and rectum cancer), endocrine cancer (including, but not imited to, thyroid cancer, and adrenal gland cancer), eye cancer (including, but not limited to, retinoblastoma), female genitourinary cancer (including, but not limited to, cancer of the placenta, uterus, vulva, ovary, cervix), head and neck cancer (including, but not limited to, cancer of the pharynx, oesophagus, and tongue), liver cancer, lung cancer (including, but not limited to, non-small cell lung cancer (NSCLC), small cell lung cancer (SCLC), mucoepidermoid, bronchogenic, squamous cell carcinoma (SQCC), and analplastic/NSCLC), skin cancer (including, but not limited to, melanoma, and SQCC), soft tissue cancer (including but not limited to, sarcoma, Ewing's sarcoma, and rhabdomyosarcoma), bone cancer (including, but not limited to, sarcoma, Ewing's sarcoma, and osteosarcoma), squamous cell cancer (including, but not limited to, lung, esophageal, cervical, and head and neck cancer), pancreas cancer, kidney cancer (including, but not limited to, renal Wilm's tumor and renal cell carcinoma), and prostate cancer. In one embodiment, the solid tumor is not triple negative breast cancer (TNBC). In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

As used herein "hematological cancer" includes, but is not limited to, leukemia (including, but not limited to, acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including but not limited to Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), large cell immunoblastic lymphoma), and multiple myeloma.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no | ≥50% decrease in SPD of nodules (for single nodule in greatest | Irrelevant if positive prior to therapy; cell type should be specified |

| Response | Definition | Nodal Masses | Spleen, liver | Bone Marrow |
|---|---|---|---|---|
| | | increase in size of other nodes (a) FDG-avid or PET positive prior to therapy; one or more PET positive at previously involved site (b) Variably FDG-avid or PET negative; regression on CT | transverse diameter); no increase in size of liver or spleen | |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [$^{18}$F]fluorodeoxyglucose; PET, positron emission tomography; CT, computed tomography; PR, partial remission; SPD, sum of the product of the diameters; SD, stable disease; PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations: CR: complete remission; PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or >50% improvement over baseline | |

Group A criteria define the tumor load; Group B criteria define the function of the hematopoietic system (or marrow). CR (complete remission): all of the criteria have to be met, and patients have to lack disease-related constitutional symptoms; PR (partial remission): at least two of the criteria of group A plus one of the criteria of group B have to be met; SD is absence of progressive disease (PD) and failure to achieve at least a PR; PD: at least one of the above criteria of group A or group B has to be met. Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100mg per 24 h |
| PR | ≥50% reduction of serum M-protein and reduction in 24-h urinary M-protein by ≥90% or to <200 mg per 24 h If the serum and urine M-protein are unmeasurable,[d] a ≥50% decrease in the difference between involved and uninvolved FLC levels is required in place of the M-protein criteria If serum and urine M-protein are unmeasurable, and serum free light assay is also unmeasurable, ≥50% reduction in plasma cells is required in place of M-protein, provided baseline bone marrow plasma cell percentage was ≥30% In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations: CR, complete response; FLC, free light chain; PR, partial response; SD, stable disease; sCR, stringent complete response; VGPR, very good partial response; [a]All response categories require two consecutive assessments made at anytime before the institution of any new therapy; all categories also require no known evidence of progressive or new bone lesions if radiographic studies were performed. Radiographic studies are not required to satisfy these response requirements; [b]Confirmation with repeat bone marrow biopsy not needed; [c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2. [d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |

| Target lesions | Non-target lesions | New lesions | Overall response |
|---|---|---|---|
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (i.e., less than 5 mm by 5 mm), nonenhancing lesions (e.g., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (e.g., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

TTK (also known as Mps1, hMps1 or PYT) is a dual specificity protein kinase with the ability to phosphorylate tyrosine, serine and threonine. Associated with cell proliferation, this protein is essential for chromosome alignment at the centromere during mitosis and is required for centrosome duplication. It has been found to be a critical mitotic checkpoint protein for accurate segregation of chromosomes during mitosis. Tumorigenesis may occur when this protein fails to degrade and produces excess centrosomes resulting in aberrant mitotic spindles. Alternative splicing results in multiple transcript variants. [RefSeq, November 2009]. TTK is essential for spindle checkpoint function and its inhibition accelerates cell progression through mitosis. TTK also plays an important role for cancer stem cell survival.

CLK1 is a member of the CDC2-like (or LAMMER) family of dual specificity protein kinases. In the nucleus, the encoded protein phosphorylates serine/arginine-rich (SR) proteins involved in pre-mRNA processing, releasing them into the nucleoplasm. The choice of splice sites during pre-mRNA processing may be regulated by the concentration and localization of splicing factors, including serine/arginine rich (SR) proteins. Therefore, the encoded protein may play an indirect role in governing splice site selection. Multiple transcript variants encoding different isoforms have been found for this gene. [provided by RefSeq, June 2009]

CLK2 is a member of the CLK family of dual specificity protein kinases. CLK family members have been shown to interact with, and phosphorylate, serine/arginine-rich (SR) proteins of the spliceosomal complex, which is a part of the regulatory mechanism that enables the SR proteins to control RNA splicing. This protein kinase is involved in the regulation of several cellular processes and may serve as a link between cell cycle progression, apoptosis, and telomere length regulation [RefSeq, July 2008]. Inhibition of CLK2 changes the expression of protein isoforms, many of which contribute to the oncogenic phenotype.

CAMKK2 belongs to the serine/threonine-specific protein kinase family, and to the Ca$^{++}$/calmodulin-dependent protein kinase subfamily. This protein plays a role in the calcium/calmodulin-dependent (CaM) kinase cascade by phosphorylating the downstream kinases CaMK1 and CaMK4 [RefSeq, July 2012]. CAMKK2 reportedly plays a role in tumor energy homeostasis.

Pyrrolopyrimidine Compounds

Provided herein are compounds having the following formula (I):

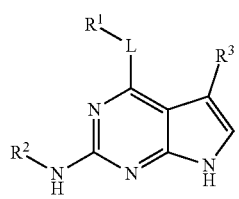

and pharmaceutically acceptable salts, tautomers, stereoisomers, enantiomers, and isotopologues thereof, wherein:
$R^1$ is substituted or unsubstituted $C_{1-8}$ alkyl, substituted or unsubstituted $C_{3-8}$ cycloalkyl, or substituted or unsubstituted non-aromatic heterocyclyl;
$R^2$ is substituted or unsubstituted aryl, or substituted or unsubstituted heteroaryl;
$R^3$ is substituted or unsubstituted heterocyclyl or substituted or unsubstituted aryl, and
L is NH or O;
provided that when L is NH, $R^3$ is not pyridyl.

Provided herein are compounds having the following formula (I):

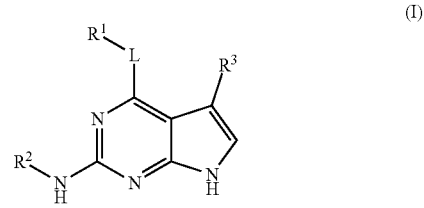

and pharmaceutically acceptable salts, tautomers, stereoisomers, enantiomers, and isotopologues thereof, wherein:
$R^1$ is substituted or unsubstituted $C_{1-8}$ alkyl, substituted or unsubstituted $C_{3-8}$ cycloalkyl, or substituted or unsubstituted non-aromatic heterocyclyl;
$R^2$ is substituted or unsubstituted aryl, or substituted or unsubstituted heteroaryl;
$R^3$ is substituted or unsubstituted heterocyclyl or substituted or unsubstituted aryl, and
L is NH or O;
provided
$R^3$ is not pyridyl when L is NH or when $R^2$ is pyrazolyl; and
the compound is not
N-methyl-N-[trans-3-[[5-(1-methyl-1H-pyrazol-4-yl)-2-[(1-methyl-1Hpyrazol-4-yl)amino]-7H-pyrrolo[2,3-d]pyrimidin-4-yl]oxy]cyclobutyl]-2-propenamide; or
N-methyl-N-[trans-3-[[5-(1-methyl-1H-pyrazol-3-yl)-2-[(1-methyl-1Hpyrazol-4-yl)amino]-7H-pyrrolo[2,3-d]pyrimidin-4-yl]oxy]cyclobutyl]-2-propenamide.

The compound as described herein is not a compound selected from:

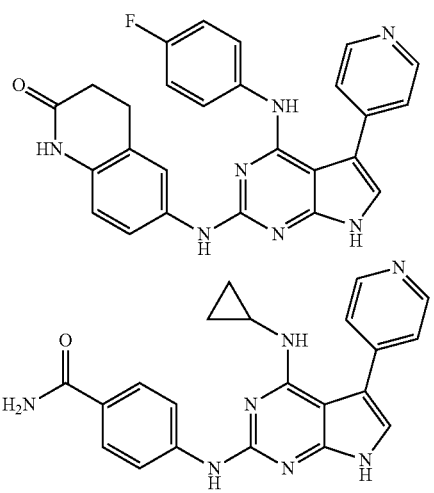

-continued
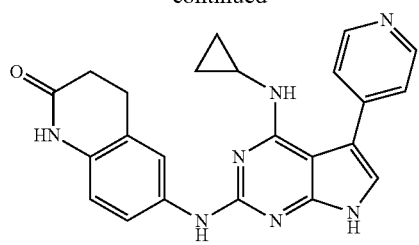
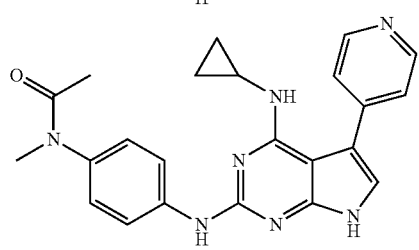
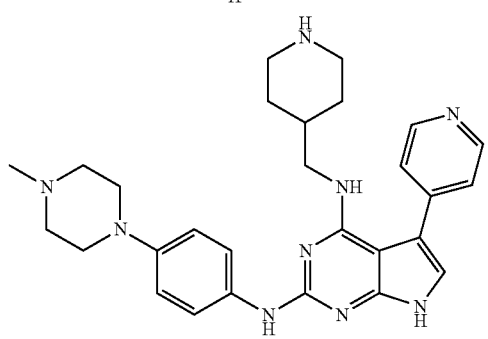
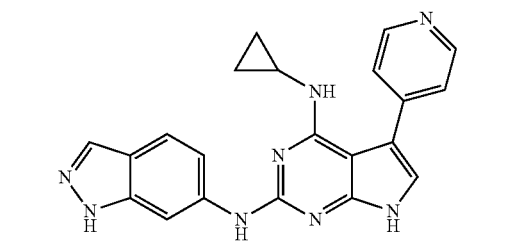
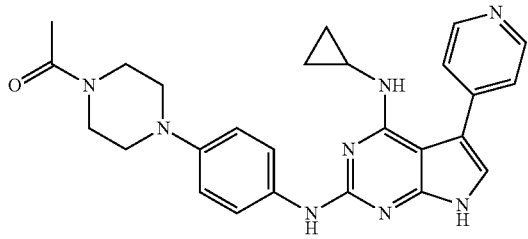
-continued
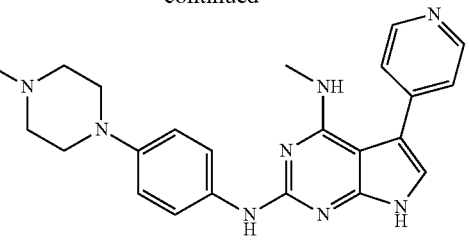
As described herein, the compound is not
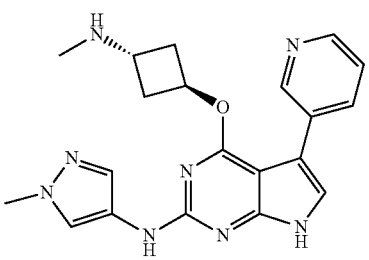
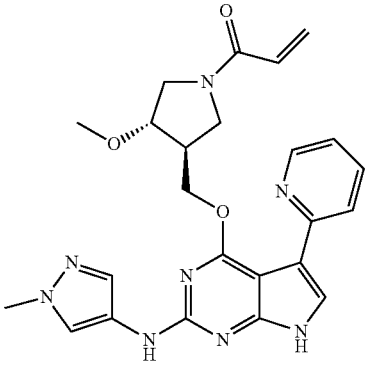
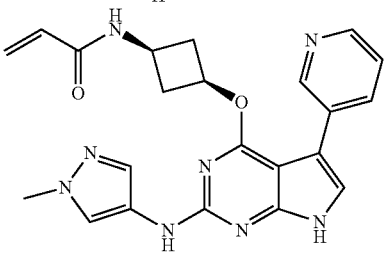
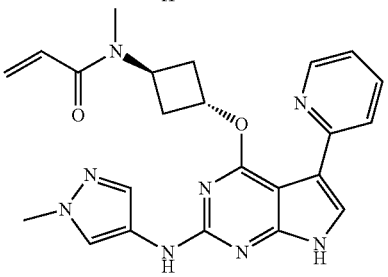

-continued

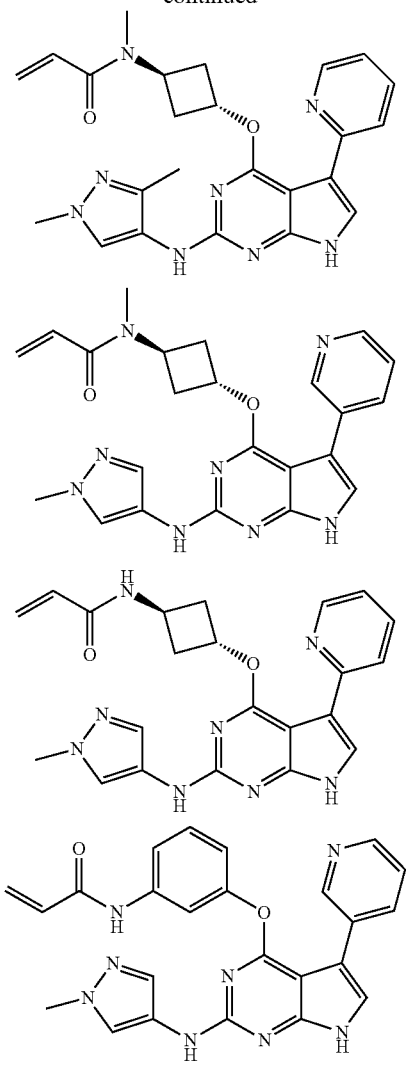

In one embodiment, the compound is not N-methyl-N-[trans-3-[[5-(1-methyl-1H-pyrazol-4-yl)-2-[(1-methyl-1Hpyrazol-4-yl)amino]-7H-pyrrolo[2,3-d]pyrimidin-4-yl]oxy]cyclobutyl]-2-propenamide (also named N-methyl-N-((1r,3r)-3-((5-(1-methyl-1H-pyrazol-4-yl)-2-((1-methyl-1H-pyrazol-4-yl)amino)-7H-pyrrolo[2,3-d]pyrimidin-4-yl)oxy)cyclobutyl)acrylamide)

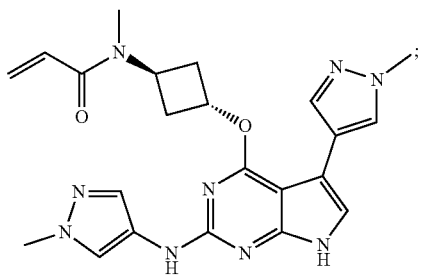 [SMILES: C=CC(=O)N(C)[C@H]1C[C@H](Oc2nc(Nc3cnn(C)c3)nc3[nH]cc(-c4cnn(C)c4)c23)C1]

or N-methyl-N-[trans-3-[[5-(1-methyl-1H-pyrazol-3-yl)-2-[(1-methyl-1Hpyrazol-4-yl)amino]-7H-pyrrolo[2,3-d]pyrimidin-4-yl]oxy]cyclobutyl]-2-propenamide (also named N-methyl-N-((1r,3r)-3-((5-(1-methyl-1H-pyrazol-3-yl)-2-((1-methyl-1H-pyrazol-4-yl)amino)-7H-pyrrolo[2,3-d]pyrimidin-4-yl)oxy)cyclobutyl)acrylamide)

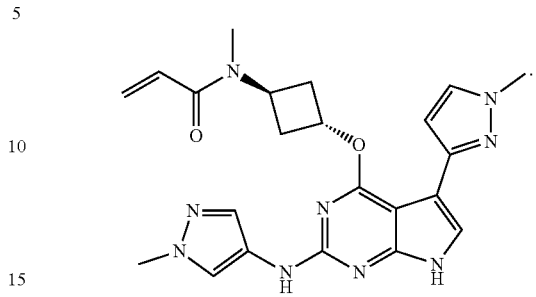

In yet another embodiment, the compound is not

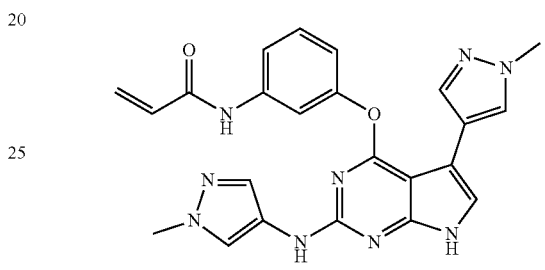

In one embodiment, provided herein are compounds of formula (I), wherein L is O.

In some embodiments of compounds of formula (I), $R^1$ is substituted or unsubstituted alkyl, for example, $R^1$ is substituted or unsubstituted methyl, ethyl, propyl, isopropyl, n-butyl, sec-butyl, tert-butyl, n-pentyl, sec-pentyl, tert-pentyl, or 2,2-dimethylpropyl. In some embodiments, $R^1$ is substituted or unsubstituted methyl, ethyl, isopropyl, sec-butyl, t-butyl, or 2,2-dimethylpropyl. In some embodiments of formula (I), wherein $R^1$ is alkyl, the alkyl is substituted with one or more —OR or —$NR_2$, wherein each R is independently —H or substituted or unsubstituted ($C_{1-4}$) alkyl. For example $R^1$ is —$CH_2CH_2OH$, —$CH_2CH_2OCH_3$, or —$CH_2CH_2NHCH_3$. In other embodiments of compounds of formula (I), $R^1$ is substituted or unsubstituted $C_{3-8}$ cycloalkyl, for example, $R^1$ is substituted or unsubstituted cyclopropyl, cyclobutyl, cyclopentyl, cyclohexyl, or cycloheptyl. In some such embodiments, the cycloalkyl is substituted with one or more —CN, halogen, —OR or a substituted or unsubstituted $C_{1-3}$ alkyl, wherein each R is independently —H or substituted or unsubstituted ($C_{1-4}$) alkyl. For example, in some embodiments the cycloalkyl is substituted with one or more —CN, —F, —OH, or —$CH_3$. In some other embodiments of compounds of formula (I), $R^1$ is substituted or unsubstituted non-aromatic heterocyclyl, for example, $R^1$ is substituted or unsubstituted oxetanyl, tetrahydrofuranyl, tetrahydropyranyl, or piperidinyl.

In some other embodiments of compounds of formula (I), $R^1$ is substituted or unsubstituted $C_{1-8}$ alkyl,

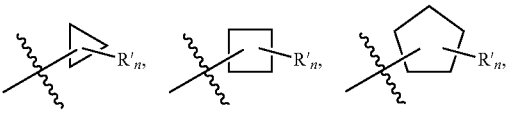

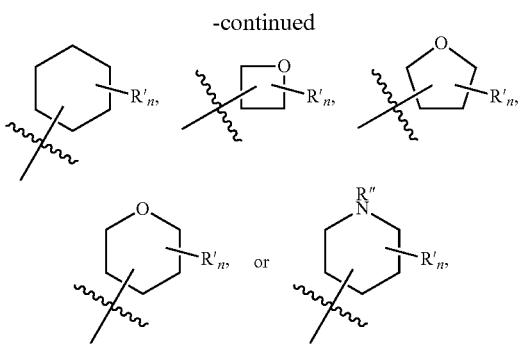

wherein
each R' is independently —CN, halogen, —OR or $C_{1-3}$ alkyl;
R" is —H or $C_{1-3}$ alkyl;
each R is independently —H or substituted or unsubstituted $(C_{1-4})$alkyl; and
n is 0-2.

In some such embodiments, $R^1$ is substituted or unsubstituted methyl, ethyl, isopropyl, sec-butyl, t-butyl, or 2,2-dimethylpropyl,

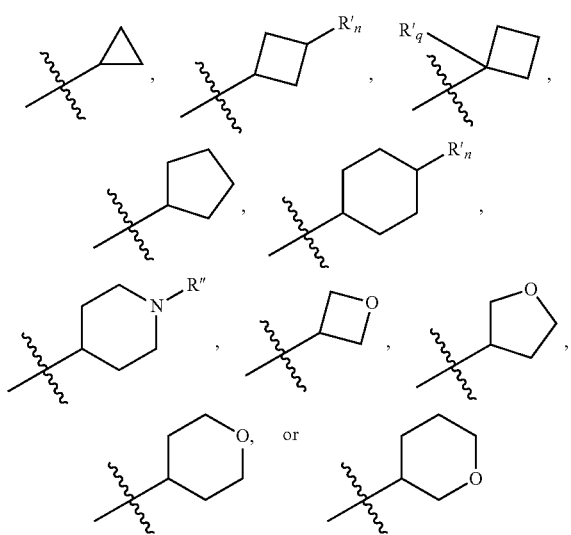

and R' is —CN, —F, —OH, or —$CH_3$;
R" is —$CH_3$;
n is 0, 1 or 2; and
q is 0 or 1.

Also provided herein are compounds of formula (I), wherein $R^2$ is substituted phenyl. In some such embodiments, $R^2$ is phenyl, substituted with one or more substituted or unsubstituted $C_{1-6}$ alkyl, halogen, —CN, —$OR^5$, —C(=O)$NR^5_2$, —C(=O) (substituted or unsubstituted heterocyclyl), —C(=O) (substituted or unsubstituted alkylheterocyclyl), —NHC(=O)$R^5$, —$SO_2NR^5_2$, or substituted or unsubstituted heteroaryl, wherein each $R^5$ is independently —H, substituted or unsubstituted alkyl, substituted or unsubstituted cycloalkyl, substituted or unsubstituted heterocyclyl, or substituted or unsubstituted alkylheterocyclyl. For example, $R^2$ is phenyl, substituted with one or more —($C_{1-3}$ alkyl), —($C_{1-3}$ alkyl)$NR_2$, —$CF_3$, —Cl, —F, —CN, —$OCH_3$, —$OCF_3$, —C(=O)$NR_2$, —C(=O)NR (substituted or unsubstituted cycloalkyl), —C(=O)NR $(CH_2)_{0-2}CR_2(CH_2)_{0-2}$OR, —C(=O)NR$(CH_2)_{0-2}$ $CR_2(CH_2)_{0-2}NR_2$, —C(=O)NR$(CH_2)_{0-2}CR_2(CH_2)_{0-2}$C (=O)$NR_2$, —C(=O)N (substituted or unsubstituted cycloalkyl)$(CH_2)_{0-2}$OR, —C(=O)NR$(CH_2)_{0-3}$ (substituted or unsubstituted heterocyclyl), —C(=O)$(CH_2)_{0-3}$ (substituted or unsubstituted heterocyclyl), —C(=NR)$NR_2$, —NRC(=O)R, —$SO_2NR_2$, —$SO_2R$, or substituted or unsubstituted heterocyclyl, wherein each R is independently —H or substituted or unsubstituted $(C_{1-4})$alkyl. In some such embodiments, each R is independently —H or —$CH_3$.

In some embodiments of compounds of formula (I), $R^2$ is phenyl, substituted with one or more —$CH_3$, —$CH_2CH_3$, —$CH_2CH_2CH_3$, —$CH(CH_3)_2$, —$CH_2NH_2$, —$CF_3$, —Cl, —F, —CN, —$OCH_3$, —$OCF_3$, —C(=O)$NH_2$, —C(=O) $NHCH_3$, —C(=O)N$(CH_3)_2$, —C(=O)NC$(CH_3)_3$, —C(=O)$NHCH_2CH_2F$, —C(=O)$NHCH_2CHF_2$, —C(=O)$NHCH_2CF_3$, —C(=O)$NHCH_2CF_2CH_3$, —C(=O)$NHCH_2CN$, —C(=O)N$(CH_3)CH_2CN$, —C(=O)$NHCH_2CH_2CN$, —C(=O)N$(CH_3)CH_2CH_2CN$, —C(=O)NH-cyclobutyl, —C(=O)NH-(hydroxy-cyclobutyl), —C(=O)NH-cyclopentyl, —C(=O)NH-(hydroxyl-cyclopentyl), —C(=O)$NHCH_2CH_2OH$, —C(=O) $NHCH_2CH_2OCH_3$, —C(=O)N$(CH_3)CH_2CH_2OH$, —C(=O)N$(CH_3)CH_2CH_2OCH_3$, —C(=O) $NHCH_2CH_2CH_2OH$, —C(=O)N$(CH_3)CH_2CH_2CH_2OH$, —C(=O)N$(CH_3)CH_2CH_2CH_2OCH_3$, —C(=O) $NHCH_2CH(CH_3)OH$, —C(=O)$NHCH_2C(CH_3)_2OH$, —C(=O)$NHCH(CH_3)CH_2OH$, —C(=O)$NHC(CH_3)_2$ $CH_2OH$, —C(=O)$NHCH_2CH_2NH_2$, —C(=O) $NHCH_2CH_2NH(CH_3)$, —C(=O)$NHCH_2CH_2N(CH_3)_2$, —C(=O)$NHCH_2C(=O)NH_2$, —C(=O)N$(CH_3)CH_2C$ (=O)$NH_2$, —C(=O)$NHCH_2CH_2C(=O)NH_2$, —C(=O)N $(CH_3)CH_2CH_2C(=O)NH_2$, —C(=O)N(cyclopropyl) $CH_2CH_2OH$, —C(=O)NH-oxetanyl, —C(=O)N$(CH_3)$-oxetanyl, —C(=O)NH-(methyl-oxetanyl), —C(=O)NH-azetidinyl, —C(=O)NH-(methylazetidinyl), —C(=O)NH-(1-acetylazetidinyl), —C(=O)NH-pyrrolidyl, —C(=O) NH-piperidyl, —C(=O)NH-tetrahydrofuranyl, —C(=O)N $(CH_3)$-tetrahydrofuranyl, —C(=O)NH-tetrahydropyranyl, —C(=O)N$(CH_3)$-tetrahydropyranyl, —C(=O)$NHCH_2$-oxetanyl, —C(=O)N$(CH_3)CH_2$-oxetanyl, —C(=O) $NHCH_2$-(methyl-oxetanyl), —C(=O)N$(CH_3)CH_2$-(methyl-oxetanyl), —C(=O)$NHCH_2$-tetrahydrofuranyl, —C(=O) $NHCH_2$-tetrahydropyranyl, —C(=O)$NHCH_2$-dioxanyl, —C(=O)aziridinyl, —C(=O)(methyl-aziridinyl), —C(=O)(dimethyl-aziridinyl), —C(=O)(hydroxymethyl-aziridinyl), —C(=O)azetidinyl, —C(=O)pyrrolidinyl, —C(=O)(hydroxyl-pyrrolidinyl), —C(=O)(hydroxyl, methoxypyrrolidinyl), —C(=O)(dimethoxypyrrolidinyl), —C(=O)morpholinyl, —C(=O)piperazinyl, —C(=O) (methylpiperazinyl), —C(=O)(hydroxy-piperidyl), —C(=O)(fluoropiperidinyl), —(C=O)(methoxy-piperidyl), —C(=NH)$NH_2$, —NHC(=O)$CH_3$, —$SO_2NHCH_3$, —$SO_2CH_3$, or substituted or unsubstituted pyrazolyl. In some other embodiments, $R^2$ is phenyl, substituted with one or more —$CH_3$, —$CH_2CH_3$, —$CH_2CH_2CH_3$, —$CH(CH_3)_2$, —$CH_2NH_2$, —$CF_3$, —Cl, —F, —CN, —$OCH_3$, —$OCF_3$, —C(=O)$NH_2$, —C(=O)$NHCH_3$, —C(=O)N$(CH_3)_2$, —C(=O)NC$(CH_3)_3$, —C(=O)$NHCH_2CH_2F$, —C(=O) $NHCH_2CF_2CH_3$, —C(=O)N$(CH_3)CH_2CN$, —C(=O)N $(CH_3)CH_2CH_2CN$, —C(=O)NH-(3-hydroxy-cyclobutyl), —C(=O)NH-cyclopentyl, —C(=O)NH-(2-hydroxycyclopentyl), —C(=O)$NHCH_2CH_2OH$, —C(=O) $NHCH_2CH_2OCH_3$, —C(=O)N$(CH_3)CH_2CH_2OH$, —C(=O)N$(CH_3)CH_2CH_2OCH_3$, —C(=O) $NHCH_2CH_2CH_2OH$, —C(=O)N$(CH_3)CH_2CH_2CH_2OH$, —C(=O)$NHCH_2CH(CH_3)OH$, —C(=O)$NHCH_2$ C(CH₃)₂OH, —C(=O)NHCH(CH₃)CH₂OH, —C(=O)NHC(CH₃)₂CH₂OH, —C(=O)NHCH₂CH₂NH₂, —C(=O)NHCH₂CH₂NH(CH₃), —C(=O)NHCH₂CH₂N(CH₃)₂, —C(=O)N(CH₃)CH₂C(=O)NH₂, —C(=O)N(CH₃)CH₂CH₂C(=O)NH₂, —C(=O)N(cyclopropyl)CH₂CH₂OH, —C(=O)NH-oxetanyl, —C(=O)N(CH₃)-oxetanyl, —C(=O)NH-(3-methyl-oxetanyl), —C(=O)NH-(1-methylazetidinyl), —C(=O)NH-(1-acetylazetidinyl), —C(=O)NH-piperidyl, —C(=O)NH-tetrahydrofuranyl, —C(=O)NH-tetrahydropyranyl, —C(=O)N(CH₃)-tetrahydropyranyl, —C(=O)NHCH₂-oxetanyl, —C(=O)N(CH₃)CH₂-(3-methyl-oxetanyl), —C(=O)NHCH₂-tetrahydrofuranyl, —C(=O)NHCH₂-tetrahydropyranyl, —C(=O)NHCH₂-dioxanyl, —C(=O)aziridinyl, —C(=O)(2-methyl-aziridinyl), —C(=O)(2,2-dimethyl-aziridinyl), —C(=O)(2-(hydroxymethyl)aziridinyl), —C(=O)azetidinyl, —C(=O)pyrrolidinyl, —C(=O)(3-hydroxy-4-methoxypyrrolidinyl), —C(=O)(3,4-dimethoxypyrrolidinyl), —C(=O)morpholinyl, —C(=O)piperazinyl, —C(=O)(4-methylpiperazinyl), —C(=O)(4-hydroxy-piperidyl), —C(=O)(4,4-difluoropiperidinyl), —(C=O)(4-methoxy-piperidyl), —C(=NH)NH₂, —NHC(=O)CH₃, —SO₂NHCH₃, —SO₂CH₃, or substituted or unsubstituted pyrazolyl.

In some embodiments of compounds of formula (I), $R^2$ is substituted or unsubstituted pyrazolyl, substituted or unsubstituted pyridyl, substituted or unsubstituted indazolyl or substituted or unsubstituted isoindolinone. In some such embodiments, $R^2$ is substituted with one or more halogen, substituted or unsubstituted $(C_{1-4})$alkyl, —OR, —C(=O)NR₂, or substituted or unsubstituted heterocyclyl, wherein each R is independently —H or substituted or unsubstituted $(C_{1-4})$alkyl. For example, $R^2$ is pyrazolyl substituted with one or more —Cl, —CH₃, —CH₂CH₃, —CH(CH₃)₂, —CH₂CH₂OCH₃, —CH₂C(CH₃)₂OH, or tetrahydropyranyl. Alternatively, $R^2$ is pyridyl, substituted with one or more —OCH₃, C(=O)NHCH₃, or tetrahydropyranyl. In yet other embodiments, $R^2$ is indazolyl or isoindolinone, substituted with one or more —CH₃.

In some such embodiments of $R^2$, $R^1$ is substituted or unsubstituted $C_{1-8}$ alkyl,

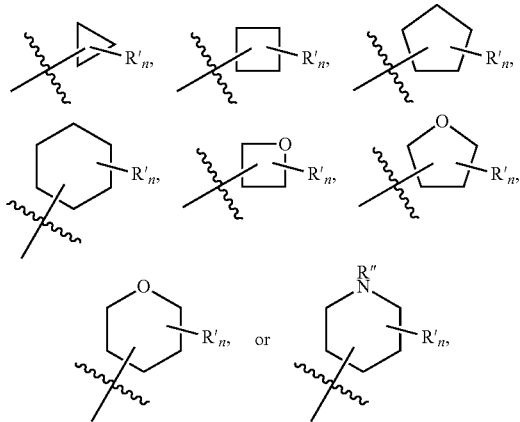

wherein
each R' is independently —OR or $C_{1-3}$ alkyl;
R" is —H or $C_{1-3}$ alkyl;
each R is independently —H or substituted or unsubstituted $(C_{1-4})$alkyl; and
n is 0-2.

In yet other embodiments of compounds of formula (I), $R^3$ is substituted or unsubstituted heterocyclyl, for example, substituted or unsubstituted pyrazolyl, oxazolyl, isoxazolyl, oxadiazolyl, pyridyl, pyridazinyl, pyrimidyl, pyrazinyl, benztriazolyl, indazolyl, indolyl, benzoxazolyl, benzisoxazolyl, benzthiazolyl, benzoxazolonyl, benzoxadiazolyl, benzimidazolyl, or quinolyl. In some such embodiments, the heterocyclyl is substituted with one or more substituents selected from substituted or unsubstituted $(C_{1-4})$alkyl, halogen, —OR, —CN, —NR₂, —C(=O)NR₂, —NRC(=O)R, or substituted or unsubstituted triazolyl, wherein each R is independently —H or substituted or unsubstituted $(C_{1-4})$alkyl. For example, the heterocyclyl is substituted with one or more substituents selected from —CH₃, —CH(CH₃)₂, —F, —Cl, —OH, —OCH₃, —OCH₂CH₃, —CN, —NH₂, —NHCH₃, —N(CH₃)₂, —C(=O)NH(CH₃), —NHC(=O)CH₃, or substituted or unsubstituted triazolyl. In some such embodiments, the pyrazolyl is substituted with one or more —CH₃, or —Cl. In others, the pyridyl is substituted with one or more —CH₃, —F, —Cl, —OH, —OCH₃, —OCH₂CH₃, —CN, —NH₂, —NHCH₃, —N(CH₃)₂, —C(=O)NH(CH₃), or —NHC(=O)CH₃. In still others, the benzoxazolyl is substituted with one or more —CH₃, —CH(CH₃)₂, —F or —OCH₂CH₃.

In other embodiments of compounds of formula (I), $R^3$ is substituted or unsubstituted aryl, for example, $R^3$ is substituted or unsubstituted phenyl. In some such embodiments, the phenyl is substituted with one or more substituents selected from substituted or unsubstituted $C_{1-4}$ alkyl, halogen, —CN, —OR, —NR₂, —NRSO₂R', —NR(C=O)NR₂, —NR(C=O)R', —COOR, —(C=O)NR₂, —C(=NH)NR₂, —SO₂R', or substituted or unsubstituted heteroaryl, wherein each R is independently —H or substituted or unsubstituted $(C_{1-4})$alkyl, and R' is $C_{1-3}$ alkyl. In yet other embodiments, the phenyl is substituted with one or more substituents selected from —CH₃, —CH₂OH, —CH(OH)CH₃, —C(CH₃)₂OH, —CN, —F, —Cl, —OH, —OCH₃, —NH₂, —N(CH₃)₂, —NHSO₂CH₃, —NH(C=O)NH₂, —NH(C=O)CH₃, —COOCH₃, —(C=O)NHCH₃, —C(=N)NH₂, —SO₂CH₃, substituted or unsubstituted triazolyl, substituted or unsubstituted pyrazolyl, or substituted or unsubstituted imidazolyl.

In some such embodiments of $R^3$, $R^1$ is substituted or unsubstituted $C_{1-8}$ alkyl,

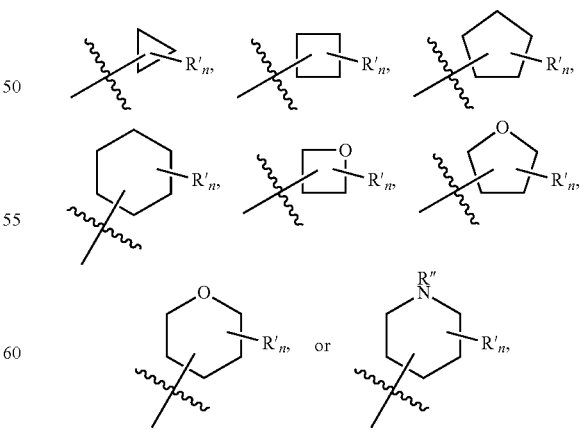

wherein
each R' is independently —OR or $C_{1-3}$ alkyl;
R" is —H or $C_{1-3}$ alkyl;

each R is independently —H or substituted or unsubstituted ($C_{1-4}$)alkyl; and n is 0-2.

In some such embodiments, $R^2$ is phenyl, substituted with one or more —($C_{1-3}$ alkyl), —($C_{1-3}$ alkyl)$NR_2$, —$CF_3$, —Cl, —F, —CN, —$OCH_3$, —$OCF_3$, —C(=O)$NR_2$, —C(=O)NR (substituted or unsubstituted cycloalkyl), —C(=O)NR($CH_2$)$_{0-2}$C$R_2$($CH_2$)$_{0-2}$OR, —C(=O)NR($CH_2$)$_{0-2}$C$R_2$($CH_2$)$_{0-2}$N$R_2$, —C(=O)NR($CH_2$)$_{0-2}$C$R_2$($CH_2$)$_{0-2}$C(=O)$NR_2$, —C(=O)N (substituted or unsubstituted cycloalkyl)($CH_2$)$_{0-2}$OR, —C(=O)NR($CH_2$)$_{0-3}$ (substituted or unsubstituted heterocyclyl), —C(=O)($CH_2$)$_{0-3}$ (substituted or unsubstituted heterocyclyl), —C(=NR)$NR_2$, —NRC(=O)R, —$SO_2NR_2$, —$SO_2R$, or substituted or unsubstituted heterocyclyl, wherein each R is independently —H or substituted or unsubstituted ($C_{1-4}$)alkyl.

Further embodiments provided herein include combinations of one or more of the particular embodiments set forth above.

In some embodiments of compounds of formula (I), the compound is selected from Table A, or a pharmaceutically acceptable salt, tautomer, stereoisomer, enantiomer, or isotopologue thereof.

Pyrrolopyrimidine Compounds set forth in Table A were tested in the assays described herein and were found to have activity as cancer treatment agents, in particular for the treatment of solid tumors and hematological cancers as described herein. In some embodiments, the solid tumor is bladder cancer (including superficial bladder cancer), breast cancer (including luminal B type, ER+, PR+ and Her2+ breast cancer), central nervous system cancer (including glioblastoma multiforme (GBM), glioma, medulloblastoma, and astrocytoma), colorectal cancer, gastrointestinal cancer (including stomach cancer, oesophagus cancer, and rectum cancer), endocrine cancer (including thyroid cancer, and adrenal gland cancer), eye cancer (including retinoblastoma), female genitourinary cancer (including cancer of the placenta, uterus, vulva, ovary, cervix), head and neck cancer (including cancer of the pharynx, oesophagus, and tongue), liver cancer, lung cancer (including non-small cell lung cancer (NSCLC), small cell lung cancer (SCLC), mucoepidermoid, bronchogenic, squamous cell carcinoma (SQCC), and analplastic/NSCLC), skin cancer (including melanoma, and SQCC), soft tissue cancer (including sarcoma, Ewing's sarcoma, and rhabdomyosarcoma), bone cancer (including sarcoma, Ewing's sarcoma, and osteosarcoma), squamous cell cancer (including lung, esophageal, cervical, and head and neck cancer), pancreas cancer, kidney cancer (including renal Wilm's tumor and renal cell carcinoma), or prostate cancer. In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

In some embodiments, the hematological cancer is leukemia (including acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), and large cell immunoblastic lymphoma), or multiple myeloma.

In one embodiment, the Pyrrolopyrimidine Compound is a compound as described herein, wherein the compound at a concentration of 10 μM inhibits cancer cell proliferation, for example solid tumor or hematological cancer cell proliferation, as described herein, by at least about 50% or more.

TABLE A

| Cmpd No. | Structure | Name |
|---|---|---|
| 1 | 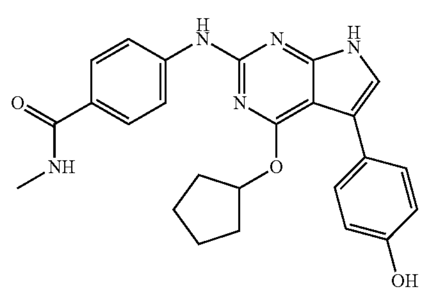 [SMILES: CNC(=O)c1ccc(Nc2nc(OC3CCCC3)c3c(-c4ccc(O)cc4)c[nH]c3n2)cc1] | 4-(4-(cyclopentyloxy)-5-(4-hydroxyphenyl)-7H-pyrrolo[2,3-d]pyrimidin-2-ylamino)-N-methylbenzamide |
| 2 | 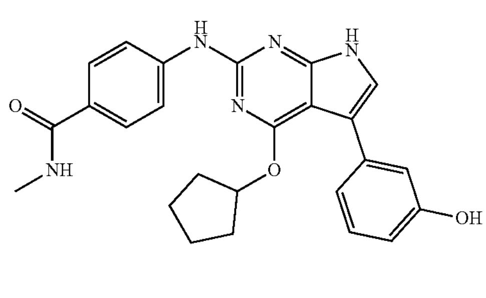 [SMILES: CNC(=O)c1ccc(Nc2nc(OC3CCCC3)c3c(-c4cccc(O)c4)c[nH]c3n2)cc1] | 4-(4-(cyclopentyloxy)-5-(3-hydroxyphenyl)-7H-pyrrolo[2,3-d]pyrimidin-2-ylamino)-N-methylbenzamide |

TABLE A-continued

| Cmpd No. | Structure | Name |
|---|---|---|
| 3 | 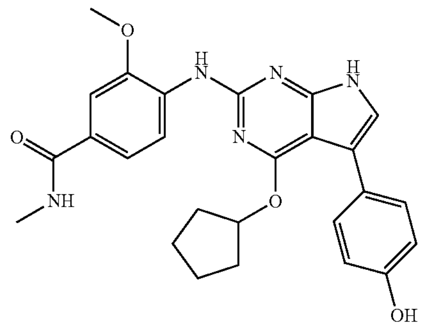 [SMILES: CNC(=O)c1ccc(Nc2nc(OC3CCCC3)c3c(-c4ccc(O)cc4)c[nH]c3n2)c(OC)c1] | 4-(4-(cyclopentyloxy)-5-(4-hydroxyphenyl)-7H-pyrrolo[2,3-d]pyrimidin-2-ylamino)-3-methoxy-N-methylbenzamide |
| 4 | 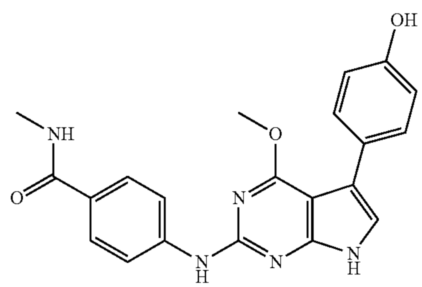 [SMILES: CNC(=O)c1ccc(Nc2nc(OC)c3c(-c4ccc(O)cc4)c[nH]c3n2)cc1] | 4-(5-(4-hydroxyphenyl)-4-methoxy-7H-pyrrolo[2,3-d]pyrimidin-2-ylamino)-N-methylbenzamide |
| 5 | 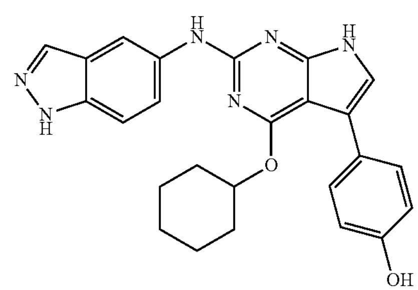 [SMILES: Oc1ccc(-c2c[nH]c3nc(Nc4ccc5[nH]ncc5c4)nc(OC4CCCCC4)c23)cc1] | 4-(2-(1H-indazol-5-ylamino)-4-(cyclohexyloxy)-7H-pyrrolo[2,3-d]pyrimidin-5-yl)phenol |
| 6 | 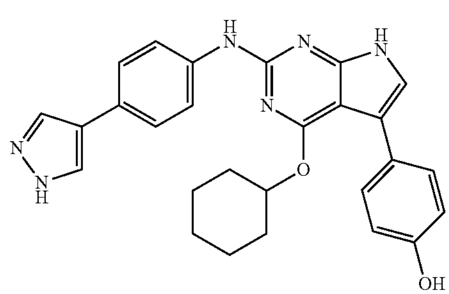 [SMILES: Oc1ccc(-c2c[nH]c3nc(Nc4ccc(-c5cn[nH]c5)cc4)nc(OC4CCCCC4)c23)cc1] | 4-(2-(4-(1H-pyrazol-4-yl)phenylamino)-4-(cyclohexyloxy)-7H-pyrrolo[2,3-d]pyrimidin-5-yl)phenol |

TABLE A-continued

| Cmpd No. | Structure | Name |
| --- | --- | --- |
| 7 | 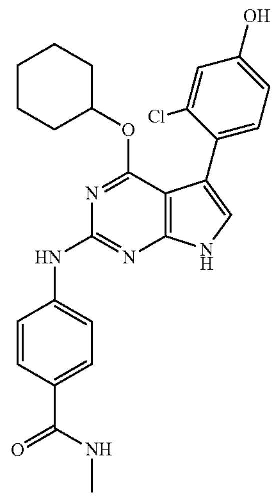 [SMILES: CNC(=O)c1ccc(Nc2nc(OC3CCCCC3)c3c(-c4ccc(O)cc4Cl)c[nH]c3n2)cc1] | 4-(5-(2-chloro-4-hydroxyphenyl)-4-(cyclohexyloxy)-7H-pyrrolo[2,3-d]pyrimidin-2-ylamino)-N-methylbenzamide |
| 8 | 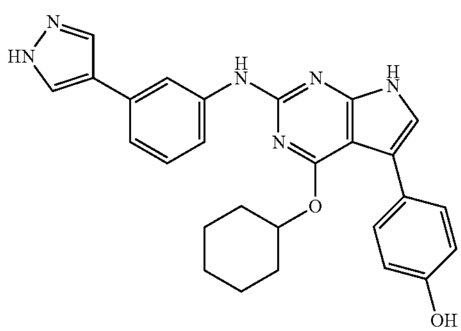 [SMILES: Oc1ccc(-c2c[nH]c3nc(Nc4cccc(-c5cn[nH]c5)c4)nc(OC4CCCCC4)c23)cc1] | 4-(2-(3-(1H-pyrazol-4-yl)phenylamino)-4-(cyclohexyloxy)-7H-pyrrolo[2,3-d]pyrimidin-5-yl)phenol |
| 9 | 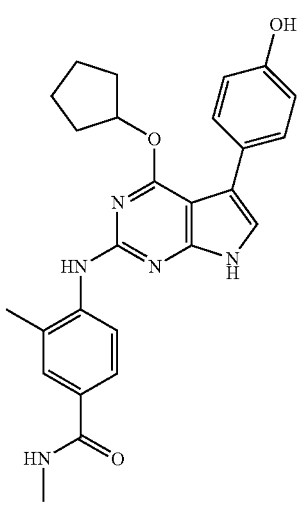 [SMILES: CNC(=O)c1ccc(Nc2nc(OC3CCCC3)c3c(-c4ccc(O)cc4)c[nH]c3n2)c(C)c1] | 4-(4-(cyclopentyloxy)-5-(4-hydroxyphenyl)-7H-pyrrolo[2,3-d]pyrimidin-2-ylamino)-N,3-diethylbenzamide |

TABLE A-continued
| Cmpd No. | Structure | Name |
|---|---|---|
| 10 | 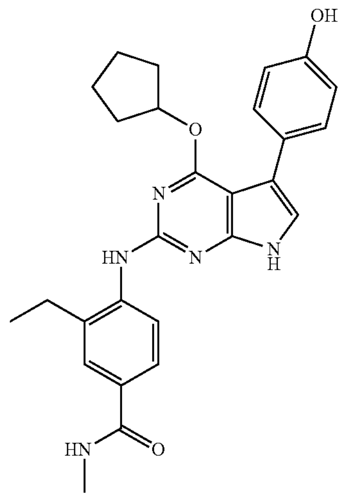 [SMILES: CCc1cc(C(=O)NC)ccc1Nc1nc(OC2CCCC2)c2c(-c3ccc(O)cc3)c[nH]c2n1] | 4-(4-(cyclopentyloxy)-5-(4-hydroxyhenyl)-7H-pyrrolo[2,3-d]pyrimidin-2-ylamino)-3-ethyl-N-methylbenzamide |
| 11 | 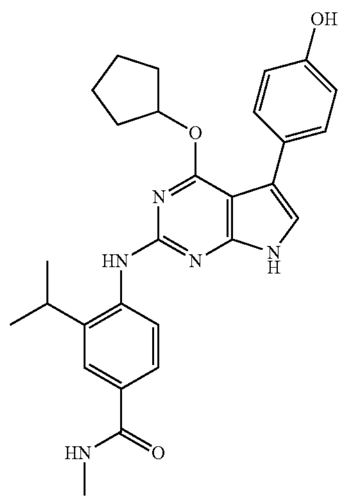 [SMILES: CNC(=O)c1ccc(Nc2nc(OC3CCCC3)c3c(-c4ccc(O)cc4)c[nH]c3n2)c(C(C)C)c1] | 4-(4-(cyclopentyloxy)-5-(4-hydroxyphenyl)-7H-pyrrolo[2,3-d]pyrimidin-2-ylamino)-3-isopropyl-N-methylbenzamide |
| 12 | 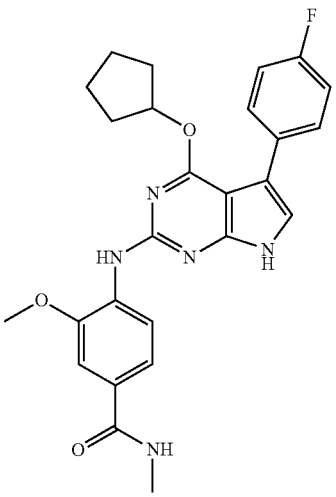 [SMILES: CNC(=O)c1ccc(Nc2nc(OC3CCCC3)c3c(-c4ccc(F)cc4)c[nH]c3n2)c(OC)c1] | 4-(4-(cyclopentyloxy)-5-(4-fluorophenyl)-7H-pyrrolo[2,3-d]pyrimidin-2-ylamino)-3-methoxy-N-methylbenzamide |

TABLE A-continued

| Cmpd No. | Structure | Name |
|---|---|---|
| 13 | 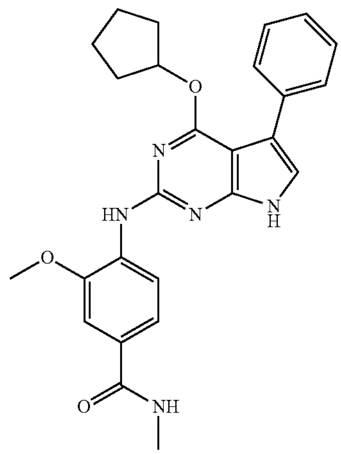 [SMILES: CNC(=O)c1ccc(Nc2nc(OC3CCCC3)c3c(-c4ccccc4)c[nH]c3n2)c(OC)c1] | 4-(4-(cyclopentyloxy)-5-phenyl-7H-pyrrolo[2,3-d]pyrimidin-2-ylamino)-3-methoxy-N-methylbenzamide |
| 14 | 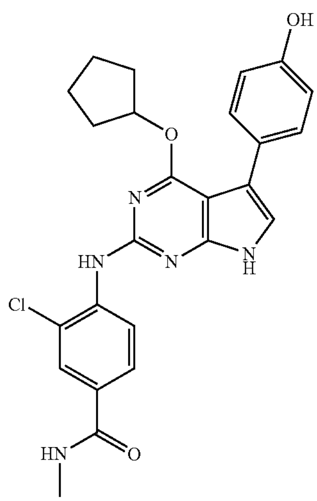 [SMILES: CNC(=O)c1ccc(Nc2nc(OC3CCCC3)c3c(-c4ccc(O)cc4)c[nH]c3n2)c(Cl)c1] | 3-chloro-4-(4-(cyclopentyloxy)-5-(4-hydroxyphenyl)-7H-pyrrolo[2,3-d]pyrimidin-2-ylamino)-N-methylbenzamide |
| 15 | 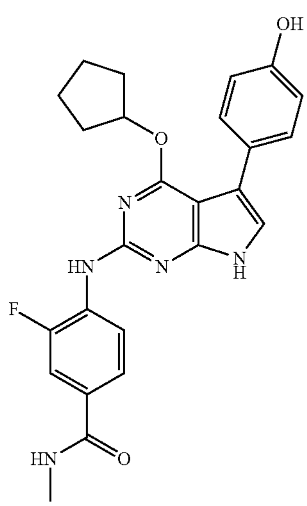 [SMILES: CNC(=O)c1ccc(Nc2nc(OC3CCCC3)c3c(-c4ccc(O)cc4)c[nH]c3n2)c(F)c1] | 4-(4-(cyclopentyloxy)-5-(4-hydroxyphenyl)-7H-pyrrolo[2,3-d]pyrimidin-2-ylamino)-3-fluoro-N-methylbenzamide |

TABLE A-continued

| Cmpd No. | Structure | Name |
|---|---|---|
| 16 | 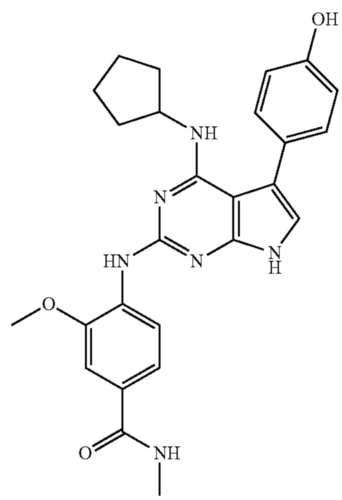 [SMILES: CNC(=O)c1ccc(Nc2nc(NC3CCCC3)c3c(-c4ccc(O)cc4)c[nH]c3n2)c(OC)c1] | 4-(4-(cyclopentylamino)-5-(4-hydroxyphenyl)-7H-pyrrolo[2,3-d]pyrimidin-2-ylamino)-3-methoxy-N-methylbenzamide |
| 17 | 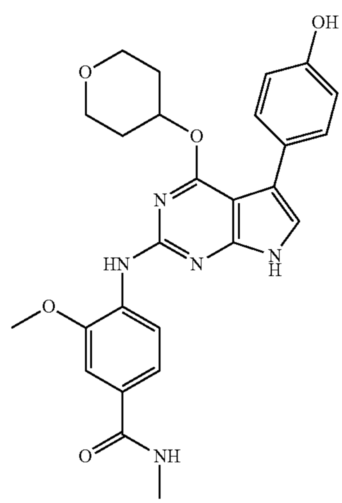 [SMILES: CNC(=O)c1ccc(Nc2nc(OC3CCOCC3)c3c(-c4ccc(O)cc4)c[nH]c3n2)c(OC)c1] | 4-(5-(4-hydroxyphenyl)-4-(tetrahydro-2H-pyran-4-yloxy)-7H-pyrrolo[2,3-d]pyrimidin-2-ylamino)-3-methoxy-N-methylbenzamide |
| 18 | 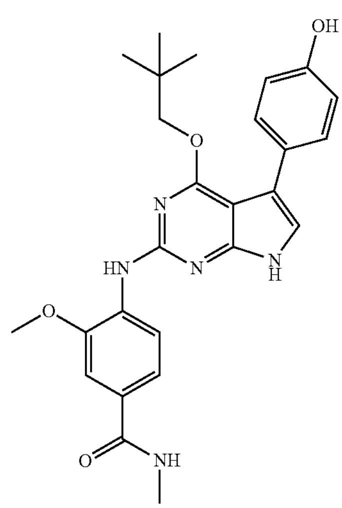 [SMILES: CNC(=O)c1ccc(Nc2nc(OCC(C)(C)C)c3c(-c4ccc(O)cc4)c[nH]c3n2)c(OC)c1] | 4-(5-(4-hydroxyphenyl)-4-(neopentyloxy)-7H-pyrrolo[2,3-d]pyrimidin-2-ylamino)-3-methoxy-N-methylbenzamide |

TABLE A-continued
| Cmpd No. | Structure | Name |
|---|---|---|
| 19 | 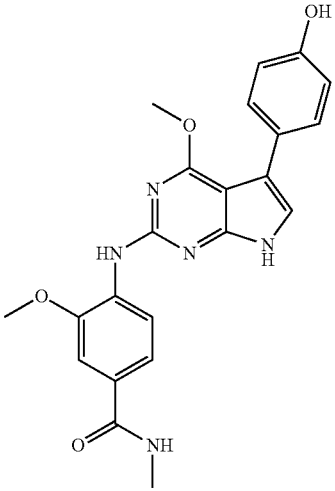 [SMILES: CNC(=O)c1ccc(Nc2nc(OC)c3c(-c4ccc(O)cc4)c[nH]c3n2)c(OC)c1] | 4-(5-(4-hydroxyphenyl)-4-methoxy-7H-pyrrolo[2,3-d]pyrimidin-2-ylamino)-3-methoxy-N-methylbenzamide |
| 20 | 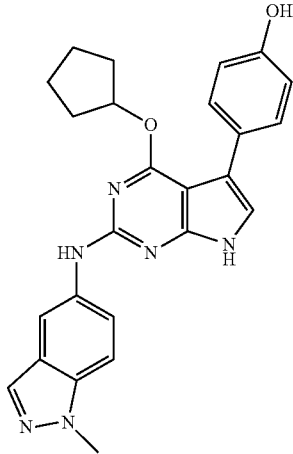 [SMILES: Cn1ncc2cc(Nc3nc(OC4CCCC4)c4c(-c5ccc(O)cc5)c[nH]c4n3)ccc21] | 4-(4-(cyclopentyloxy)-2-(1-methyl-1H-indazol-5-ylamino)-7H-pyrrolo[2,3-d]pyrimidin-5-yl)phenol |
| 21 | 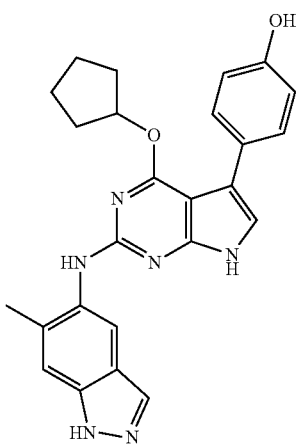 [SMILES: Cc1cc2[nH]ncc2cc1Nc1nc(OC2CCCC2)c2c(-c3ccc(O)cc3)c[nH]c2n1] | 4-(4-(cyclopentyloxy)-2-(6-methyl-1H-indazol-5-ylamino)-7H-pyrrolo[2,3-d]pyrimidin-5-yl)phenol |

TABLE A-continued

| Cmpd No. | Structure | Name |
|---|---|---|
| 22 | 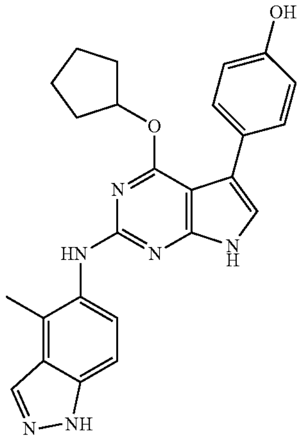 [SMILES: Cc1c(Nc2nc(OC3CCCC3)c3c(-c4ccc(O)cc4)c[nH]c3n2)ccc2[nH]ncc12] | 4-(4-(cyclopentyloxy)-2-(4-methyl-1H-indazol-5-ylamino)-7H-pyrrolo[2,3-d]pyrimidin-5-yl)phenol |
| 23 | 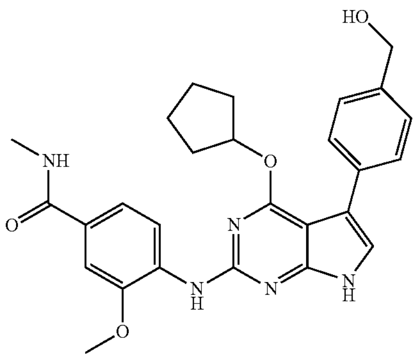 [SMILES: CNC(=O)c1ccc(Nc2nc(OC3CCCC3)c3c(-c4ccc(CO)cc4)c[nH]c3n2)c(OC)c1] | 4-(4-(cyclopentyloxy)-5-(4-(hydroxymethyl)phenyl)-7H-pyrrolo[2,3-d]pyrimidin-2-ylamino)-3-methoxy-N-methylbenzamide |
| 24 | 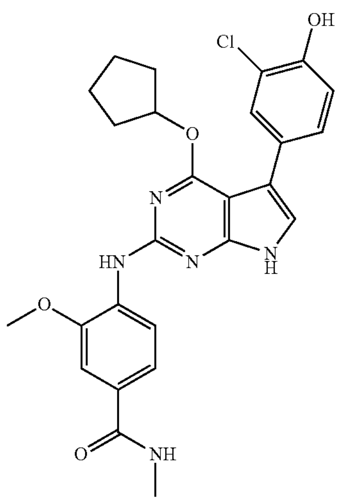 [SMILES: CNC(=O)c1ccc(Nc2nc(OC3CCCC3)c3c(-c4ccc(O)c(Cl)c4)c[nH]c3n2)c(OC)c1] | 4-(5-(3-chloro-4-hydroxyphenyl)-4-(cyclopentyloxy)-7H-pyrrolo[2,3-d]pyrimidin-2-ylamino)-3-methoxy-N-methylbenzamide |
| 25 | 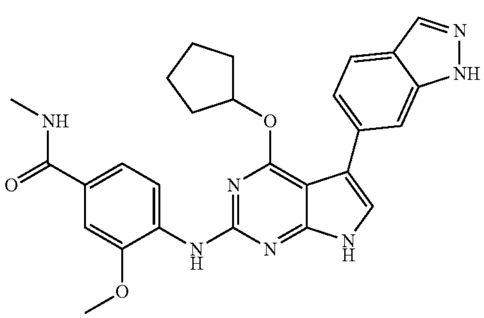 [SMILES: CNC(=O)c1ccc(Nc2nc(OC3CCCC3)c3c(-c4ccc5cn[nH]c5c4)c[nH]c3n2)c(OC)c1] | 4-(4-(cyclopentyloxy)-5-(1H-indazol-6-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 26 | 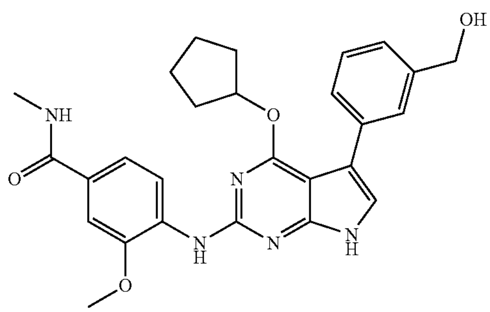 [SMILES: CNC(=O)c1ccc(Nc2nc(OC3CCCC3)c3c(-c4cccc(CO)c4)c[nH]c3n2)c(OC)c1] | 4-(4-(cyclopentyloxy)-5-(3-(hydroxymethyl)phenyl)-7H-pyrrolo[2,3-d]pyrimidin-2-ylamino)-3-methoxy-N-methylbenzamide |
| 27 | 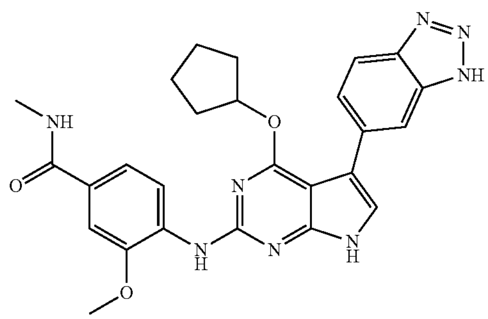 [SMILES: CNC(=O)c1ccc(Nc2nc(OC3CCCC3)c3c(-c4ccc5nn[nH]c5c4)c[nH]c3n2)c(OC)c1] | 4-(5-(1H-benzo[d][1,2,3]triazol-6-yl)-4-(cyclopentyloxy)-7H-pyrrolo[2,3-d]pyrimidin-2-ylamino)-3-methoxy-N-methylbenzamide |
| 28 | 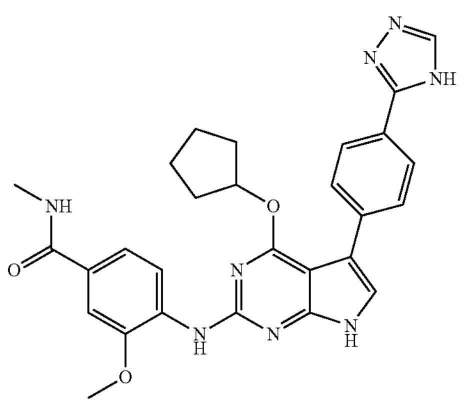 [SMILES: CNC(=O)c1ccc(Nc2nc(OC3CCCC3)c3c(-c4ccc(-c5nnc[nH]5)cc4)c[nH]c3n2)c(OC)c1] | 4-(5-(4-(4H-1,2,4-triazol-3-yl)phenyl)-4-(cyclopentyloxy)-7H-pyrrolo[2,3-d]pyrimidin-2-ylamino)-3-methoxy-N-methylbenzamide |
| 29 | 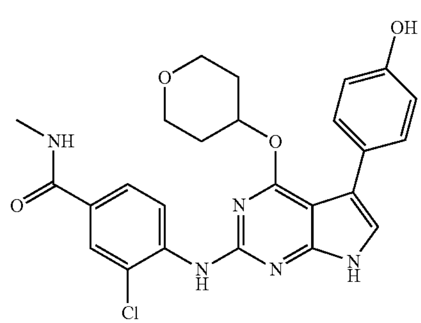 [SMILES: CNC(=O)c1ccc(Nc2nc(OC3CCOCC3)c3c(-c4ccc(O)cc4)c[nH]c3n2)c(Cl)c1] | 3-chloro-4-(5-(4-hydroxyphenyl)-4-(tetrahydro-2H-pyran-4-yloxy)-7H-pyrrolo[2,3-d]pyrimidin-2-ylamino)-N-methylbenzamide |

TABLE A-continued

| Cmpd No. | Structure | Name |
|---|---|---|
| 30 | 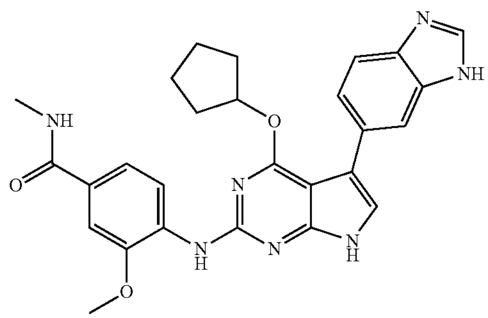 [SMILES: CNC(=O)c1ccc(Nc2nc(OC3CCCC3)c3c(-c4ccc5nc[nH]c5c4)c[nH]c3n2)c(OC)c1] | 4-(5-(1H-benzo[d]imidazol-6-yl)-4-(cyclopentyloxy)-7H-pyrrolo[2,3-d]pyrimidin-2-ylamino)-3-methoxy-N-methylbenzamide |
| 31 | 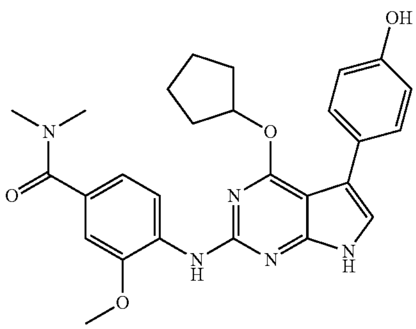 [SMILES: COc1cc(C(=O)N(C)C)ccc1Nc1nc(OC2CCCC2)c2c(-c3ccc(O)cc3)c[nH]c2n1] | 4-(4-(cyclopentyloxy)-5-(4-hydroxyphenyl)-7H-pyrrolo[2,3-d]pyrimidin-2-ylamino)-3-methoxy-N,N-dimethylbenzamide |
| 32 | 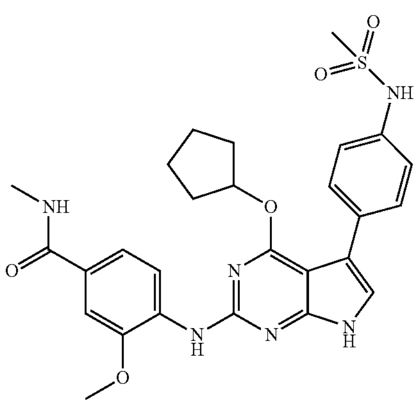 [SMILES: CNC(=O)c1ccc(Nc2nc(OC3CCCC3)c3c(-c4ccc(NS(C)(=O)=O)cc4)c[nH]c3n2)c(OC)c1] | 4-(4-(cyclopentyloxy)-5-(4-(methylsulfonamido)phenyl)-7H-pyrrolo[2,3-d]pyrimidin-2-ylamino)-3-methoxy-N-methylbenzamide |
| 33 | 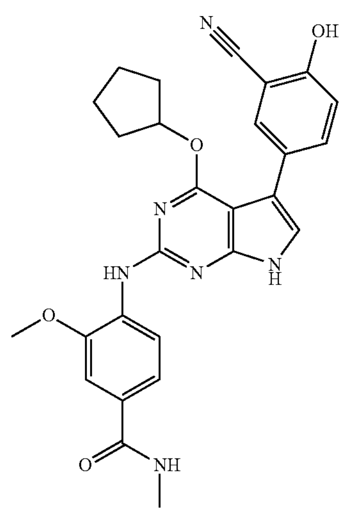 [SMILES: CNC(=O)c1ccc(Nc2nc(OC3CCCC3)c3c(-c4ccc(O)c(C#N)c4)c[nH]c3n2)c(OC)c1] | 4-(5-(3-cyano-4-hydroxyphenyl)-4-(cyclopentyloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 34 | 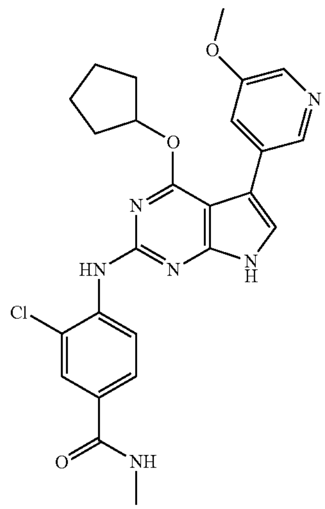 [SMILES: CNC(=O)c1ccc(Nc2nc(OC3CCCC3)c3c(-c4cncc(OC)c4)c[nH]c3n2)c(Cl)c1] | 3-chloro-4-(4-(cyclopentyloxy)-5-(5-methoxypyridin-3-yl)-7H-pyrrolo[2,3-d]pyrimidin-2-ylamino)-N-methylbenzamide |
| 35 | 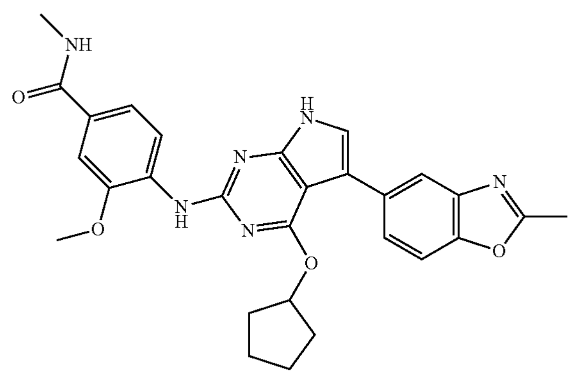 [SMILES: CNC(=O)c1ccc(Nc2nc(OC3CCCC3)c3c(-c4ccc5oc(C)nc5c4)c[nH]c3n2)c(OC)c1] | 4-(4-(cyclopentyloxy)-5-(2-methylbenzo[d]oxazol-5-yl)-7H-pyrrolo[2,3-d]pyrimidin-2-ylamino)-3-methoxy-N-methylbenzamide |
| 36 | 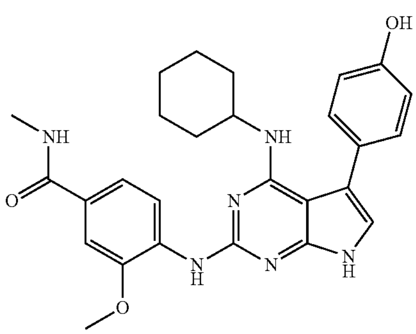 | 4-(4-(cyclohexylamino)-5-(4-hydroxyphenyl)-7H-pyrrolo[2,3-d]pyrimidin-2-ylamino)-3-methoxy-N-methylbenzamide |
| 37 | 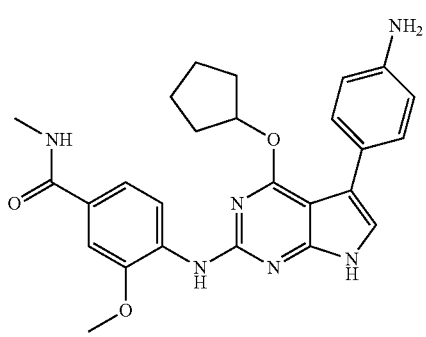 [SMILES: CNC(=O)c1ccc(Nc2nc(OC3CCCC3)c3c(-c4ccc(N)cc4)c[nH]c3n2)c(OC)c1] | 4-(5-(aminophenyl)-4-(cyclopentyloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 38 | 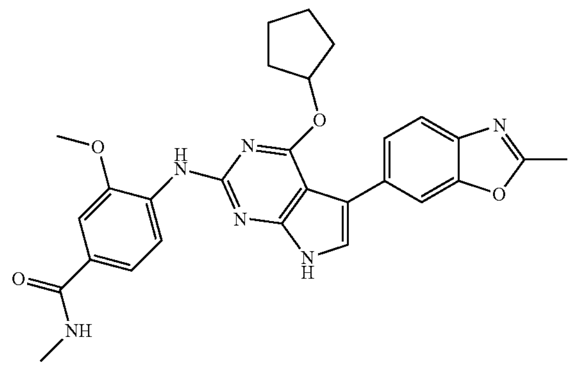 [SMILES: CNC(=O)c1ccc(Nc2nc(OC3CCCC3)c3c(-c4ccc5nc(C)oc5c4)c[nH]c3n2)c(OC)c1] | 4-(4-(cyclopentyloxy)-5-(2-methylbenzo[d]oxazol-6-yl)-7H-pyrrolo[2,3-d]pyrimidin-2-ylamino)-3-methoxy-N-methylbenzamide |
| 39 | 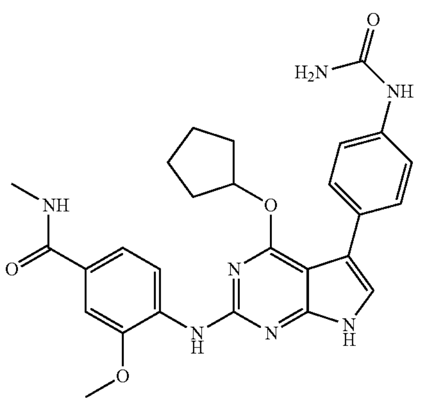 [SMILES: CNC(=O)c1ccc(Nc2nc(OC3CCCC3)c3c(-c4ccc(NC(N)=O)cc4)c[nH]c3n2)c(OC)c1] | 4-(4-(cyclopentyloxy)-5-(4-ureidophenyl)-7H-pyrrolo[2,3-d]pyrimidin-2-ylamino)-3-methoxy-N-methylbenzamide |
| 40 | 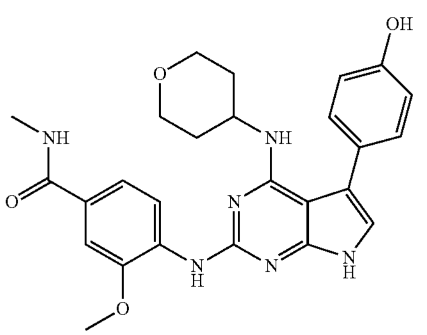 [SMILES: CNC(=O)c1ccc(Nc2nc(NC3CCOCC3)c3c(-c4ccc(O)cc4)c[nH]c3n2)c(OC)c1] | 4-(5-(4-hydroxyphenyl)-4-(tetrahydro-2H-pyran-4-ylamino)-7H-pyrrolo[2,3-d]pyrimidin-2-ylamino)-3-methoxy-N-methylbenzamide |
| 41 | 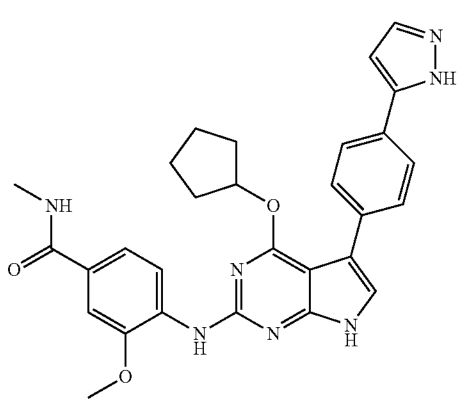 [SMILES: CNC(=O)c1ccc(Nc2nc(OC3CCCC3)c3c(-c4ccc(-c5ccn[nH]5)cc4)c[nH]c3n2)c(OC)c1] | 4-(5-(4-(1H-pyrazol-5-yl)phenyl)-4-(cyclopentyloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 42 | 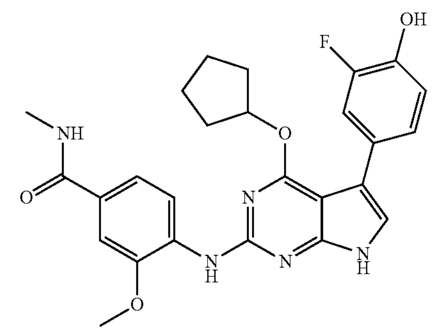 [SMILES: CNC(=O)c1ccc(Nc2nc(OC3CCCC3)c3c(-c4ccc(O)c(F)c4)c[nH]c3n2)c(OC)c1] | 4-(4-(cyclopentyloxy)-5-(3-fluoro-4-hydroxyphenyl)-7H-pyrrolo[2,3-d]pyrimidin-2-ylamino)-3-methoxy-N-methylbenzamide |
| 43 | 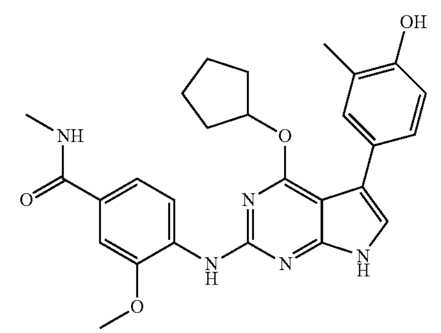 [SMILES: CNC(=O)c1ccc(Nc2nc(OC3CCCC3)c3c(-c4ccc(O)c(C)c4)c[nH]c3n2)c(OC)c1] | 4-(4-(cyclopentyloxy)-5-(4-hydroxy-3-methylphenyl)-7H-pyrrolo[2,3-d]pyrimidin-2-ylamino)-3-methoxy-N-methylbenzamide |
| 44 | 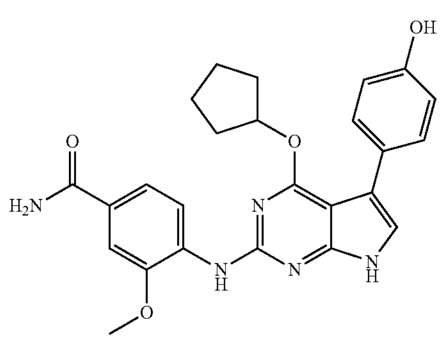 [SMILES: COc1cc(C(N)=O)ccc1Nc1nc(OC2CCCC2)c2c(-c3ccc(O)cc3)c[nH]c2n1] | 4-(4-(cyclopentyloxy)-5-(4-hydroxyphenyl)-7H-pyrrolo[2,3-d]pyrimidin-2-ylamino)-3-methoxybenzamide |
| 45 | 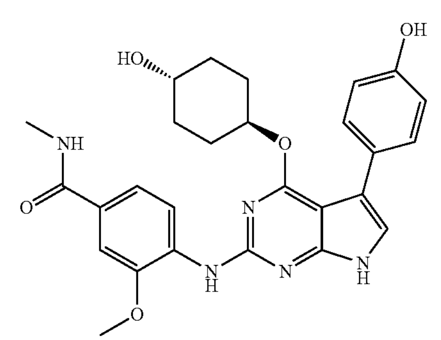 [SMILES: CNC(=O)c1ccc(Nc2nc(O[C@H]3CC[C@H](O)CC3)c3c(-c4ccc(O)cc4)c[nH]c3n2)c(OC)c1] | 4-(4-((1r,4r)-4-hydroxycyclohexyloxy)-5-(4-hydroxyphenyl)-7H-pyrrolo[2,3-d]pyrimidin-2-ylamino)-3-methoxy-N-methylbenzamide |

TABLE A-continued

| Cmpd No. | Structure | Name |
|---|---|---|
| 46 | 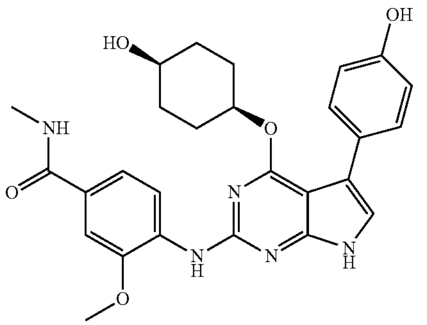 [SMILES: CNC(=O)c1ccc(Nc2nc(O[C@H]3CC[C@@H](O)CC3)c3c(-c4ccc(O)cc4)c[nH]c3n2)c(OC)c1] | 4-(4-((1s,4s)-4-hydroxycyclohexyloxy)-5-(4-hydroxyphenyl)-7H-pyrrolo[2,3-d]pyrimidin-2-ylamino)-3-methoxy-N-methylbenzamide |
| 47 | 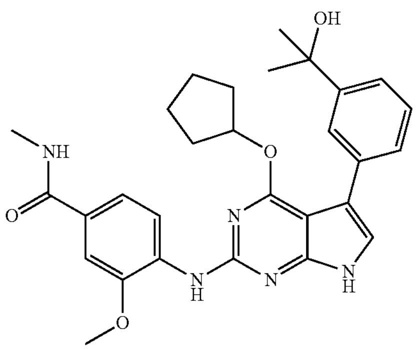 [SMILES: CNC(=O)c1ccc(Nc2nc(OC3CCCC3)c3c(-c4cccc(C(C)(C)O)c4)c[nH]c3n2)c(OC)c1] | 4-(4-(cyclopentyloxy)-5-(3-(2-hydroxypropan-2-yl)phenyl)-7H-pyrrolo[2,3-d]pyrimidin-2-ylamino)-3-methoxy-N-methylbenzamide |
| 48 | 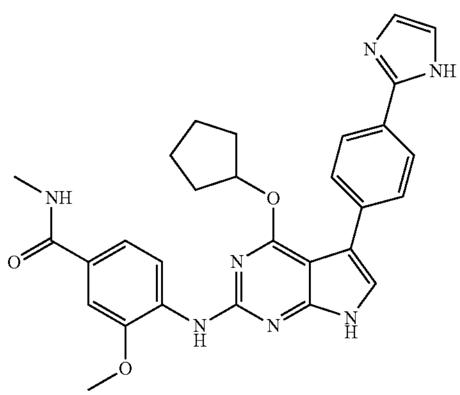 [SMILES: CNC(=O)c1ccc(Nc2nc(OC3CCCC3)c3c(-c4ccc(-c5ncc[nH]5)cc4)c[nH]c3n2)c(OC)c1] | 4-(5-(4-(1H-imidazol-2-yl)phenyl)-4-(cyclopentyloxy)-7H-pyrrolo[2,3-d]pyrimidin-2-ylamino)-3-methoxy-N-methylbenzamide |
| 49 | 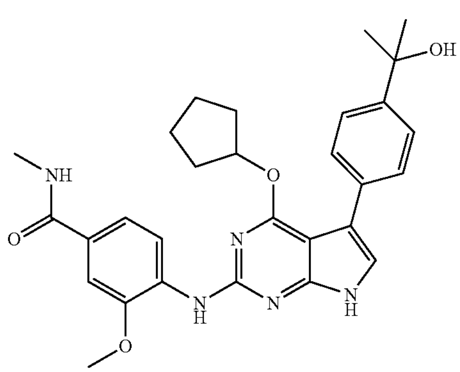 [SMILES: CNC(=O)c1ccc(Nc2nc(OC3CCCC3)c3c(-c4ccc(C(C)(C)O)cc4)c[nH]c3n2)c(OC)c1] | 4-(4-(cyclopentyloxy)-5-(4-(2-hydroxypropan-2-yl)phenyl)-7H-pyrrolo[2,3-d]pyrimidin-2-ylamino)-3-methoxy-N-methylbenzamide |

TABLE A-continued

| Cmpd No. | Structure | Name |
|---|---|---|
| 50 | 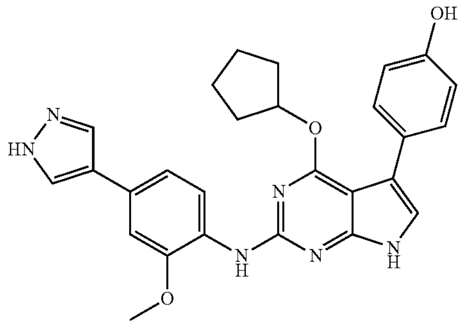 [SMILES: COc1cc(-c2cn[nH]c2)ccc1Nc1nc(OC2CCCC2)c2c(-c3ccc(O)cc3)c[nH]c2n1] | 4-(4-(cyclopentyloxy)-2-(2-methoxy-4-(1H-pyrazol-4-yl)phenylamino)-7H-pyrrolo[2,3-d]pyrimidin-5-yl)phenol |
| 51 | 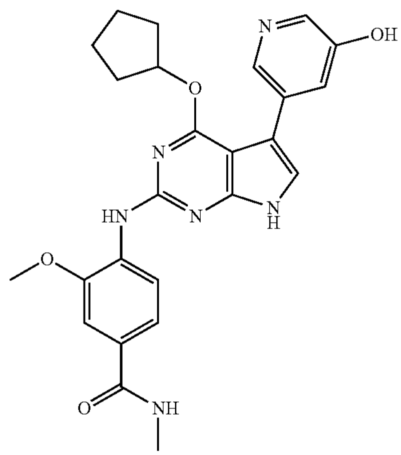 [SMILES: CNC(=O)c1ccc(Nc2nc(OC3CCCC3)c3c(-c4cncc(O)c4)c[nH]c3n2)c(OC)c1] | 4-(4-(cyclopentyloxy)-5-(5-hydroxypyridin-3-yl)-7H-pyrrolo[2,3-d]pyrimidin-2-ylamino)-3-methoxy-N-methylbenzamide |
| 52 | 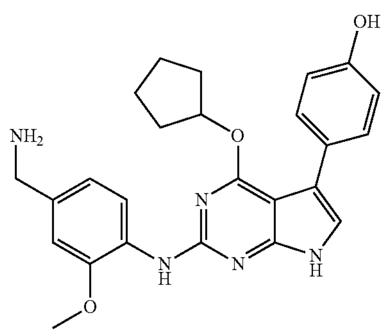 [SMILES: COc1cc(CN)ccc1Nc1nc(OC2CCCC2)c2c(-c3ccc(O)cc3)c[nH]c2n1] | 4-(2-(4-(aminomethyl)-2-methoxyphenylamino)-4-(cyclopentyloxy)-7H-pyrrolo[2,3-d]pyrimidin-5-yl)phenol |
| 53 | 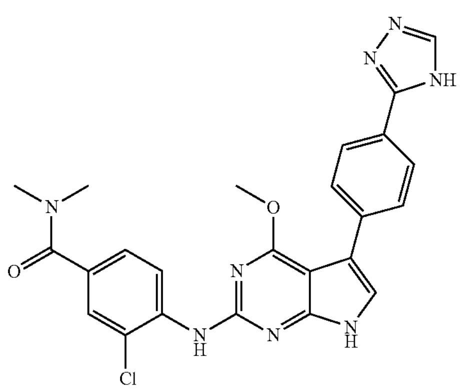 [SMILES: COc1nc(Nc2ccc(C(=O)N(C)C)cc2Cl)nc2[nH]cc(-c3ccc(-c4nnc[nH]4)cc3)c12] | 4-(5-(4-(4H-1,2,4-triazol-3-yl)phenyl)-4-methoxy-7H-pyrrolo[2,3-d]pyrimidin-2-ylamino)-3-chloro-N,N-dimethylbenzamide |

TABLE A-continued

| Cmpd No. | Structure | Name |
| --- | --- | --- |
| 54 | 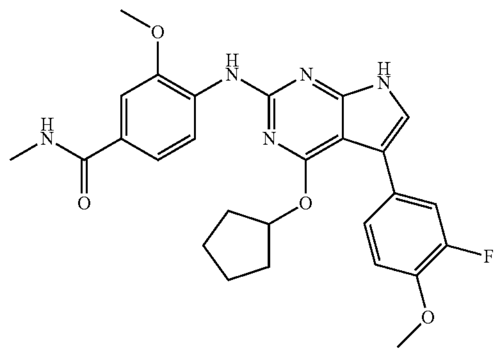 [SMILES: CNC(=O)c1ccc(Nc2nc(OC3CCCC3)c3c(-c4ccc(OC)c(F)c4)c[nH]c3n2)c(OC)c1] | 4-(4-(cyclopentyloxy)-5-(3-fluoro-4-methoxyphenyl)-7H-pyrrolo[2,3-d]pyrimidin-2-ylamino)-3-methoxy-N-methylbenzamide |
| 55 | 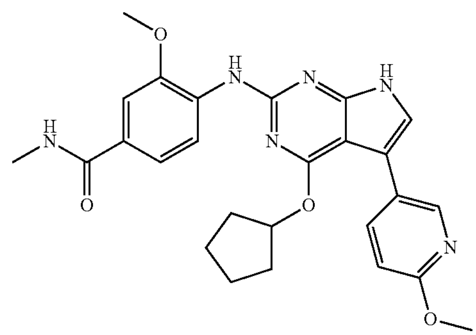 | 4-(4-(cyclopentyloxy)-5-(6-methoxypyridin-3-yl)-7H-pyrrolo[2,3-d]pyrimidin-2-ylamino)-3-methoxy-N-methylbenzamide |
| 56 | 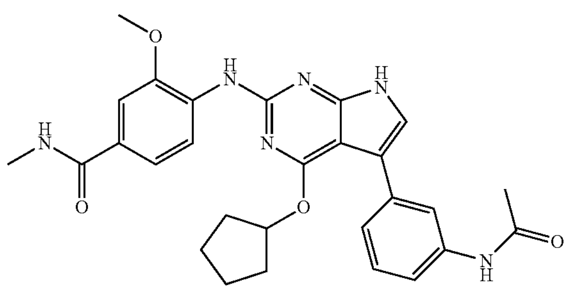 [SMILES: CNC(=O)c1ccc(Nc2nc(OC3CCCC3)c3c(-c4cccc(NC(C)=O)c4)c[nH]c3n2)c(OC)c1] | 4-(5-(3-acetamidophenyl)-4-(cyclopentyloxy)-7H-pyrrolo[2,3-d]pyrimidin-2-ylamino)-3-methoxy-N-methylbenzamide |
| 57 | 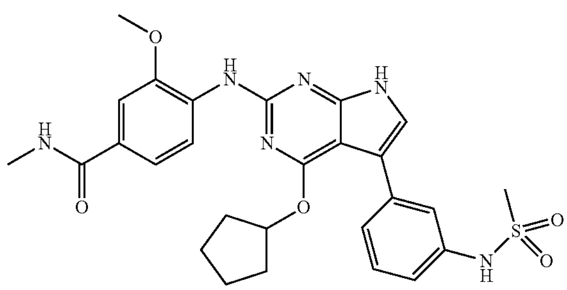 [SMILES: CNC(=O)c1ccc(Nc2nc(OC3CCCC3)c3c(-c4cccc(NS(C)(=O)=O)c4)c[nH]c3n2)c(OC)c1] | 4-(4-(cyclopentyloxy)-5-(3-(methylsulfonamido)phenyl)-7H-pyrrolo[2,3-d]pyrimidin-2-ylamino)-3-methoxy-N-methylbenzamide |
| 58 | 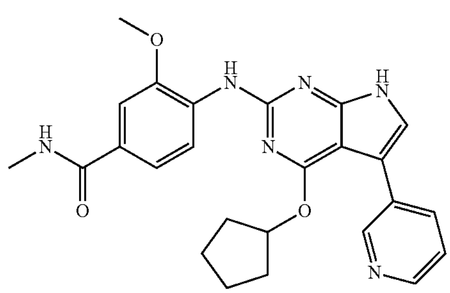 [SMILES: CNC(=O)c1ccc(Nc2nc(OC3CCCC3)c3c(-c4cccnc4)c[nH]c3n2)c(OC)c1] | 4-(4-(cyclopentyloxy)-5-(pyridin-3-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 59 | 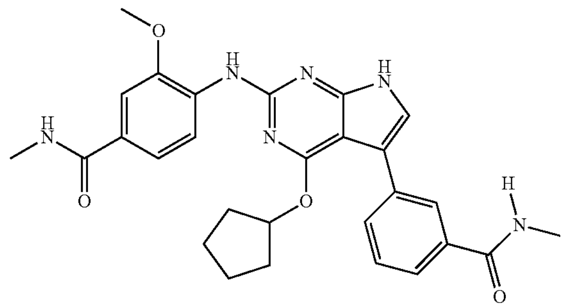 | 4-(4-(cyclopentyloxy)-5-(3-(methylcarbamoyl)phenyl)-7H-pyrrolo[2,3-d]pyrimidin-2-ylamino)-3-methoxy-N-methylbenzamide |
| 60 | 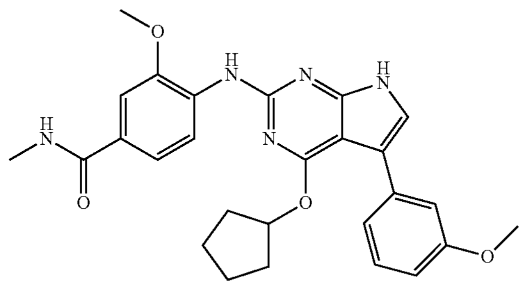 | 4-(4-(cyclopentyloxy)-5-(3-methoxyphenyl)-7H-pyrrolo[2,3-d]pyrimidin-2-ylamino)-3-methoxy-N-methylbenzamide |
| 61 | 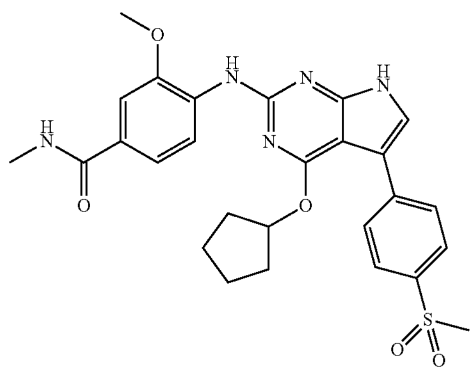 | 4-(4-(cyclopentyloxy)-5-(4-(methylsulfonyl)phenyl)-7H-pyrrolo[2,3-d]pyrimidin-2-ylamino)-3-methoxy-N-methylbenzamide |
| 62 | 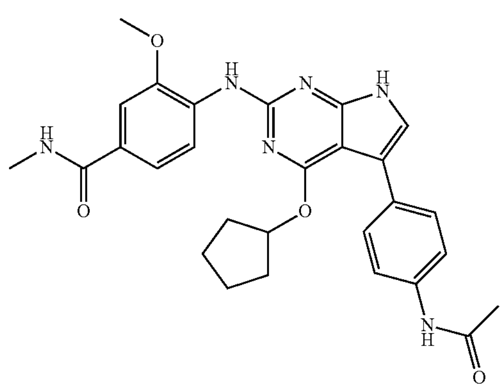 [SMILES: CNC(=O)c1ccc(Nc2nc(OC3CCCC3)c3c(-c4ccc(NC(C)=O)cc4)c[nH]c3n2)c(OC)c1] | 4-(5-(4-acetamidophenyl)-4-(cyclopentyloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 63 | 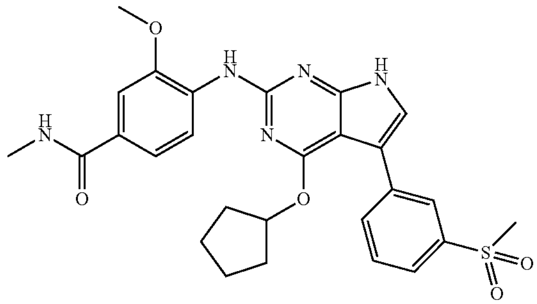 [SMILES: CNC(=O)c1ccc(Nc2nc(OC3CCCC3)c3c(-c4cccc(S(C)(=O)=O)c4)c[nH]c3n2)c(OC)c1] | 4-(4-(cyclopentyloxy)-5-(3-(methylsulfonyl)phenyl)-7H-pyrrolo[2,3-d]pyrimidin-2-ylamino)-3-methoxy-N-methylbenzamide |
| 64 | 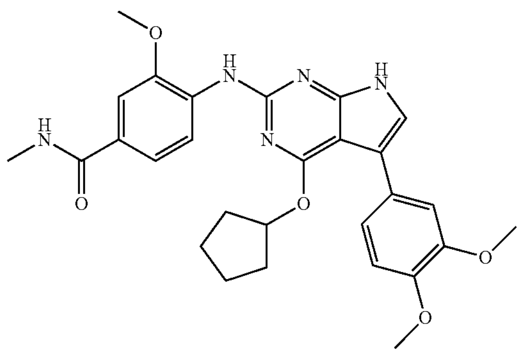 | 4-(4-(cyclopentyloxy)-5-(3,4-dimethoxyphenyl)-7H-pyrrolo[2,3-d]pyrimidin-2-ylamino)-3-methoxy-N-methylbenzamide |
| 65 | 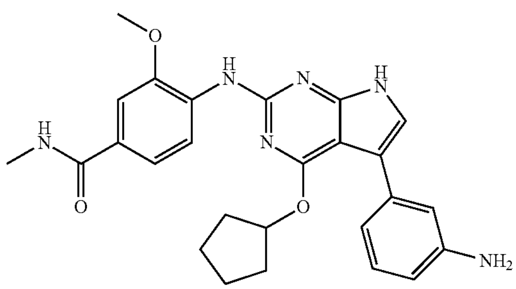 [SMILES: CNC(=O)c1ccc(Nc2nc(OC3CCCC3)c3c(-c4cccc(N)c4)c[nH]c3n2)c(OC)c1] | 4-(5-(3-aminophenyl)-4-(cyclopentyloxy)-7H-pyrrolo[2,3-d]pyrimidin-2-ylamino)-3-methoxy-N-methylbenzamide |
| 66 | 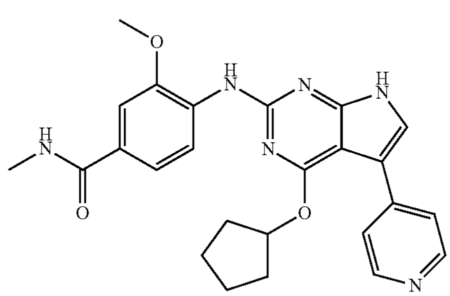 [SMILES: CNC(=O)c1ccc(Nc2nc(OC3CCCC3)c3c(-c4ccncc4)c[nH]c3n2)c(OC)c1] | 4-(4-(cyclopentyloxy)-5-(pyridin-4-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 67 | 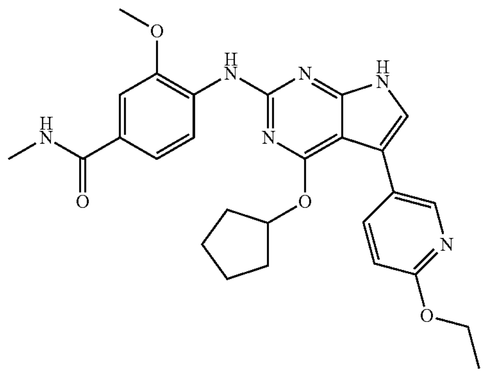 [SMILES: CCOc1ccc(-c2c[nH]c3nc(Nc4ccc(C(=O)NC)cc4OC)nc(OC4CCCC4)c23)cn1] | 4-(4-(cyclopentyloxy)-5-(6-ethoxypyridin-3-yl)-7H-pyrrolo[2,3-d]pyrimidin-2-ylamino)-3-methoxy-N-methylbenzamide |
| 68 | 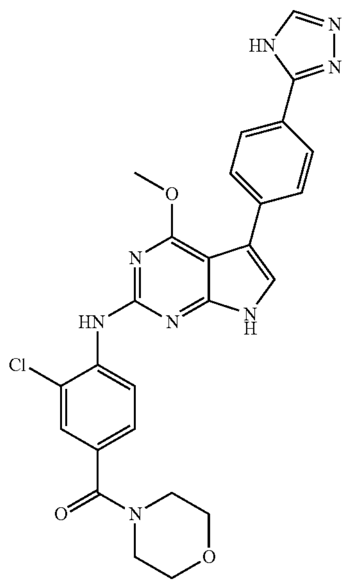 [SMILES: COc1nc(Nc2ccc(C(=O)N3CCOCC3)cc2Cl)nc2[nH]cc(-c3ccc(-c4nnc[nH]4)cc3)c12] | (4-(5-(4-(4H-1,2,4-triazol-3-yl)phenyl)-4-methoxy-7H-pyrrolo[2,3-d]pyrimidin-2-ylamino)-3-chlorophenyl)(morpholino)methanone |
| 69 | 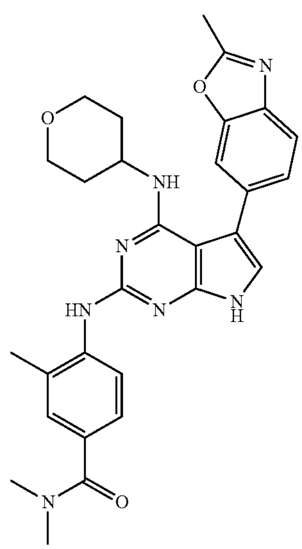 [SMILES: Cc1nc2ccc(-c3c[nH]c4nc(Nc5ccc(C(=O)N(C)C)cc5C)nc(NC5CCOCC5)c34)cc2o1] | N,N,3-trimethyl-4-(5-(2-methylbenzo[d]oxazol-6-yl)-4-(tetrahydro-2H-pyran-4-ylamino)-7H-pyrrolo[2,3-dpyrimidin-2-ylamino)benzamide |

TABLE A-continued

| Cmpd No. | Structure | Name |
|---|---|---|
| 70 | 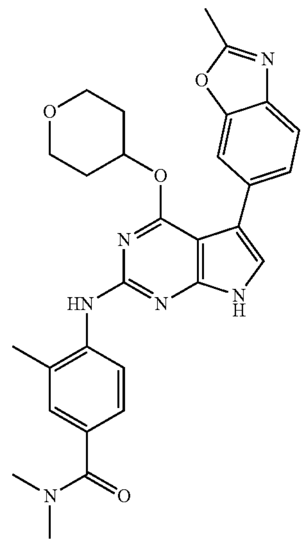 [SMILES: Cc1nc2ccc(-c3c[nH]c4nc(Nc5ccc(C(=O)N(C)C)cc5C)nc(OC5CCOCC5)c34)cc2o1] | N,N,3-trimethyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 71 | 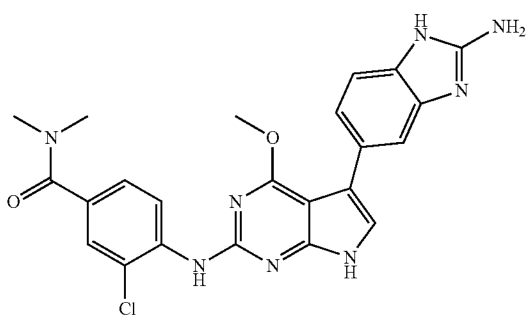 [SMILES: COc1nc(Nc2ccc(C(=O)N(C)C)cc2Cl)nc2[nH]cc(-c3ccc4[nH]c(N)nc4c3)c12] | 4-(5-(2-amino-1H-benzo[d]imidazol-5-yl)-4-methoxy-7H-pyrrolo[2,3-d]pyrimidin-2-ylamino)-3-chloro-N,N-dimethylbenzamide |
| 72 | 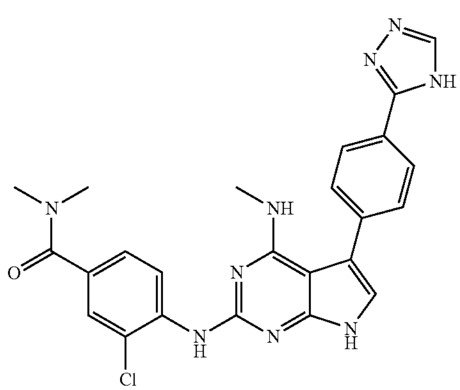 [SMILES: CNc1nc(Nc2ccc(C(=O)N(C)C)cc2Cl)nc2[nH]cc(-c3ccc(-c4nnc[nH]4)cc3)c12] | 4-(5-(4-(4H-1,2,4-triazol-3-yl)phenyl)-4-(methylamino)-7H-pyrrolo[2,3-d]pyrimidin-2-ylamino)-3-chloro-N,N-dimethylbenzamide |

TABLE A-continued

| Cmpd No. | Structure | Name |
|---|---|---|
| 73 | 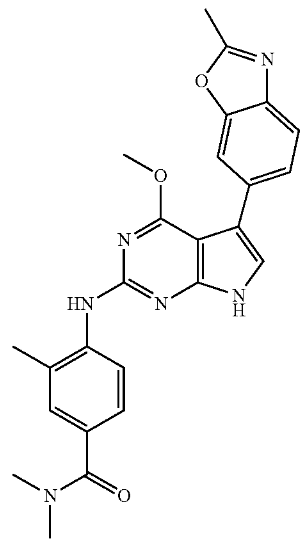 [SMILES: COc1nc(Nc2ccc(C(=O)N(C)C)cc2C)nc2[nH]cc(-c3ccc4nc(C)oc4c3)c12] | 4-(4-methoxy-5-(2-methylbenzo[d]oxazol-6-yl)-7H-pyrrolo[2,3-d]pyrimidin-2-ylamino)-N,N,3-trimethylbenzamide |
| 74 | 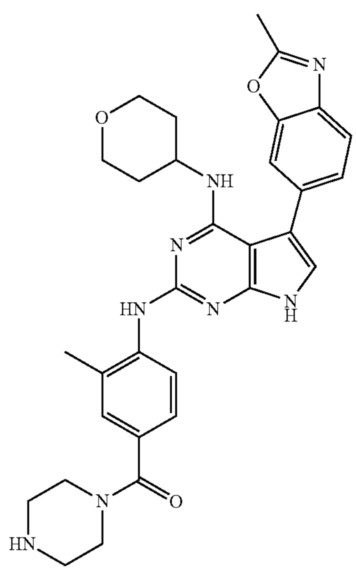 [SMILES: Cc1nc2ccc(-c3c[nH]c4nc(Nc5ccc(C(=O)N6CCNCC6)cc5C)nc(NC5CCOCC5)c34)cc2o1] | (3-methyl-4-(5-(2-methylbenzo[d]oxazol-6-yl)-4-(tetrahydro-2H-pyran-4-ylamino)-7H-pyrrolo[2,3-d]pyrimidin-2-ylamino)phenyl)(piperazin-1-yl)methanone |
| 75 | 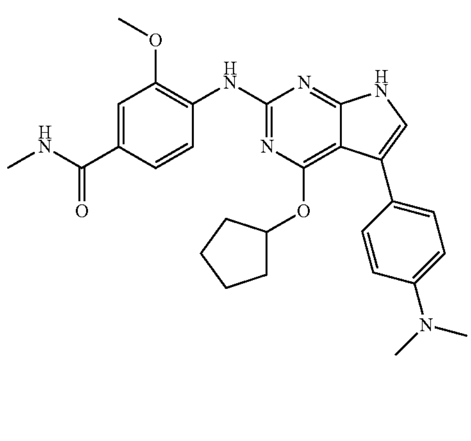 | 4-(4-(cyclopentyloxy)-5-(4-(dimethylamino)phenyl)-7H-pyrrolo[2,3-d]pyrimidin-2-ylamino)-3-methoxy-N-methylbenzamide |

TABLE A-continued

| Cmpd No. | Structure | Name |
|---|---|---|
| 76 | 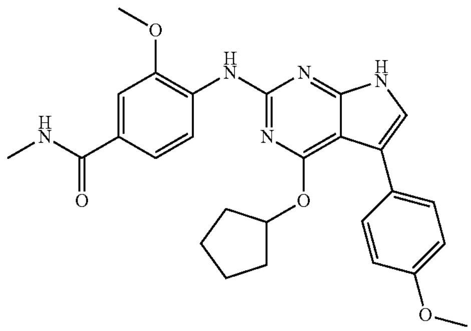 | 4-(4-(cyclopentyloxy)-5-(4-methoxyphenyl)-7H-pyrrolo[2,3-d]pyrimidin-2-ylamino)-3-methoxy-N-methylbenzamide |
| 77 | 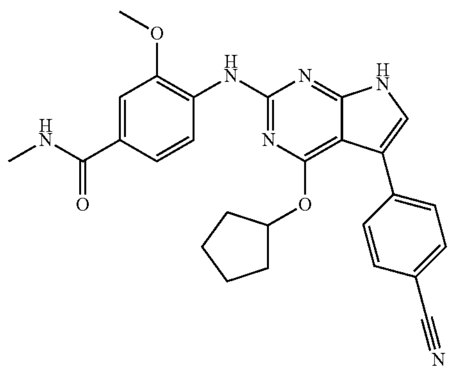 [SMILES: CNC(=O)c1ccc(Nc2nc(OC3CCCC3)c3c(-c4ccc(C#N)cc4)c[nH]c3n2)c(OC)c1] | 4-(5-(4-cyanophenyl)-4-(cyclopentyloxy)-7H-pyrrolo[2,3-d]pyrimidin-2-ylamino)-3-methoxy-N-methylbenzamide |
| 78 | 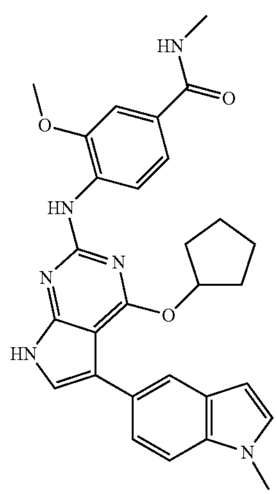 [SMILES: CNC(=O)c1ccc(Nc2nc(OC3CCCC3)c3c(-c4ccc5c(ccn5C)c4)c[nH]c3n2)c(OC)c1] | 4-(4-(cyclopentyloxy)-5-(1-methyl-1H-indol-5-yl)-7H-pyrrolo[2,3-d]pyrimidin-2-ylamino)-3-methoxy-N-methylbenzamide |
| 79 | 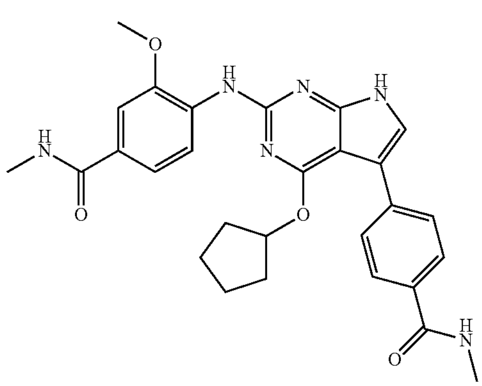 | 4-(4-(cyclopentyloxy)-5-(4-(methylcarbamoyl)phenyl)-7H-pyrrolo[2,3-d]pyrimidin-2-ylamino)-3-methoxy-N-methylbenzamide |

TABLE A-continued

| Cmpd No. | Structure | Name |
| --- | --- | --- |
| 80 | 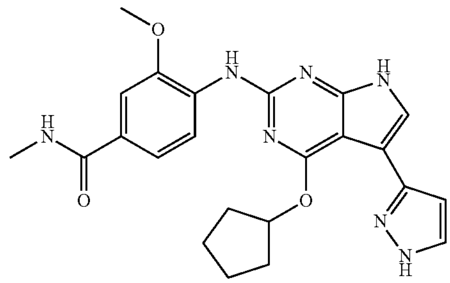 [SMILES: CNC(=O)c1ccc(Nc2nc(OC3CCCC3)c3c(-c4cc[nH]n4)c[nH]c3n2)c(OC)c1] | 4-(4-(cyclopentyloxy)-5-(1H-pyrazol-3-yl)-7H-pyrrolo[2,3-d]pyrimidin-2-ylamino)-3-methoxy-N-methylbenzamide |
| 81 | 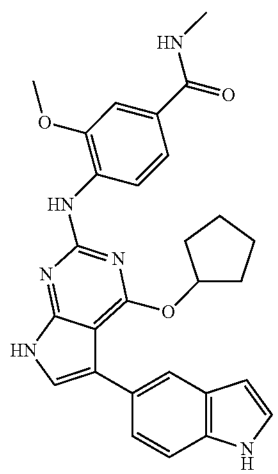 [SMILES: CNC(=O)c1ccc(Nc2nc(OC3CCCC3)c3c(-c4ccc5[nH]ccc5c4)c[nH]c3n2)c(OC)c1] | 4-(4-(cyclopentyloxy)-5-(1H-indol-5-yl)-7H-pyrrolo[2,3-d]pyrimidin-2-ylamino)-3-methoxy-N-methylbenzamide |
| 82 | 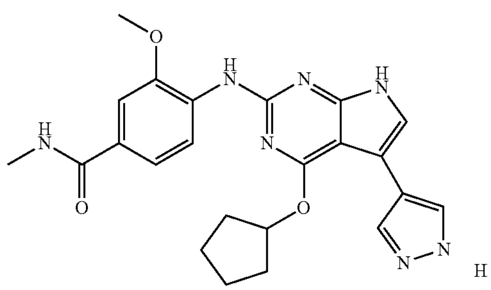 | 4-(4-(cyclopentyloxy)-5-(1H-pyrazol-4-yl)-7H-pyrrolo[2,3-d]pyrimidin-2-ylamino)-3-methoxy-N-methylbenzamide |
| 83 | 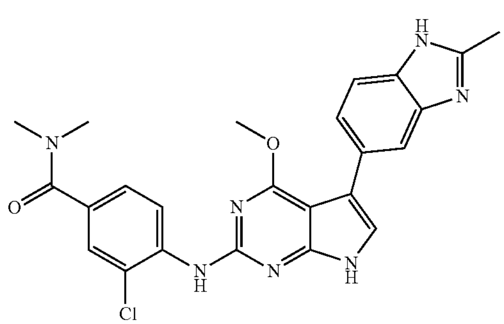 [SMILES: COc1nc(Nc2ccc(C(=O)N(C)C)cc2Cl)nc2[nH]cc(-c3ccc4[nH]c(C)nc4c3)c12] | 3-chloro-4-(4-methoxy-5-(2-methyl-1H-benzo[d]imidazol-5-yl)-7H-pyrrolo[2,3-d]pyrimidin-2-ylamino)-N,N-dimethylbenzamide |

TABLE A-continued

| Cmpd No. | Structure | Name |
|---|---|---|
| 84 | 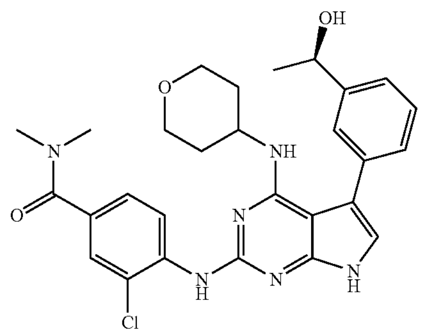 [SMILES: C[C@@H](O)c1cccc(-c2c[nH]c3nc(Nc4ccc(C(=O)N(C)C)cc4Cl)nc(NC4CCOCC4)c23)c1] | (R)-3-chloro-4-(5-(3-(1-hydroxyethyl)phenyl)-4-(tetrahydro-2H-pyran-4-ylamino)-7H-pyrrolo[2,3-d]pyrimidin-2-ylamino)-N,N-dimethylbenzamide |
| 85 | 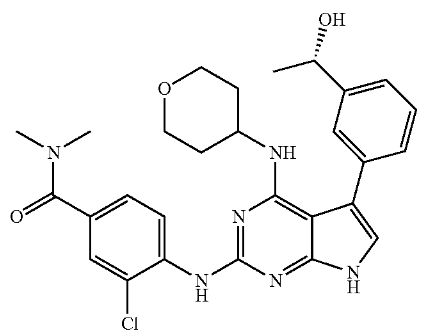 [SMILES: C[C@H](O)c1cccc(-c2c[nH]c3nc(Nc4ccc(C(=O)N(C)C)cc4Cl)nc(NC4CCOCC4)c23)c1] | (S)-3-chloro-4-(5-(3-(1-hydroxyethyl)phenyl)-4-(tetrahydro-2H-pyran-4-ylamino)-7H-pyrrolo[2,3-d]pyrimidin-2-ylamino)-N,N-dimethylbenzamide |
| 86 | 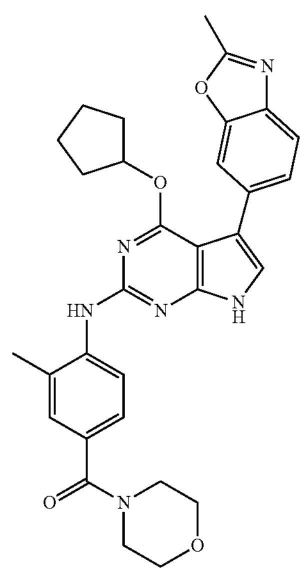 [SMILES: Cc1nc2ccc(-c3c[nH]c4nc(Nc5ccc(C(=O)N6CCOCC6)cc5C)nc(OC5CCCC5)c34)cc2o1] | (4-(4-(cyclopentyloxy)-5-(2-methylbenzo[d]oxazol-6-yl)-7H-pyrrolo[2,3-d]pyrimidin-2-ylamino)-3-methylphenyl)(morpholino)methanone |
| 87 | 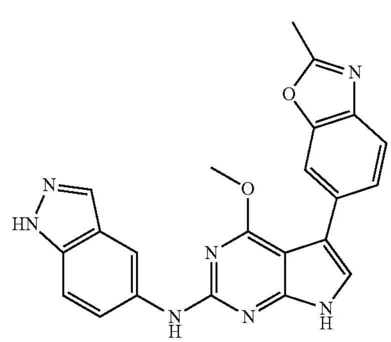 [SMILES: COc1nc(Nc2ccc3[nH]ncc3c2)nc2[nH]cc(-c3ccc4nc(C)oc4c3)c12] | N-(1H-indazol-5-yl)-4-methoxy-5-(2-methylbenzo[d]oxazol-6-yl)-7H-pyrrolo[2,3-d]pyrimidin-2-amine |

TABLE A-continued

| Cmpd No. | Structure | Name |
|---|---|---|
| 88 | 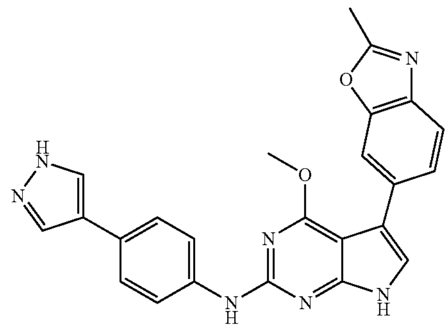 [SMILES: COc1nc(Nc2ccc(-c3cn[nH]c3)cc2)nc2[nH]cc(-c3ccc4nc(C)oc4c3)c12] | N-(4-(1H-pyrazol-4-yl)phenyl)-4-methoxy-5-(2-methylbenzo[d]oxazol-6-yl)-7H-pyrrolo[2,3-d]pyrimidin-2-amine |
| 89 | 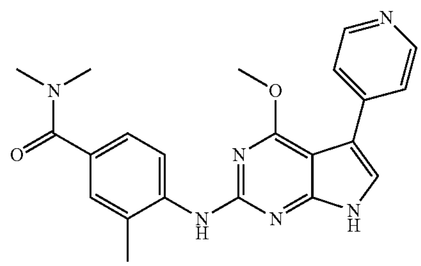 [SMILES: COc1nc(Nc2ccc(C(=O)N(C)C)cc2C)nc2[nH]cc(-c3ccncc3)c12] | 4-(4-methoxy-5-(pyridin-4-yl)-7H-pyrrolo[2,3-d]pyrimidin-2-ylamino)-N,N,3-trimethylbenzamide |
| 90 | 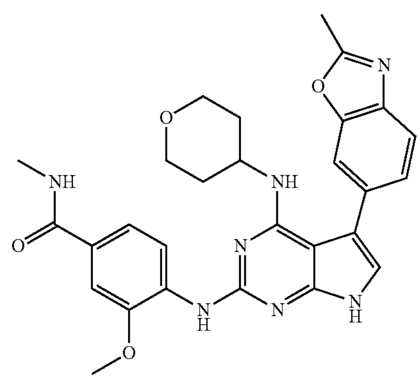 [SMILES: CNC(=O)c1ccc(Nc2nc(NC3CCOCC3)c3c(-c4ccc5nc(C)oc5c4)c[nH]c3n2)c(OC)c1] | 3-methoxy-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 91 | 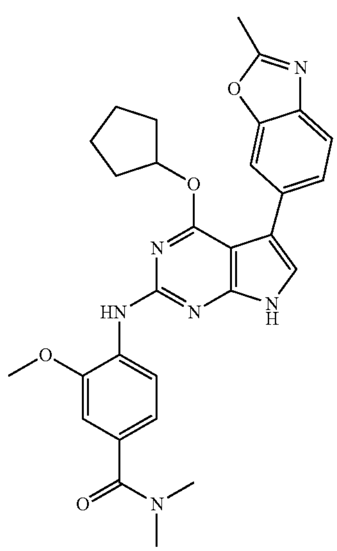 [SMILES: COc1cc(C(=O)N(C)C)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N,N-dimethylbenzamide |

TABLE A-continued

| Cmpd No. | Structure | Name |
|---|---|---|
| 92 | 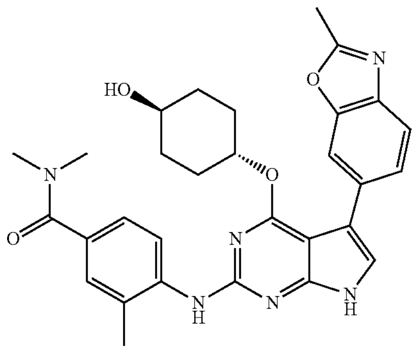 [SMILES: Cc1nc2ccc(-c3c[nH]c4nc(Nc5ccc(C(=O)N(C)C)cc5C)nc(O[C@H]5CC[C@H](O)CC5)c34)cc2o1] | 4-(4-((1r,4r)-4-hydroxycyclohexyloxy)-5-(2-methylbenzo[d]oxazol-6-yl)-7H-pyrrolo[2,3-d]pyrimidin-2-ylamino)-N,N,3-trimethylbenzamide |
| 93 | 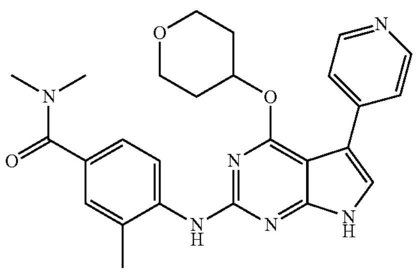 [SMILES: Cc1cc(C(=O)N(C)C)ccc1Nc1nc(OC2CCOCC2)c2c(-c3ccncc3)c[nH]c2n1] | N,N,3-trimethyl-4-(5-(pyridin-4-yl)-4-(tetrahydro-2H-pyran-4-yloxy)-7H-pyrrolo[2,3-d]pyrimidin-2-ylamino)benzamide |
| 94 | 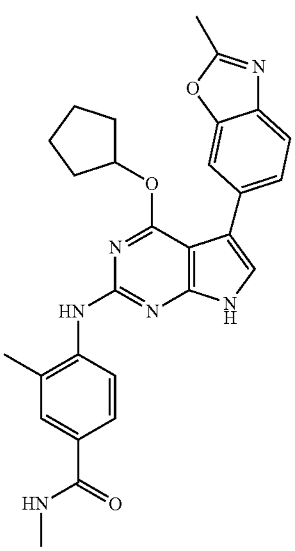 [SMILES: CNC(=O)c1ccc(Nc2nc(OC3CCCC3)c3c(-c4ccc5nc(C)oc5c4)c[nH]c3n2)c(C)c1] | 4-(4-(cyclopentyloxy)-5-(2-methylbenzo[d]oxazol-6-yl)-7H-pyrrolo[2,3-d]pyrimidin-2-ylamino)-N,3-dimethylbenzamide |

TABLE A-continued
| Cmpd No. | Structure | Name |
|---|---|---|
| 95 | 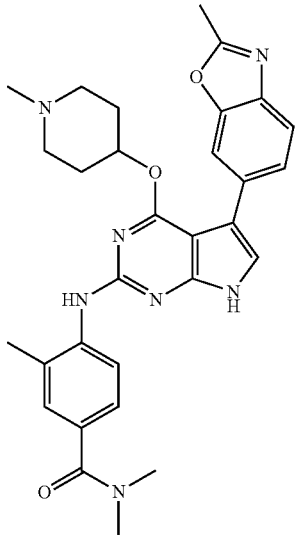 [SMILES: Cc1nc2ccc(-c3c[nH]c4nc(Nc5ccc(C(=O)N(C)C)cc5C)nc(OC5CCN(C)CC5)c34)cc2o1] | N,N,3-trimethyl-4-(5-(2-methylbenzo[d]oxazol-6-yl)-4-(1-methylpiperidin-4-yloxy)-7H-pyrrolo[2,3-d]pyrimidin-2-ylamino)benzamide |
| 96 | 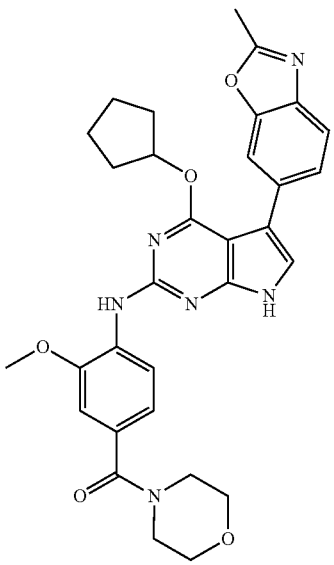 [SMILES: COc1cc(C(=O)N2CCOCC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(morpholino)methanone |

TABLE A-continued

| Cmpd No. | Structure | Name |
|---|---|---|
| 97 | 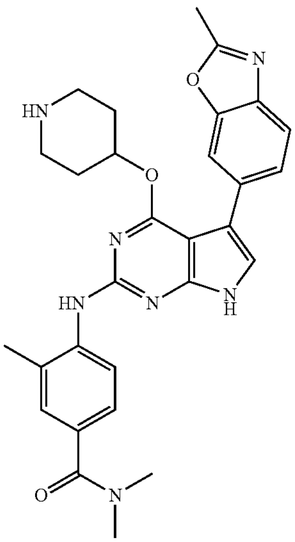 [SMILES: Cc1nc2ccc(-c3c[nH]c4nc(Nc5ccc(C(=O)N(C)C)cc5C)nc(OC5CCNCC5)c34)cc2o1] | N,N,3-trimethyl-4-(5-(2-methylbenzo[d]oxazol-6-yl)-4-(piperidin-4-yloxy)-7H-pyrrolo[2,3-d]pyrimidin-2-ylamino)benzamide |
| 98 | 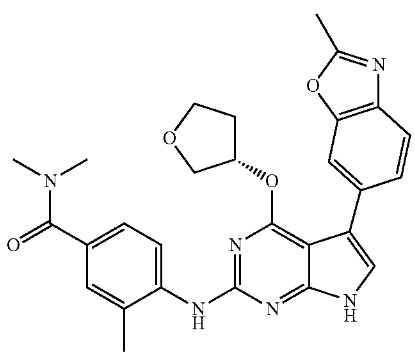 [SMILES: Cc1nc2ccc(-c3c[nH]c4nc(Nc5ccc(C(=O)N(C)C)cc5C)nc(O[C@H]5CCOC5)c34)cc2o1] | (S)-N,N,3-trimethyl-4-(5-(2-methylbenzo[d]oxazol-6-yl)-4-(tetrahydrofuran-3-yloxy)-7H-pyrrolo[2,3-d]pyrimidin-2-ylamino)benzamide |
| 99 | 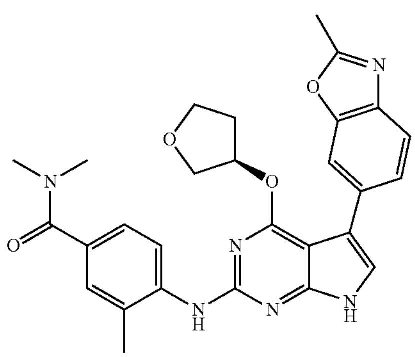 [SMILES: Cc1nc2ccc(-c3c[nH]c4nc(Nc5ccc(C(=O)N(C)C)cc5C)nc(O[C@@H]5CCOC5)c34)cc2o1] | (R)-N,N,3-trimethyl-4-(5-(2-methylbenzo[d]oxazol-6-yl)-4-(tetrahydrofuran-3-yloxy)-7H-pyrrolo[2,3-d]pyrimidin-2-ylamino)benzamide |

TABLE A-continued

| Cmpd No. | Structure | Name |
|---|---|---|
| 100 | 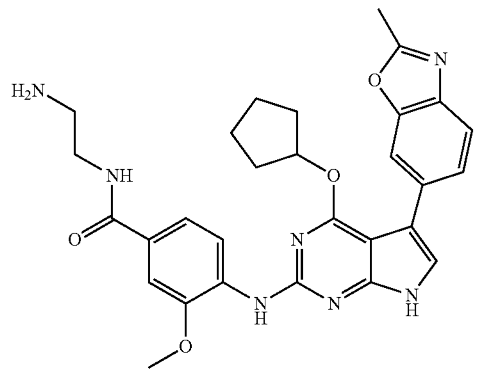 [SMILES: COc1cc(C(=O)NCCN)ccc1Nc1nc(OC2CCCC2)c2c(-c3ccc4nc(C)oc4c3)c[nH]c2n1] | N-(2-aminoethyl)-4-(4-(cyclopentyloxy)-5-(2-methylbenzo[d]oxazol-6-yl)-7H-pyrrolo[2,3-d]pyrimidin-2-ylamino)-3-methoxybenzamide |
| 101 | 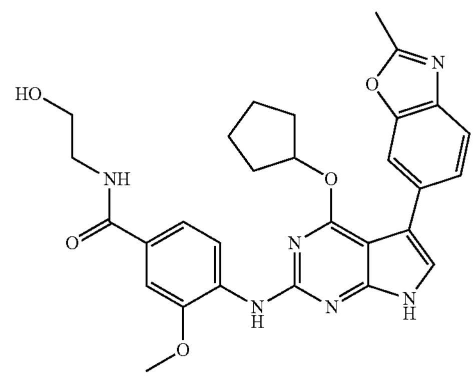 [SMILES: COc1cc(C(=O)NCCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(2-hydroxyethyl)-3-methoxybenzamide |
| 102 | 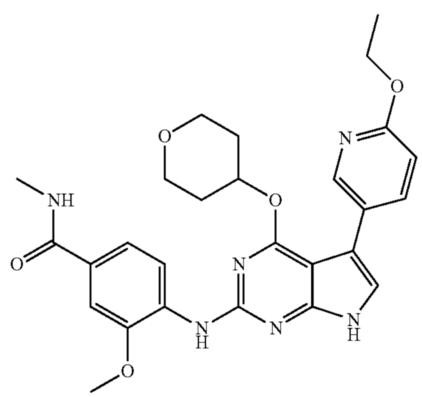 [SMILES: CCOc1ccc(-c2c[nH]c3nc(Nc4ccc(C(=O)NC)cc4OC)nc(OC4CCOCC4)c23)cn1] | 4-(5-(6-ethoxypyridin-3-yl)-4-(tetrahydro-2H-pyran-4-yloxy)-7H-pyrrolo[2,3-d]pyrimidin-2-ylamino)-3-methoxy-N-methylbenzamide |
| 103 | 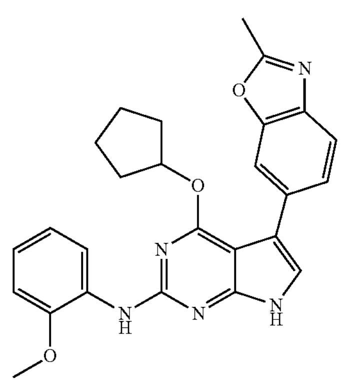 [SMILES: COc1ccccc1Nc1nc(OC2CCCC2)c2c(-c3ccc4nc(C)oc4c3)c[nH]c2n1] | 4-(cyclopentyloxy)-N-(2-methoxyphenyl)-5-(2-methylbenzo[d]oxazol-6-yl)-7H-pyrrolo[2,3-d]pyrimidin-2-amine |

TABLE A-continued

| Cmpd No. | Structure | Name |
|---|---|---|
| 104 | 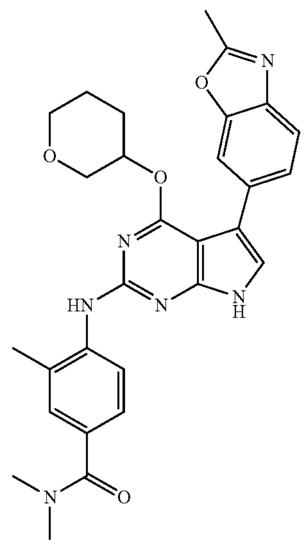 [SMILES: Cc1nc2ccc(-c3c[nH]c4nc(Nc5ccc(C(=O)N(C)C)cc5C)nc(OC5CCCOC5)c34)cc2o1] | (S)-N,N,3-trimethyl-4-(5-(2-methylbenzo[d]oxazol-6-yl)-4-(tetrahydro-2H-pyran-3-yloxy)-7H-pyrrolo[2,3-d]pyrimidin-2-ylamino)benzamide |
| 105 | 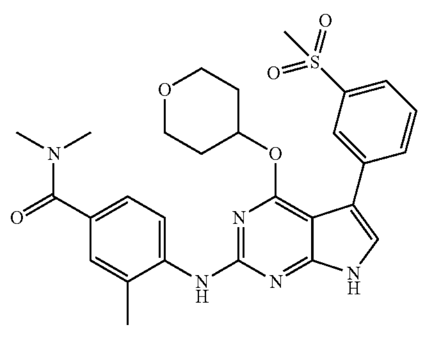 [SMILES: Cc1cc(C(=O)N(C)C)ccc1Nc1nc(OC2CCOCC2)c2c(-c3cccc(S(C)(=O)=O)c3)c[nH]c2n1] | N,N,3-trimethyl-4-(5-(3-(methylsulfonyl)phenyl)-4-(tetrahydro-2H-pyran-4-yloxy)-7H-pyrrolo[2,3-d]pyrimidin-2-ylamino)benzamide |
| 106 | 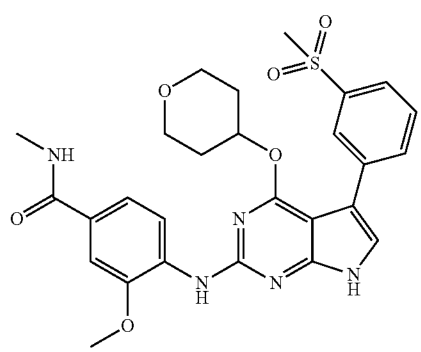 [SMILES: CNC(=O)c1ccc(Nc2nc(OC3CCOCC3)c3c(-c4cccc(S(C)(=O)=O)c4)c[nH]c3n2)c(OC)c1] | 3-methoxy-N-methyl-4-(5-(3-(methylsulfonyl)phenyl)-4-(tetrahydro-2H-pyran-4-yloxy)-7H-pyrrolo[2,3-d]pyrimidin-2-ylamino)benzamide |

| Cmpd No. | Structure | Name |
|---|---|---|
| 107 | 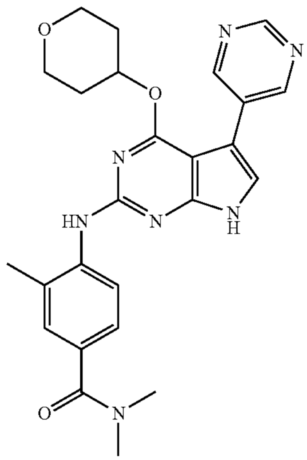 [SMILES: Cc1cc(C(=O)N(C)C)ccc1Nc1nc(OC2CCOCC2)c2c(-c3cncnc3)c[nH]c2n1] | N,N,3-trimethyl-4-(5-(pyrimidin-5-yl)-4-(tetrahydro-2H-pyran-4-yloxy)-7H-pyrrolo[2,3-d]pyrimidin-2-ylamino)benzamide |
| 108 | 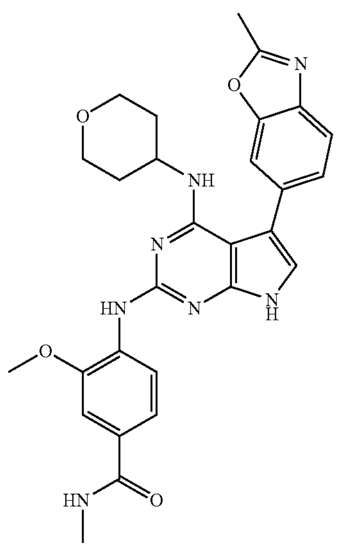 [SMILES: CNC(=O)c1ccc(Nc2nc(NC3CCOCC3)c3c(-c4ccc5nc(C)oc5c4)c[nH]c3n2)c(OC)c1] | 3-methoxy-N-methyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide |
| 109 | 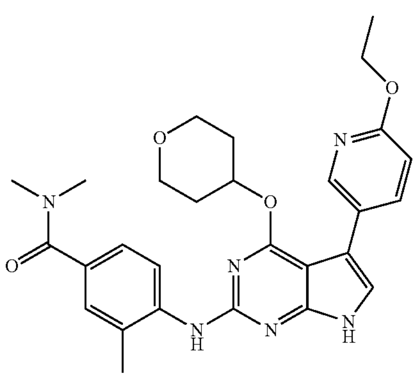 [SMILES: CCOc1ccc(-c2c[nH]c3nc(Nc4ccc(C(=O)N(C)C)cc4C)nc(OC4CCOCC4)c23)cn1] | 4-(5-(6-ethoxypyridin-3-yl)-4-(tetrahydro-2H-pyran-4-yloxy)-7H-pyrrolo[2,3-d]pyrimidin-2-ylamino)-N,N,3-trimethylbenzamide |

TABLE A-continued

| Cmpd No. | Structure | Name |
|---|---|---|
| 110 | 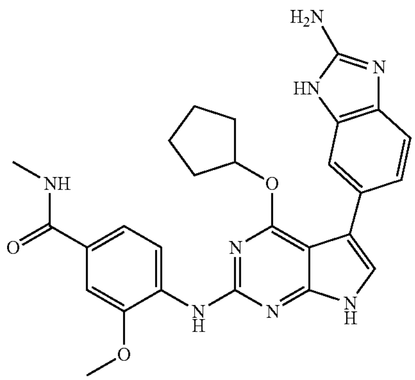 [SMILES: CNC(=O)c1ccc(Nc2nc(OC3CCCC3)c3c(-c4ccc5nc(N)[nH]c5c4)c[nH]c3n2)c(OC)c1] | 4-(5-(2-amino-1H-benzo[d]imidazol-6-yl)-4-(cyclopentyloxy)-7H-pyrrolo[2,3-d]pyrimidin-2-ylamino)-3-methoxy-N-methylbenzamide |
| 111 | 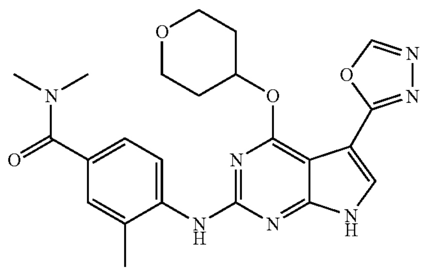 [SMILES: Cc1cc(C(=O)N(C)C)ccc1Nc1nc(OC2CCOCC2)c2c(-c3nnco3)c[nH]c2n1] | 4-(5-(1,3,4-oxadiazol-2-yl)-4-(tetrahydro-2H-pyran-4-yloxy)-7H-pyrrolo[2,3-d]pyrimidin-2-ylamino)-N,N,3-trimethylbenzamide |
| 112 | 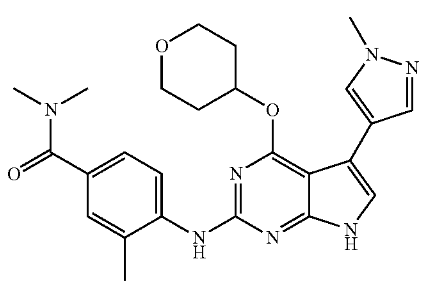 [SMILES: Cc1cc(C(=O)N(C)C)ccc1Nc1nc(OC2CCOCC2)c2c(-c3cnn(C)c3)c[nH]c2n1] | N,N,3-trimethyl-4-(5-(1-methyl-1H-pyrazol-4-yl)-4-(tetrahydro-2H-pyran-4-yloxy)-7H-pyrrolo[2,3-d]pyrimidin-2-ylamino)benzamide |
| 113 | 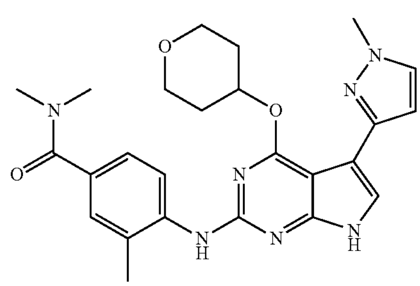 [SMILES: Cc1cc(C(=O)N(C)C)ccc1Nc1nc(OC2CCOCC2)c2c(-c3ccn(C)n3)c[nH]c2n1] | N,N,3-trimethyl-4-(5-(1-methyl-1H-pyrazol-3-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 114 | 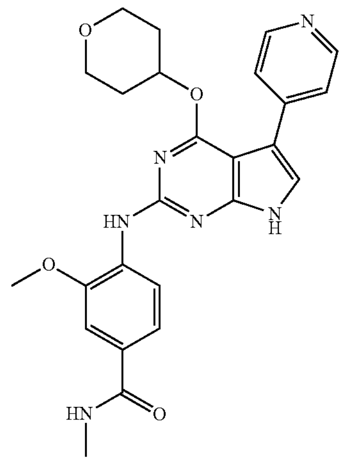 [SMILES: CNC(=O)c1ccc(Nc2nc(OC3CCOCC3)c3c(-c4ccncc4)c[nH]c3n2)c(OC)c1] | 3-methoxy-N-methyl-4-(5-(pyridin-4-yl)-4-(tetrahydro-2H-pyran-4-yloxy)-7H-pyrrolo[2,3-d]pyrimidin-2-ylamino)benzamide |
| 115 | 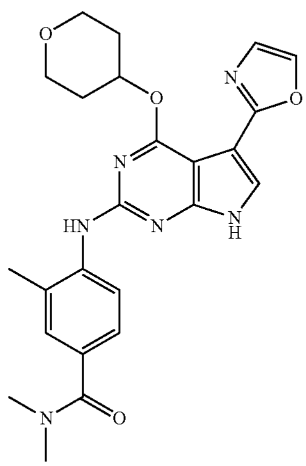 [SMILES: Cc1cc(C(=O)N(C)C)ccc1Nc1nc(OC2CCOCC2)c2c(-c3ncco3)c[nH]c2n1] | N,N,3-trimethyl-4-(5-(oxazol-2-yl)-4-(tetrahydro-2H-pyran-4-yloxy)-7H-pyrrolo[2,3-d]pyrimidin-2-ylamino)benzamide |
| 116 | 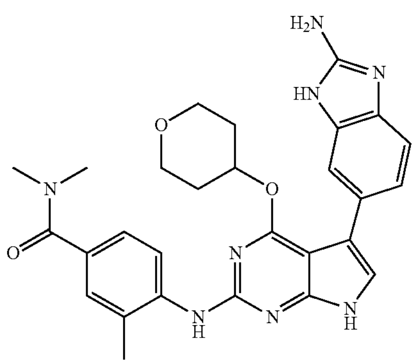 [SMILES: Cc1cc(C(=O)N(C)C)ccc1Nc1nc(OC2CCOCC2)c2c(-c3ccc4nc(N)[nH]c4c3)c[nH]c2n1] | 4-(5-(2-amino-1H-benzo[d]imidazol-6-yl)-4-(tetrahydro-2H-pyran-4-yloxy)-7H-pyrrolo[2,3-d]pyrimidin-2-ylamino)-N,N,3-trimethylbenzamide |
| 117 | 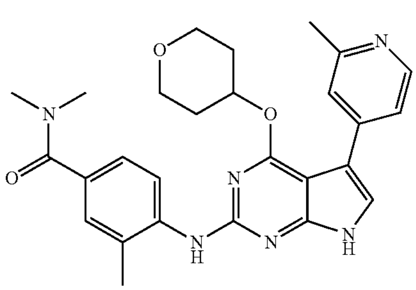 [SMILES: Cc1cc(-c2c[nH]c3nc(Nc4ccc(C(=O)N(C)C)cc4C)nc(OC4CCOCC4)c23)ccn1] | N,N,3-trimethyl-4-(5-(2-methylpyridin-4-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 118 | 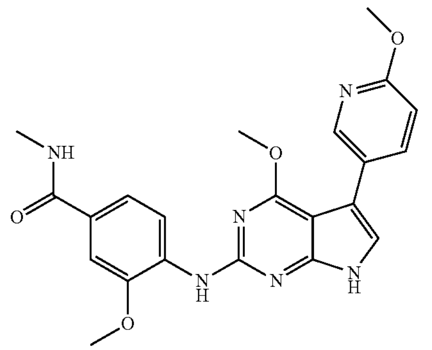 [SMILES: CNC(=O)c1ccc(Nc2nc(OC)c3c(-c4ccc(OC)nc4)c[nH]c3n2)c(OC)c1] | 3-methoxy-4-(4-methoxy-5-(6-methoxypyridin-3-yl)-7H-pyrrolo[2,3-d]pyrimidin-2-ylamino)-N-methylbenzamide |
| 119 | 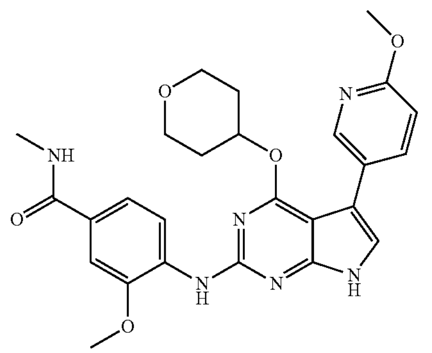 [SMILES: CNC(=O)c1ccc(Nc2nc(OC3CCOCC3)c3c(-c4ccc(OC)nc4)c[nH]c3n2)c(OC)c1] | 3-methoxy-4-(5-(6-methoxypyridin-3-yl)-4-(tetrahydro-2H-pyran-4-yloxy)-7H-pyrrolo[2,3-d]pyrimidin-2-ylamino)-N-methylbenzamide |
| 120 | 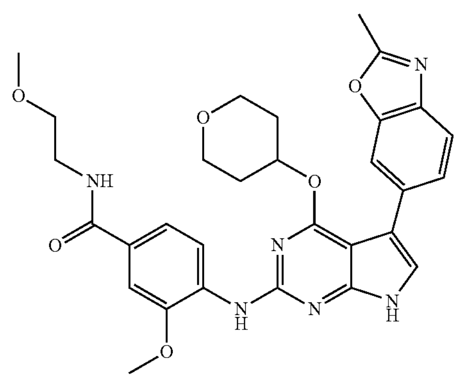 [SMILES: COCCNC(=O)c1ccc(Nc2nc(OC3CCOCC3)c3c(-c4ccc5nc(C)oc5c4)c[nH]c3n2)c(OC)c1] | 3-methoxy-N-(2-methoxyethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide |

| Cmpd No. | Structure | Name |
|---|---|---|
| 121 | 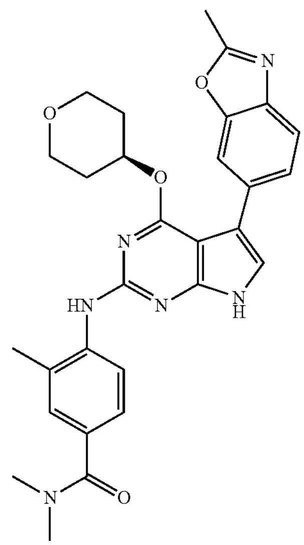 | (R)-N,N,3-trimethyl-4-(5-(2-methylbenzo[d]oxazol-6-yl)-4-(tetrahydro-2H-pyran-3-yloxy)-7H-pyrrolo[2,3-d]pyrimidin-2-ylamino)benzamide |
| 122 | 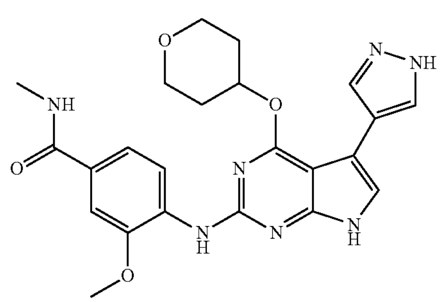 [SMILES: CNC(=O)c1ccc(Nc2nc(OC3CCOCC3)c3c(-c4cn[nH]c4)c[nH]c3n2)c(OC)c1] | 4-(5-(1H-pyrazol-4-yl)-4-(tetrahydro-2H-pyran-4-yloxy)-7H-pyrrolo[2,3-d]pyrimidin-2-ylamino)-3-methoxy-N-methylbenzamide |
| 123 | 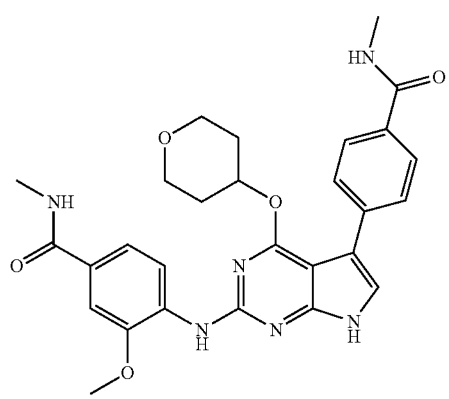 [SMILES: CNC(=O)c1ccc(-c2c[nH]c3nc(Nc4ccc(C(=O)NC)cc4OC)nc(OC4CCOCC4)c23)cc1] | 3-methoxy-N-methyl-4-(5-(4-(methylcarbamoyl)phenyl)-4-(tetrahydro-2H-pyran-4-yloxy)-7H-pyrrolo[2,3-d]pyrimidin-2-ylamino)benzamide |

| Cmpd No. | Structure | Name |
|---|---|---|
| 124 | 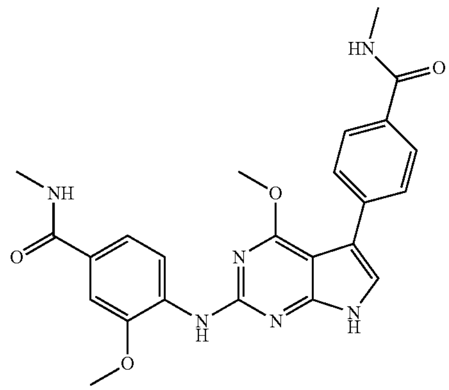 [SMILES: CNC(=O)c1ccc(-c2c[nH]c3nc(Nc4ccc(C(=O)NC)cc4OC)nc(OC)c23)cc1] | 3-methoxy-4-(4-methoxy-5-(4-(methylcarbamoyl)phenyl)-7H-pyrrolo[2,3-d]pyrimidin-2-ylamino)-N-methylbenzamide |
| 125 | 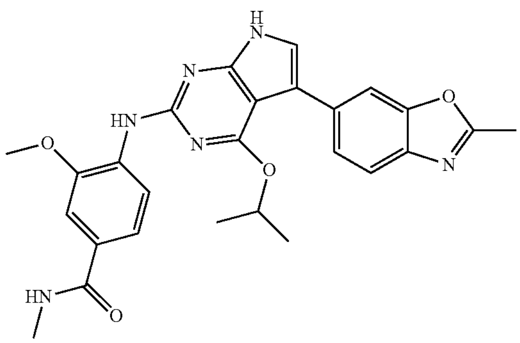 | 4-(4-isopropoxy-5-(2-methylbenzo[d]oxazol-6-yl)-7H-pyrrolo[2,3-d]pyrimidin-2-ylamino)-3-methoxy-N-methylbenzamide |
| 126 | 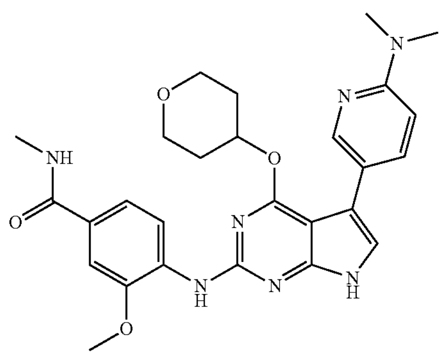 [SMILES: CNC(=O)c1ccc(Nc2nc(OC3CCOCC3)c3c(-c4ccc(N(C)C)nc4)c[nH]c3n2)c(OC)c1] | 4-(5-(6-(dimethylamino)pyridin-3-yl)-4-(tetrahydro-2H-pyran-4-yloxy)-7H-pyrrolo[2,3-d]pyrimidin-2-ylamino)-3-methoxy-N-methylbenzamide |
| 127 | 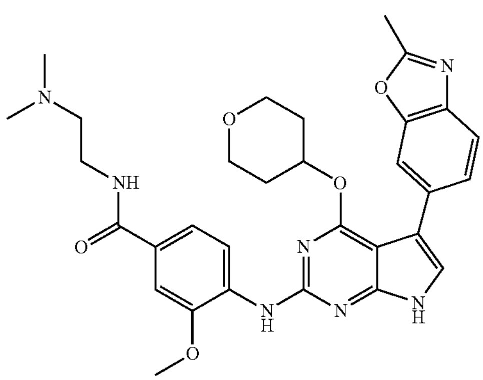 [SMILES: COc1cc(C(=O)NCCN(C)C)ccc1Nc1nc(OC2CCOCC2)c2c(-c3ccc4nc(C)oc4c3)c[nH]c2n1] | N-(2-(dimethylamino)ethyl)-3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 128 | 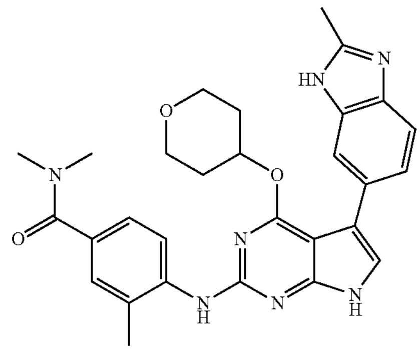 [SMILES: Cc1nc2ccc(-c3c[nH]c4nc(Nc5ccc(C(=O)N(C)C)cc5C)nc(OC5CCOCC5)c34)cc2[nH]1] | N,N,3-trimethyl-4-(5-(2-methyl-1H-benzo[d]imidazol-6-yl)-4-(tetrahydro-2H-pyran-4-yloxy)-7H-pyrrolo[2,3-d]pyrimidin-2-ylamino)benzamide |
| 129 | 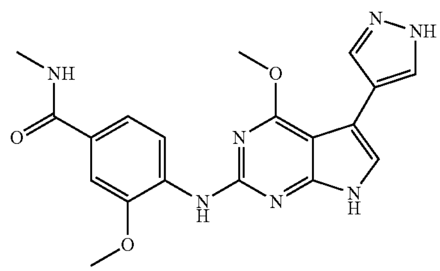 [SMILES: CNC(=O)c1ccc(Nc2nc(OC)c3c(-c4cn[nH]c4)c[nH]c3n2)c(OC)c1] | 3-methoxy-4-(4-methoxy-5-(1H-pyrazol-4-yl)-7H-pyrrolo[2,3-d]pyrimidin-2-ylamino)-N-methylbenzamide |
| 130 | 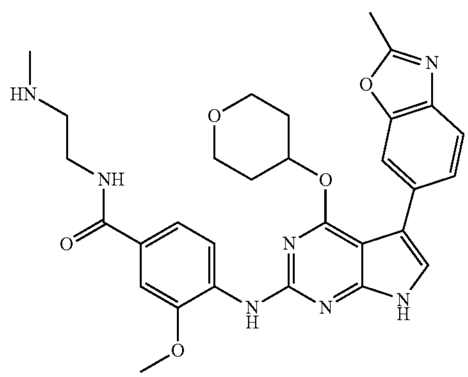 [SMILES: CNCCNC(=O)c1ccc(Nc2nc(OC3CCOCC3)c3c(-c4ccc5nc(C)oc5c4)c[nH]c3n2)c(OC)c1] | 3-methoxy-N-(2-(methylamino)ethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 131 | 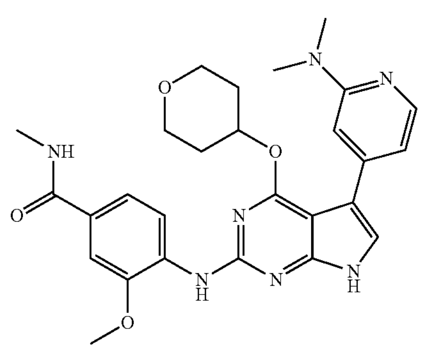 [SMILES: CNC(=O)c1ccc(Nc2nc(OC3CCOCC3)c3c(-c4ccnc(N(C)C)c4)c[nH]c3n2)c(OC)c1] | 4-(5-(2-(dimethylamino)pyridin-4-yl)-4-(tetrahydro-2H-pyran-4-yloxy)-7H-pyrrolo[2,3-d]pyrimidin-2-ylamino)-3-methoxy-N-methylbenzamide |

TABLE A-continued
| Cmpd No. | Structure | Name |
|---|---|---|
| 132 | 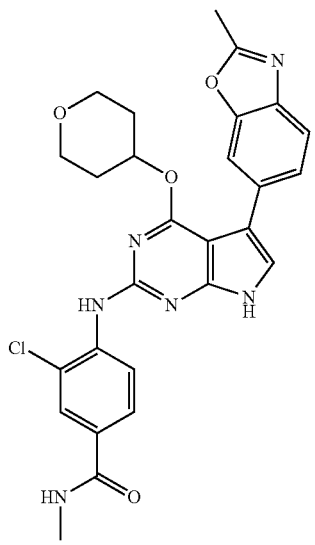 [SMILES: CNC(=O)c1ccc(Nc2nc(OC3CCOCC3)c3c(-c4ccc5nc(C)oc5c4)c[nH]c3n2)c(Cl)c1] | 3-chloro-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 133 | 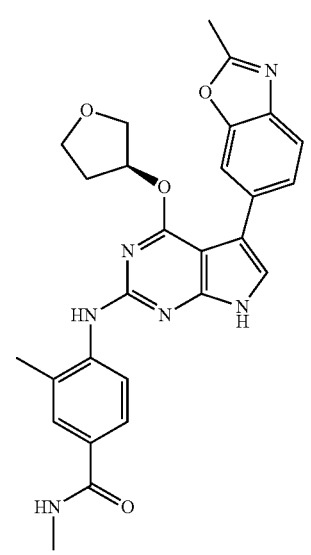 [SMILES: CNC(=O)c1ccc(Nc2nc(O[C@H]3CCOC3)c3c(-c4ccc5nc(C)oc5c4)c[nH]c3n2)c(C)c1] | (S)-N,3-dimethyl-4-(5-(2-methylbenzo[d]oxazol-6-yl)-4-(tetrahydrofuran-3-yloxy)-7H-pyrrolo[2,3-d]pyrimidin-2-ylamino)benzamide |

| Cmpd No. | Structure | Name |
|---|---|---|
| 134 | 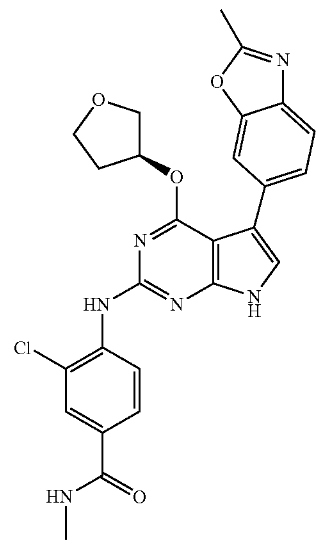 [SMILES: CNC(=O)c1ccc(Nc2nc(O[C@H]3CCOC3)c3c(-c4ccc5nc(C)oc5c4)c[nH]c3n2)c(Cl)c1] | (S)-3-chloro-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide |
| 135 | 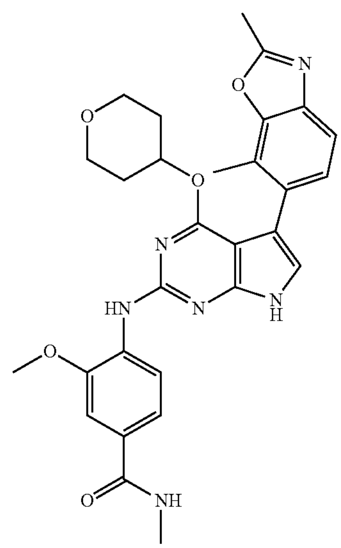 [SMILES: CNC(=O)c1ccc(Nc2nc(OC3CCOCC3)c3c(-c4ccc5nc(C)oc5c4C)c[nH]c3n2)c(OC)c1] | 4-(5-(2,7-dimethylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide |
| 136 | 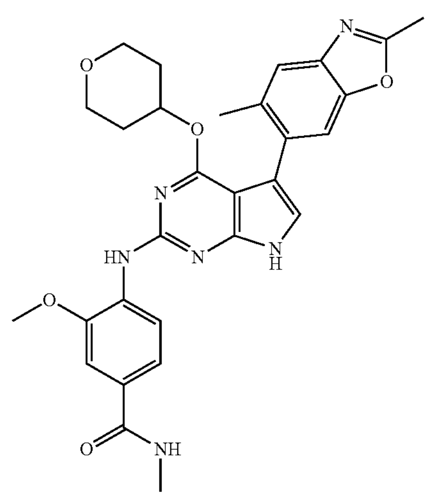 | 4-(5-(2,5-dimethylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide |

| Cmpd No. | Structure | Name |
|---|---|---|
| 137 | 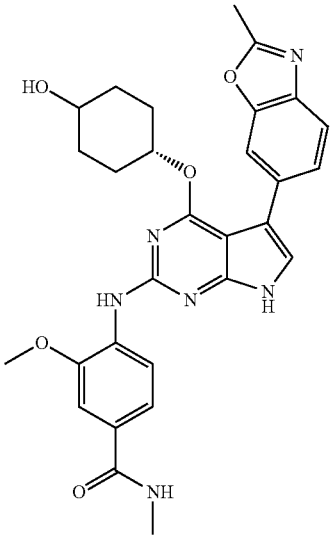 | 4-(4-(((1r,4r)-4-hydroxycyclohexyloxy)-5-(2-methylbenzo[d]oxazol-6-yl)-7H-pyrrolo[2,3-d]pyrimidin-2-ylamino)-3-methoxy-N-methylbenzamide |
| 138 | 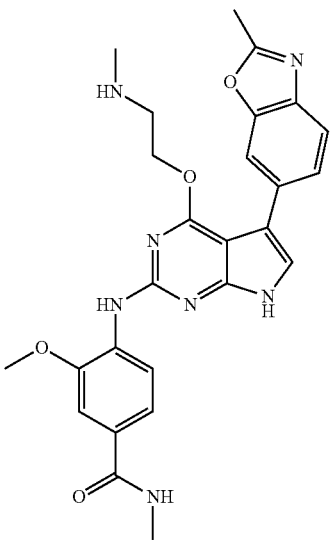 [SMILES: CNCCOc1nc(Nc2ccc(C(=O)NC)cc2OC)nc2[nH]cc(-c3ccc4nc(C)oc4c3)c12] | 3-methoxy-N-methyl-4-(4-(2-(methylamino)ethoxy)-5-(2-methylbenzo[d]oxazol-6-yl)-7H-pyrrolo[2,3-d]pyrimidin-2-ylamino)benzamide |

TABLE A-continued

| Cmpd No. | Structure | Name |
|---|---|---|
| 139 | 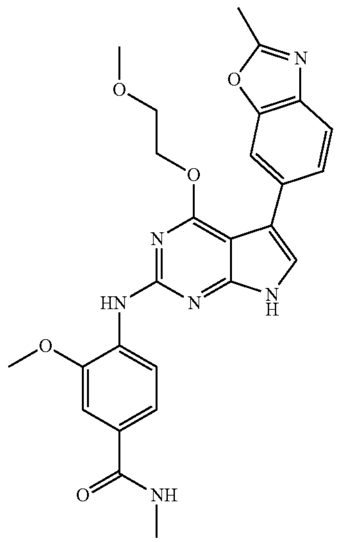 [SMILES: CNC(=O)c1ccc(Nc2nc(OCCOC)c3c(-c4ccc5nc(C)oc5c4)c[nH]c3n2)c(OC)c1] | 3-methoxy-4-(4-(2-methoxyethoxy)-5-(2-methylbenzo[d]oxazol-6-yl)-7H-pyrrolo[2,3-d]pyrimidin-2-ylamino)-N-methylbenzamide |
| 140 | 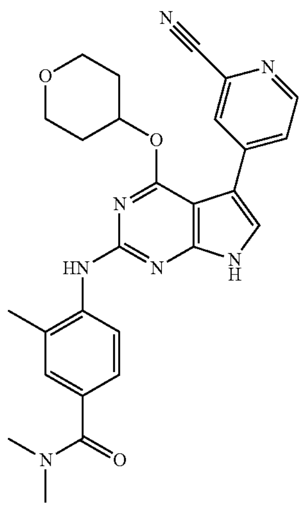 [SMILES: Cc1cc(C(=O)N(C)C)ccc1Nc1nc(OC2CCOCC2)c2c(-c3ccnc(C#N)c3)c[nH]c2n1] | 4-(5-(2-cyanopyridin-4-yl)-4-(tetrahydro-2H-pyran-4-yloxy)-7H-pyrrolo[2,3-d]pyrimidin-2-ylamino)-N,N,3-trimethylbenzamide |
| 141 | 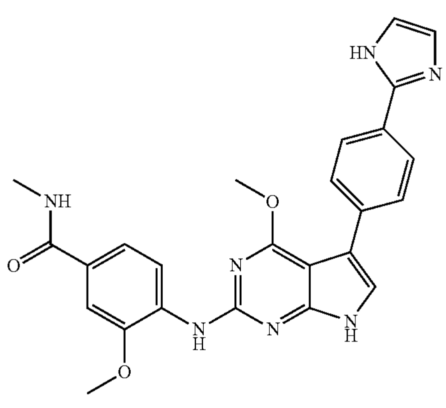 [SMILES: CNC(=O)c1ccc(Nc2nc(OC)c3c(-c4ccc(-c5ncc[nH]5)cc4)c[nH]c3n2)c(OC)c1] | 4-(5-(4-(1H-imidazol-2-yl)phenyl)-4-methoxy-7H-pyrrolo[2,3-d]pyrimidin-2-ylamino)-3-methoxy-N-methylbenzamide |

TABLE A-continued

| Cmpd No. | Structure | Name |
|---|---|---|
| 142 | 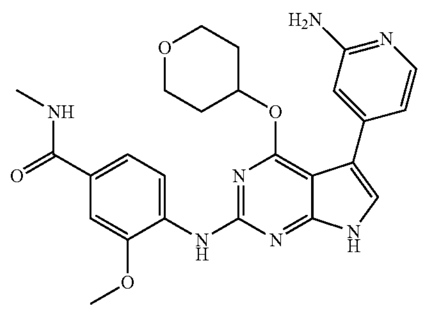 [SMILES: CNC(=O)c1ccc(Nc2nc(OC3CCOCC3)c3c(-c4ccnc(N)c4)c[nH]c3n2)c(OC)c1] | 4-(5-(2-aminopyridin-4-yl)-4-(tetrahydro-2H-pyran-4-yloxy)-7H-pyrrolo[2,3-d]pyrimidin-2-ylamino)-3-methoxy-N-methylbenzamide |
| 143 | 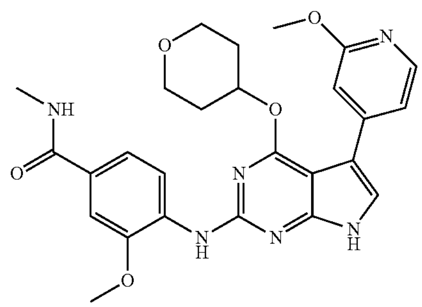 [SMILES: CNC(=O)c1ccc(Nc2nc(OC3CCOCC3)c3c(-c4ccnc(OC)c4)c[nH]c3n2)c(OC)c1] | 3-methoxy-4-(5-(2-methoxypyridin-4-yl)-4-(tetrahydro-2H-pyran-4-yloxy)-7H-pyrrolo[2,3-d]pyrimidin-2-ylamino)-N-methylbenzamide |
| 144 | 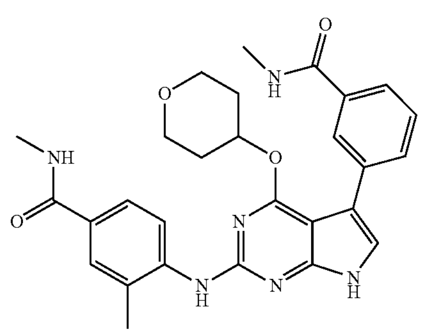 [SMILES: CNC(=O)c1cccc(-c2c[nH]c3nc(Nc4ccc(C(=O)NC)cc4C)nc(OC4CCOCC4)c23)c1] | N,3-dimethyl-4-(5-(3-(methylcarbamoyl)phenyl)-4-(tetrahydro-2H-pyran-4-yloxy)-7H-pyrrolo[2,3-d]pyrimidin-2-ylamino)benzamide |
| 145 | 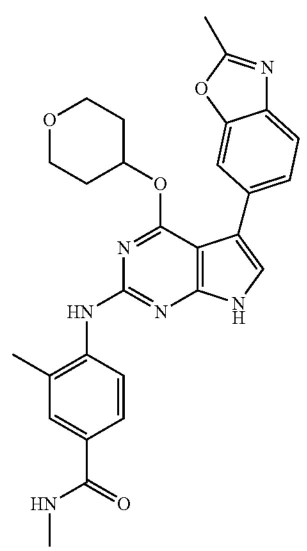 [SMILES: CNC(=O)c1ccc(Nc2nc(OC3CCOCC3)c3c(-c4ccc5nc(C)oc5c4)c[nH]c3n2)c(C)c1] | N,3-dimethyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 146 | 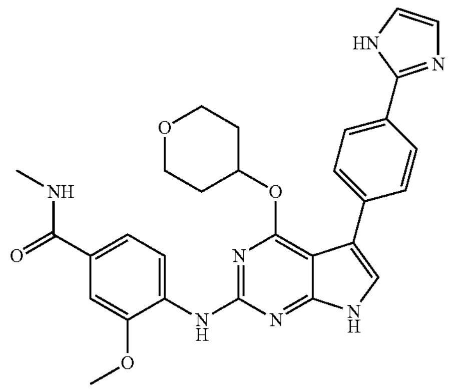 [SMILES: CNC(=O)c1ccc(Nc2nc(OC3CCOCC3)c3c(-c4ccc(-c5ncc[nH]5)cc4)c[nH]c3n2)c(OC)c1] | 4-(5-(4-(1H-imidazol-2-yl)phenyl)-4-(tetrahydro-2H-pyran-4-yloxy)-7H-pyrrolo[2,3-d]pyrimidin-2-ylamino)-3-methoxy-N-methylbenzamide |
| 147 | 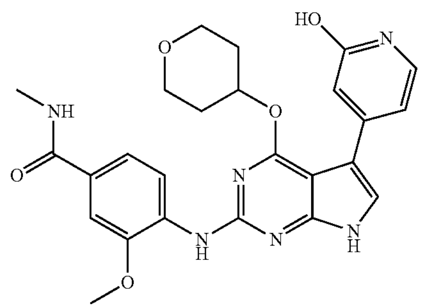 | 4-(5-(2-hydroxypyridin-4-yl)-4-(tetrahydro-2H-pyran-4-yloxy)-7H-pyrrolo[2,3-d]pyrimidin-2-ylamino)-3-methoxy-N-methylbenzamide |
| 148 | 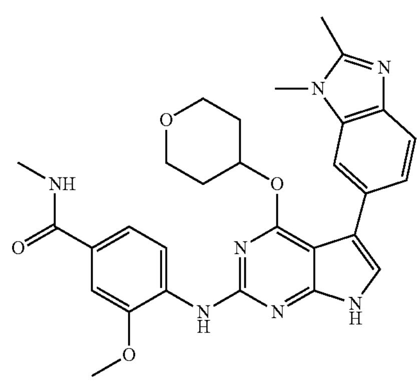 [SMILES: CNC(=O)c1ccc(Nc2nc(OC3CCOCC3)c3c(-c4ccc5nc(C)n(C)c5c4)c[nH]c3n2)c(OC)c1] | 4-(5-(1,2-dimethyl-1H-benzo[d]imidazol-6-yl)-4-(tetrahydro-2H-pyran-4-yloxy)-7H-pyrrolo[2,3-d]pyrimidin-2-ylamino)-3-methoxy-N-methylbenzamide |
| 149 | 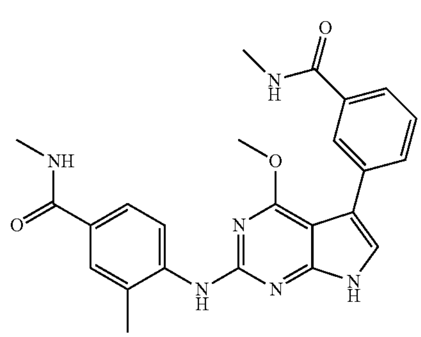 [SMILES: CNC(=O)c1cccc(-c2c[nH]c3nc(Nc4ccc(C(=O)NC)cc4C)nc(OC)c23)c1] | 4-(4-methoxy-5-(3-(methylcarbamoyl)phenyl)-7H-pyrrolo[2,3-d]pyrimidin-2-ylamino)-N,3-dimethylbenzamide |

TABLE A-continued

| Cmpd No. | Structure | Name |
|---|---|---|
| 150 | 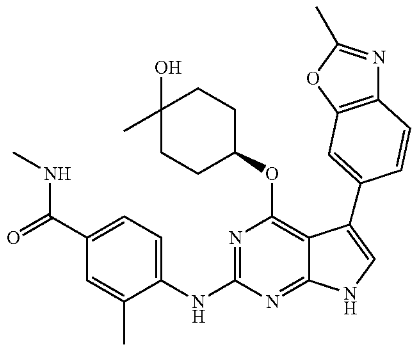 | 4-(4-((1r,4r)-4-hydroxy-4-methylcyclohexyloxy)-5-(2-methylbenzo[d]oxazol-6-yl)-7H-pyrrolo[2,3-d]pyrimidin-2-ylamino)-N,3-dimethylbenzamide |
| 151 | 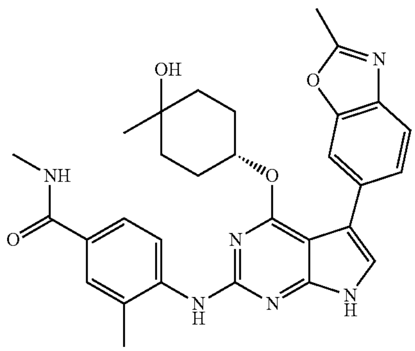 | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-N,3-dimethylbenzamide |
| 152 | 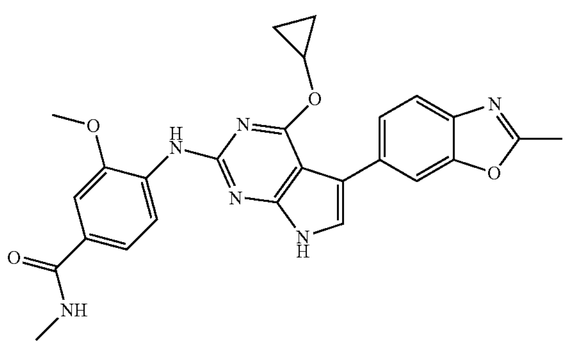 [SMILES: CNC(=O)c1ccc(Nc2nc(OC3CC3)c3c(-c4ccc5nc(C)oc5c4)c[nH]c3n2)c(OC)c1] | 4-(4-cyclopropoxy-5-(2-methylbenzo[d]oxazol-6-yl)-7H-pyrrolo[2,3-d]pyrimidin-2-ylamino)-3-methoxy-N-methylbenzamide |
| 153 | 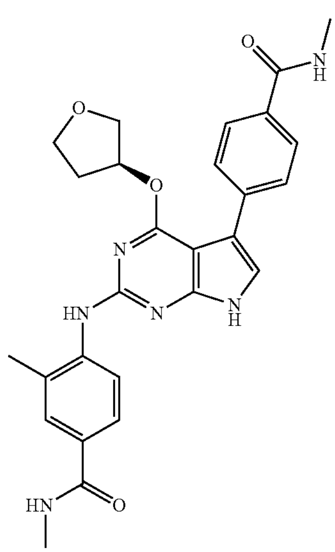 | (S)-N,3-dimethyl-4-(5-(4-(methylcarbamoyl)phenyl)-4-(tetrahydrofuran-3-yloxy)-7H-pyrrolo[2,3-d]pyrimidin-2-ylamino)benzamide |

| Cmpd No. | Structure | Name |
|---|---|---|
| 154 | 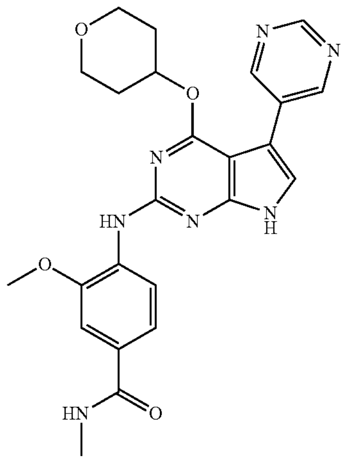 [SMILES: CNC(=O)c1ccc(Nc2nc(OC3CCOCC3)c3c(-c4cncnc4)c[nH]c3n2)c(OC)c1] | 3-methoxy-N-methyl-4-(5-(pyrimidin-5-yl)-4-(tetrahydro-2H-pyran-4-yloxy)-7H-pyrrolo[2,3-d]pyrimidin-2-ylamino)benzamide |
| 155 | 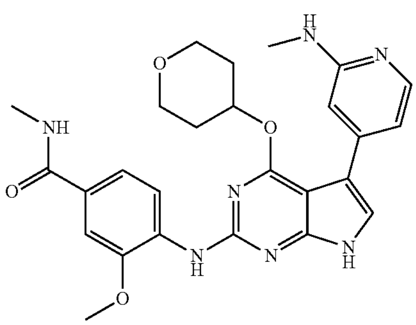 [SMILES: CNC(=O)c1ccc(Nc2nc(OC3CCOCC3)c3c(-c4ccnc(NC)c4)c[nH]c3n2)c(OC)c1] | 3-methoxy-N-methyl-4-(5-(2-(methylamino)pyridin-4-yl)-4-(tetrahydro-2H-pyran-4-yloxy)-7H-pyrrolo[2,3-d]pyrimidin-2-ylamino)benzamide |
| 156 | 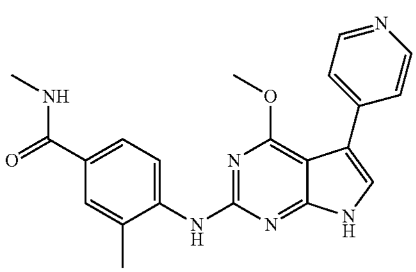 [SMILES: CNC(=O)c1ccc(Nc2nc(OC)c3c(-c4ccncc4)c[nH]c3n2)c(C)c1] | 4-(4-methoxy-5-(pyridin-4-yl)-7H-pyrrolo[2,3-d]pyrimidin-2-ylamino)-N,3-dimethylbenzamide |
| 157 | 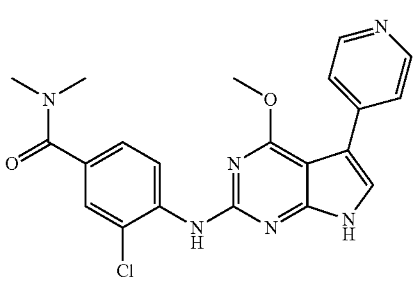 [SMILES: COc1nc(Nc2ccc(C(=O)N(C)C)cc2Cl)nc2[nH]cc(-c3ccncc3)c12] | 3-chloro-4-(4-methoxy-5-(pyridin-4-yl)-7H-pyrrolo[2,3-d]pyrimidin-2-ylamino)-N,N-dimethylbenzamide |

TABLE A-continued

| Cmpd No. | Structure | Name |
|---|---|---|
| 158 | 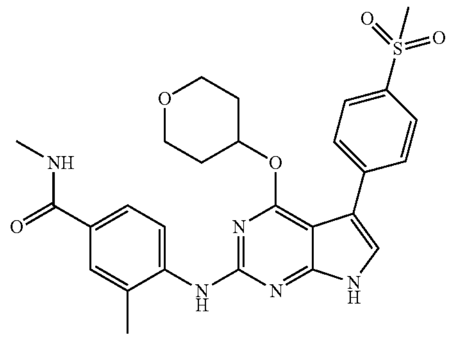 [SMILES: CNC(=O)c1ccc(Nc2nc(OC3CCOCC3)c3c(-c4ccc(S(C)(=O)=O)cc4)c[nH]c3n2)c(C)c1] | N,3-dimethyl-4-(5-(4-(methylsulfonyl)phenyl)-4-(tetrahydro-2H-pyran-4-yloxy)-7H-pyrrolo[2,3-d]pyrimidin-2-ylamino)benzamide |
| 159 | 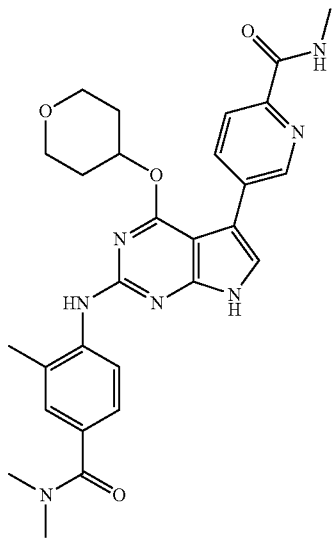 | 5-(2-(4-(dimethylcarbamoyl)-2-methylphenylamino)-4-(tetrahydro-2H-pyran-4-yloxy)-7H-pyrrolo[2,3-d]pyrimidin-5-yl)-N-methylpicolinamide |
| 160 | 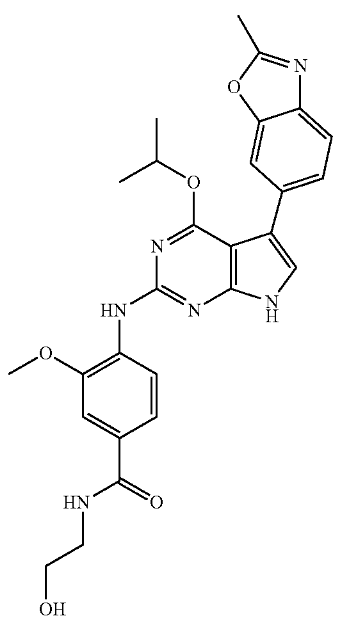 [SMILES: COc1cc(C(=O)NCCO)ccc1Nc1nc(OC(C)C)c2c(-c3ccc4nc(C)oc4c3)c[nH]c2n1] | N-(2-hydroxyethyl)-4-(4-isopropoxy-5-(2-methylbenzo[d]oxazol-6-yl)-7H-pyrrolo[2,3-d]pyrimidin-2-ylamino)-3-methoxybenzamide |

| Cmpd No. | Structure | Name |
|---|---|---|
| 161 | 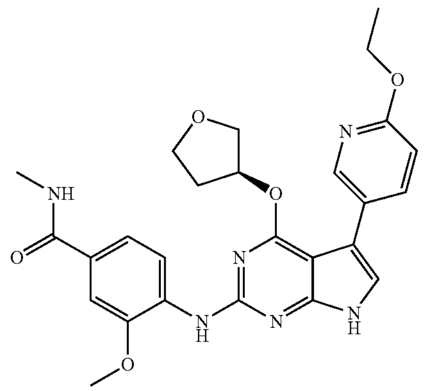 [SMILES: CCOc1ccc(-c2c[nH]c3nc(Nc4ccc(C(=O)NC)cc4OC)nc(O[C@H]4CCOC4)c23)cn1] | (S)-4-(5-(6-ethoxypyridin-3-yl)-4-(tetrahydrofuran-3-yloxy)-7H-pyrrolo[2,3-d]pyrimidin-2-ylamino)-3-methoxy-N-methylbenzamide |
| 162 | 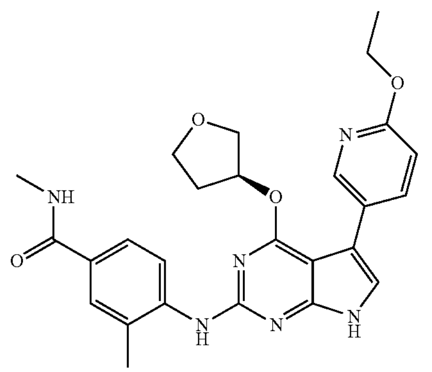 [SMILES: CCOc1ccc(-c2c[nH]c3nc(Nc4ccc(C(=O)NC)cc4C)nc(O[C@H]4CCOC4)c23)cn1] | (S)-4-(5-(6-ethoxypyridin-3-yl)-4-(tetrahydrofuran-3-yloxy)-7H-pyrrolo[2,3-d]pyrimidin-2-ylamino)-N,3-dimethylbenzamide |
| 163 | 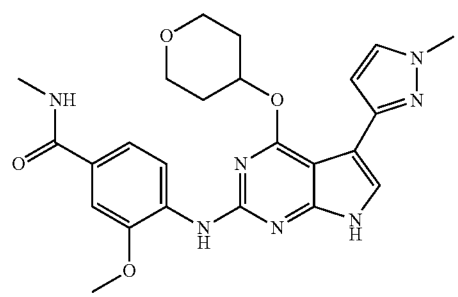 [SMILES: CNC(=O)c1ccc(Nc2nc(OC3CCOCC3)c3c(-c4ccn(C)n4)c[nH]c3n2)c(OC)c1] | 3-methoxy-N-methyl-4-(5-(1-methyl-1H-pyrazol-3-yl)-4-(tetrahydro-2H-pyran-4-yloxy)-7H-pyrrolo[2,3-d]pyrimidin-2-ylamino)benzamide |
| 164 | 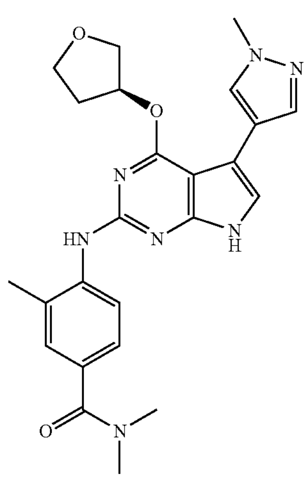 [SMILES: Cc1cc(C(=O)N(C)C)ccc1Nc1nc(O[C@H]2CCOC2)c2c(-c3cnn(C)c3)c[nH]c2n1] | (S)-N,N,3-trimethyl-4-(5-(1-methyl-1H-pyrazol-4-yl)-4-(tetrahydrofuran-3-yloxy)-7H-pyrrolo[2,3-d]pyrimidin-2-ylamino)benzamide |

TABLE A-continued

| Cmpd No. | Structure | Name |
|---|---|---|
| 165 | 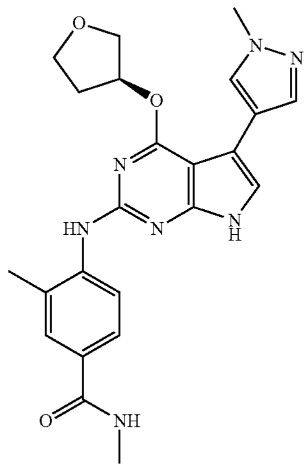 [SMILES: CNC(=O)c1ccc(Nc2nc(O[C@H]3CCOC3)c3c(-c4cnn(C)c4)c[nH]c3n2)c(C)c1] | (S)-N,3-dimethyl-4-(5-(1-methyl-1H-pyrazol-4-yl)-4-(tetrahydrofuran-3-yloxy)-7H-pyrrolo[2,3-d]pyrimidin-2-ylamino)benzamide |
| 166 | 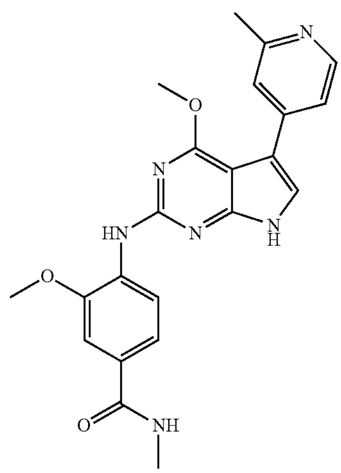 [SMILES: CNC(=O)c1ccc(Nc2nc(OC)c3c(-c4ccnc(C)c4)c[nH]c3n2)c(OC)c1] | 3-methoxy-4-(4-methoxy-5-(2-methylpyridin-4-yl)-7H-pyrrolo[2,3-d]pyrimidin-2-ylamino)-N-methylbenzamide |
| 167 | 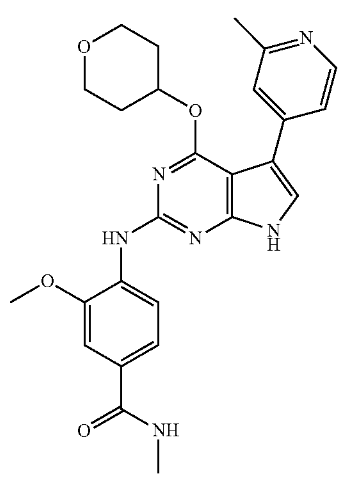 [SMILES: CNC(=O)c1ccc(Nc2nc(OC3CCOCC3)c3c(-c4ccnc(C)c4)c[nH]c3n2)c(OC)c1] | 3-methoxy-N-methyl-4-(5-(2-methylpyridin-4-yl)-4-(tetrahydro-2H-pyran-4-yloxy)-7H-pyrrolo[2,3-d]pyrimidin-2-ylamino)benzamide |

| Cmpd No. | Structure | Name |
|---|---|---|
| 168 | 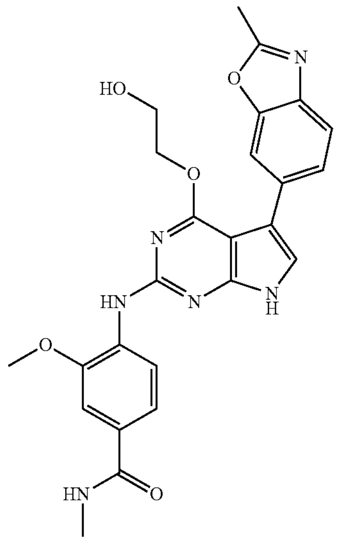 [SMILES: CNC(=O)c1ccc(Nc2nc(OCCO)c3c(-c4ccc5nc(C)oc5c4)c[nH]c3n2)c(OC)c1] | 4-(4-(2-hydroxyethoxy)-5-(2-methylbenzo[d]oxazol-6-yl)-7H-pyrrolo[2,3-d]pyrimidin-2-ylamino)-3-methoxy-N-methylbenzamide |
| 169 | 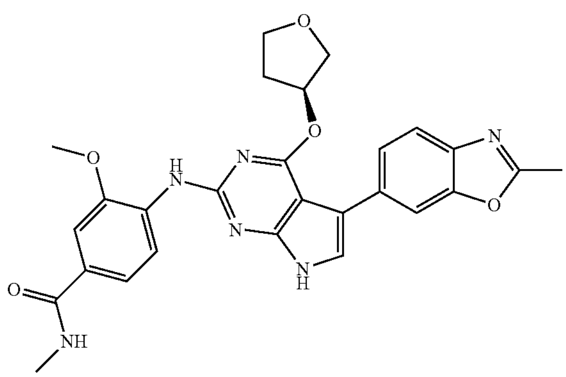 [SMILES: CNC(=O)c1ccc(Nc2nc(O[C@H]3CCOC3)c3c(-c4ccc5nc(C)oc5c4)c[nH]c3n2)c(OC)c1] | (S)-3-methoxy-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide |
| 170 | 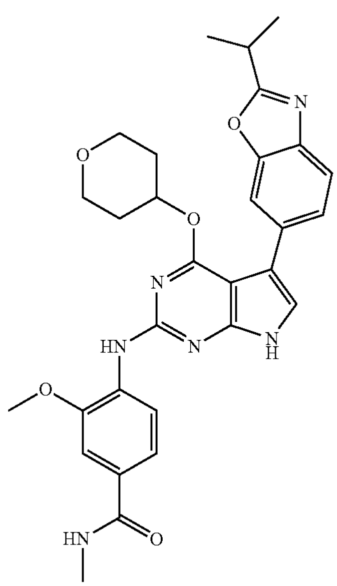 [SMILES: CNC(=O)c1ccc(Nc2nc(OC3CCOCC3)c3c(-c4ccc5nc(C(C)C)oc5c4)c[nH]c3n2)c(OC)c1] | 4-(5-(2-isopropylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 171 | 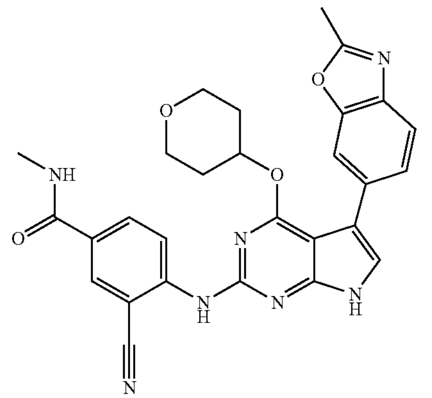 [SMILES: CNC(=O)c1ccc(Nc2nc(OC3CCOCC3)c3c(-c4ccc5nc(C)oc5c4)c[nH]c3n2)c(C#N)c1] | 3-cyano-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 172 | 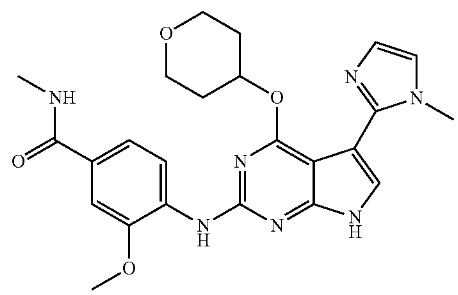 [SMILES: CNC(=O)c1ccc(Nc2nc(OC3CCOCC3)c3c(-c4nccn4C)c[nH]c3n2)c(OC)c1] | 3-methoxy-N-methyl-4-(5-(1-methyl-1H-imidazol-2-yl)-4-(tetrahydro-2H-pyran-4-yloxy)-7H-pyrrolo[2,3-d]pyrimidin-2-ylamino)benzamide |
| 173 | 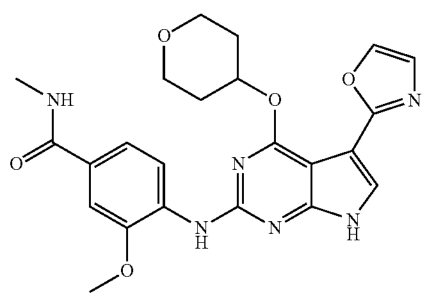 [SMILES: CNC(=O)c1ccc(Nc2nc(OC3CCOCC3)c3c(-c4ncco4)c[nH]c3n2)c(OC)c1] | 3-methoxy-N-methyl-4-(5-(oxazol-2-yl)-4-(tetrahydro-2H-pyran-4-yloxy)-7H-pyrrolo[2,3-d]pyrimidin-2-ylamino)benzamide |
| 174 | 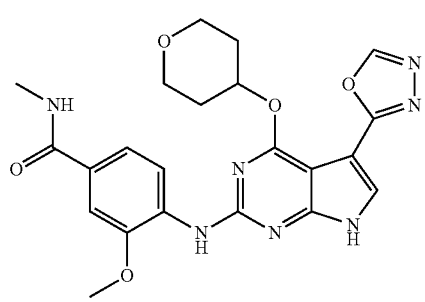 | 4-(5-(1,3,4-oxadiazol-2-yl)-4-(tetrahydro-2H-pyran-4-yloxy)-7H-pyrrolo[2,3-d]pyrimidin-2-ylamino)-3-methoxy-N-methylbenzamide |

| Cmpd No. | Structure | Name |
|---|---|---|
| 175 | 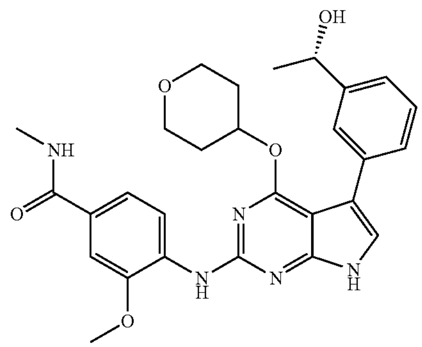 [SMILES: CNC(=O)c1ccc(Nc2nc(OC3CCOCC3)c3c(-c4cccc([C@H](C)O)c4)c[nH]c3n2)c(OC)c1] | (S)-4-(5-(3-(1-hydroxyethyl)phenyl)-4-(tetrahydro-2H-pyran-4-yloxy)-7H-pyrrolo[2,3-d]pyrimidin-2-ylamino)-3-methoxy-N-methylbenzamide |
| 176 | 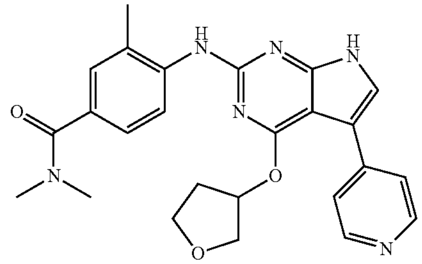 [SMILES: Cc1cc(C(=O)N(C)C)ccc1Nc1nc(OC2CCOC2)c2c(-c3ccncc3)c[nH]c2n1] | (S)-N,N,3-trimethyl-4-(5-(pyridin-4-yl)-4-(tetrahydrofuran-3-yloxy)-7H-pyrrolo[2,3-d]pyrimidin-2-ylamino)benzamide |
| 177 | 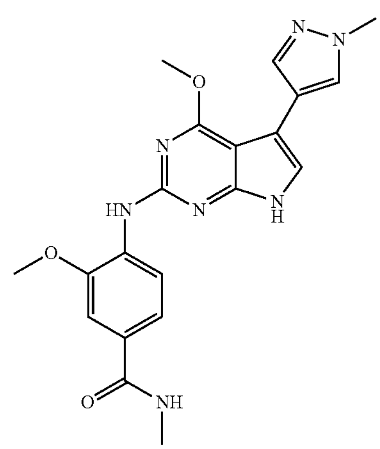 | 3-methoxy-4-(4-methoxy-5-(1-methyl-1H-pyrazol-4-yl)-7H-pyrrolo[2,3-d]pyrimidin-2-ylamino)-N-methylbenzamide |
| 178 | 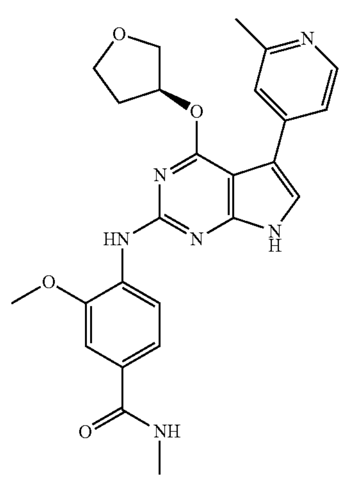 [SMILES: CNC(=O)c1ccc(Nc2nc(O[C@H]3CCOC3)c3c(-c4ccnc(C)c4)c[nH]c3n2)c(OC)c1] | (S)-3-methoxy-N-methyl-4-(5-(2-methylpyridin-4-yl)-4-(tetrahydrofuran-3-yloxy)-7H-pyrrolo[2,3-d]pyrimidin-2-ylamino)benzamide |

| Cmpd No. | Structure | Name |
|---|---|---|
| 179 | 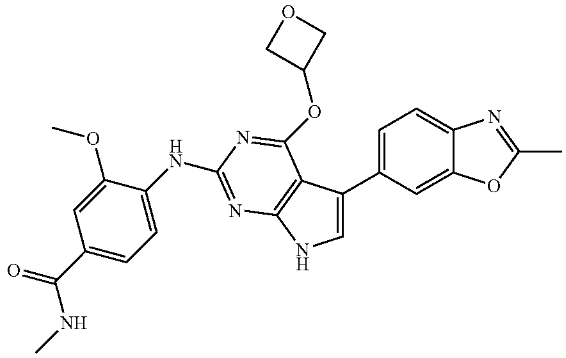 [SMILES: CNC(=O)c1ccc(Nc2nc(OC3COC3)c3c(-c4ccc5nc(C)oc5c4)c[nH]c3n2)c(OC)c1] | 3-methoxy-N-methyl-4-(5-(2-methylbenzo[d]oxazol-6-yl)-4-(oxetan-3-yloxy)-7H-pyrrlo[2,3-d]pyrimidin-2-ylamino)benzamide |
| 180 | 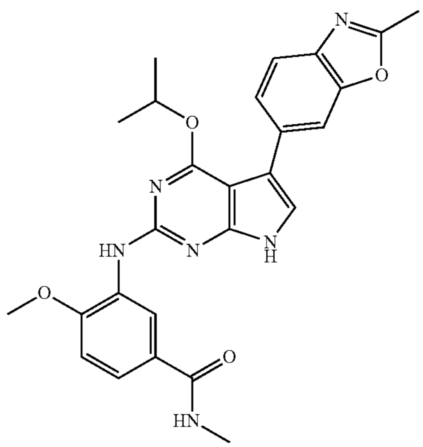 | 3-(4-isopropoxy-5-(2-methylbenzo[d]oxazol-6-yl)-7H-pyrrolo[2,3-d]pyrimidin-2-ylamino)-4-methoxy-N-methylbenzamide |
| 181 | 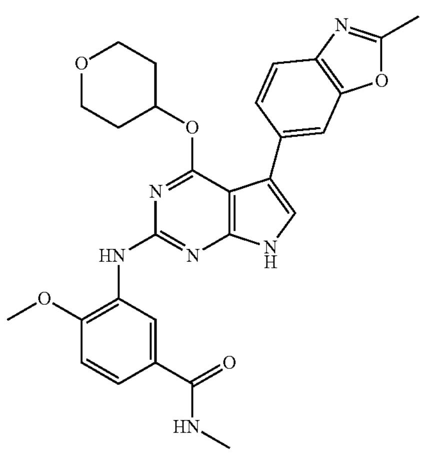 | 4-methoxy-N-methyl-3-(5-(2-methylbenzo[d]oxazol-6-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 182 | 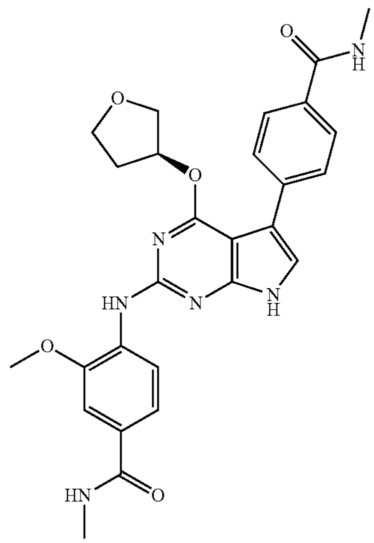 | (S)-3-methoxy-N-methyl-4-(5-(4-(methylcarbamoyl)phenyl)-4-(tetrahydrofuran-3-yloxy)-7H-pyrrolo[2,3-d]pyrimidin-2-ylamino)benzamide |
| 183 | 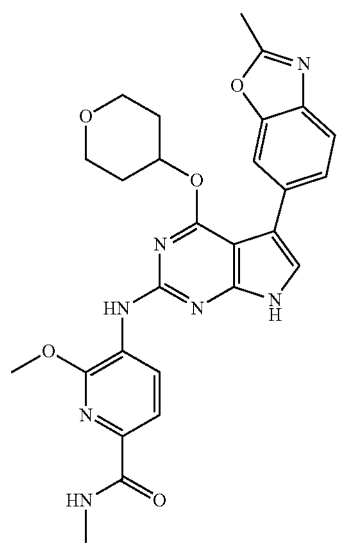 [SMILES: CNC(=O)c1ccc(Nc2nc(OC3CCOCC3)c3c(-c4ccc5nc(C)oc5c4)c[nH]c3n2)c(OC)n1] | 6-methoxy-N-methyl-5-(5-(2-methylbenzo[d]oxazol-6-yl)-4-(tetrahydro-2H-pyran-4-yloxy)-7H-pyrrolo[2,3-d]pyrimidin-2-ylamino)picolinamide |
| 184 | 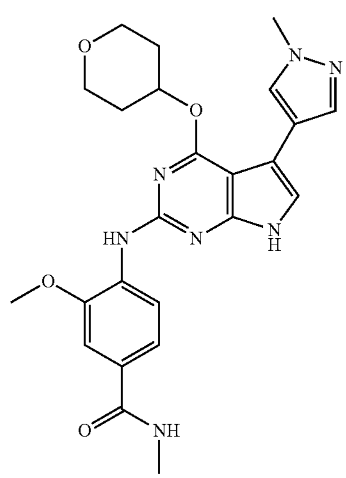 [SMILES: CNC(=O)c1ccc(Nc2nc(OC3CCOCC3)c3c(-c4cnn(C)c4)c[nH]c3n2)c(OC)c1] | 3-methoxy-N-methyl-4-(5-(1-methyl-1H-pyrazol-4-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 185 | 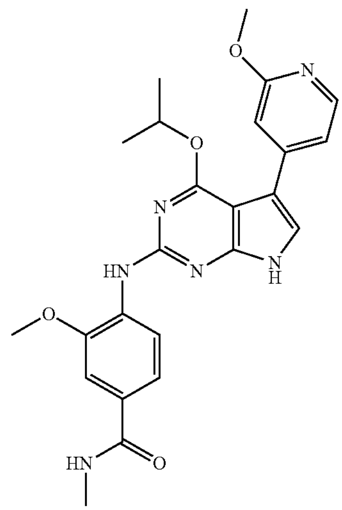 [SMILES: CNC(=O)c1ccc(Nc2nc(OC(C)C)c3c(-c4ccnc(OC)c4)c[nH]c3n2)c(OC)c1] | 4-(4-isopropoxy-5-(2-methoxypyridin-4-yl)-7H-pyrrolo[2,3-d]pyrimidin-2-ylamino)-3-methoxy-N-methylbenzamide |
| 186 | 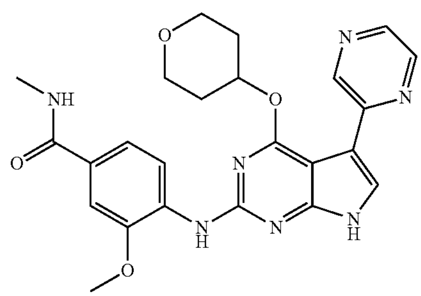 [SMILES: CNC(=O)c1ccc(Nc2nc(OC3CCOCC3)c3c(-c4cnccn4)c[nH]c3n2)c(OC)c1] | 3-methoxy-N-methyl-4-(5-(pyrazin-2-yl)-4-(tetrahydro-2H-pyran-4-yloxy)-7H-pyrrolo[2,3-d]pyrimidin-2-ylamino)benzamide |
| 187 | 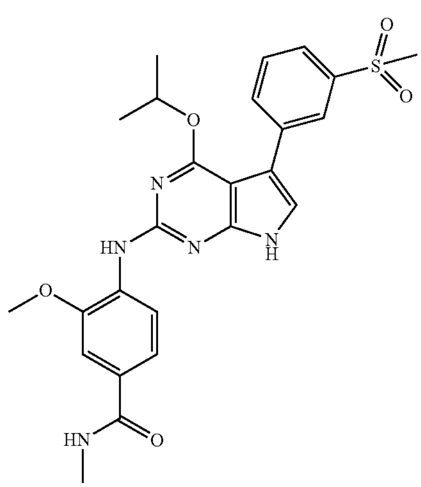 | 4-(4-isopropoxy-5-(3-(methylsulfonyl)phenyl)-7H-pyrrolo[2,3-d]pyrimidin-2-ylamino)-3-methoxy-N-methylbenzamide |

| Cmpd No. | Structure | Name |
|---|---|---|
| 188 | 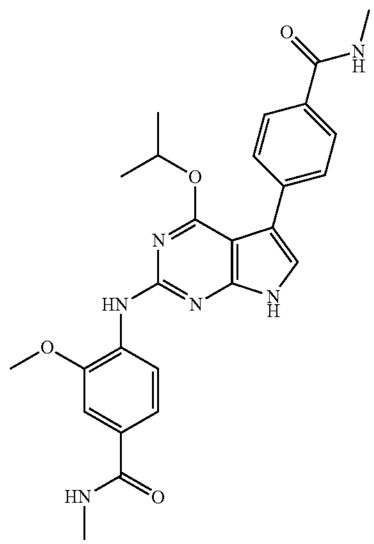 | 4-(4-isopropoxy-5-(4-(methylcarbamoyl)phenyl)-7H-pyrrolo[2,3-d]pyrimidin-2-ylamino)-3-methoxy-N-methylbenzamide |
| 189 | 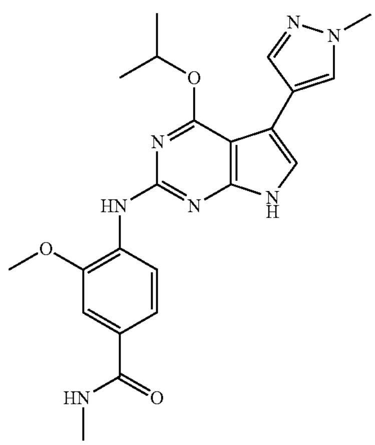 | 4-(4-isopropoxy-5-(1-methyl-1H-pyrazol-4-yl)-7H-pyrrolo[2,3-d]pyrimidin-2-ylamino)-3-methoxy-N-methylbenzamide |
| 190 | 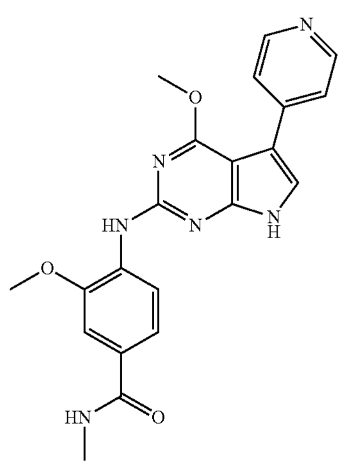 [SMILES: CNC(=O)c1ccc(Nc2nc(OC)c3c(-c4ccncc4)c[nH]c3n2)c(OC)c1] | 3-methoxy-4-(4-methoxy-5-(pyridin-4-yl)-7H-pyrrolo[2,3-d]pyrimidin-2-ylamino)-N-methylbenzamide |

| Cmpd No. | Structure | Name |
|---|---|---|
| 191 | 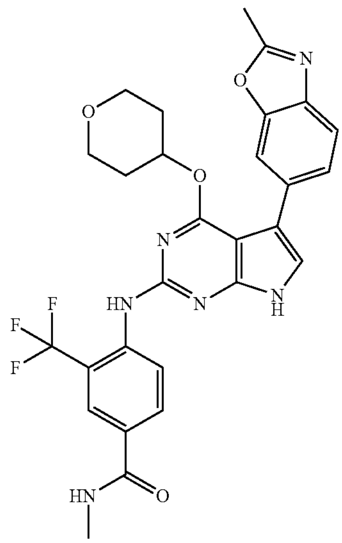 [SMILES: CNC(=O)c1ccc(Nc2nc(OC3CCOCC3)c3c(-c4ccc5nc(C)oc5c4)c[nH]c3n2)c(C(F)(F)F)c1] | N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-(trifluoromethyl)benzamide |
| 192 | 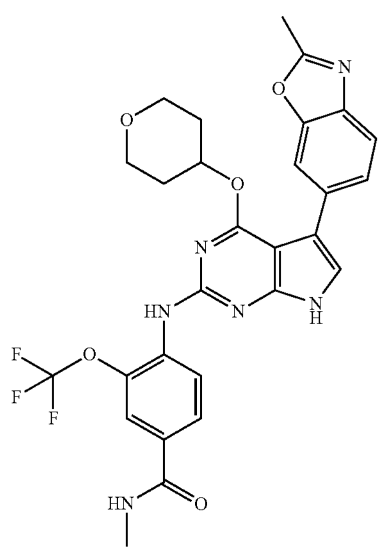 [SMILES: CNC(=O)c1ccc(Nc2nc(OC3CCOCC3)c3c(-c4ccc5nc(C)oc5c4)c[nH]c3n2)c(OC(F)(F)F)c1] | N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-(trifluoromethoxy)benzamide |

| Cmpd No. | Structure | Name |
|---|---|---|
| 193 | 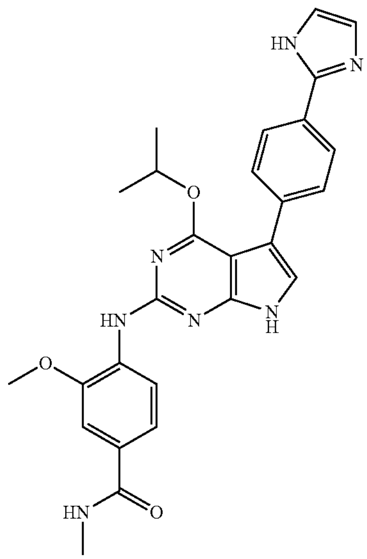 [SMILES: CNC(=O)c1ccc(Nc2nc(OC(C)C)c3c(-c4ccc(-c5ncc[nH]5)cc4)c[nH]c3n2)c(OC)c1] | 4-(5-(4-(1H-imidazol-2-yl)phenyl)-4-isopropoxy-7H-pyrrolo[2,3-d]pyrimidin-2-ylamino)-3-methoxy-N-methylbenzamide |
| 194 | 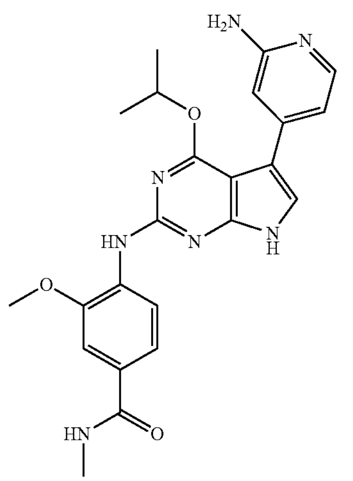 [SMILES: CNC(=O)c1ccc(Nc2nc(OC(C)C)c3c(-c4ccnc(N)c4)c[nH]c3n2)c(OC)c1] | 4-(5-(2-aminopyridin-4-yl)-4-isopropoxy-7H-pyrrolo[2,3-d]pyrimidin-2-ylamino)-3-methoxy-N-methylbenzamide |
| 195 | 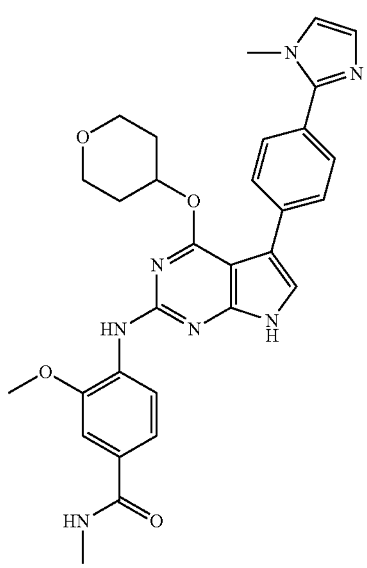 [SMILES: CNC(=O)c1ccc(Nc2nc(OC3CCOCC3)c3c(-c4ccc(-c5nccn5C)cc4)c[nH]c3n2)c(OC)c1] | 3-methoxy-N-methyl-4-(5-(4-(1-methyl-1H-imidazol-2-yl)phenyl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 196 | 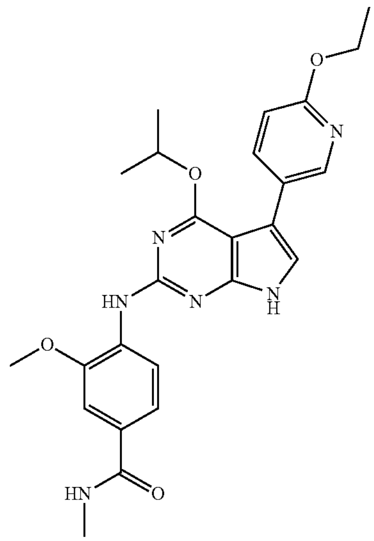 [SMILES: CCOc1ccc(-c2c[nH]c3nc(Nc4ccc(C(=O)NC)cc4OC)nc(OC(C)C)c23)cn1] | 4-(5-(6-ethoxypyridin-3-yl)-4-isopropoxy-7H-pyrrolo[2,3-d]pyrimidin-2-ylamino)-3-methoxy-N-methylbenzamide |
| 197 | 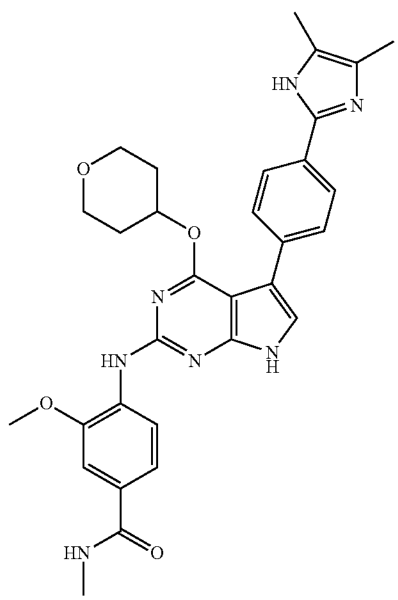 | 4-(5-(4-(4,5-dimethyl-1H-imidazol-2-yl)phenyl)-4-(tetrahydro-2H-pyran-4-yloxy)-7H-pyrrolo[2,3-d]pyrimidin-2-ylamino)-3-methoxy-N-methylbenzamide |
| 198 | 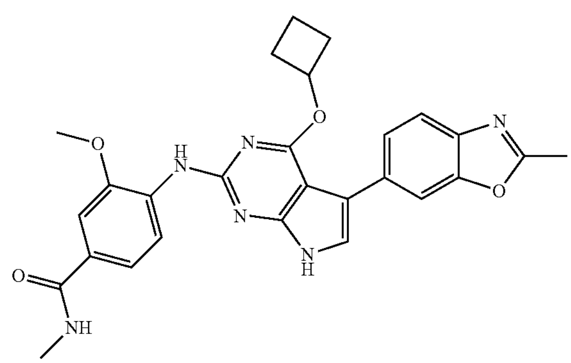 [SMILES: CNC(=O)c1ccc(Nc2nc(OC3CCC3)c3c(-c4ccc5nc(C)oc5c4)c[nH]c3n2)c(OC)c1] | 4-(4-cyclobutoxy-5-(2-methylbenzo[d]oxazol-6-yl)-7H-pyrrolo[2,3-d]pyrimidin-2-ylamino)-3-methoxy-N-methylbenzamide |

TABLE A-continued
| Cmpd No. | Structure | Name |
|---|---|---|
| 199 | 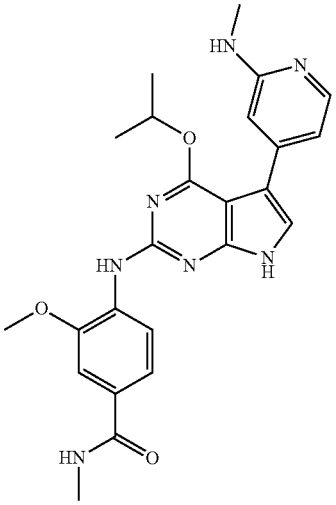 [SMILES: CNC(=O)c1ccc(Nc2nc(OC(C)C)c3c(-c4ccnc(NC)c4)c[nH]c3n2)c(OC)c1] | 4-(4-isopropoxy-5-(2-(methylamino)pyridin-4-yl)-7H-pyrrolo[2,3-d]pyrimidin-2-ylamino)-3-methoxy-N-methylbenzamide |
| 200 | 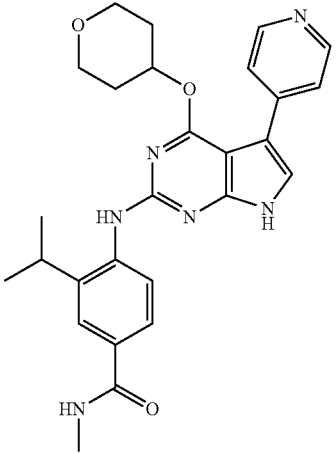 [SMILES: CNC(=O)c1ccc(Nc2nc(OC3CCOCC3)c3c(-c4ccncc4)c[nH]c3n2)c(C(C)C)c1] | 3-isopropyl-N-methyl-4-(5-(pyridin-4-yl)-4-(tetrahydro-2H-pyran-4-yloxy)-7H-pyrrolo[2,3-d]pyrimidin-2-ylamino)benzamide |
| 201 | 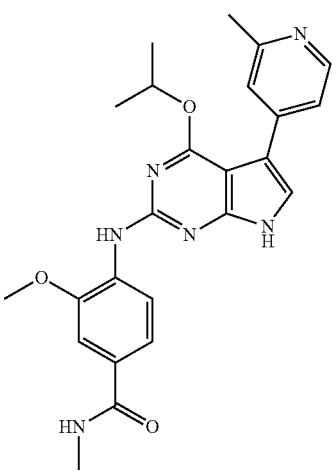 [SMILES: CNC(=O)c1ccc(Nc2nc(OC(C)C)c3c(-c4ccnc(C)c4)c[nH]c3n2)c(OC)c1] | 4-(4-isopropoxy-5-(2-methylpyridin-4-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 202 | 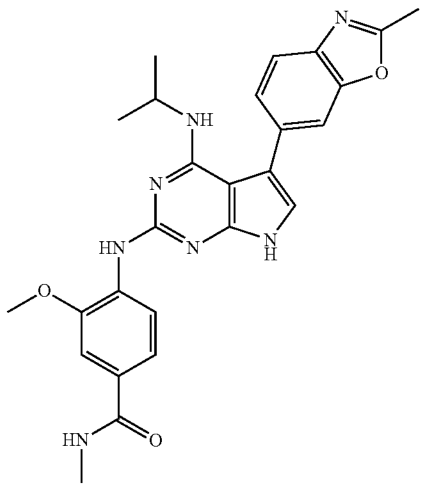 | 4-(4-(isopropylamino)-5-(2-methylbenzo[d]oxazol-6-yl)-7H-pyrrolo[2,3-d]pyrimidin-2-ylamino)-3-methoxy-N-methylbenzamide |
| 203 | 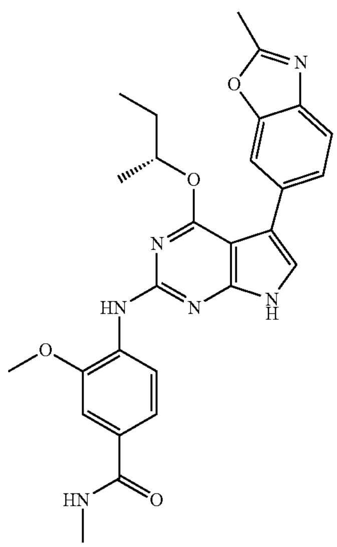 [SMILES: CC[C@@H](C)Oc1nc(Nc2ccc(C(=O)NC)cc2OC)nc2[nH]cc(-c3ccc4nc(C)oc4c3)c12] | (R)-4-(4-sec-butoxy-5-(2-methylbenzo[d]oxazol-6-yl)-7H-pyrrolo[2,3-d]pyrimidin-2-ylamino)-3-methoxy-N-methylbenzamide |
| 204 | 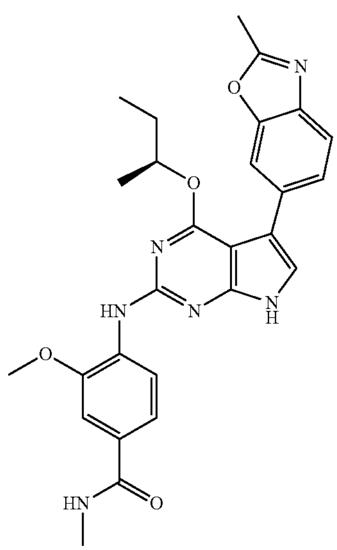 [SMILES: CC[C@H](C)Oc1nc(Nc2ccc(C(=O)NC)cc2OC)nc2[nH]cc(-c3ccc4nc(C)oc4c3)c12] | (S)-4-(4-sec-butoxy-5-(2-methylbenzo[d]oxazol-6-yl)-7H-pyrrolo[2,3-d]pyrimidin-2-ylamino)-3-methoxy-N-methylbenzamide |

US 9,623,028 B2
149                                                                                      150
TABLE A-continued
| Cmpd No. | Structure | Name |
|---|---|---|
| 205 | 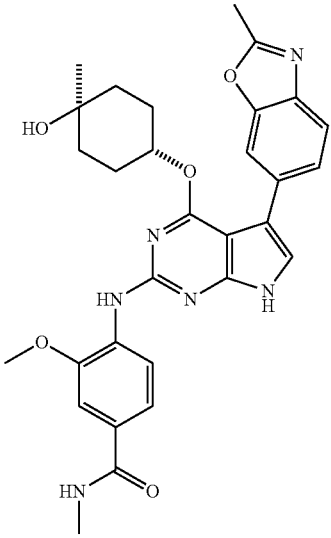 | 4-(4-((1r,4r)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-methylbenzamide |
| 206 | 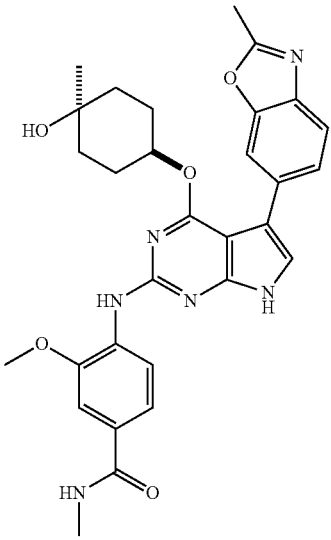 | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 207 | 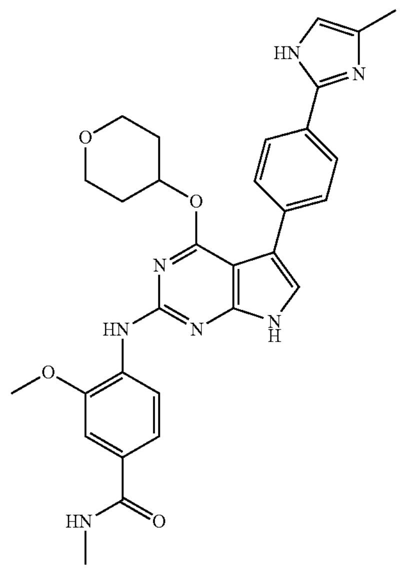 | 3-methoxy-N-methyl-4-(5-(4-(4-methyl-1H-imidazol-2-yl)phenyl)-4-(tetrahydro-2H-pyran-4-yloxy)-7H-pyrrolo[2,3-d]pyrimidin-2-ylamino)benzamide |
| 208 | 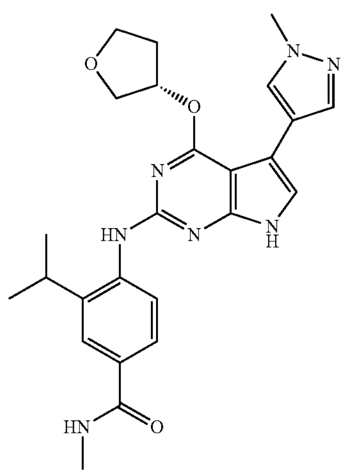 [SMILES: CNC(=O)c1ccc(Nc2nc(O[C@H]3CCOC3)c3c(-c4cnn(C)c4)c[nH]c3n2)c(C(C)C)c1] | (S)-3-isopropyl-N-methyl-4-(5-(1-methyl-1H-pyrazol-4-yl)-4-(tetrahydrofuran-3-yloxy)-7H-pyrrolo[2,3-d]pyrimidin-2-ylamino)benzamide |
| 209 | 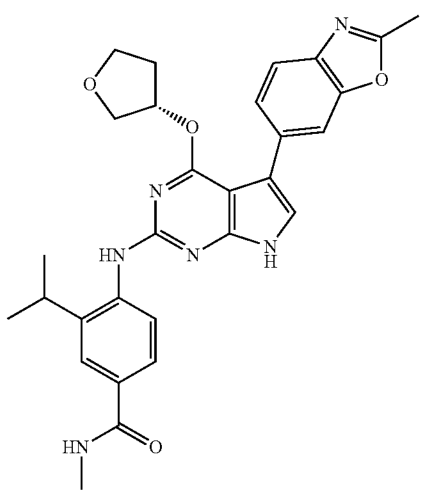 [SMILES: CNC(=O)c1ccc(Nc2nc(O[C@H]3CCOC3)c3c(-c4ccc5nc(C)oc5c4)c[nH]c3n2)c(C(C)C)c1] | (S)-3-isopropyl-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide |

TABLE A-continued

| Cmpd No. | Structure | Name |
|---|---|---|
| 210 | 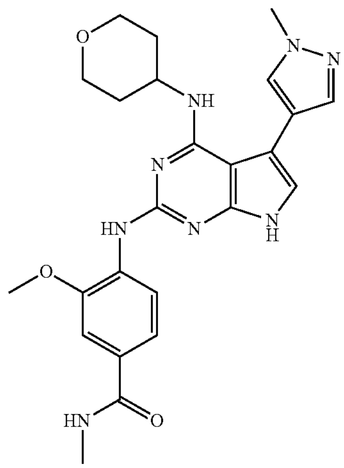 [SMILES: CNC(=O)c1ccc(Nc2nc(NC3CCOCC3)c3c(-c4cnn(C)c4)c[nH]c3n2)c(OC)c1] | 3-methoxy-N-methyl-4-(5-(1-methyl-1H-pyrazol-4-yl)-4-(tetrahydro-2H-pyran-4-ylamino)-7H-pyrrolo[2,3-d]pyrimidin-2-ylamino)benzamide |
| 211 | 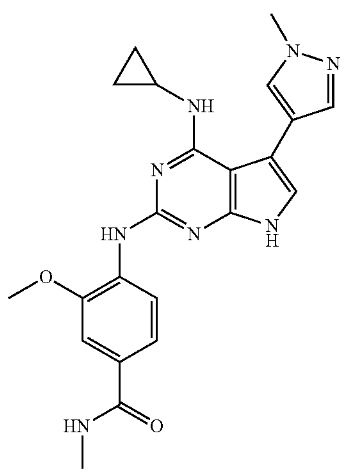 [SMILES: CNC(=O)c1ccc(Nc2nc(NC3CC3)c3c(-c4cnn(C)c4)c[nH]c3n2)c(OC)c1] | 4-(4-(cyclopropylamino)-5-(1-methyl-1H-pyrazol-4-yl)-7H-pyrrolo[2,3-d]pyrimidin-2-ylamino)-3-methoxy-N-methylbenzamide |
| 212 | 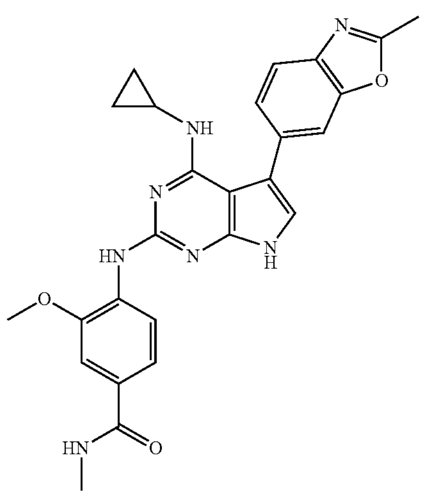 | 4-(4-(cyclopropylamino)-5-(2-methylbenzo[d]oxazol-6-yl)-7H-pyrrolo[2,3-d]pyrimidin-2-ylamino)-3-methoxy-N-methylbenzamide |

| Cmpd No. | Structure | Name |
|---|---|---|
| 213 | 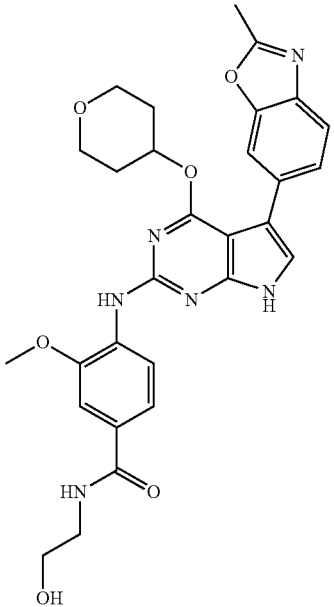 [SMILES: COc1cc(C(=O)NCCO)ccc1Nc1nc(OC2CCOCC2)c2c(-c3ccc4nc(C)oc4c3)c[nH]c2n1] | N-(2-hydroxyethyl)-3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 214 | 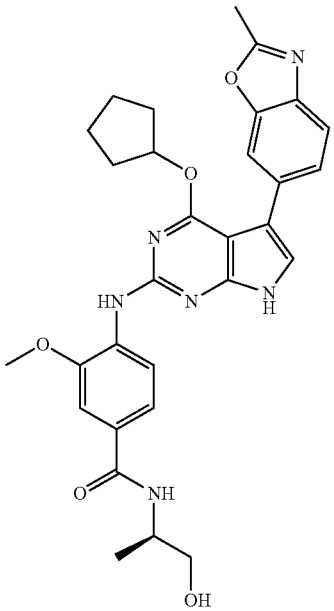 [SMILES: COc1cc(C(=O)N[C@H](C)CO)ccc1Nc1nc(OC2CCCC2)c2c(-c3ccc4nc(C)oc4c3)c[nH]c2n1] | (R)-4-(4-(cyclopentyloxy)-5-(2-methylbenzo[d]oxazol-6-yl)-7H-pyrrolo[2,3-d]pyrimidin-2-ylamino)-N-(1-hydroxypropan-2-yl)-3-methoxybenzamide |

| Cmpd No. | Structure | Name |
|---|---|---|
| 215 | 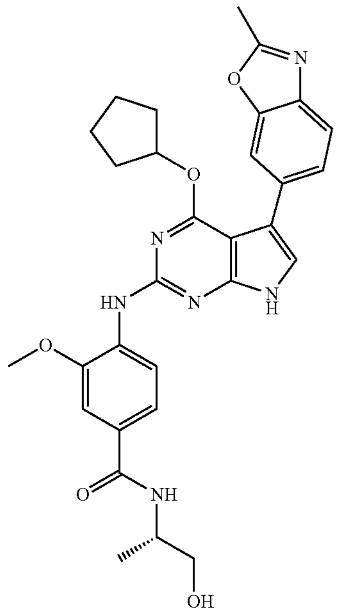 [SMILES: COc1cc(C(=O)N[C@@H](C)CO)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-N-(1-hydroxypropan-2-yl)-3-methoxybenzamide |
| 216 | 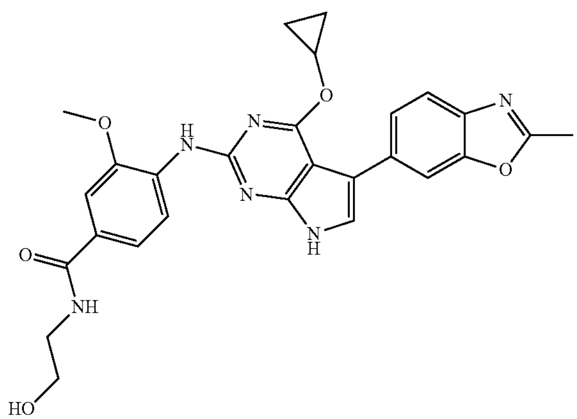 [SMILES: COc1cc(C(=O)NCCO)ccc1Nc1nc(OC2CC2)c2c(-c3ccc4nc(C)oc4c3)c[nH]c2n1] | 4-(4-cyclopropoxy-5-(2-methylbenzo[d]oxazol-6-yl)-7H-pyrrolo[2,3-d]pyrimidin-2-ylamino)-N-(2-hydroxyethyl)-3-methoxybenzamide |
| 217 | 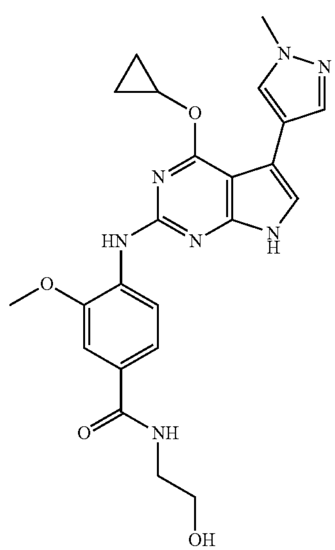 [SMILES: COc1cc(C(=O)NCCO)ccc1Nc1nc(OC2CC2)c2c(-c3cnn(C)c3)c[nH]c2n1] | 4-(4-cyclopropoxy-5-(1-methyl-1H-pyrazol-4-yl)-7H-pyrrolo[2,3-d]pyrimidin-2-ylamino)-N-(2-hydroxyethyl)-3-methoxybenzamide |

TABLE A-continued

| Cmpd No. | Structure | Name |
|---|---|---|
| 218 | 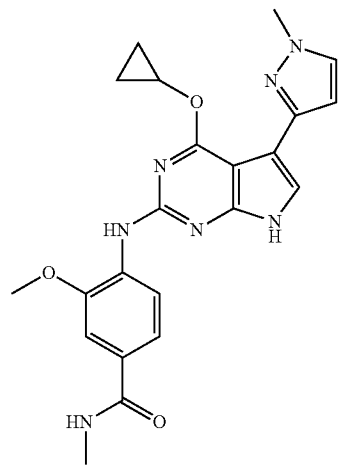 [SMILES: CNC(=O)c1ccc(Nc2nc(OC3CC3)c3c(-c4ccn(C)n4)c[nH]c3n2)c(OC)c1] | 4-(4-cyclopropoxy-5-(1-methyl-1H-pyrazol-3-yl)-7H-pyrrolo[2,3-d]pyrimidin-2-ylamino)-3-methoxy-N-methylbenzamide |
| 219 | 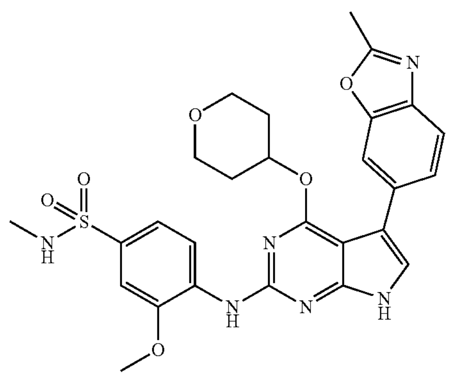 [SMILES: CNS(=O)(=O)c1ccc(Nc2nc(OC3CCOCC3)c3c(-c4ccc5nc(C)oc5c4)c[nH]c3n2)c(OC)c1] | 3-methoxy-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzenesulfonamide |
| 220 | 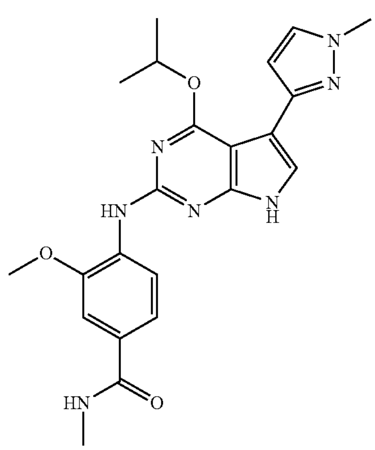 | 4-(4-isopropoxy-5-(1-methyl-1H-pyrazol-3-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 221 | 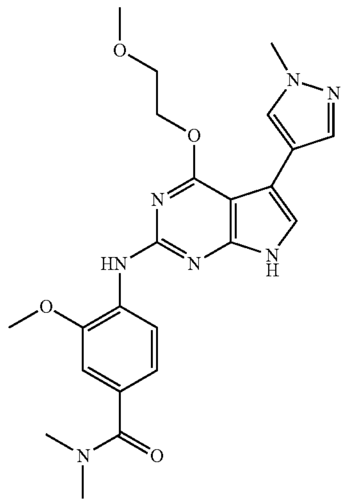 [SMILES: COCCOc1nc(Nc2ccc(C(=O)N(C)C)cc2OC)nc2[nH]cc(-c3cnn(C)c3)c12] | 3-methoxy-4-(4-(2-methoxyethoxy)-5-(1-methyl-1H-pyrazol-4-yl)-7H-pyrrolo[2,3-d]pyrimidin-2-ylamino)-N,N-dimethylbenzamide |
| 222 | 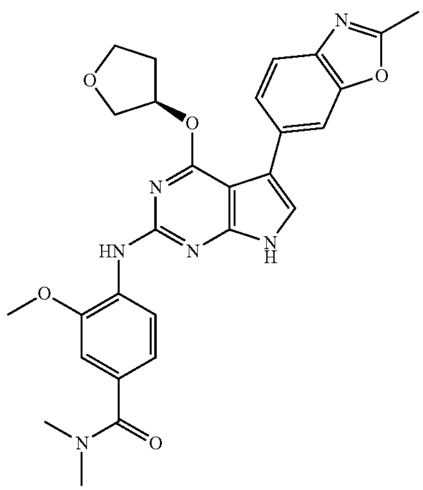 | (R)-3-methoxy-N,N-dimethyl-4-(5-(2-methylbenzo[d]oxazol-6-yl)-4-(tetrahydrofuran-3-yloxy)-7H-pyrrolo[2,3-d]pyrimidin-2-ylamino)benzamide |
| 223 | 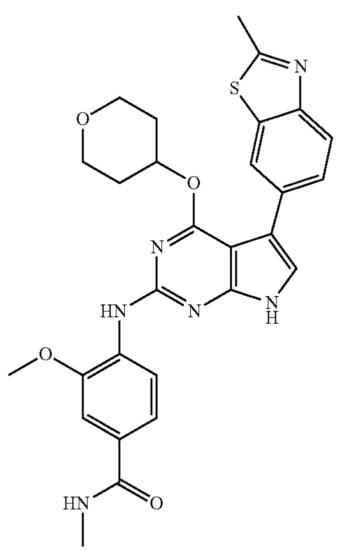 [SMILES: CNC(=O)c1ccc(Nc2nc(OC3CCOCC3)c3c(-c4ccc5nc(C)sc5c4)c[nH]c3n2)c(OC)c1] | 3-methoxy-N-methyl-4-(5-(2-methylbenzo[d]thiazol-6-yl)-4-(tetrahydro-2H-pyran-4-yloxy)-7H-pyrrolo[2,3-d]pyrimidin-2-ylamino)benzamide |

TABLE A-continued
| Cmpd No. | Structure | Name |
|---|---|---|
| 224 | 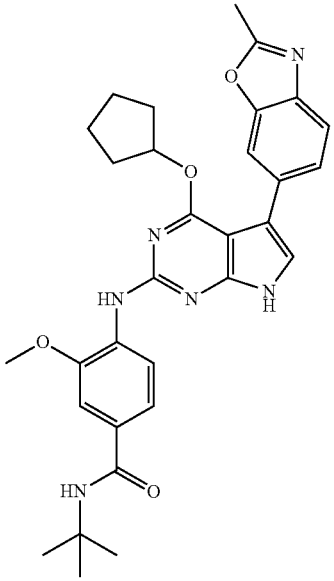 [SMILES: COc1cc(C(=O)NC(C)(C)C)ccc1Nc1nc(OC2CCCC2)c2c(-c3ccc4nc(C)oc4c3)c[nH]c2n1] | N-tert-butyl-4-(4-(cyclopentyloxy)-5-(2-methylbenzo[d]oxazol-6-yl)-7H-pyrrolo[2,3-d]pyrimidin-2-ylamino)-3-methoxybenzamide |
| 225 | 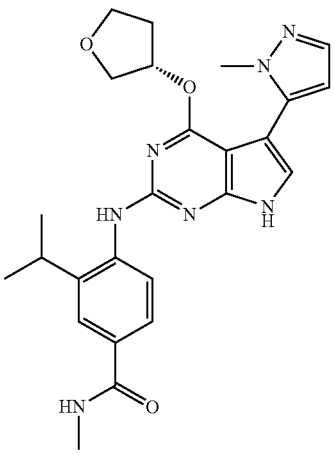 [SMILES: CNC(=O)c1ccc(Nc2nc(O[C@H]3CCOC3)c3c(-c4ccnn4C)c[nH]c3n2)c(C(C)C)c1] | (S)-3-isopropyl-N-methyl-4-(5-(1-methyl-1H-pyrazol-5-yl)-4-(tetrahydrofuran-3-yloxy)-7H-pyrrolo[2,3-d]pyrimidin-2-ylamino)benzamide |
| 226 | 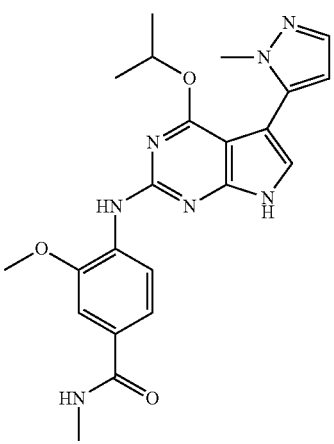 [SMILES: CNC(=O)c1ccc(Nc2nc(OC(C)C)c3c(-c4ccnn4C)c[nH]c3n2)c(OC)c1] | 4-(4-isopropoxy-5-(1-methyl-1H-pyrazol-5-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 227 | 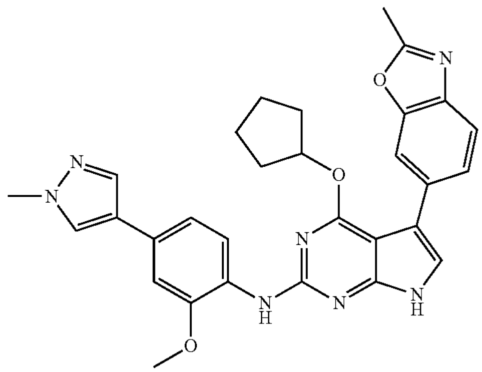 [SMILES: COc1cc(-c2cnn(C)c2)ccc1Nc1nc(OC2CCCC2)c2c(-c3ccc4nc(C)oc4c3)c[nH]c2n1] | 4-(cyclopentyloxy)-N-(2-methoxy-4-(1-methyl-1H-pyrazol-4-yl)phenyl)-5-(2-methylbenzo[d]oxazol-6-yl)-7H-pyrrolo[2,3-d]pyrimidin-2-amine |
| 228 | 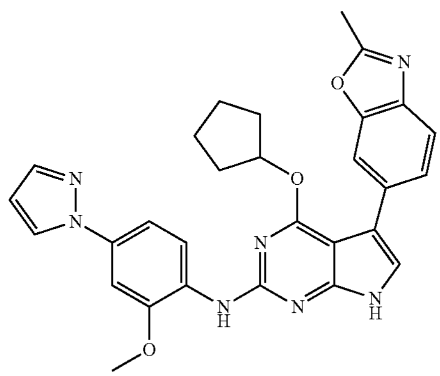 [SMILES: COc1cc(-n2cccn2)ccc1Nc1nc(OC2CCCC2)c2c(-c3ccc4nc(C)oc4c3)c[nH]c2n1] | 4-(cyclopentyloxy)-N-(2-methoxy-4-(1H-pyrazol-1-yl)phenyl)-5-(2-methylbenzo[d]oxazol-6-yl)-7H-pyrrolo[2,3-d]pyrimidin-2-amine |
| 229 | 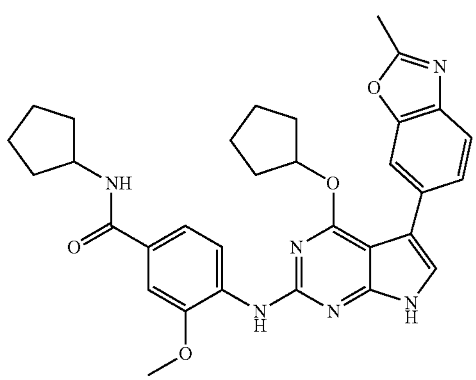 [SMILES: COc1cc(C(=O)NC2CCCC2)ccc1Nc1nc(OC2CCCC2)c2c(-c3ccc4nc(C)oc4c3)c[nH]c2n1] | N-cyclopentyl-4-(4-(cyclopentyloxy)-5-(2-methylbenzo[d]oxazol-6-yl)-7H-pyrrolo[2,3-d]pyrimidin-2-ylamino)-3-methoxybenzamide |
| 230 | 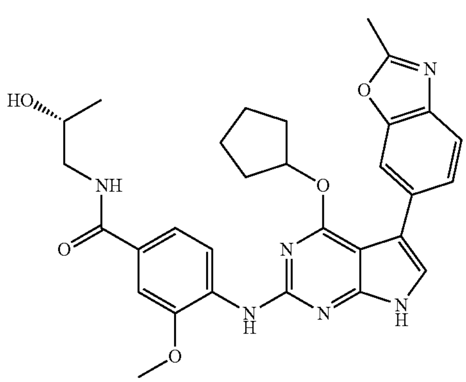 [SMILES: COc1cc(C(=O)NC[C@@H](C)O)ccc1Nc1nc(OC2CCCC2)c2c(-c3ccc4nc(C)oc4c3)c[nH]c2n1] | (R)-4-(4-(cyclopentyloxy)-5-(2-methylbenzo[d]oxazol-6-yl)-7H-pyrrolo[2,3-d]pyrimidin-2-ylamino)-N-(2-hydroxypropyl)-3-methoxybenzamide |

TABLE A-continued

| Cmpd No. | Structure | Name |
|---|---|---|
| 231 | 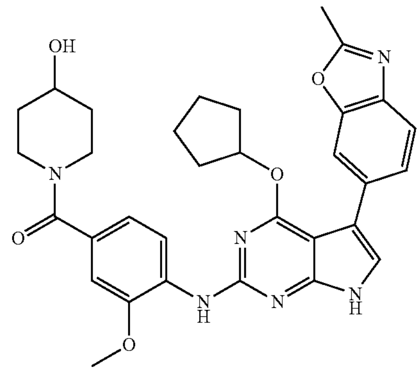 [SMILES: COc1cc(C(=O)N2CCC(O)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4-hydroxypiperidin-1-yl)methanone |
| 232 | 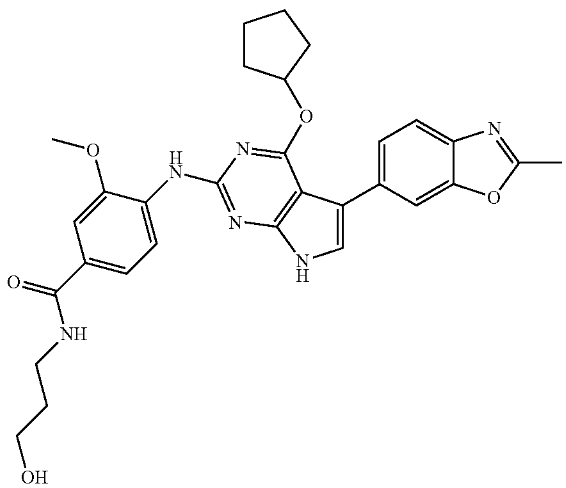 [SMILES: COc1cc(C(=O)NCCCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(3-hydroxypropyl)-3-methoxybenzamide |
| 233 | 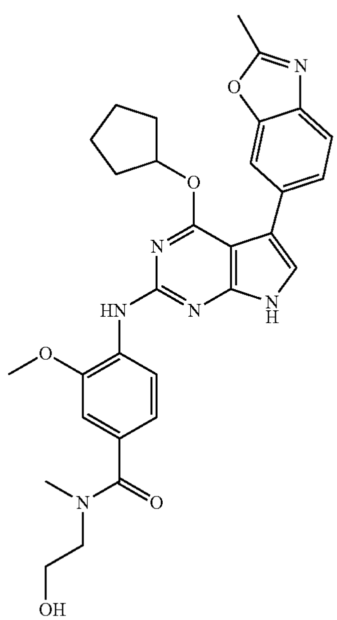 [SMILES: COc1cc(C(=O)N(C)CCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(2-hydroxyethyl)-3-methoxy-N-methylbenzamide |

TABLE A-continued
| Cmpd No. | Structure | Name |
|---|---|---|
| 234 | 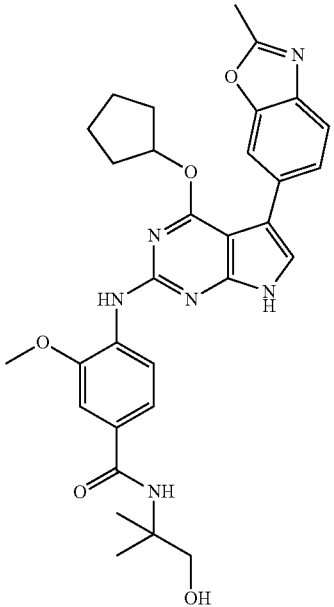 [SMILES: COc1cc(C(=O)NC(C)(C)CO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(1-hydroxy-2-methylpropan-2-yl)-3-methoxybenzamide |
| 235 | 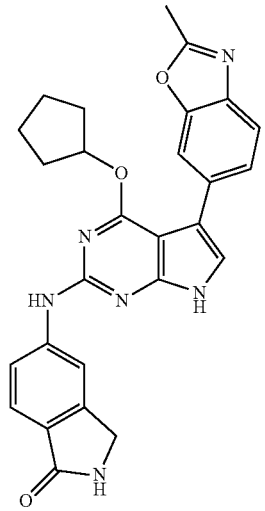 [SMILES: Cc1nc2ccc(-c3c[nH]c4nc(Nc5ccc6c(c5)CNC6=O)nc(OC5CCCC5)c34)cc2o1] | 5-(4-(cyclopentyloxy)-5-(2-methylbenzo[d]oxazol-6-yl)-7H-pyrrolo[2,3-d]pyrimidin-2-ylamino)isoindolin-1-one |

TABLE A-continued

| Cmpd No. | Structure | Name |
|---|---|---|
| 236 | 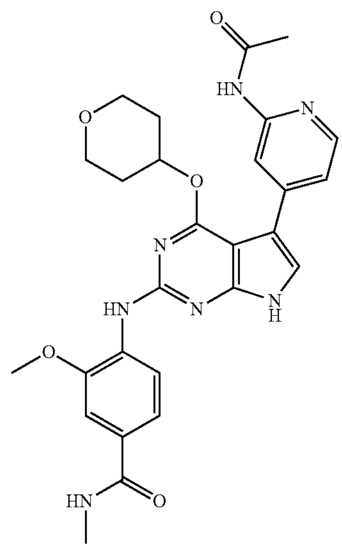 [SMILES: CNC(=O)c1ccc(Nc2nc(OC3CCOCC3)c3c(-c4ccnc(NC(C)=O)c4)c[nH]c3n2)c(OC)c1] | 4-(5-(2-acetamidopyridin-4-yl)-4-(tetrahydro-2H-pyran-4-yloxy)-7H-pyrrolo[2,3-d]pyrimidin-2-ylamino)-3-methoxy-N-methylbenzamide |
| 237 | 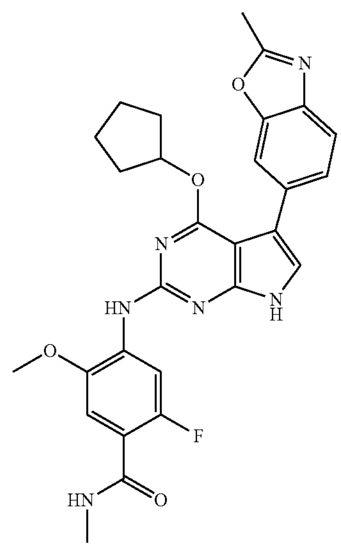 [SMILES: CNC(=O)c1cc(OC)c(Nc2nc(OC3CCCC3)c3c(-c4ccc5nc(C)oc5c4)c[nH]c3n2)cc1F] | 4-(4-(cyclopentyloxy)-5-(2-methylbenzo[d]oxazol-6-yl)-7H-pyrrolo[2,3-d]pyrimidin-2-ylamino)-2-fluoro-5-methoxy-N-methylbenzamide |
| 238 | 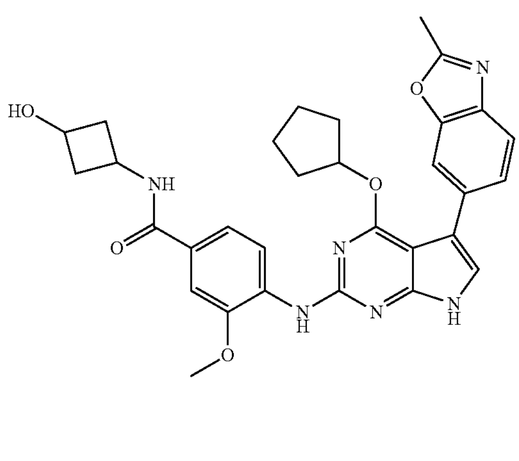 [SMILES: COc1cc(C(=O)NC2CC(O)C2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1s,3s)-3-hydroxycyclobutyl)-3-methoxybenzamide |

| Cmpd No. | Structure | Name |
|---|---|---|
| 239 | 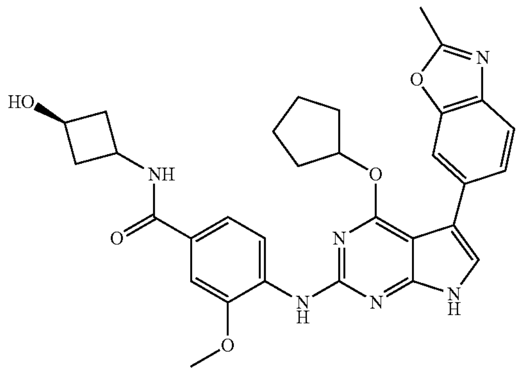 | 4-(4-(cyclopentyloxy)-5-(2-methylbenzo[d]oxazol-6-yl)-7H-pyrrolo[2,3-d]pyrimidin-2-ylamino)-N-((1r,3r)-3-hydroxycyclobutyl)-3-methoxybenzamide |
| 240 | 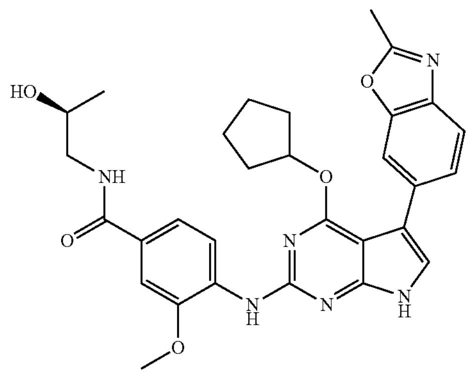 [SMILES: COc1cc(C(=O)NC[C@H](C)O)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-N-(2-hydroxypropyl)-3-methoxybenzamide |
| 241 | 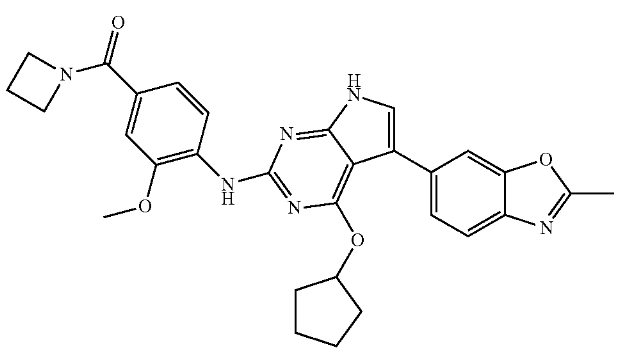 [SMILES: COc1cc(C(=O)N2CCC2)ccc1Nc1nc(OC2CCCC2)c2c(-c3ccc4nc(C)oc4c3)c[nH]c2n1] | azetidin-1-yl(4-(4-(cyclopentyloxy)-5-(2-methylbenzo[d]oxazol-6-yl)-7H-pyrrolo[2,3-d]pyrimidin-2-ylamino)-3-methoxyphenyl)methanone |
| 242 | 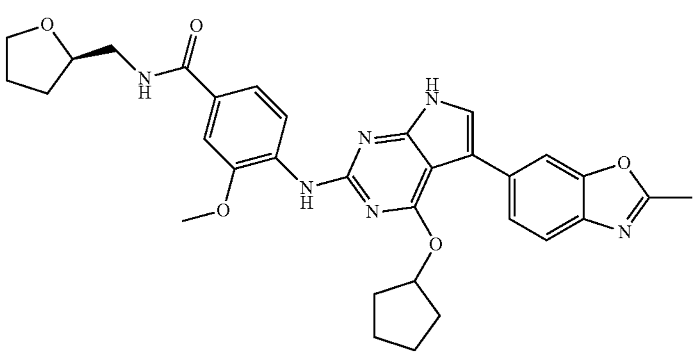 [SMILES: COc1cc(C(=O)NC[C@H]2CCCO2)ccc1Nc1nc(OC2CCCC2)c2c(-c3ccc4nc(C)oc4c3)c[nH]c2n1] | (R)-4-(4-(cyclopentyloxy)-5-(2-methylbenzo[d]oxazol-6-yl)-7H-pyrrolo[2,3-d]pyrimidin-2-ylamino)-3-methoxy-N-((tetrahydrofuran-2-yl)methyl)benzamide |

TABLE A-continued

| Cmpd No. | Structure | Name |
|---|---|---|
| 243 | 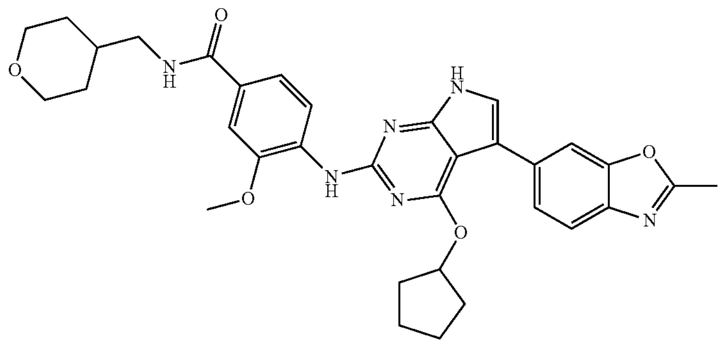 [SMILES: COc1cc(C(=O)NCC2CCOCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-((tetrahydro-2H-pyran-4-yl)methyl)benzamide |
| 244 | 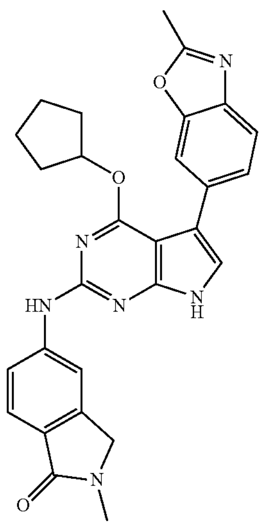 [SMILES: Cc1nc2ccc(-c3c[nH]c4nc(Nc5ccc6c(c5)CN(C)C6=O)nc(OC5CCCC5)c34)cc2o1] | 5-(4-(cyclopentyloxy)-5-(2-methylbenzo[d]oxazol-6-yl)-7H-pyrrolo[2,3-d]pyrimidin-2-ylamino)-2-methylisoindolin-1-one |
| 245 | 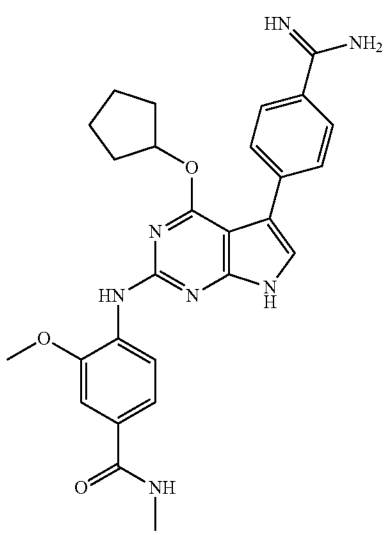 [SMILES: CNC(=O)c1ccc(Nc2nc(OC3CCCC3)c3c(-c4ccc(C(=N)N)cc4)c[nH]c3n2)c(OC)c1] | 4-(5-(4-carbamimidoylphenyl)-4-(cyclopentyloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 246 | 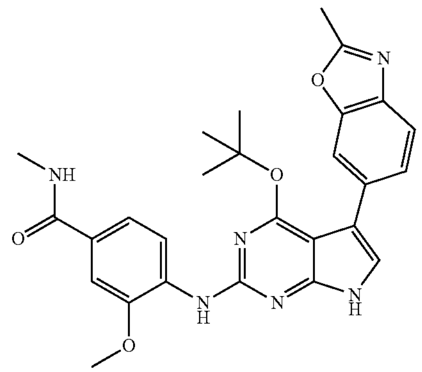 [SMILES: CNC(=O)c1ccc(Nc2nc(OC(C)(C)C)c3c(-c4ccc5nc(C)oc5c4)c[nH]c3n2)c(OC)c1] | 4-(4-tert-butoxy-5-(2-methylbenzo[d]oxazol-6-yl)-7H-pyrrolo[2,3-d]pyrimidin-2-ylamino)-3-methoxy-N-methylbenzamide |
| 247 | 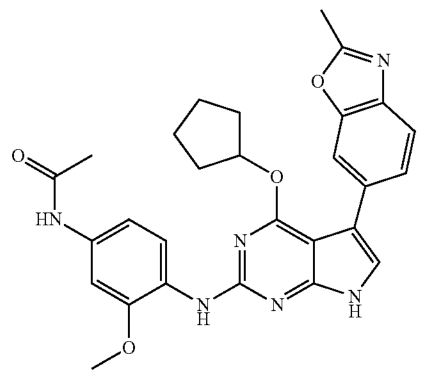 [SMILES: COc1cc(NC(C)=O)ccc1Nc1nc(OC2CCCC2)c2c(-c3ccc4nc(C)oc4c3)c[nH]c2n1] | N-(4-(4-(cyclopentyloxy)-5-(2-methylbenzo[d]oxazol-6-yl)-7H-pyrrolo[2,3-d]pyrimidin-2-ylamino)-3-methoxyphenyl)acetamide |
| 248 | 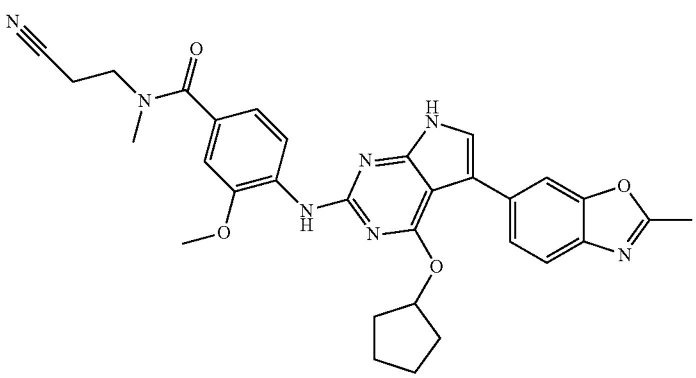 [SMILES: COc1cc(C(=O)N(C)CCC#N)ccc1Nc1nc(OC2CCCC2)c2c(-c3ccc4nc(C)oc4c3)c[nH]c2n1] | N-(2-cyanoethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide |
| 249 | 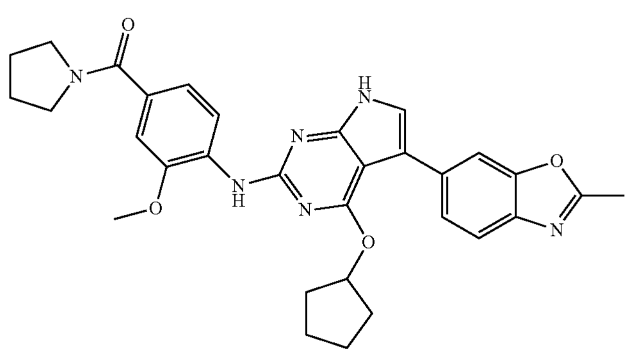 [SMILES: COc1cc(C(=O)N2CCCC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(pyrrolidin-1-yl)methanone |

| Cmpd No. | Structure | Name |
|---|---|---|
| 250 | 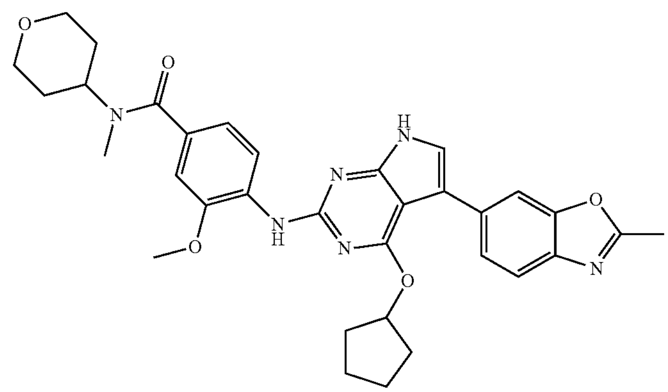 [SMILES: COc1cc(C(=O)N(C)C2CCOCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-methyl-N-(tetrahydro-2H-pyran-4-yl)benzamide |
| 251 | 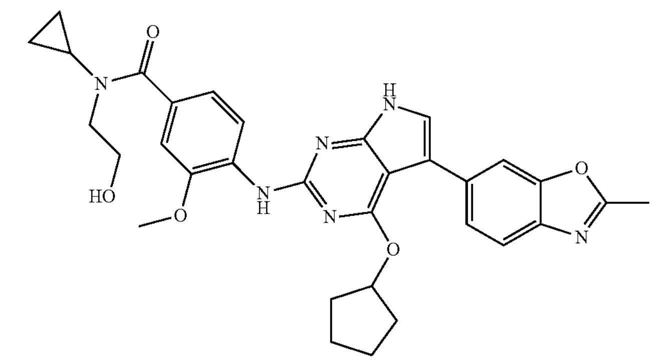 [SMILES: COc1cc(C(=O)N(CCO)C2CC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-cyclopropyl-N-(2-hydroxyethyl)-3-methoxybenzamide |
| 252 | 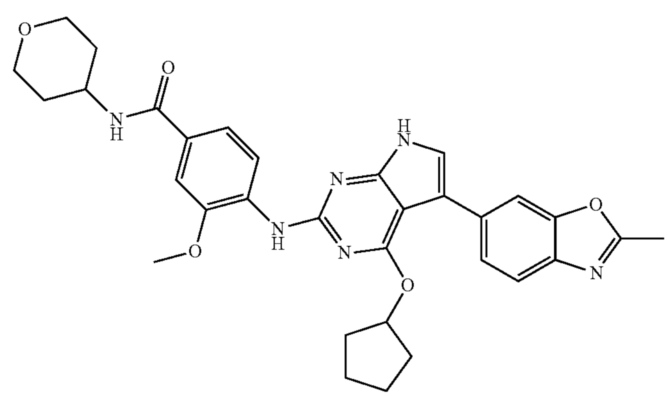 [SMILES: COc1cc(C(=O)NC2CCOCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-4-yl)benzamide |
| 253 | 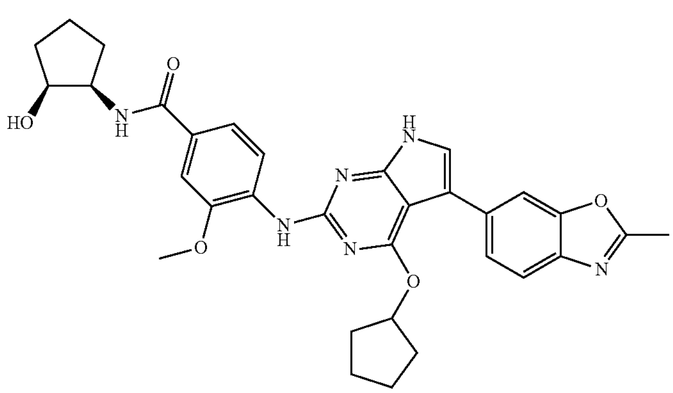 [SMILES: COc1cc(C(=O)N[C@@H]2CCC[C@@H]2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1R,2S)-2-hydroxycyclopentyl)-3-methoxybenzamide |

TABLE A-continued

| Cmpd No. | Structure | Name |
|---|---|---|
| 254 | 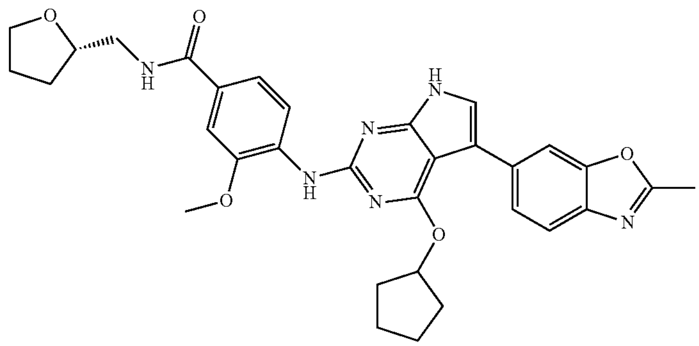 [SMILES: COc1cc(C(=O)NC[C@@H]2CCCO2)ccc1Nc1nc(OC2CCCC2)c2c(-c3ccc4nc(C)oc4c3)c[nH]c2n1] | (S)-4-(4-(cyclopentyloxy)-5-(2-methylbenzo[d]oxazol-6-yl)-7H-pyrrolo[2,3-d]pyrimidin-2-ylamino)-3-methoxy-N-((tetrahydrofuran-2-yl)methyl)benzamide |
| 255 | 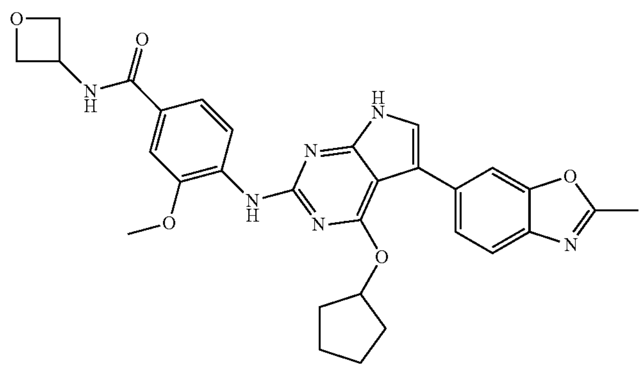 | 4-(4-(cyclopentyloxy)-5-(2-methylbenzo[d]oxazol-6-yl)-7H-pyrrolo[2,3-d]pyrimidin-2-ylamino)-3-methoxy-N-(oxetan-3-yl)benzamide |
| 256 | 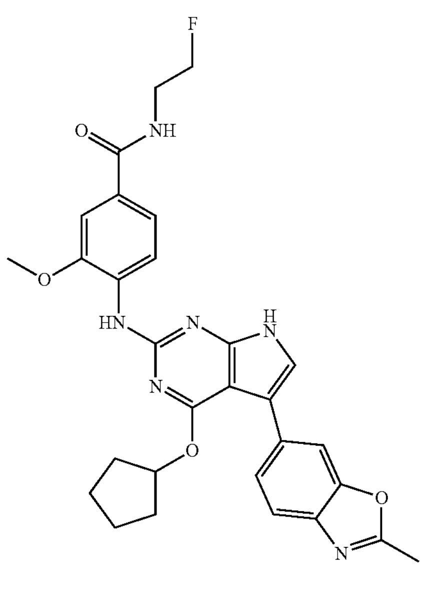 | 4-(4-(cyclopentyloxy)-5-(2-methylbenzo[d]oxazol-6-yl)-7H-pyrrolo[2,3-d]pyrimidin-2-ylamino)-N-(2-fluoroethyl)-3-methoxybenzamide |

TABLE A-continued

| Cmpd No. | Structure | Name |
|---|---|---|
| 257 | 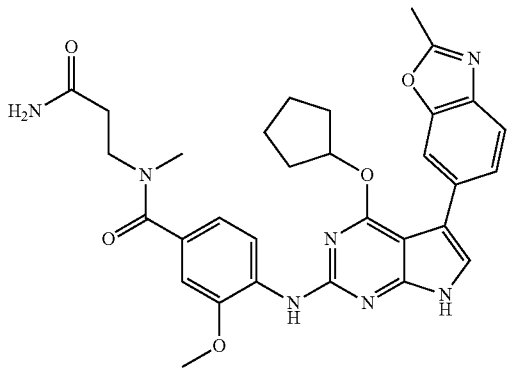 [SMILES: COc1cc(C(=O)N(C)CCC(N)=O)ccc1Nc1nc(OC2CCCC2)c2c(-c3ccc4nc(C)oc4c3)c[nH]c2n1] | N-(3-amino-3-oxopropyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide |
| 258 | 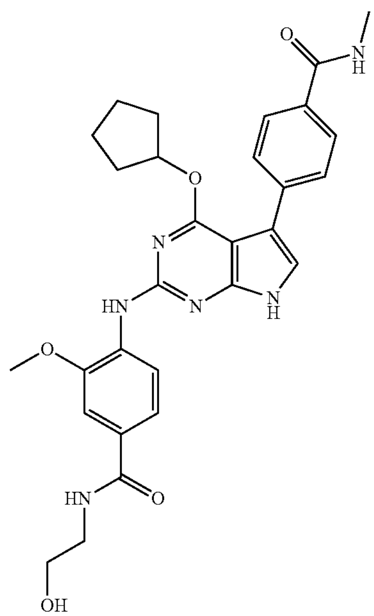 | 4-(4-(cyclopentyloxy)-5-(4-(methylcarbamoyl)phenyl)-7H-pyrrolo[2,3-d]pyrimidin-2-ylamino)-N-(2-hydroxyethyl)-3-methoxybenzamide |
| 259 | 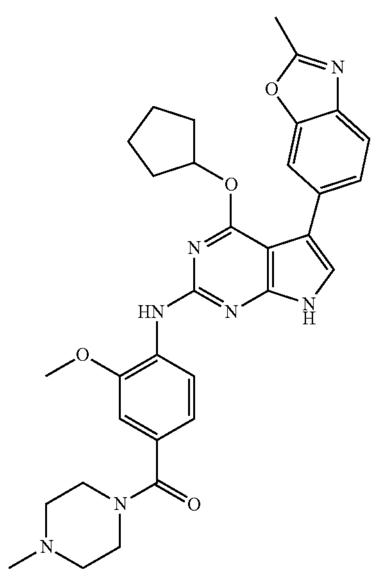 [SMILES: COc1cc(C(=O)N2CCN(C)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4-methylpiperazin-1-yl)methanone |

TABLE A-continued

| Cmpd No. | Structure | Name |
|---|---|---|
| 260 | 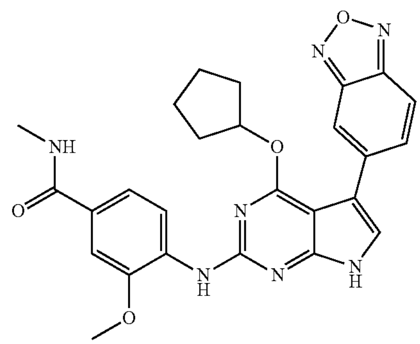 [SMILES: CNC(=O)c1ccc(Nc2nc(OC3CCCC3)c3c(-c4ccc5nonc5c4)c[nH]c3n2)c(OC)c1] | 4-(5-(benzo[c][1,2,5]oxadiazol-5-yl)-4-(cyclopentyloxy)-7H-pyrrolo[2,3-d]pyrimidin-2-ylamino)-3-methoxy-N-methylbenzamide |
| 261 | 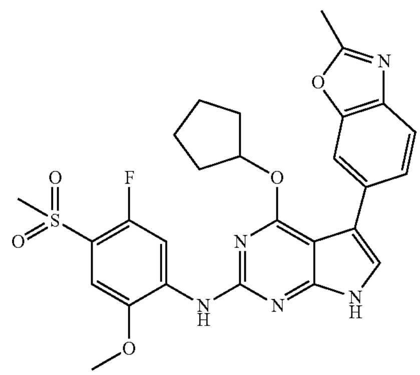 [SMILES: COc1cc(S(C)(=O)=O)c(F)cc1Nc1nc(OC2CCCC2)c2c(-c3ccc4nc(C)oc4c3)c[nH]c2n1] | 4-(cyclopentyloxy)-N-(5-fluoro-2-methoxy-4-(methylsulfonyl)phenyl)-5-(2-methylbenzo[d]oxazol-6-yl)-7H-pyrrolo[2,3-d]pyrimidin-2-amine |
| 262 | 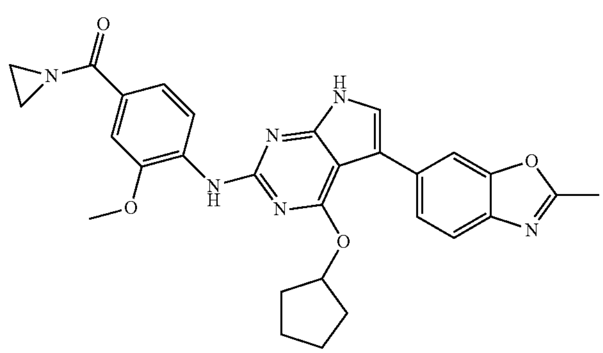 [SMILES: COc1cc(C(=O)N2CC2)ccc1Nc1nc(OC2CCCC2)c2c(-c3ccc4nc(C)oc4c3)c[nH]c2n1] | aziridin-1-yl(4-(4-(cyclopentyloxy)-5-(2-methylbenzo[d]oxazol-6-yl)-7H-pyrrolo[2,3-d]pyrimidin-2-ylamino)-3-methoxyphenyl)methanone |
| 263 | 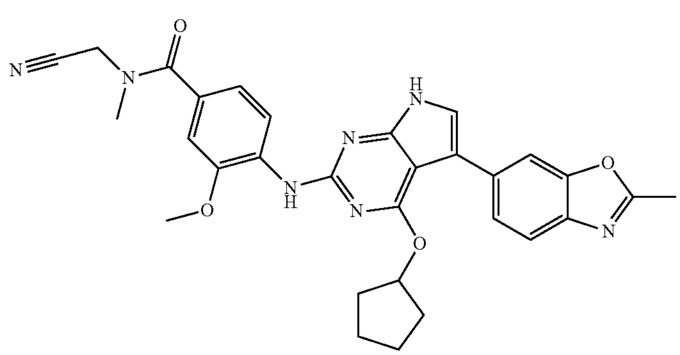 [SMILES: COc1cc(C(=O)N(C)CC#N)ccc1Nc1nc(OC2CCCC2)c2c(-c3ccc4nc(C)oc4c3)c[nH]c2n1] | N-(cyanomethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 264 | 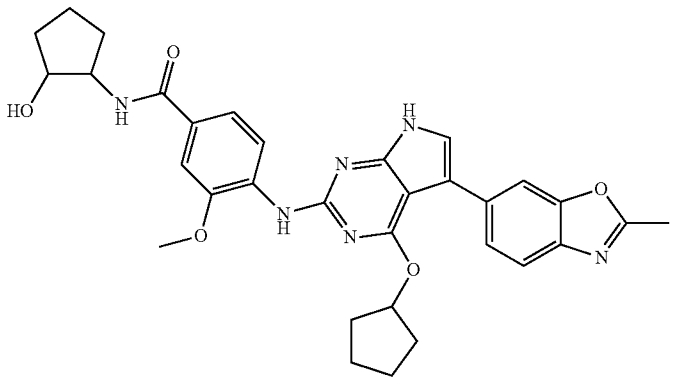 [SMILES: COc1cc(C(=O)NC2CCCC2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1S,2R)-2-hydroxycyclopentyl)-3-methoxybenzamide |
| 265 | 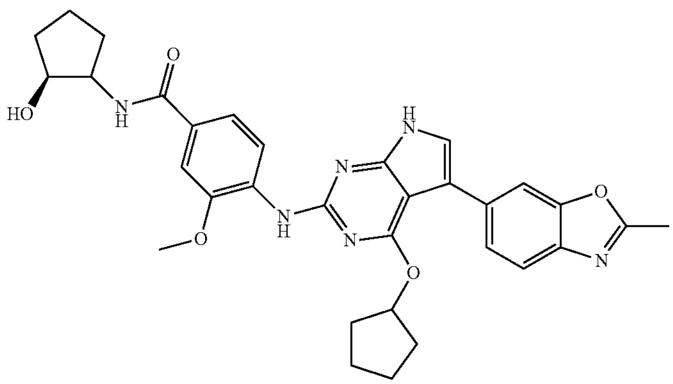 [SMILES: COc1cc(C(=O)NC2CCC[C@@H]2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1S,2S)-2-hydroxycyclopentyl)-3-methoxybenzamide |
| 266 | 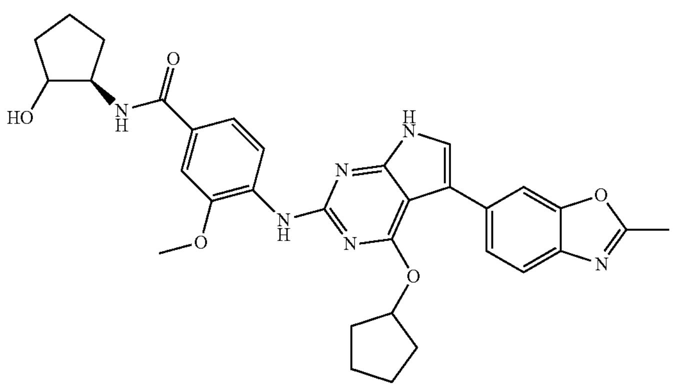 [SMILES: COc1cc(C(=O)N[C@@H]2CCCC2O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-((1R,2R)-2-hydroxycyclopentyl)-3-methoxybenzamide |
| 267 | 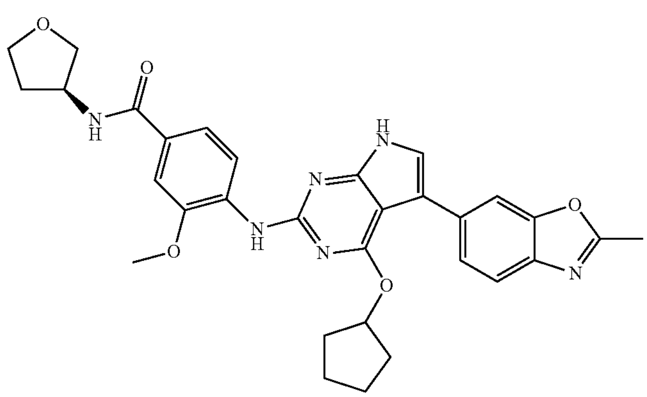 [SMILES: COc1cc(C(=O)N[C@H]2CCOC2)ccc1Nc1nc(OC2CCCC2)c2c(-c3ccc4nc(C)oc4c3)c[nH]c2n1] | (S)-4-(4-(cyclopentyloxy)-5-(2-methoxybenzo[d]oxazol-6-yl)-7H-pyrrolo[2,3-d]pyrimidin-2-ylamino)-3-methoxy-N-(tetrahydrofuran-3-yl)benzamide |

TABLE A-continued

| Cmpd No. | Structure | Name |
|---|---|---|
| 268 | 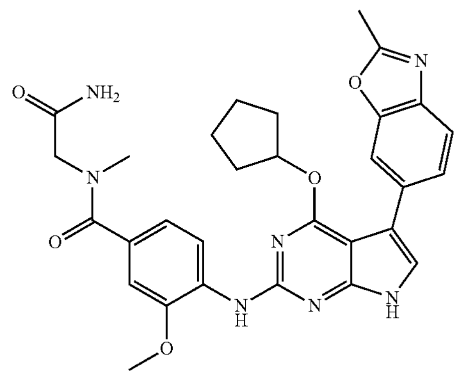 [SMILES: COc1cc(C(=O)N(C)CC(N)=O)ccc1Nc1nc(OC2CCCC2)c2c(-c3ccc4nc(C)oc4c3)c[nH]c2n1] | N-(2-amino-2-oxoethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide |
| 269 | 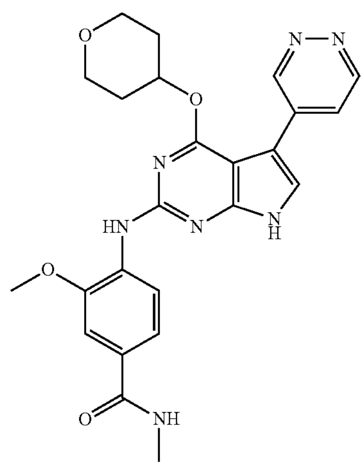 [SMILES: CNC(=O)c1ccc(Nc2nc(OC3CCOCC3)c3c(-c4ccnnc4)c[nH]c3n2)c(OC)c1] | 3-methoxy-N-methyl-4-(5-(pyridazin-4-yl)-4-(tetrahydro-2H-pyran-4-yloxy)-7H-pyrrolo[2,3-d]pyrimidin-2-ylamino)benzamide |
| 270 | 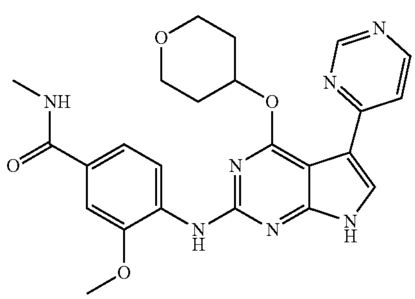 [SMILES: CNC(=O)c1ccc(Nc2nc(OC3CCOCC3)c3c(-c4ccncn4)c[nH]c3n2)c(OC)c1] | 3-methoxy-N-methyl-4-(5-(pyrimidin-4-yl)-4-(tetrahydro-2H-pyran-4-yloxy)-7H-pyrrolo[2,3-d]pyrimidin-2-ylamino)benzamide |
| 271 | 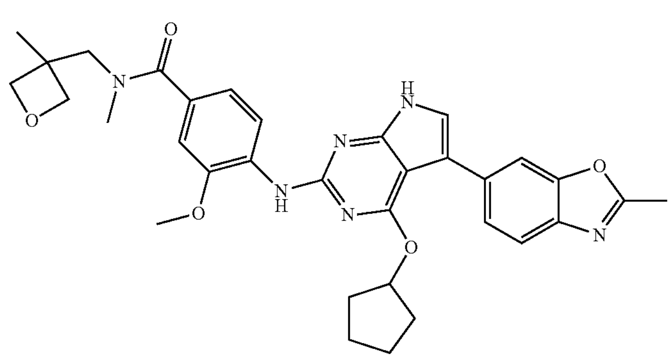 [SMILES: COc1cc(C(=O)N(C)CC2(C)COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-methyl-N-((3-methyloxetan-3-yl)methyl)benzamide |

TABLE A-continued

| Cmpd No. | Structure | Name |
|---|---|---|
| 272 | 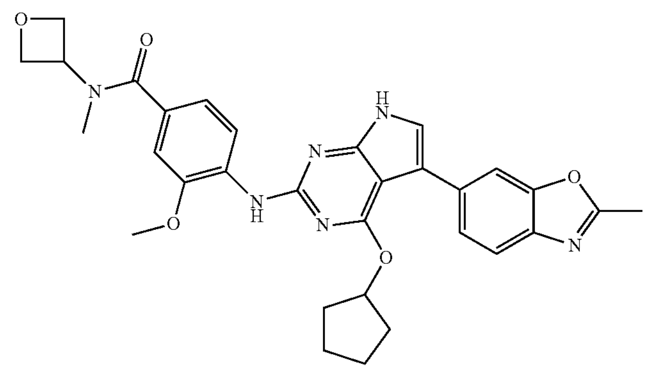 [SMILES: COc1cc(C(=O)N(C)C2COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-methyl-N-(oxetan-3-yl)benzamide |
| 273 | 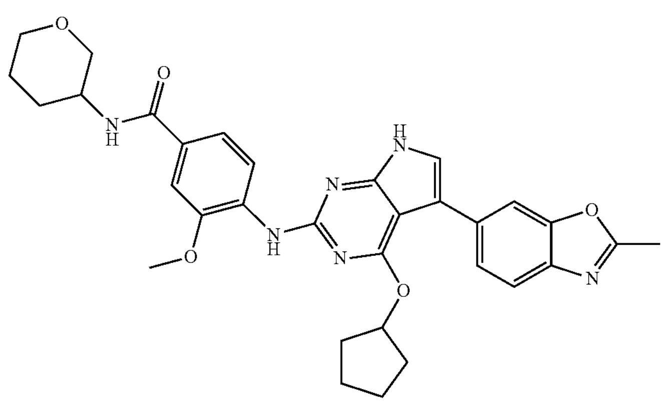 [SMILES: COc1cc(C(=O)NC2CCCOC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-3-yl)benzamide |
| 274 | 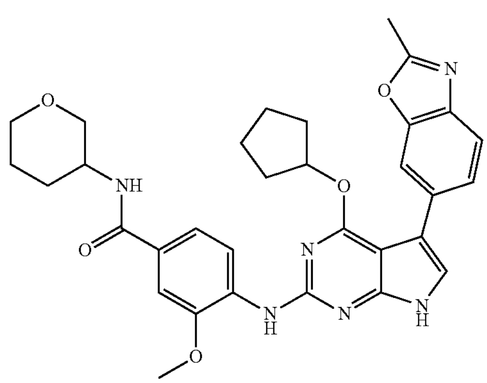 [SMILES: COc1cc(C(=O)NC2CCCOC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-3-yl)benzamide |

| Cmpd No. | Structure | Name |
|---|---|---|
| 275 | 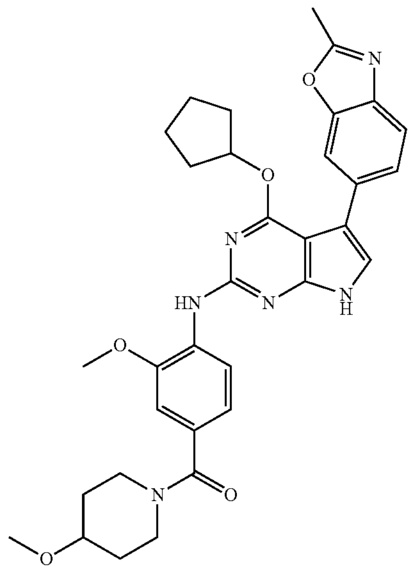 [SMILES: COc1cc(C(=O)N2CCC(OC)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4-methoxypiperidin-1-yl)methanone |
| 276 | 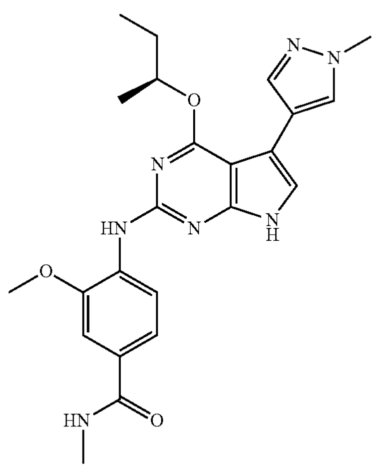 | (S)-4-(4-sec-butoxy-5-(1-methyl-1H-pyrazol-4-yl)-7H-pyrrolo[2,3-d]pyrimidin-2-ylamino)-3-methoxy-N-methylbenzamide |
| 277 | 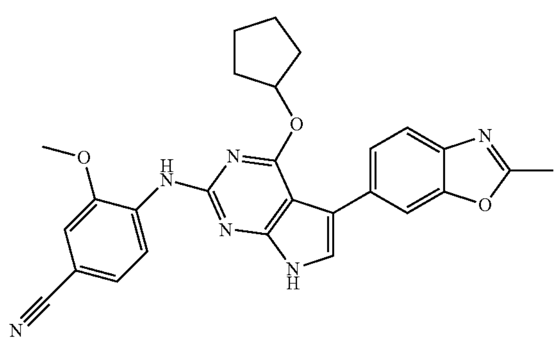 [SMILES: COc1cc(C#N)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxybenzonitrile |

TABLE A-continued

| Cmpd No. | Structure | Name |
|---|---|---|
| 278 | 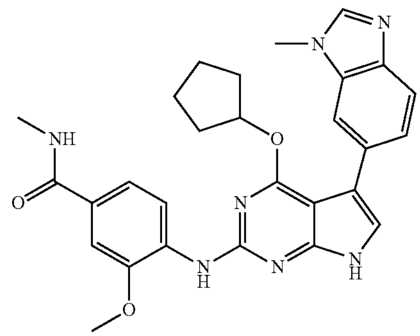 [SMILES: CNC(=O)c1ccc(Nc2nc(OC3CCCC3)c3c(-c4ccc5ncn(C)c5c4)c[nH]c3n2)c(OC)c1] | 4-(4-(cyclopentyloxy)-5-(1-methyl-1H-indazol-6-yl)-7H-pyrrolo[2,3-d]pyrimidin-2-ylamino)-3-methoxy-N-methylbenzamide |
| 279 | 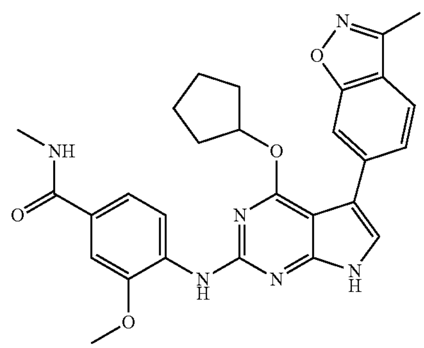 | 4-(4-(cyclopentyloxy)-5-(3-methylbenzo[d]isoxazol-6-yl)-7H-pyrrolo[2,3-d]pyrimidin-2-ylamino)-3-methoxy-N-methylbenzamide |
| 280 | 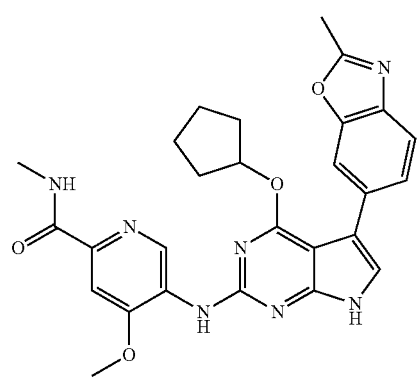 [SMILES: CNC(=O)c1cc(OC)c(Nc2nc(OC3CCCC3)c3c(-c4ccc5nc(C)oc5c4)c[nH]c3n2)cn1] | 5-(4-(cyclopentyloxy)-5-(2-methylbenzo[d]oxazol-6-yl)-7H-pyrrolo[2,3-d]pyrimidin-2-ylamino)-4-methoxy-N-methylpicolinamide |

TABLE A-continued

| Cmpd No. | Structure | Name |
|---|---|---|
| 281 | 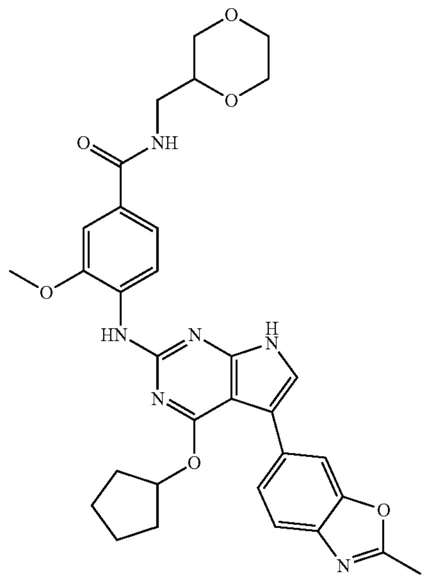 | N-((1,4-dioxan-2-yl)methyl)-4-(4-(cyclopentyloxy)-5-(2-methylbenzo[d]oxazol-6-yl)-7H-pyrrolo[2,3-d]pyrimidin-2-ylamino)-3-methoxybenzamide |
| 282 | 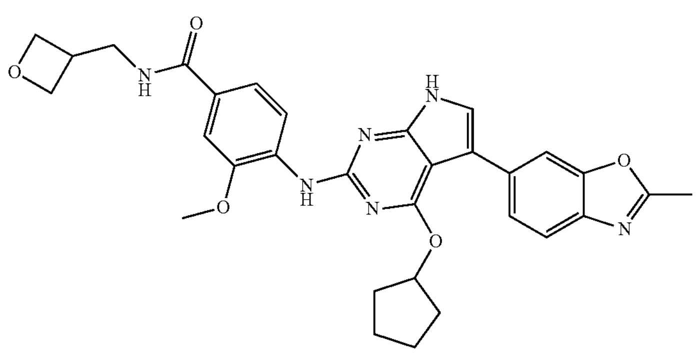 [SMILES: COc1cc(C(=O)NCC2COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(oxetan-3-ylmethyl)benzamide |
| 283 | 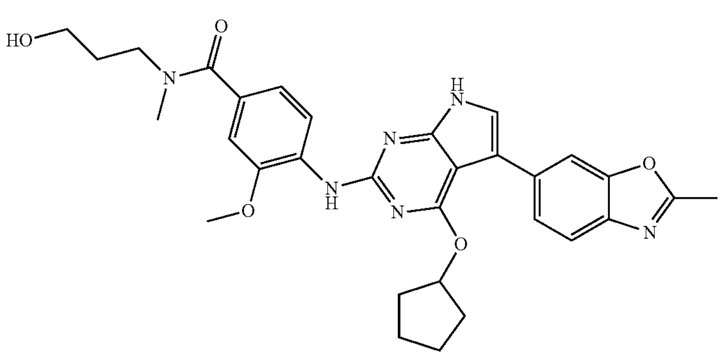 [SMILES: COc1cc(C(=O)N(C)CCCO)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(3-hydroxypropyl)-3-methoxy-N-methylbenzamide |

TABLE A-continued

| Cmpd No. | Structure | Name |
|---|---|---|
| 284 | 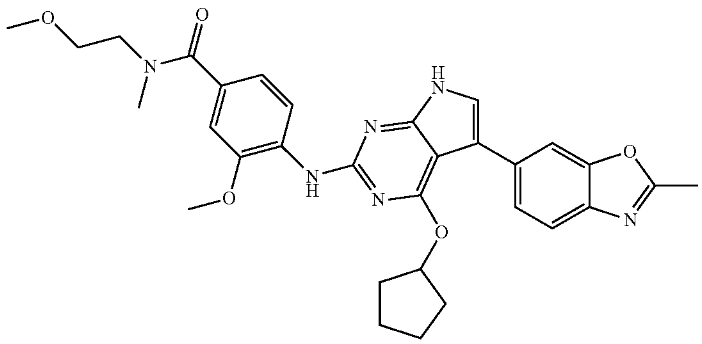 | 4-(4-(cyclopentyloxy)-5-(2-methylbenzo[d]oxazol-6-yl)-7H-pyrrolo[2,3-d]pyrimidin-2-ylamino)-3-methoxy-N-(2-methoxyethyl)-N-methylbenzamide |
| 285 | 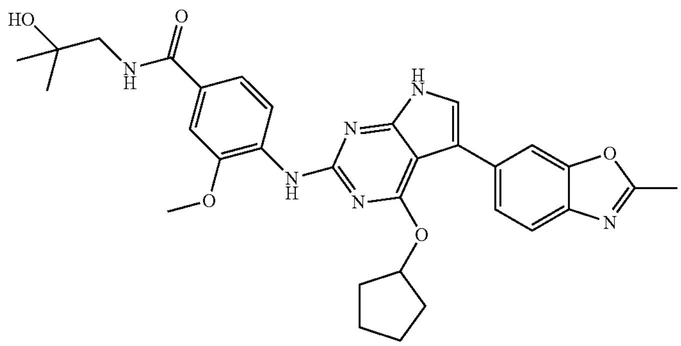 [SMILES: COc1cc(C(=O)NCC(C)(C)O)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-N-(2-hydroxy-2-methylpropyl)-3-methoxybenzamide |
| 286 | 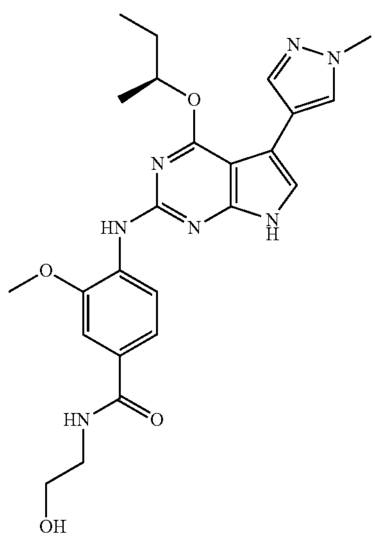 | (S)-4-(4-sec-butoxy-5-(1-methyl-1H-pyrazol-4-yl)-7H-pyrrolo[2,3-d]pyrimidin-2-ylamino)-N-(2-hydroxyethyl)-3-methoxybenzamide |
| 287 | 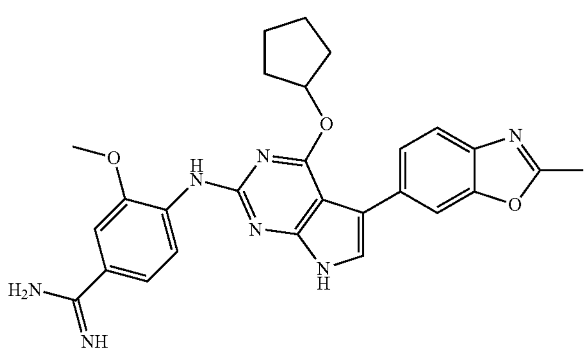 [SMILES: COc1cc(C(=N)N)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxybenzimidamide |

TABLE A-continued
| Cmpd No. | Structure | Name |
|---|---|---|
| 288 | 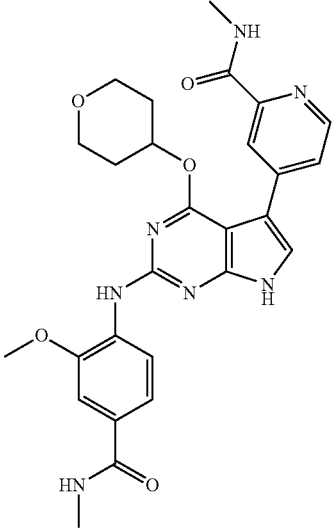 [SMILES: CNC(=O)c1ccc(Nc2nc(OC3CCOCC3)c3c(-c4ccnc(C(=O)NC)c4)c[nH]c3n2)c(OC)c1] | 4-(2-(2-methoxy-4-(methylcarbamoyl)phenylamino)-4-(tetrahydro-2H-pyran-4-yloxy)-7H-pyrrolo[2,3-d]pyrimidin-5-yl)-N-methylpicolinamide |
| 289 | 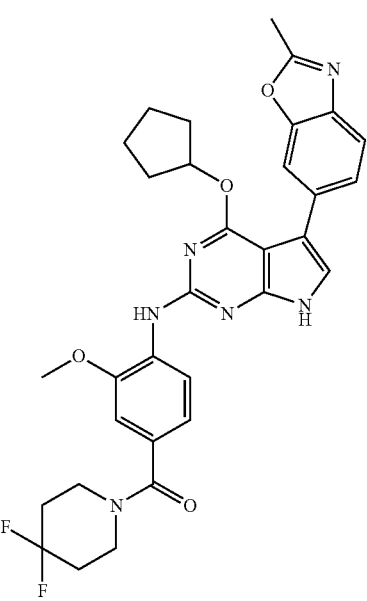 [SMILES: COc1cc(C(=O)N2CCC(F)(F)CC2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(4,4-difluoropiperidin-1-yl)methanone |

TABLE A-continued

| Cmpd No. | Structure | Name |
|---|---|---|
| 290 | 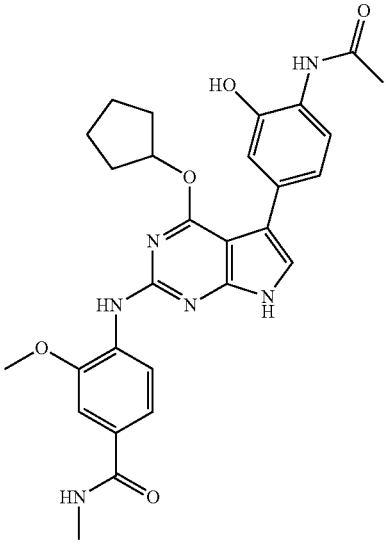 [SMILES: CNC(=O)c1ccc(Nc2nc(OC3CCCC3)c3c(-c4ccc(NC(C)=O)c(O)c4)c[nH]c3n2)c(OC)c1] | 4-(5-(4-acetamido-3-hydroxyphenyl)-4-(cyclopentyloxy)-7H-pyrrolo[2,3-d]pyrimidin-2-ylamino)-3-methoxy-N-methylbenzamide |
| 291 | 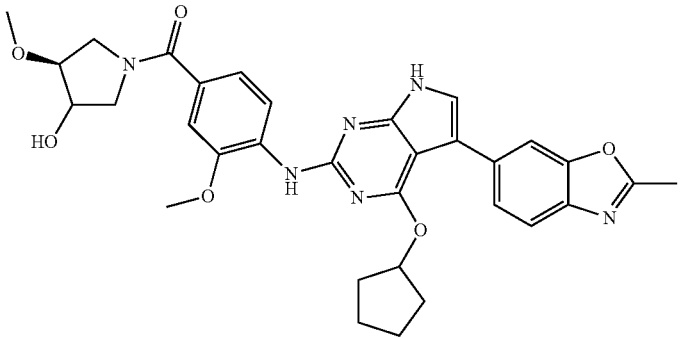 | (4-(4-(cyclopentyloxy)-5-(2-methylbenzo[d]oxazol-6-yl)-7H-pyrrolo[2,3-d]pyrimidin-2-ylamino)-3-methoxyphenyl)((3R,4R)-3-hydroxy-4-methoxypyrrolidin-1-yl)methanone |
| 292 | 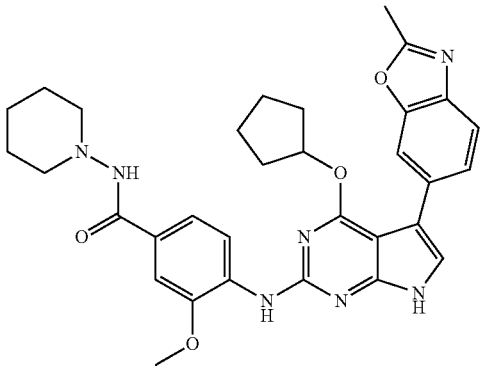 [SMILES: COc1cc(C(=O)NN2CCCCC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(piperidin-1-yl)benzamide |

| Cmpd No. | Structure | Name |
|---|---|---|
| 293 | 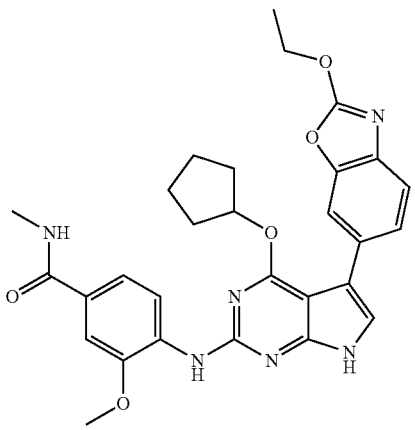 [SMILES: CCOc1nc2ccc(-c3c[nH]c4nc(Nc5ccc(C(=O)NC)cc5OC)nc(OC5CCCC5)c34)cc2o1] | 4-(4-(cyclopentyloxy)-5-(2-ethoxybenzo[d]oxazol-6-yl)-7H-pyrrolo[2,3-d]pyrimidin-2-ylamino)-3-methoxy-N-methylbenzamide |
| 294 | 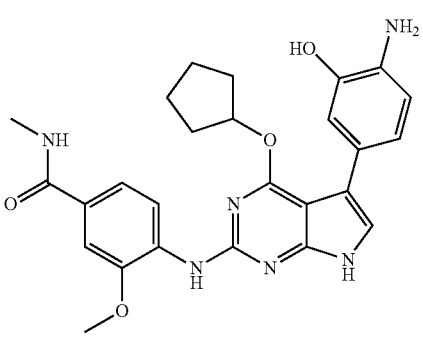 [SMILES: CNC(=O)c1ccc(Nc2nc(OC3CCCC3)c3c(-c4ccc(N)c(O)c4)c[nH]c3n2)c(OC)c1] | 4-(5-(4-amino-3-hydroxyphenyl)-4-(cyclopentyloxy)-7H-pyrrolo[2,3-d]pyrimidin-2-ylamino)-3-methoxy-N-methylbenzamide |
| 295 | 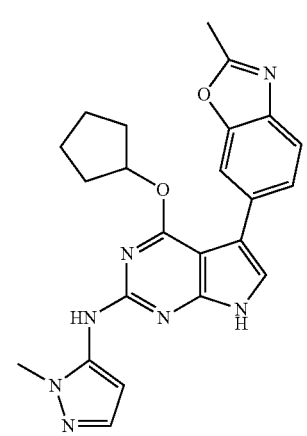 [SMILES: Cc1nc2ccc(-c3c[nH]c4nc(Nc5ccnn5C)nc(OC5CCCC5)c34)cc2o1] | 4-(cyclopentyloxy)-N-(1-methyl-1H-pyrazol-5-yl)-5-(2-methylbenzo[d]oxazol-6-yl)-7H-pyrrolo[2,3-d]pyrimidin-2-amine |

TABLE A-continued

| Cmpd No. | Structure | Name |
|---|---|---|
| 296 | 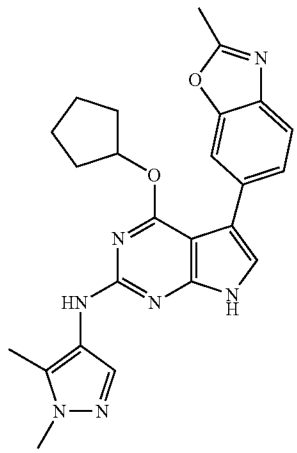 [SMILES: Cc1nc2ccc(-c3c[nH]c4nc(Nc5cnn(C)c5C)nc(OC5CCCC5)c34)cc2o1] | 4-(cyclopentyloxy)-N-(1,5-dimethyl-1H-pyrazol-4-yl)-5-(2-methylbenzo[d]oxazol-6-yl)-7H-pyrrolo[2,3-d]pyrimidin-2-amine |
| 297 | 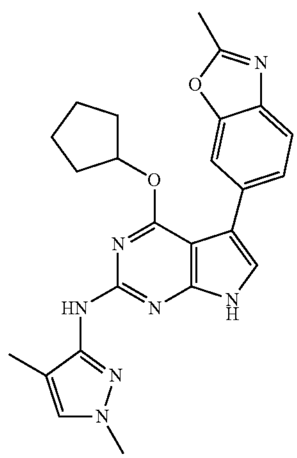 [SMILES: Cc1nc2ccc(-c3c[nH]c4nc(Nc5nn(C)cc5C)nc(OC5CCCC5)c34)cc2o1] | 4-(cyclopentyloxy)-N-(1,4-dimethyl-1H-pyrazol-3-yl)-5-(2-methylbenzo[d]oxazol-6-yl)-7H-pyrrolo[2,3-d]pyrimidin-2-amine |
| 298 | 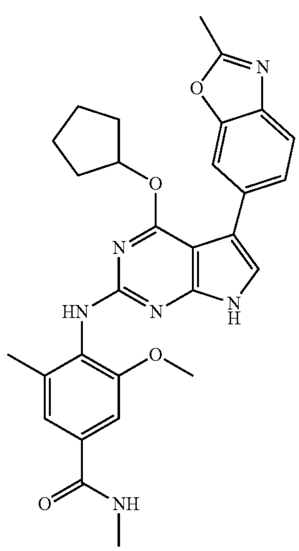 [SMILES: CNC(=O)c1cc(C)c(Nc2nc(OC3CCCC3)c3c(-c4ccc5nc(C)oc5c4)c[nH]c3n2)c(OC)c1] | 4-(4-(cyclopentyloxy)-5-(2-methylbenzo[d]oxazol-6-yl)-7H-pyrrolo[2,3-d]pyrimidin-2-ylamino)-3-methoxy-N,5-dimethylbenzamide |

TABLE A-continued

| Cmpd No. | Structure | Name |
|---|---|---|
| 299 | 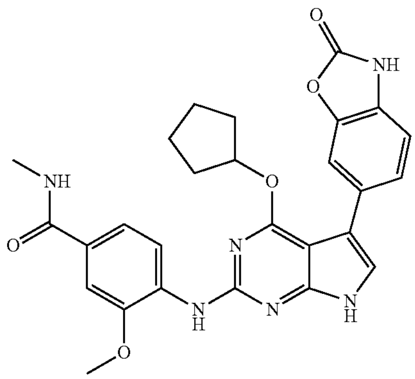 [SMILES: CNC(=O)c1ccc(Nc2nc(OC3CCCC3)c3c(-c4ccc5[nH]c(=O)oc5c4)c[nH]c3n2)c(OC)c1] | 4-(4-(cyclopentyloxy)-5-(2-oxo-2,3-dihydrobenzo[d]oxazol-6-yl)-7H-pyrrolo[2,3-d]pyrimidin-2-ylamino)-3-methoxy-N-methylbenzamide |
| 300 | 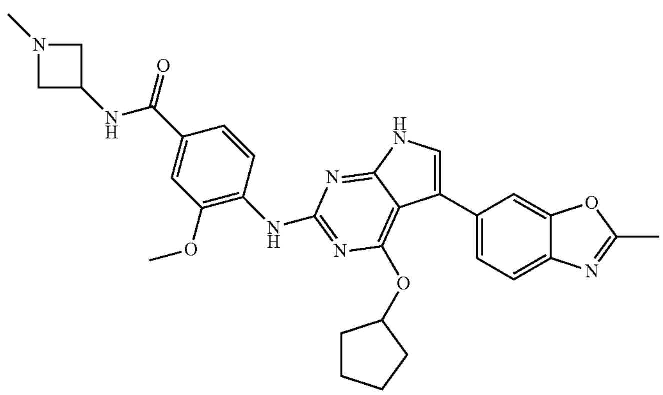 | 4-(4-(cyclopentyloxy)-5-(2-methylbenzo[d]oxazol-6-yl)-7H-pyrrolo[2,3-d]pyrimidin-2-ylamino)-3-methoxy-N-(1-methylazetidin-3-yl)benzamide |
| 301 | 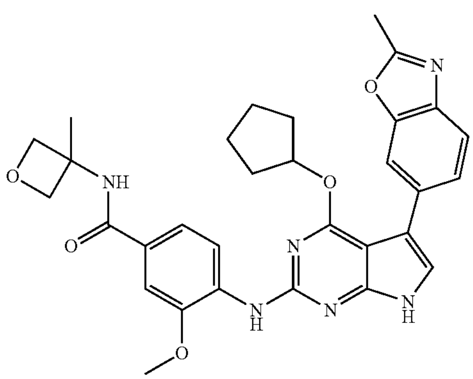 [SMILES: COc1cc(C(=O)NC2(C)COC2)ccc1Nc1nc(OC2CCCC2)c2c(-c3ccc4nc(C)oc4c3)c[nH]c2n1] | 4-(4-(cyclopentyloxy)-5-(2-methylbenzo[d]oxazol-6-yl)-7H-pyrrolo[2,3-d]pyrimidin-2-ylamino)-3-methoxy-N-(3-methyloxetan-3-yl)benzamide |
| 302 | 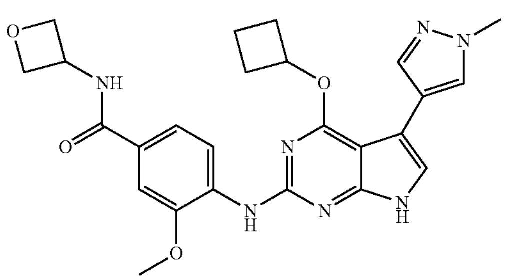 [SMILES: COc1cc(C(=O)NC2COC2)ccc1Nc1nc(OC2CCC2)c2c(-c3cnn(C)c3)c[nH]c2n1] | 4-(4-cyclobutoxy-5-(1-methyl-1H-pyrazol-4-yl)-7H-pyrrolo[2,3-d]pyrimidin-2-ylamino)-3-methoxy-N-(oxetan-3-yl)benzamide |

| Cmpd No. | Structure | Name |
|---|---|---|
| 303 | 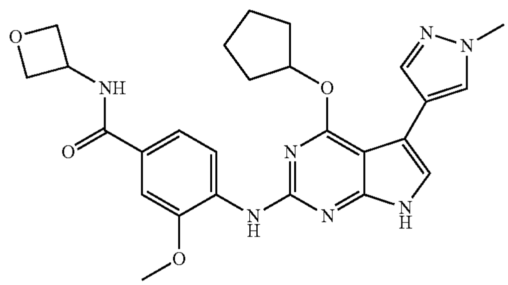 [SMILES: COc1cc(C(=O)NC2COC2)ccc1Nc1nc(OC2CCCC2)c2c(-c3cnn(C)c3)c[nH]c2n1] | 4-(4-(cyclopentyloxy)-5-(1-methyl-1H-yrazol-4-yl)7H-pyrrolo[2,3-d]pyrimidin-2-ylamino)-3-methoxy-N-(oxetan-3-yl)benzamide |
| 304 | 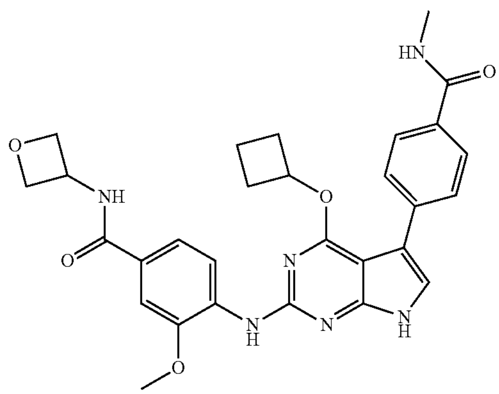 [SMILES: CNC(=O)c1ccc(-c2c[nH]c3nc(Nc4ccc(C(=O)NC5COC5)cc4OC)nc(OC4CCC4)c23)cc1] | 4-(4-cyclobutoxy-5-(4-(methylcarbamoyl)phenyl)-7H-pyrrolo[2,3-d]pyrimidin-2-ylamino)-3-methoxy-N-(oxetan-3-yl)benzamide |
| 305 | 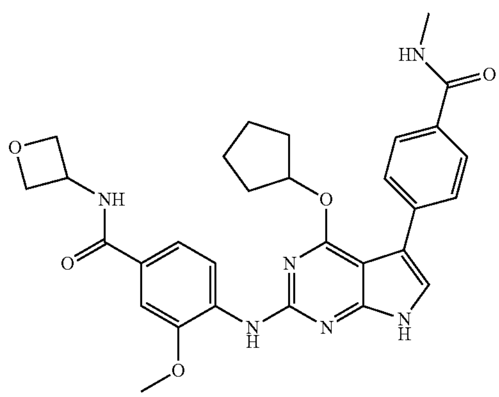 [SMILES: CNC(=O)c1ccc(-c2c[nH]c3nc(Nc4ccc(C(=O)NC5COC5)cc4OC)nc(OC4CCCC4)c23)cc1] | 4-(4-(cyclopentyloxy)-5-(4-(methylcarbamoyl)phenyl)-7H-pyrrolo[2,3-d]pyrimidin-2-ylamino)-3-methoxy-N-(oxetan-3-yl)benzamide |
| 306 | 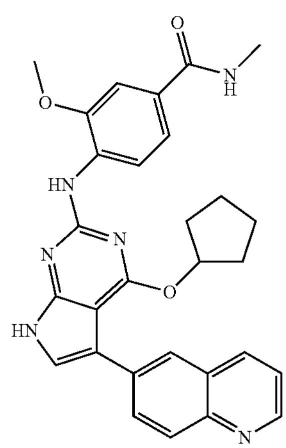 [SMILES: CNC(=O)c1ccc(Nc2nc(OC3CCCC3)c3c(-c4ccc5ncccc5c4)c[nH]c3n2)c(OC)c1] | 4-(4-(cyclopentyloxy)-5-(quinolin-6-yl)-7H-pyrrolo[2,3-d]pyrimidin-2-ylamino)-3-methoxy-N-methylbenzamide |

TABLE A-continued

| Cmpd No. | Structure | Name |
|---|---|---|
| 307 | 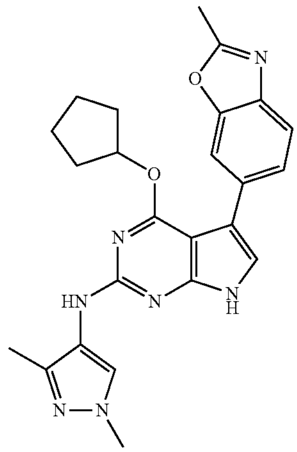 [SMILES: Cc1nc2ccc(-c3c[nH]c4nc(Nc5cn(C)nc5C)nc(OC5CCCC5)c34)cc2o1] | 4-(cyclopentyloxy)-N-(1,3-dimethyl-1H-pyrazol-4-yl)-5-(2-methylbenzo[d]oxazol-6-yl)-7H-pyrrolo[2,3-d]pyrimidin-2-amine |
| 308 | 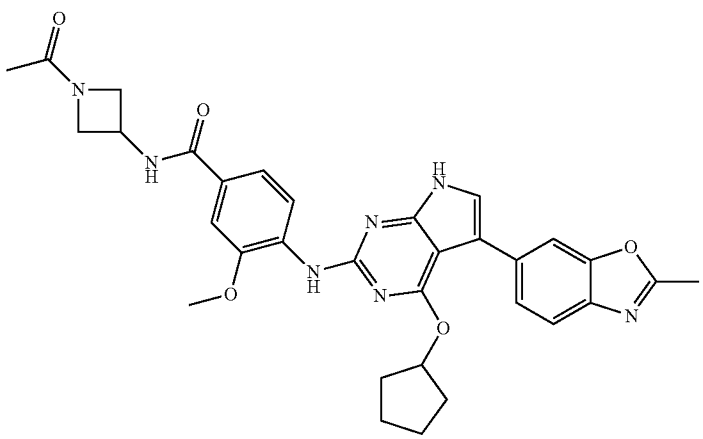 [SMILES: COc1cc(C(=O)NC2CN(C(C)=O)C2)ccc1Nc1nc(OC2CCCC2)c2c(-c3ccc4nc(C)oc4c3)c[nH]c2n1] | N-(1-acetylazetidin-3-yl)-4-(4-(cyclopentyloxy)-5-(2-methylbenzo[d]oxazol-6-yl)-7H-pyrrolo[2,3-d]pyrimidin-2-ylamino)-3-methoxybenzamide |
| 309 | 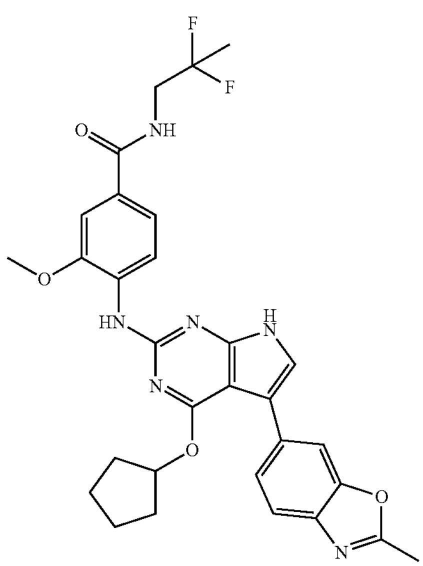 | 4-(4-(cyclopentyloxy)-5-(2-methylbenzo[d]oxazol-6-yl)-7H-pyrrolo[2,3-d]pyrimidin-2-ylamino)-N-(2,2-difluoropropyl)-3-methoxybenzamide |

TABLE A-continued

| Cmpd No. | Structure | Name |
|---|---|---|
| 310 | 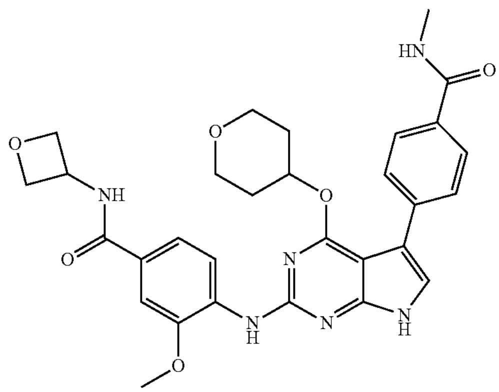 [SMILES: CNC(=O)c1ccc(-c2c[nH]c3nc(Nc4ccc(C(=O)NC5COC5)cc4OC)nc(OC4CCOCC4)c23)cc1] | 3-methoxy-4-(5-(4-(methylcarbamoyl)phenyl)-4-(tetrahydro-2H-pyran-4-yloxy)-7H-pyrrolo[2,3-d]pyrimidin-2-ylamino)-N-(oxetan-3-yl)benzamide |
| 311 | 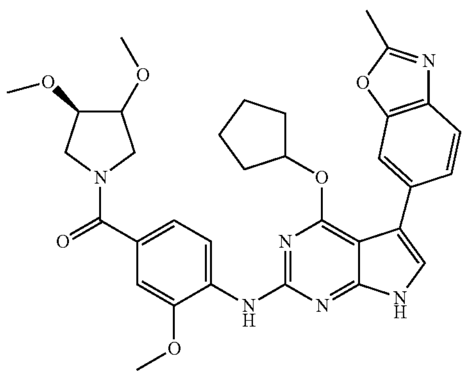 [SMILES: COc1cc(C(=O)N2CC(OC)[C@H](OC)C2)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)((3R,4R)-3,4-dimethoxypyrrolidin-1-yl)methanone |
| 312 | 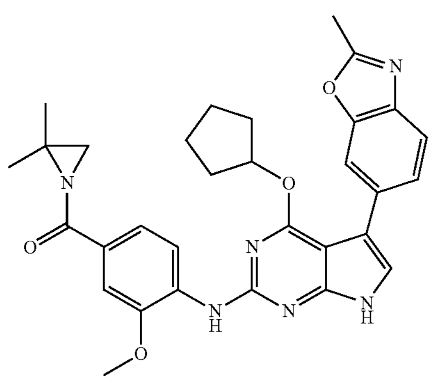 [SMILES: COc1cc(C(=O)N2CC2(C)C)ccc1Nc1nc(OC2CCCC2)c2c(-c3ccc4nc(C)oc4c3)c[nH]c2n1] | (4-(4-(cyclopentyloxy)-5-(2-methylbenzo[d]oxazol-6-yl)-7H-pyrrolo[2,3-d]pyrimidin-2-ylamino)-3-methoxyphenyl)(2,2-dimethylaziridin-1-yl)methanone |
| 313 | 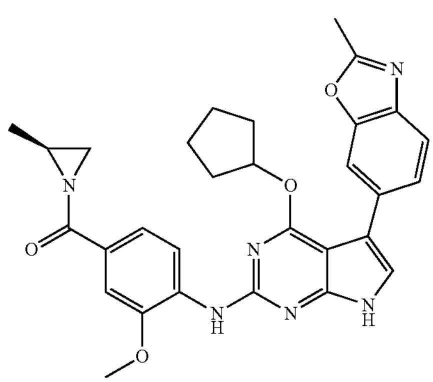 [SMILES: COc1cc(C(=O)N2C[C@@H]2C)ccc1Nc1nc(OC2CCCC2)c2c(-c3ccc4nc(C)oc4c3)c[nH]c2n1] | (S)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone |

| Cmpd No. | Structure | Name |
|---|---|---|
| 314 | 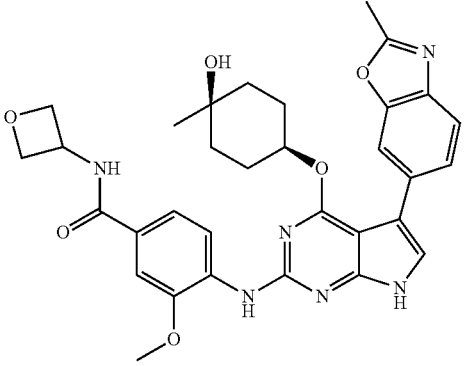 [SMILES: COc1cc(C(=O)NC2COC2)ccc1Nc1nc(O[C@H]2CC[C@@](C)(O)CC2)c2c(-c3ccc4nc(C)oc4c3)c[nH]c2n1] | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-(oxetan-3-yl)benzamide |
| 315 | 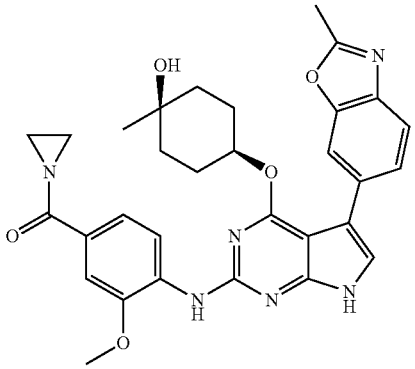 [SMILES: COc1cc(C(=O)N2CC2)ccc1Nc1nc(O[C@H]2CC[C@@](C)(O)CC2)c2c(-c3ccc4nc(C)oc4c3)c[nH]c2n1] | aziridin-1-yl(4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxyphenyl)methanone |
| 316 | 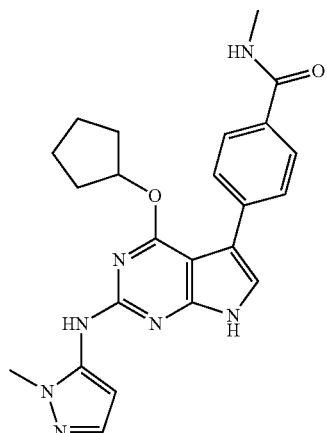 | 4-(4-(cyclopentyloxy)-2-(1-methyl-1H-pyrazol-5-ylamino)-7H-pyrrolo[2,3-d]pyrimidin-5-yl)-N-methylbenzamide |

TABLE A-continued

| Cmpd No. | Structure | Name |
|---|---|---|
| 317 | 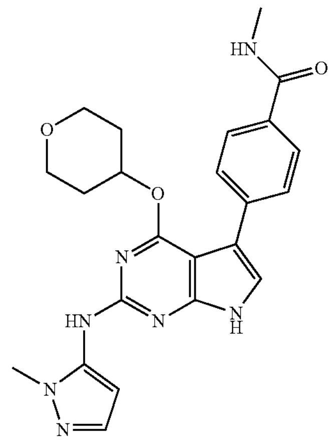 [SMILES: CNC(=O)c1ccc(-c2c[nH]c3nc(Nc4ccnn4C)nc(OC4CCOCC4)c23)cc1] | N-methyl-4-(2-(1-methyl-1H-pyrazol-5-ylamino)-4-(tetrahydro-2H-pyran-4-yloxy)-7H-pyrrolo[2,3-d]pyrimidin-5-yl)benzamide |
| 318 | 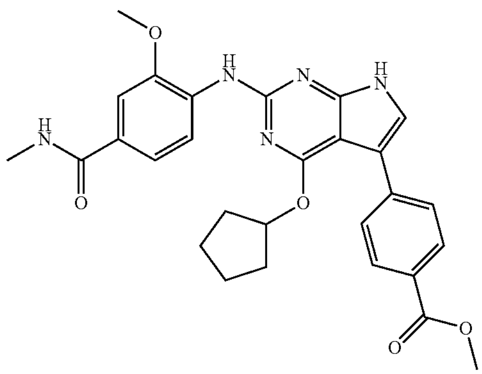 | methyl 4-(4-(cyclopentyloxy)-2-(2-methoxy-4-(methylcarbamoyl)phenylamino)-7H-pyrrolo[2,3-d]pyrimidin-5-yl)benzoate |
| 319 | 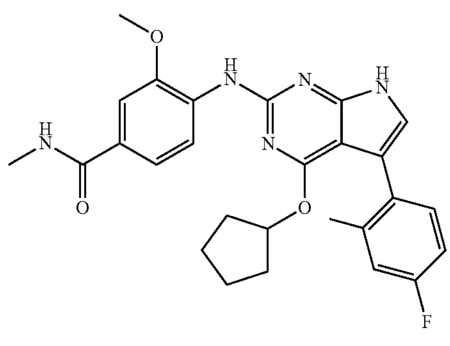 [SMILES: CNC(=O)c1ccc(Nc2nc(OC3CCCC3)c3c(-c4ccc(F)cc4C)c[nH]c3n2)c(OC)c1] | 4-(4-(cyclopentyloxy)-5-(4-fluoro-2-methylphenyl)-7H-pyrrolo[2,3-d]pyrimidin-2-ylamino)-3-methoxy-N-methylbenzamide |
| 320 | 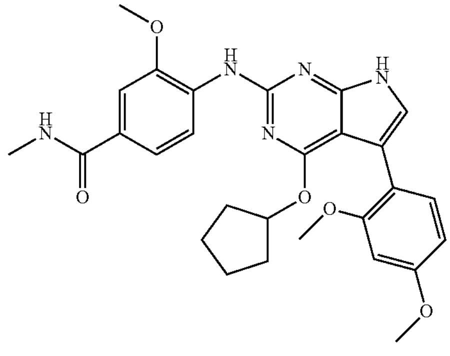 [SMILES: CNC(=O)c1ccc(Nc2nc(OC3CCCC3)c3c(-c4ccc(OC)cc4OC)c[nH]c3n2)c(OC)c1] | 4-(4-(cyclopentyloxy)-5-(2,4-dimethoxyphenyl)-7H-pyrrolo[2,3-d]pyrimidin-2-ylamino)-3-methoxy-N-methylbenzamide |

| Cmpd No. | Structure | Name |
|---|---|---|
| 321 | 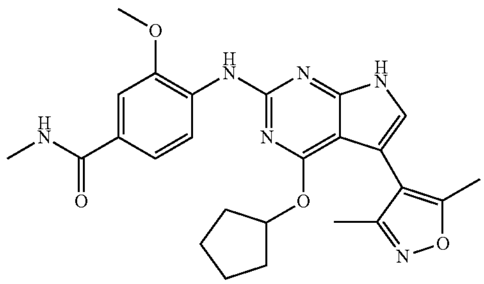 | 4-(4-(cyclopentyloxy)-5-(3,5-dimethylisoxazol-4-yl)-7H-pyrrolo[2,3-d]pyrimidin-2-ylamino)-3-methoxy-N-methylbenzamide |
| 322 | 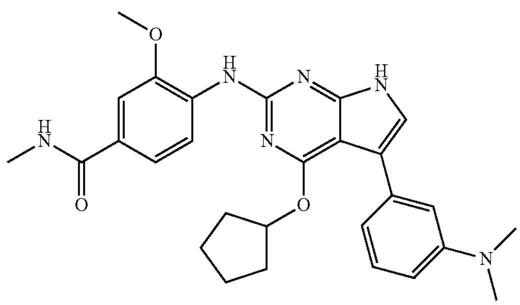 | 4-(4-(cyclopentyloxy)-5-(3-(dimethylamino)phenyl)-7H-pyrrolo[2,3-d]pyrimidin-2-ylamino)-3-methoxy-N-methylbenzamide |
| 323 | 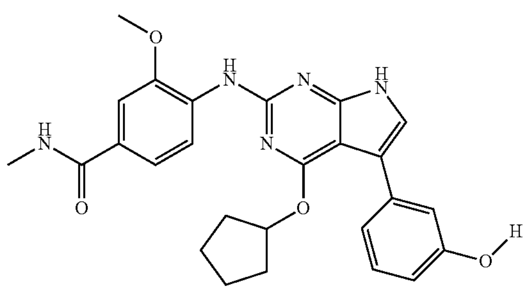 [SMILES: CNC(=O)c1ccc(Nc2nc(OC3CCCC3)c3c(-c4cccc(O)c4)c[nH]c3n2)c(OC)c1] | 4-(4-(cyclopentyloxy)-5-(3-hydroxyphenyl)-7H-pyrrolo[2,3-d]pyrimidin-2-ylamino)-3-methoxy-N-methylbenzamide |
| 324 | 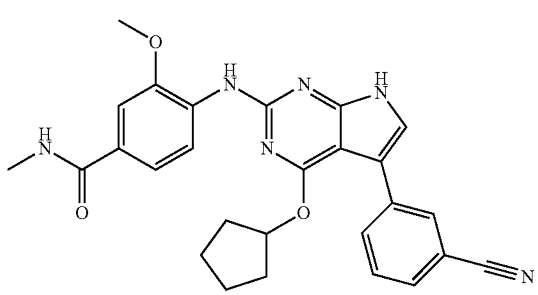 [SMILES: CNC(=O)c1ccc(Nc2nc(OC3CCCC3)c3c(-c4cccc(C#N)c4)c[nH]c3n2)c(OC)c1] | 4-(5-(3-cyanophenyl)-4-(cyclopentyloxy)-7H-pyrrolo[2,3-d]pyrimidin-2-ylamino)-3-methoxy-N-methylbenzamide |

TABLE A-continued

| Cmpd No. | Structure | Name |
|---|---|---|
| 325 | 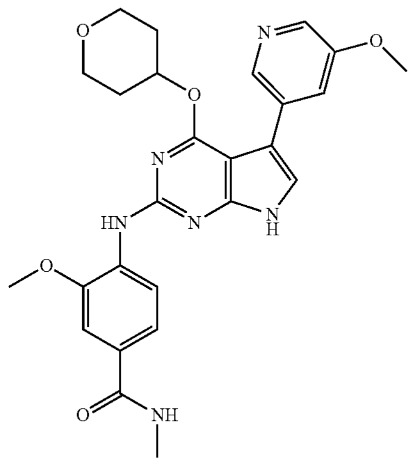 | 3-methoxy-4-(5-(5-methoxypyridin-3-yl)-4-(tetrahydro-2H-pyran-4-yloxy)-7H-pyrrolo[2,3-d]pyrimidin-2-ylamino)-N-methylbenzamide |
| 326 | 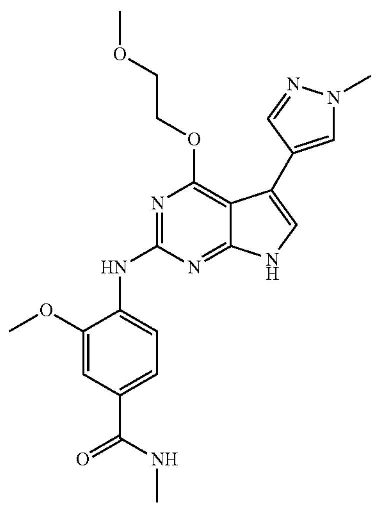 | 3-methoxy-4-(4-(2-methoxyethoxy)-5-(1-methyl-1H-pyrazol-4-yl)-7H-pyrrolo[2,3-d]pyrimidin-2-ylamino)-N-methylbenzamide |
| 327 | 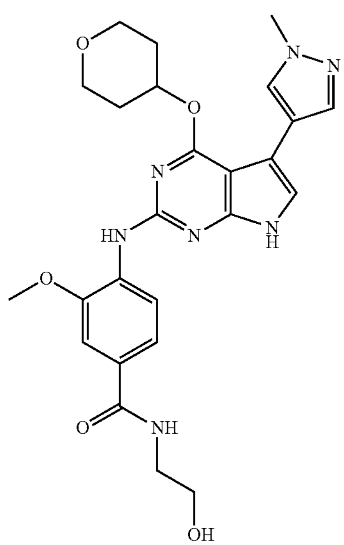 [SMILES: COc1cc(C(=O)NCCO)ccc1Nc1nc(OC2CCOCC2)c2c(-c3cnn(C)c3)c[nH]c2n1] | N-(2-hydroxyethyl)-3-methoxy-4-(5-(1-methyl-1H-pyrazol-4-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 328 | 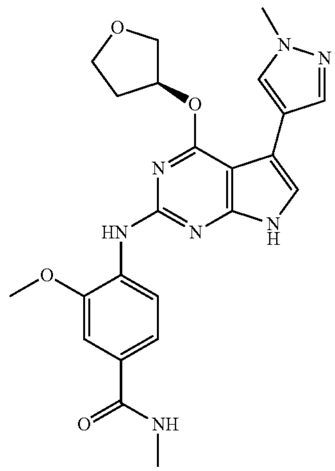 [SMILES: CNC(=O)c1ccc(Nc2nc(O[C@H]3CCOC3)c3c(-c4cnn(C)c4)c[nH]c3n2)c(OC)c1] | (S)-3-methoxy-N-methyl-4-(5-(1-methyl-1H-pyrazol-4-yl)-4-(tetrahydrofuran-3-yloxy)-7H-pyrrolo[2,3-d]pyrimidin-2-ylamino)benzamide |
| 329 | 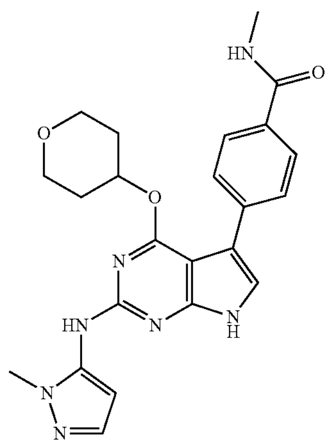 [SMILES: CNC(=O)c1ccc(-c2c[nH]c3nc(Nc4ccnn4C)nc(OC4CCOCC4)c23)cc1] | N-methyl-4-(2-(1-methyl-1H-pyrazol-5-ylamino)-4-(tetrahydro-2H-pyran-4-yloxy)-7H-pyrrolo[2,3-d]pyrimidin-5-yl)benzamide |
| 330 | 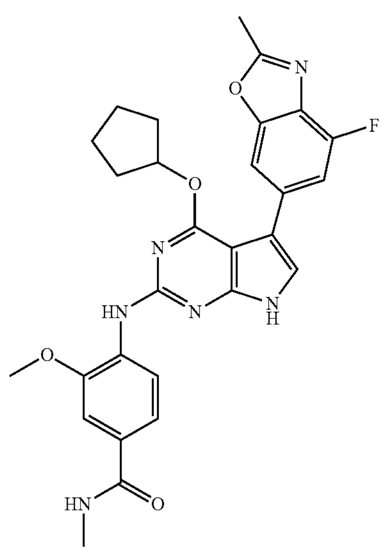 [SMILES: CNC(=O)c1ccc(Nc2nc(OC3CCCC3)c3c(-c4cc(F)c5nc(C)oc5c4)c[nH]c3n2)c(OC)c1] | 4-(4-(cyclopentyloxy)-5-(4-fluoro-2-methylbenzo[d]oxazol-6-yl)-7H-pyrrolo[2,3-d]pyrimidin-2-ylamino)-3-methoxy-N-methylbenzamide |

| Cmpd No. | Structure | Name |
|---|---|---|
| 331 | 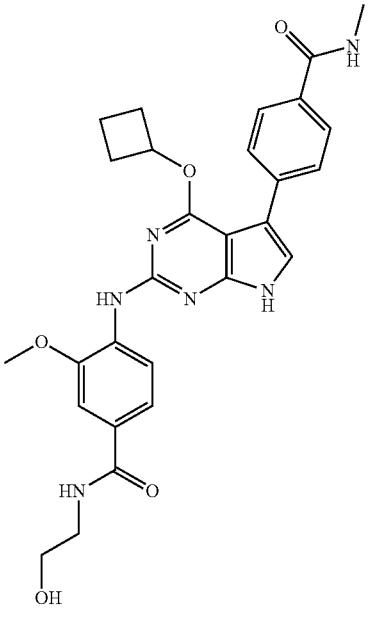 | 4-(4-cyclobutoxy-5-(4-(methylcarbamoyl)phenyl)-7H-pyrrolo[2,3-d]pyrimidin-2-ylamino)-N-(2-hydroxyethyl)-3-methoxybenzamide |
| 332 | 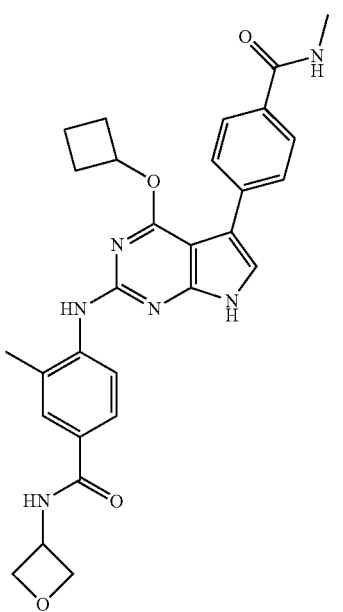 | 4-(4-cyclobutoxy-5-(4-(methylcarbamoyl)phenyl)-7H-pyrrolo[2,3-d]pyrimidin-2-ylamino)-3-methyl-N-(oxetan-3-yl)benzamide |

TABLE A-continued
| Cmpd No. | Structure | Name |
|---|---|---|
| 333 | 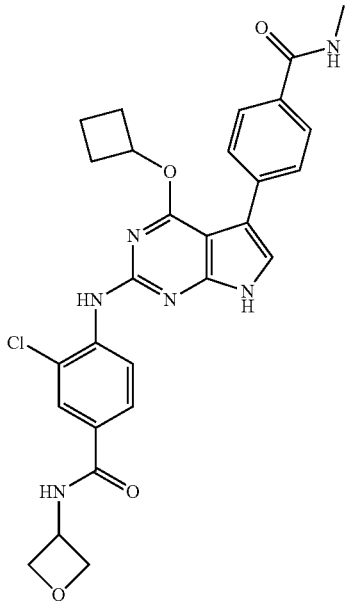 [SMILES: CNC(=O)c1ccc(-c2c[nH]c3nc(Nc4ccc(C(=O)NC5COC5)cc4Cl)nc(OC4CCC4)c23)cc1] | 3-chloro-4-(4-cyclobutoxy-5-(4-(methylcarbamoyl)phenyl)-7H-pyrrolo[2,3-d]pyrimidin-2-ylamino)-N-(oxetan-3-yl)benzamide |
| 334 | 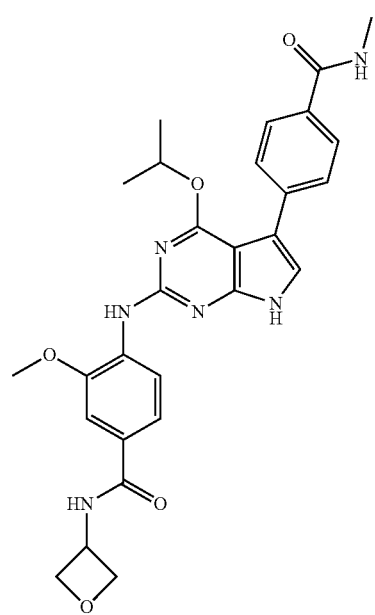 | 4-(4-isopropoxy-5-(4-(methylcarbamoyl)phenyl)-7H-pyrrolo[2,3-d]pyrimidin-2-ylamino)-3-methoxy-N-(oxetan-3-yl)benzamide |

TABLE A-continued
| Cmpd No. | Structure | Name |
|---|---|---|
| 335 | 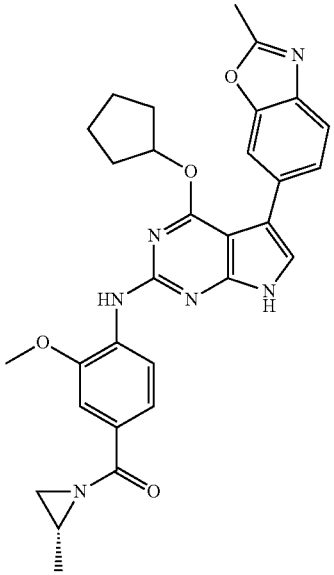 [SMILES: COc1cc(C(=O)N2C[C@H]2C)ccc1Nc1nc(OC2CCCC2)c2c(-c3ccc4nc(C)oc4c3)c[nH]c2n1] | (R)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone |
| 336 | 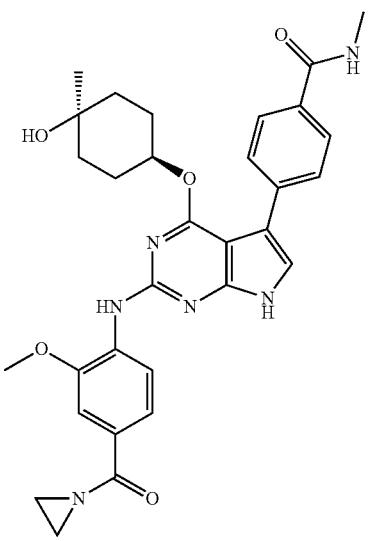 | 4-(2-(4-(aziridine-1-carbonyl)-2-methoxyphenylamino)-4-((1s,4s)-4-hydroxy-4-methylcyclohexyloxy)-7H-pyrrolo[2,3-d]pyrimidin-5-yl)-N-methylbenzamide |

TABLE A-continued
| Cmpd No. | Structure | Name |
|---|---|---|
| 337 | 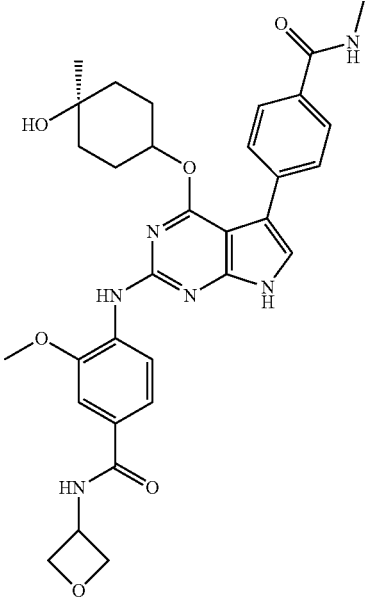 | 4-(4-((1s,4s)-4-hydroxy-4-methylcyclohexyloxy)-5-(4-(methylcarbamoyl)phenyl)-7H-pyrrolo[2,3-d]pyrimidin-2-ylamino)-3-methoxy-N-(oxetan-3-yl)benzamide |
| 338 | 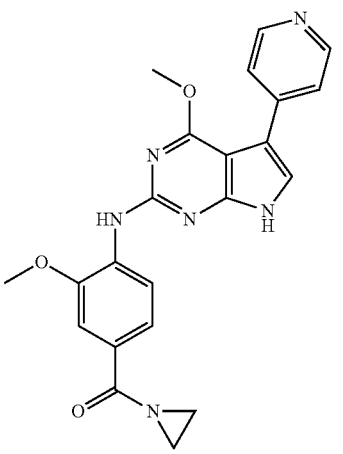 [SMILES: COc1cc(C(=O)N2CC2)ccc1Nc1nc(OC)c2c(-c3ccncc3)c[nH]c2n1] | aziridin-1-yl(3-methoxy-4-(4-methoxy-5-(pyridin-4-yl)-7H-pyrrolo[2,3-d]pyrimidin-2-ylamino)phenyl)methanone |

TABLE A-continued
| Cmpd No. | Structure | Name |
|---|---|---|
| 339 | 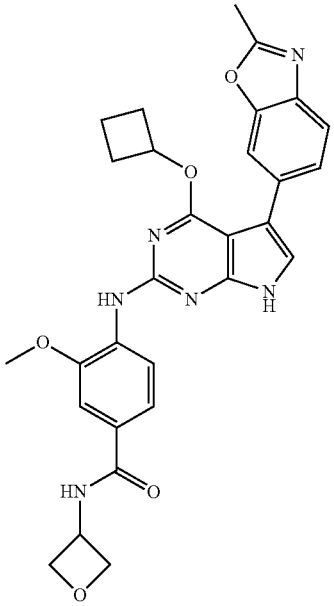 [SMILES: COc1cc(C(=O)NC2COC2)ccc1Nc1nc(OC2CCC2)c2c(-c3ccc4nc(C)oc4c3)c[nH]c2n1] | 4-(4-cyclobutoxy-5-(2-methylbenzo[d]oxazol-6-yl)-7H-pyrrolo[2,3-d]pyrimidin-2-ylamino)-3-methoxy-N-(oxetan-3-yl)benzamide |
| 340 | 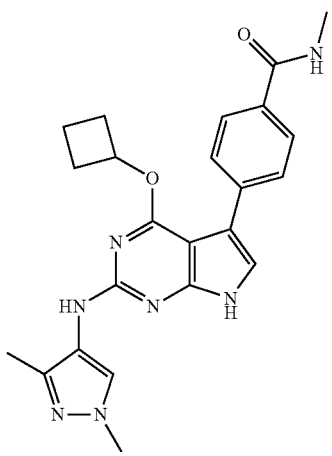 | 4-(4-cyclobutoxy-2-(1,3-dimethyl-1H-pyrazol-4-ylamino)-7H-pyrrolo[2,3-d]pyrimidin-5-yl)-N-methylbenzamide |

TABLE A-continued
| Cmpd No. | Structure | Name |
|---|---|---|
| 341 | 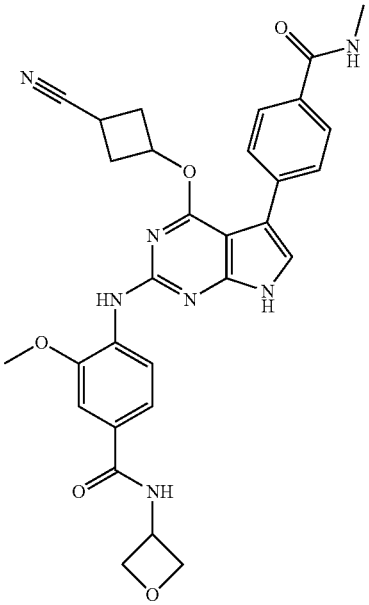 | 4-(4-(3-cyanocyclobutoxy)-5-(4-(methylcarbamoyl)phenyl)-7H-pyrrolo[2,3-d]pyimdin-2-ylamino)-3-methoxy-N-(oxetan-3-yl)benzamide |
| 342 | 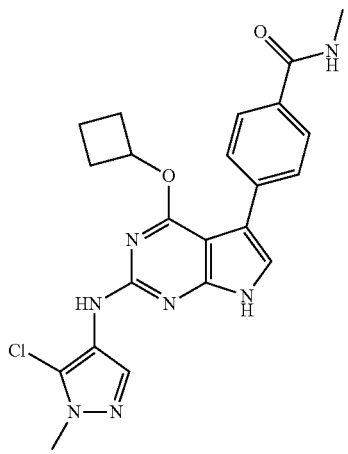 [SMILES: CNC(=O)c1ccc(-c2c[nH]c3nc(Nc4cnn(C)c4Cl)nc(OC4CCC4)c23)cc1] | 4-(2-(5-chloro-1-methyl-1H-pyrazol-4-ylamino)-4-cyclobutoxy-7H-pyrrolo[2,3-d]pyrimidin-5-yl)-N-methylbenzamide |

| Cmpd No. | Structure | Name |
|---|---|---|
| 343 | 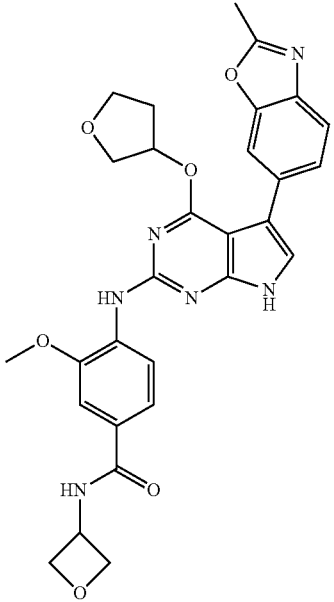 [SMILES: COc1cc(C(=O)NC2COC2)ccc1Nc1nc(OC2CCOC2)c2c(-c3ccc4nc(C)oc4c3)c[nH]c2n1] | (S)-3-methoxy-4-(5-(2-methylbenzo[d]oxazol-6-yl)-4-(tetrahydrofuran-3-yloxy)-7H-pyrrolo[2,3-d]pyrimidin-2-ylamino)-N-(oxetan-3-yl)benzamide |
| 344 | 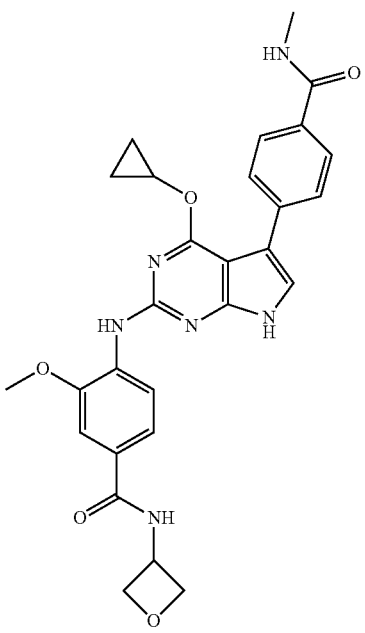 [SMILES: CNC(=O)c1ccc(-c2c[nH]c3nc(Nc4ccc(C(=O)NC5COC5)cc4OC)nc(OC4CC4)c23)cc1] | 4-(4-cyclopropoxy-5-(4-(methylcarbamoyl)phenyl)-7H-pyrrolo[2,3-d]pyrimidin-2-ylamino)-3-methoxy-N-(oxetan-3-yl)benzamide |

| Cmpd No. | Structure | Name |
|---|---|---|
| 345 | 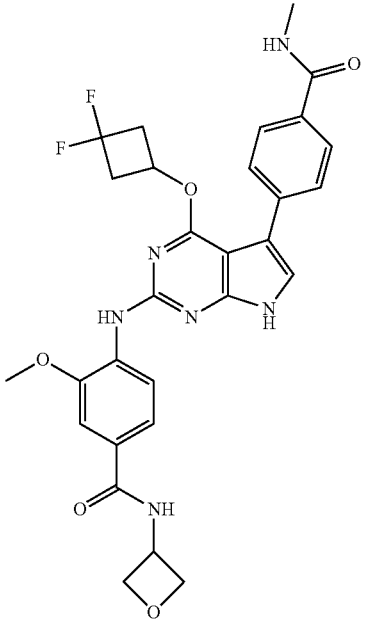 [SMILES: CNC(=O)c1ccc(-c2c[nH]c3nc(Nc4ccc(C(=O)NC5COC5)cc4OC)nc(OC4CC(F)(F)C4)c23)cc1] | 4-(4-(3,3-difluorocyclobutoxy)-5-(4-(methylcarbamoyl)phenyl)-7H-pyrrolo[2,3-d]pyrimidin-2-ylamino)-3-methoxy-N-(oxetan-3-yl)benzamide |
| 346 | 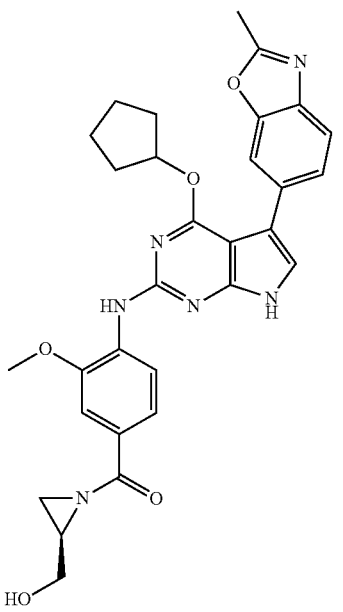 [SMILES: COc1cc(C(=O)N2C[C@@H]2CO)ccc1Nc1nc(OC2CCCC2)c2c(-c3ccc4nc(C)oc4c3)c[nH]c2n1] | (R)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-(hydroxymethyl)aziridin-1-yl)methanone |

TABLE A-continued

| Cmpd No. | Structure | Name |
|---|---|---|
| 347 | 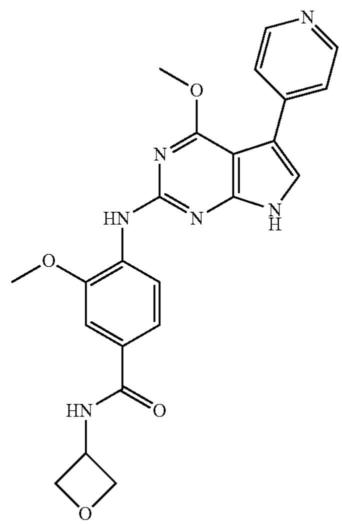 [SMILES: COc1cc(C(=O)NC2COC2)ccc1Nc1nc(OC)c2c(-c3ccncc3)c[nH]c2n1] | 3-methoxy-4-(4-methoxy-5-(pyridin-4-yl)-7H-pyrrolo[2,3-d]pyrimidin-2-ylamino)-N-(oxetan-3-yl)benzamide |
| 348 | 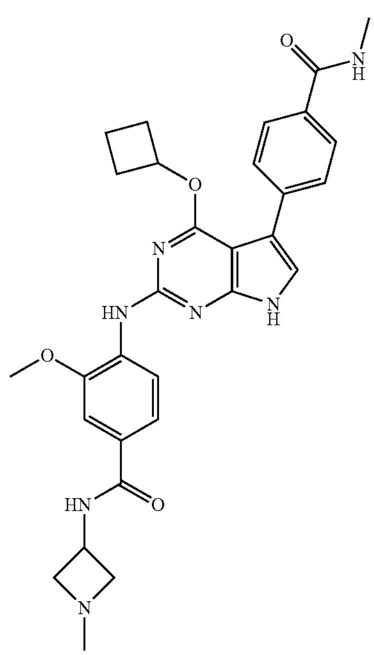 | 4-(4-cyclobutoxy-5-(4-(methylcarbamoyl)phenyl)-7H-pyrrolo[2,3-d]pyrimidin-2-ylamino)-3-methoxy-N-(1-methylazetidin-3-yl)benzamide |

| Cmpd No. | Structure | Name |
|---|---|---|
| 349 | 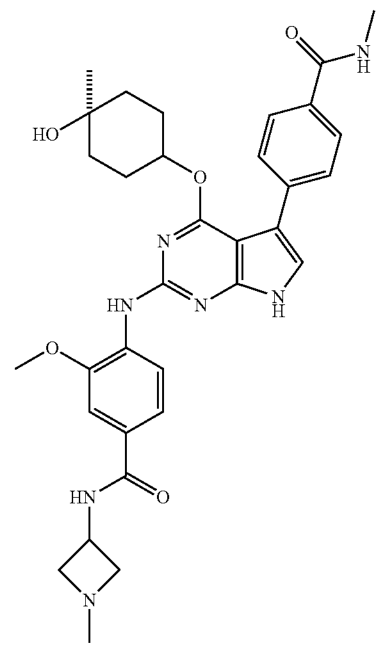 | 4-(4-((1s,4s)-4-hydroxy-4-methylcyclohexyloxy)-5-(4-(methylcarbamoyl)phenyl)-7H-pyrrolo[2,3-d]pyrimidin-2-ylamino)-3-methoxy-N-(1-methylazetidin-3-yl)benzamide |
| 350 | 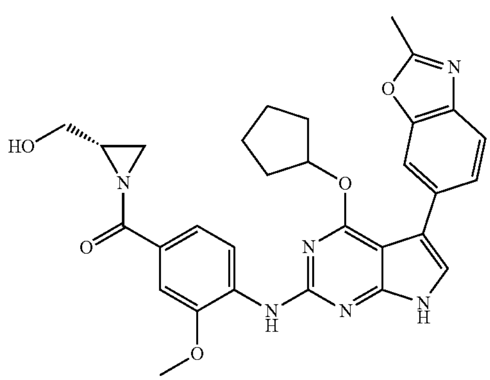 [SMILES: COc1cc(C(=O)N2C[C@H]2CO)ccc1Nc1nc(OC2CCCC2)c2c(-c3ccc4nc(C)oc4c3)c[nH]c2n1] | (S)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-(hydroxymethyl)aziridin-1-yl)methanone |
| 351 | 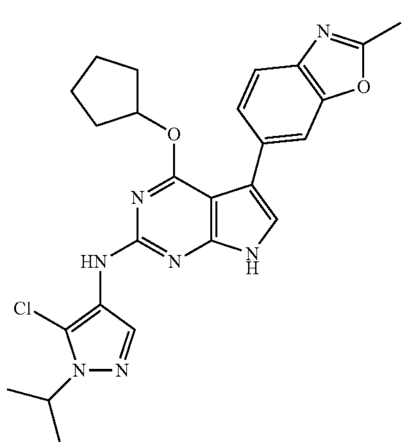 [SMILES: Cc1nc2ccc(-c3c[nH]c4nc(Nc5cnn(C(C)C)c5Cl)nc(OC5CCCC5)c34)cc2o1] | N-(5-chloro-1-isopropyl-1H-pyrazol-4-yl)-4-(cyclopentyloxy)-5-(2-methylbenzo[d]oxazol-6-yl)-7H-pyrrolo[2,3-d]pyrimidin-2-amine |

TABLE A-continued

| Cmpd No. | Structure | Name |
|---|---|---|
| 352 | 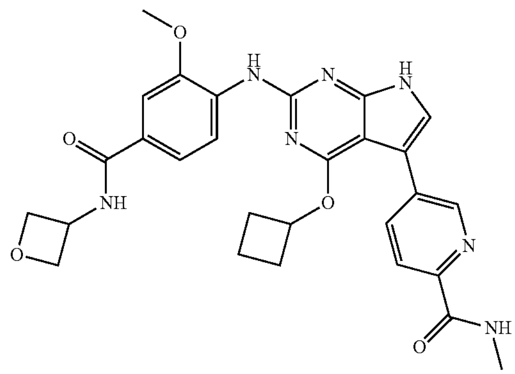 [SMILES: CNC(=O)c1ccc(-c2c[nH]c3nc(Nc4ccc(C(=O)NC5COC5)cc4OC)nc(OC4CCC4)c23)cn1] | 5-(4-cyclobutoxy-2-(2-methoxy-4-(oxetan-3-ylcarbamoyl)phenylamino)-7H-pyrrolo[2,3-d]pyrimidin-5-yl)-N-methylpicolinamide |
| 353 | 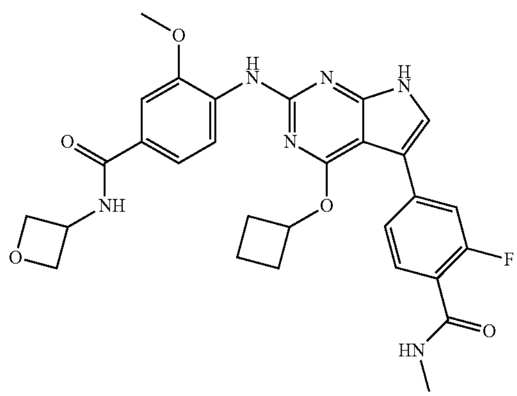 [SMILES: CNC(=O)c1ccc(-c2c[nH]c3nc(Nc4ccc(C(=O)NC5COC5)cc4OC)nc(OC4CCC4)c23)cc1F] | 4-(4-cyclobutoxy-2-(2-methoxy-4-(oxetan-3-ylcarbamoyl)phenylamino)-7H-pyrrolo[2,3-d]pyrimidin-5-yl)-2-fluoro-N-methylbenzamide |
| 354 | 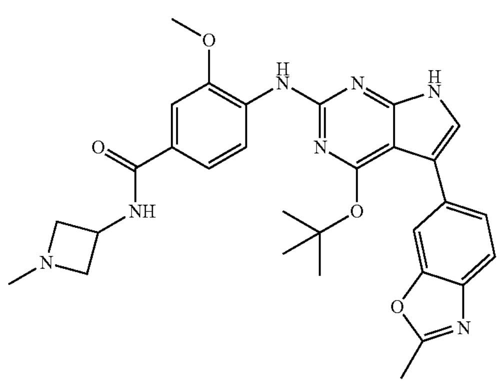 [SMILES: COc1cc(C(=O)NC2CN(C)C2)ccc1Nc1nc(OC(C)(C)C)c2c(-c3ccc4nc(C)oc4c3)c[nH]c2n1] | 4-(4-tert-butoxy-5-(2-methylbenzo[d]oxazol-6-yl)-7H-pyrrolo[2,3-d]pyrimidin-2-ylamino)-3-methoxy-N-(1-methylazetidin-3-yl)benzamide |
| 355 | 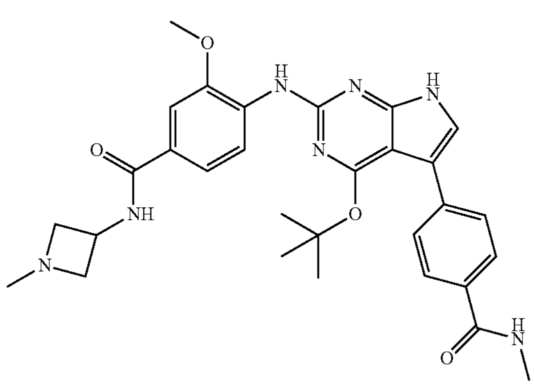 | 4-(4-tert-butoxy-5-(4-(methylcarbamoyl)phenyl)-7H-pyrrolo[2,3-d]pyrimidin-2-ylamino)-3-methoxy-N-(1-methylazetidin-3-yl)benzamide |

| Cmpd No. | Structure | Name |
|---|---|---|
| 356 | 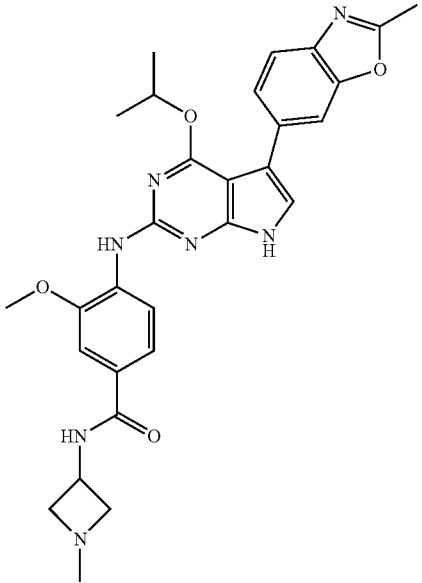 | 4-(4-isopropoxy-5-(2-methylbenzo[d]oxazol-6-yl)-7H-pyrrolo[2,3-d]pyrimidin-2-ylamino)-3-methoxy-N-(1-methylazetidin-3-yl)benzamide |
| 357 | 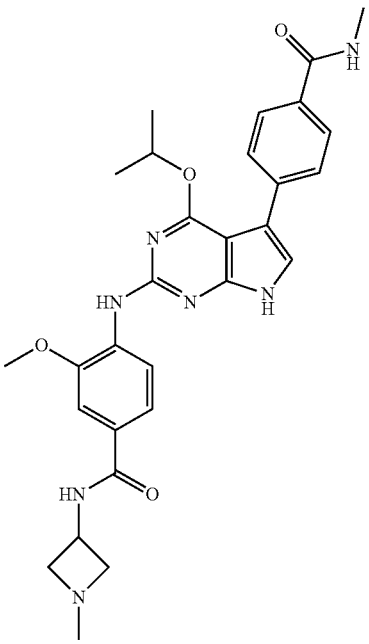 | 4-(4-isopropoxy-5-(4-(methylcarbamoyl)phenyl)-7H-pyrrolo[2,3-d]pyrimidin-2-ylamino)-3-methoxy-N-(1-methylazetidin-3-yl)benzamide |

TABLE A-continued
| Cmpd No. | Structure | Name |
|---|---|---|
| 358 | 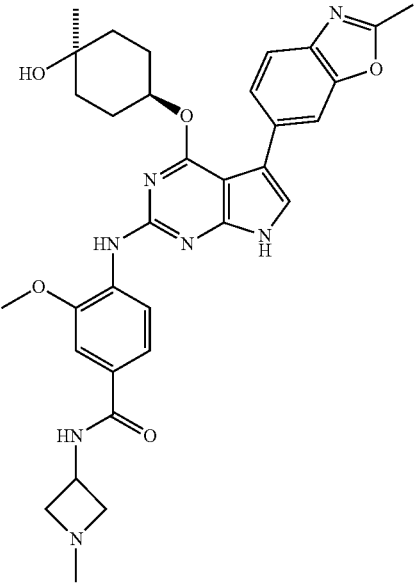 | 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-(1-methylazetidin-3-yl)benzamide |
| 359 | 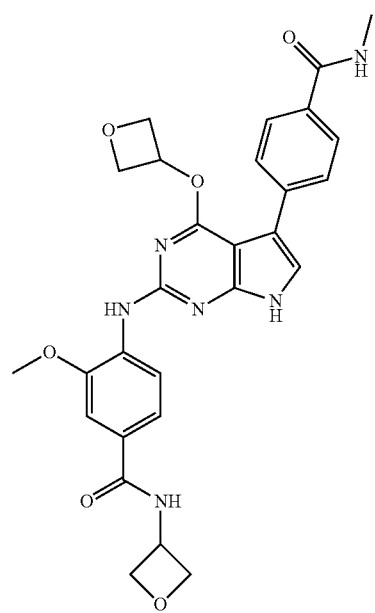 | 3-methoxy-4-(5-(4-(methylcarbamoyl)phenyl)-4-(oxetan-3-yloxy)-7H-pyrrolo[2,3-d]pyrimidin-2-ylamino)-N-(oxetan-3-yl)benzamide |

TABLE A-continued

| Cmpd No. | Structure | Name |
|---|---|---|
| 360 | 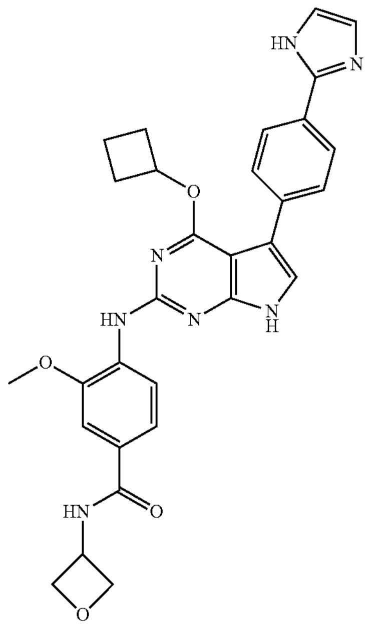 [SMILES: COc1cc(C(=O)NC2COC2)ccc1Nc1nc(OC2CCC2)c2c(-c3ccc(-c4ncc[nH]4)cc3)c[nH]c2n1] | 4-(5-(4-(1H-imidazol-2-yl)phenyl)-4-cyclobutoxy-7H-pyrrolo[2,3-d]pyrimidin-2-ylamino)-3-methoxy-N-(oxetan-3-yl)benzamide |
| 361 | 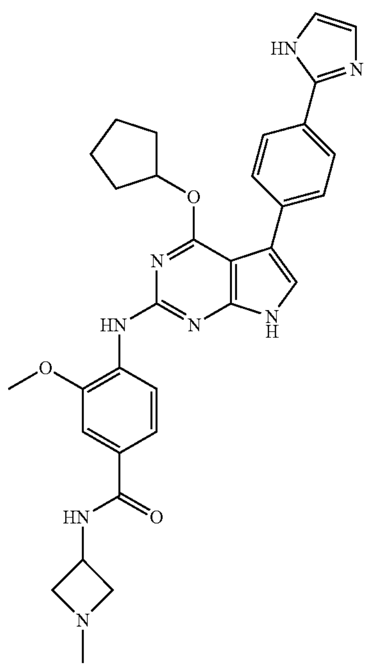 [SMILES: COc1cc(C(=O)NC2CN(C)C2)ccc1Nc1nc(OC2CCCC2)c2c(-c3ccc(-c4ncc[nH]4)cc3)c[nH]c2n1] | 4-(5-(4-(1H-imidazol-2-yl)phenyl)-4-(cyclopentyloxy)-7H-pyrrolo[2,3-d]pyrimidin-2-ylamino)-3-methoxy-N-(1-methylazetidin-3-yl)benzamide |
| 362 | 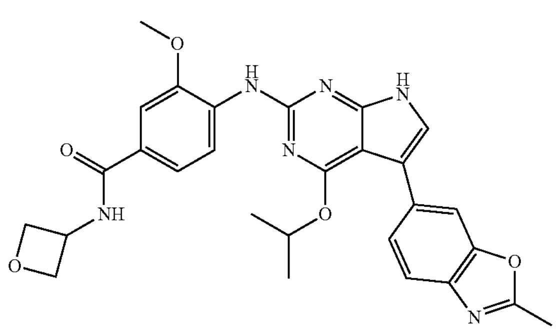 [SMILES: COc1cc(C(=O)NC2COC2)ccc1Nc1nc(OC(C)C)c2c(-c3ccc4nc(C)oc4c3)c[nH]c2n1] | 4-(4-isopropoxy-5-(2-methylbenzo[d]oxazol-6-yl)-7H-pyrrolo[2,3-d]pyrimidin-2-ylamino)-3-methoxy-N-(oxetan-3-yl)benzamide |

TABLE A-continued

| Cmpd No. | Structure | Name |
|---|---|---|
| 363 | 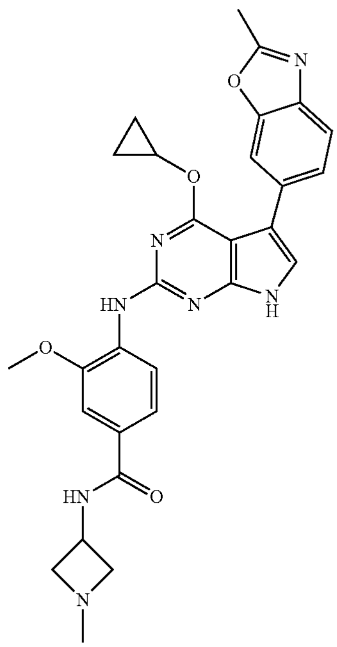 [SMILES: COc1cc(C(=O)NC2CN(C)C2)ccc1Nc1nc(OC2CC2)c2c(-c3ccc4nc(C)oc4c3)c[nH]c2n1] | 4-(4-cyclopropoxy-5-(2-methylbenzo[d]oxazol-6-yl)-7H-pyrrolo[2,3-d]pyrimidin-2-ylamino)-3-methoxy-N-(1-methylazetidin-3-yl)benzamide |
| 364 | 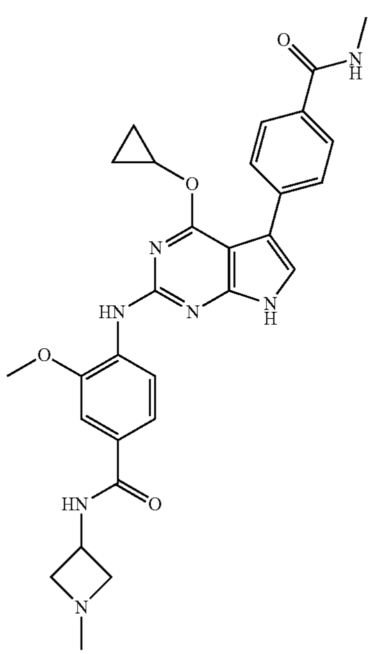 | 4-(4-cyclopropoxy-5-(4-(methylcarbamoyl)phenyl)-7H-pyrrolo[2,3-d]pyrimidin-2-ylamino)-3-methoxy-N-(1-methylazetidin-3-yl)benzamide |

TABLE A-continued
| Cmpd No. | Structure | Name |
|---|---|---|
| 365 | 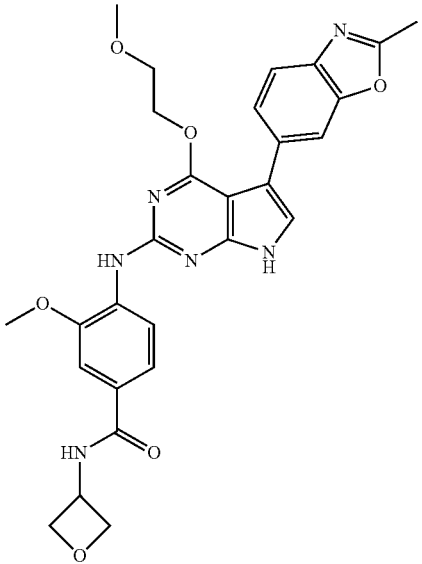 | 3-methoxy-4-(4-(2-methoxyethoxy)-5-(2-methylbenzo[d]oxazol-6-yl)-7H-pyrrolo[2,3-d]pyrimidin-2-ylamino)-N-(oxetan-3-yl)benzamide |
| 366 | 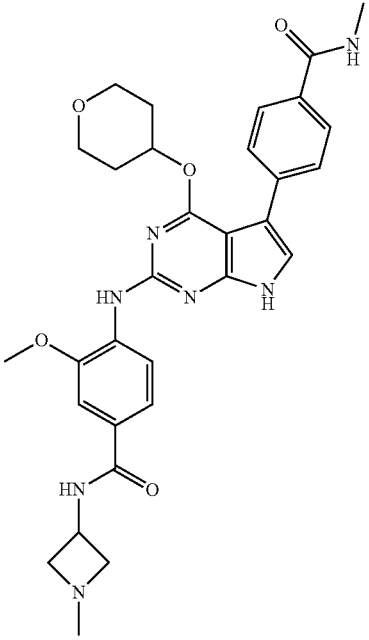 | 3-methoxy-N-(1-methylazetidin-3-yl)-4-(5-(4-(methylcarbamoyl)phenyl)-4-(tetrahydro-2H-pyran-4-yloxy)-7H-pyrrolo[2,3-d]pyrimidin-2-ylamino)benzamide |

| Cmpd No. | Structure | Name |
|---|---|---|
| 367 | 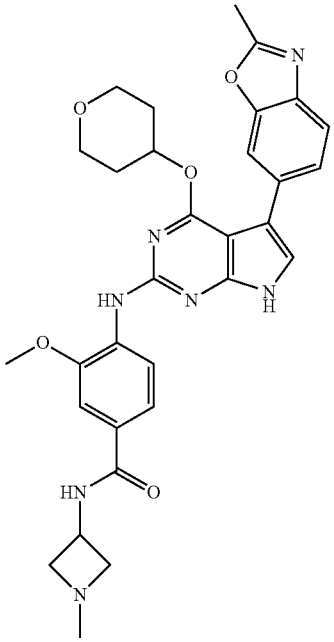 [SMILES: COc1cc(C(=O)NC2CN(C)C2)ccc1Nc1nc(OC2CCOCC2)c2c(-c3ccc4nc(C)oc4c3)c[nH]c2n1] | 3-methoxy-N-(1-methylazetidin-3-yl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide |
| 368 | 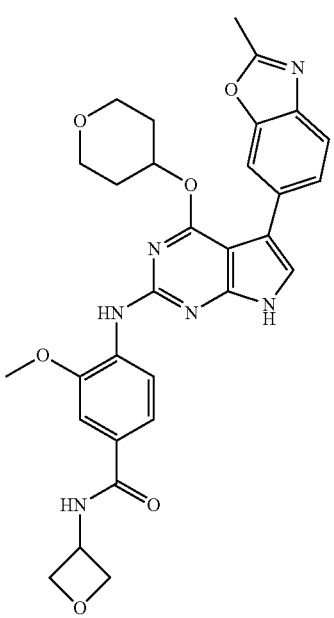 [SMILES: COc1cc(C(=O)NC2COC2)ccc1Nc1nc(OC2CCOCC2)c2c(-c3ccc4nc(C)oc4c3)c[nH]c2n1] | 3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)-N-(oxetan-3-yl)benzamide |

TABLE A-continued

| Cmpd No. | Structure | Name |
|---|---|---|
| 369 | 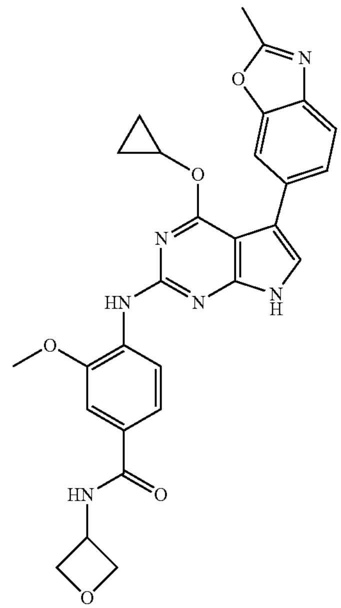 [SMILES: COc1cc(C(=O)NC2COC2)ccc1Nc1nc(OC2CC2)c2c(-c3ccc4nc(C)oc4c3)c[nH]c2n1] | 4-(4-cyclopropoxy-5-(2-methylbenzo[d]oxazol-6-yl)-7H-pyrrolo[2,3-d]pyrimidin-2-ylamino)-3-methoxy-N-(oxetan-3-yl)benzamide |
| 370 | 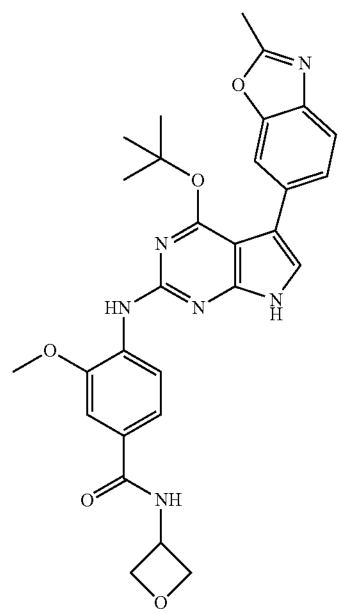 [SMILES: COc1cc(C(=O)NC2COC2)ccc1Nc1nc(OC(C)(C)C)c2c(-c3ccc4nc(C)oc4c3)c[nH]c2n1] | 4-(4-tert-butoxy-5-(2-methylbenzo[d]oxazol-6-yl)-7H-pyrrolo[2,3-d]pyrimidin-2-ylamino)-3-methoxy-N-(oxetan-3-yl)benzamide |
| 371 | 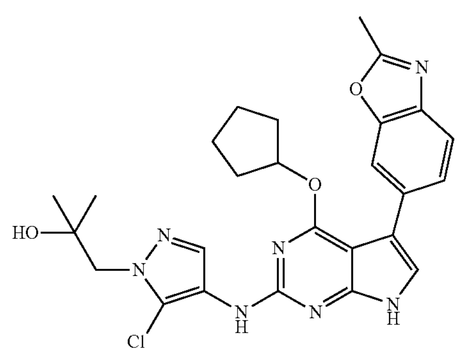 [SMILES: Cc1nc2ccc(-c3c[nH]c4nc(Nc5cnn(CC(C)(C)O)c5Cl)nc(OC5CCCC5)c34)cc2o1] | 1-(5-chloro-4-(4-(cyclopentyloxy)-5-(2-methylbenzo[d]oxazol-6-yl)-7H-pyrrolo[2,3-d]pyrimidin-2-ylamino)-1H-pyrazol-1-yl)-2-methylpropan-2-ol |

TABLE A-continued

| Cmpd No. | Structure | Name |
|---|---|---|
| 372 | 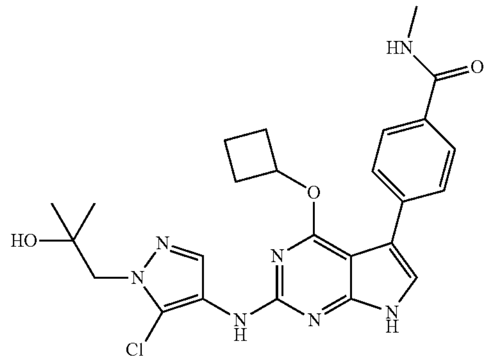 [SMILES: CNC(=O)c1ccc(-c2c[nH]c3nc(Nc4cnn(CC(C)(C)O)c4Cl)nc(OC4CCC4)c23)cc1] | 4-(2-(5-chloro-1-(2-hydroxy-2-methylpropyl)-1H-pyrazol-4-ylamino)-4-cyclobutoxy-7H-pyrrolo[2,3-d]pyrimidin-5-yl)-N-methylbenzamide |
| 373 | 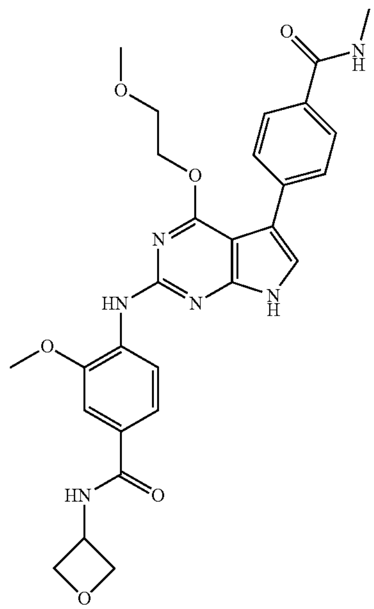 | 3-methoxy-4-(4-(2-methoxyethoxy)-5-(4-(methylcarbamoyl)phenyl)-7H-pyrrolo[2,3-d]pyrimidin-2-ylamino)-N-(oxetan-3-yl)benzamide |
| 374 | 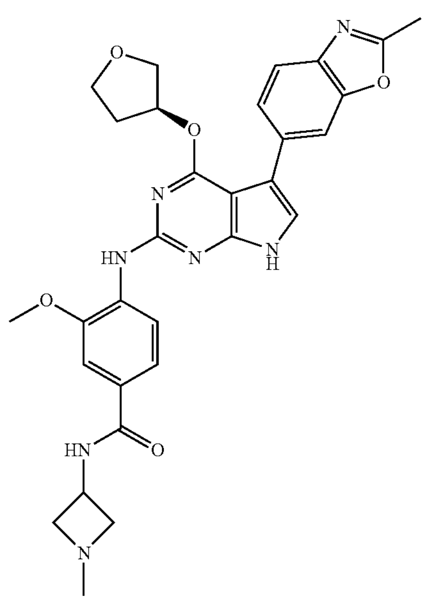 | (S)-3-methoxy-N-(1-methylazetidin-3-yl)-4-(5-(2-methylbenzo[d]oxazol-6-yl)-4-(tetrahydrofuran-3-yloxy)-7H-pyrrolo[2,3-d]pyrimidin-2-ylamino)benzamide |

| Cmpd No. | Structure | Name |
|---|---|---|
| 375 | 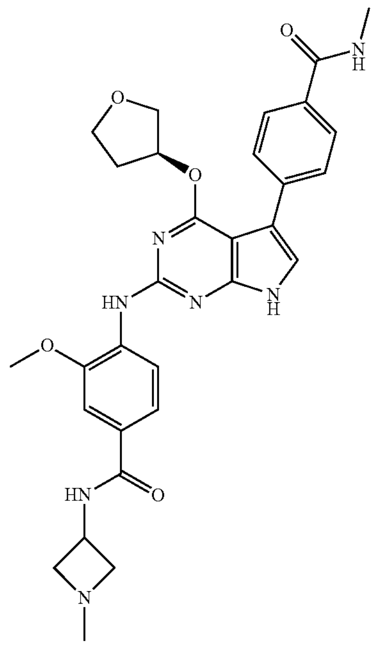 | (S)-3-methoxy-N-(1-methylazetidin-3-yl)-4-(5-(4-(methylcarbamoyl)phenyl)-4-(tetrahydrofuran-3-yloxy)-7H-pyrrolo[2,3-d]pyrimidin-2-ylamino)benzamide |
| 376 | 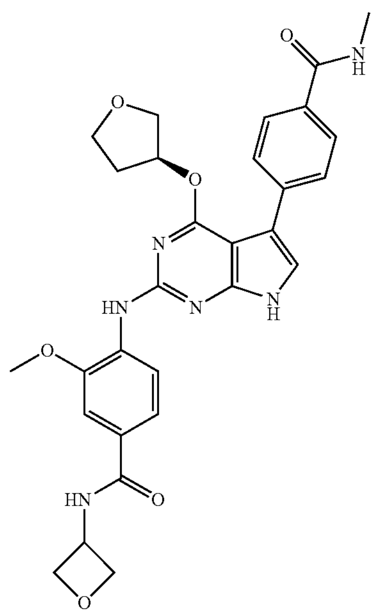 | (S)-3-methoxy-4-(5-(4-(methylcarbamoyl)phenyl)-4-(tetrahydrofuran-3-yloxy)-7H-pyrrolo[2,3-d]pyrimidin-2-ylamino)-N-(oxetan-3-yl)benzamide |
| 377 | 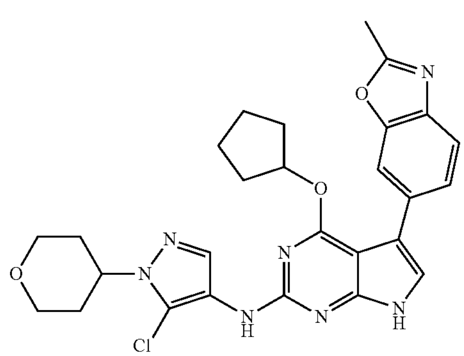 [SMILES: Cc1nc2ccc(-c3c[nH]c4nc(Nc5cnn(C6CCOCC6)c5Cl)nc(OC5CCCC5)c34)cc2o1] | N-(5-chloro-1-(tetrahydro-2H-pyran-4-yl)-1H-pyrazol-4-yl)-4-(cyclopentyloxy)-5-(2-methylbenzo[d]oxazol-6-yl)-7H-pyrrolo[2,3-d]pyrimidin-2-amine |

| Cmpd No. | Structure | Name |
|---|---|---|
| 378 | 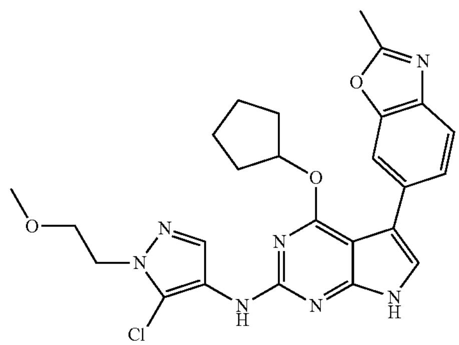 [SMILES: COCCn1ncc(Nc2nc(OC3CCCC3)c3c(-c4ccc5nc(C)oc5c4)c[nH]c3n2)c1Cl] | N-(5-chloro-1-(2-methoxyethyl)-1H-pyrazol-4-yl)-4-(cyclopentyloxy)-5-(2-methylbenzo[d]oxazol-6-yl)-7H-pyrrolo[2,3-d]pyrimidin-2-amine |
| 379 | 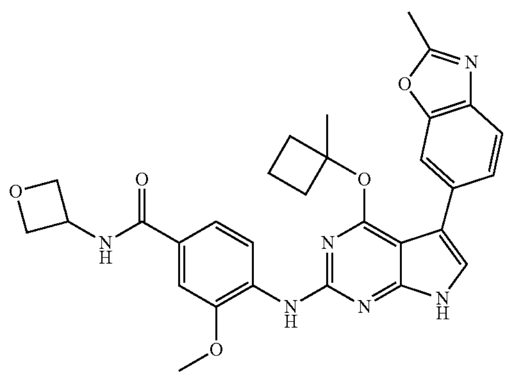 [SMILES: COc1cc(C(=O)NC2COC2)ccc1Nc1nc(OC2(C)CCC2)c2c(-c3ccc4nc(C)oc4c3)c[nH]c2n1] | 3-methoxy-4-(5-(2-methylbenzo[d]oxazol-6-yl)-4-(1-methylcyclobutoxy)-7H-pyrrolo[2,3-d]pyrimidin-2-ylamino)-N-(oxetan-3-yl)benzamide |
| 380 | 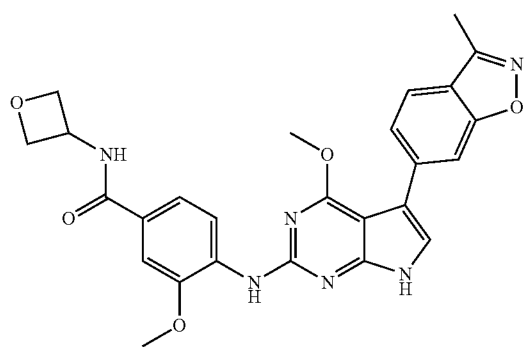 [SMILES: COc1cc(C(=O)NC2COC2)ccc1Nc1nc(OC)c2c(-c3ccc4c(C)noc4c3)c[nH]c2n1] | 3-methoxy-4-(4-methoxy-5-(3-methylbenzo[d]isoxazol-6-yl)-7H-pyrrolo[2,3-d]pyrimidin-2-ylamino)-N-(oxetan-3-yl)benzamide |
| 381 | 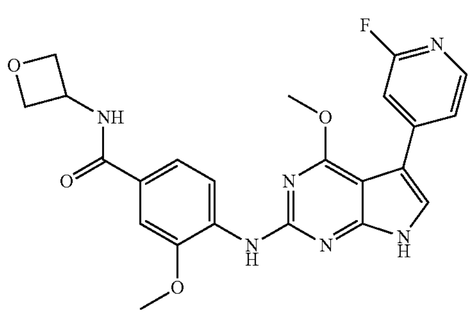 [SMILES: COc1cc(C(=O)NC2COC2)ccc1Nc1nc(OC)c2c(-c3ccnc(F)c3)c[nH]c2n1] | 4-(5-(2-fluoropyridin-4-yl)-4-methoxy-7H-pyrrolo[2,3-d]pyrimidin-2-ylamino)-3-methoxy-N-(oxetan-3-yl)benzamide |

TABLE A-continued

| Cmpd No. | Structure | Name |
|---|---|---|
| 382 | 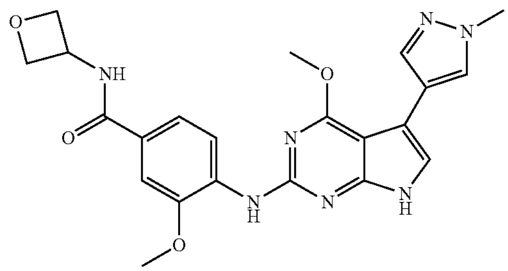 [SMILES: COc1cc(C(=O)NC2COC2)ccc1Nc1nc(OC)c2c(-c3cnn(C)c3)c[nH]c2n1] | 3-methoxy-4-(4-methoxy-5-(1-methyl-1H-pyrazol-4-yl)-7H-pyrrolo[2,3-d]pyrimidin-2-ylamino)-N-(oxetan-3-yl)benzamide |
| 383 | 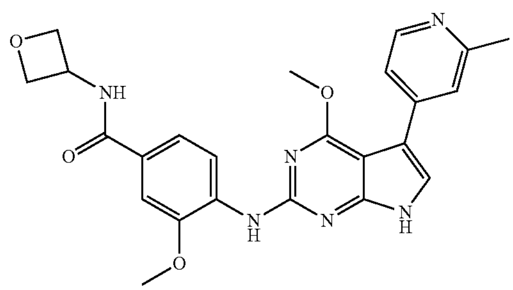 [SMILES: COc1cc(C(=O)NC2COC2)ccc1Nc1nc(OC)c2c(-c3ccnc(C)c3)c[nH]c2n1] | 3-methoxy-4-(4-methoxy-5-(2-methylpyridin-4-yl)-7H-pyrrolo[2,3-d]pyrimidin-2-ylamino)-N-(oxetan-3-yl)benzamide |
| 384 | 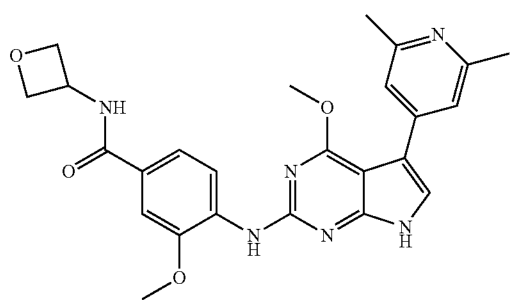 [SMILES: COc1cc(C(=O)NC2COC2)ccc1Nc1nc(OC)c2c(-c3cc(C)nc(C)c3)c[nH]c2n1] | 4-(5-(2,6-dimethylpyridin-4-yl)-4-methoxy-7H-pyrrolo[2,3-d]pyrimidin-2-ylamino)-3-methoxy-N-(oxetan-3-yl)benzamide |
| 385 | 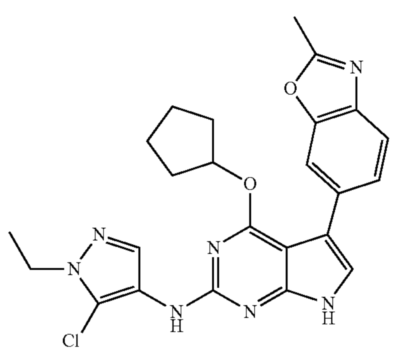 [SMILES: CCn1ncc(Nc2nc(OC3CCCC3)c3c(-c4ccc5nc(C)oc5c4)c[nH]c3n2)c1Cl] | N-(5-chloro-1-ethyl-1H-pyrazol-4-yl)-4-(cyclopentyloxy)-5-(2-methylbenzo[d]oxazol-6-yl)-7H-pyrrolo[2,3-d]pyrimidin-2-amine |

TABLE A-continued

| Cmpd No. | Structure | Name |
|---|---|---|
| 386 | 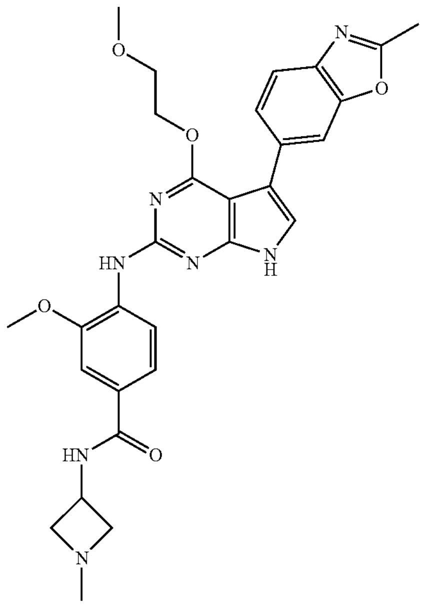 | 3-methoxy-4-(4-(2-methoxyethoxy)-5-(2-methylbenzo[d]oxazol-6-yl)-7H-pyrrolo[2,3-d]pyrimidin-2-ylamino)-N-(1-methylazetidin-3-yl)benzamide |
| 387 | 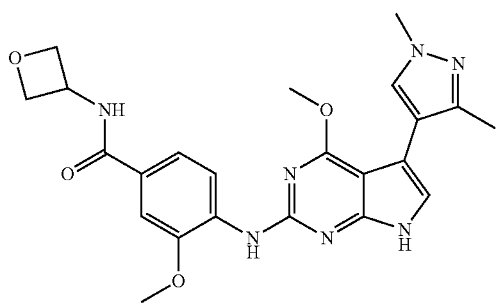 [SMILES: COc1cc(C(=O)NC2COC2)ccc1Nc1nc(OC)c2c(-c3cn(C)nc3C)c[nH]c2n1] | 4-(5-(1,3-dimethyl-1H-pyrazol-4-yl)-4-methoxy-7H-pyrrolo[2,3-d]pyrimidin-2-ylamino)-3-methoxy-N-(oxetan-3-yl)benzamide |
| 388 | 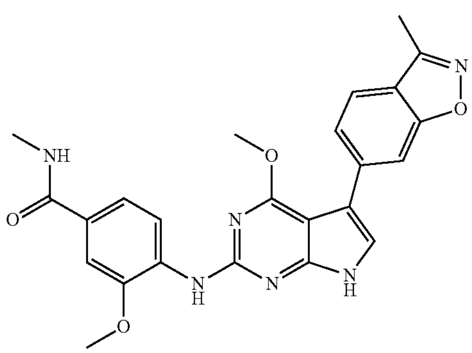 [SMILES: CNC(=O)c1ccc(Nc2nc(OC)c3c(-c4ccc5c(C)noc5c4)c[nH]c3n2)c(OC)c1] | 3-methoxy-4-(4-methoxy-5-(3-methylbenzo[d]isoxazol-6-yl)-7H-pyrrolo[2,3-d]pyrimidin-2-ylamino)-N-methylbenzamide |
| 389 | 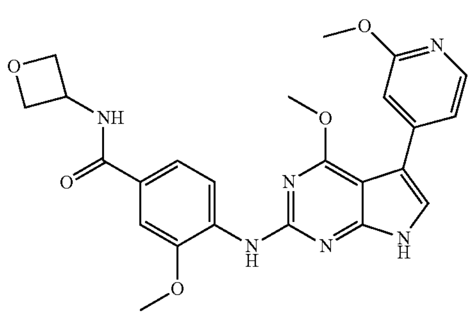 [SMILES: COc1cc(-c2c[nH]c3nc(Nc4ccc(C(=O)NC5COC5)cc4OC)nc(OC)c23)ccn1] | 3-methoxy-4-(4-methoxy-5-(2-methoxypyridin-4-yl)-7H-pyrrolo[2,3-d]pyrimidin-2-ylamino)-N-(oxetan-3-yl)benzamide |

TABLE A-continued

| Cmpd No. | Structure | Name |
| --- | --- | --- |
| 390 | 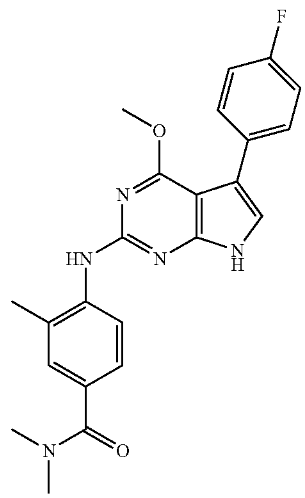 [SMILES: COc1nc(Nc2ccc(C(=O)N(C)C)cc2C)nc2[nH]cc(-c3ccc(F)cc3)c12] | 4-(5-(4-fluorophenyl)-4-methoxy-7H-pyrrolo[2,3-d]pyrimidin-2-ylamino)-N,N,3-trimethylbenzamide |
| 391 | 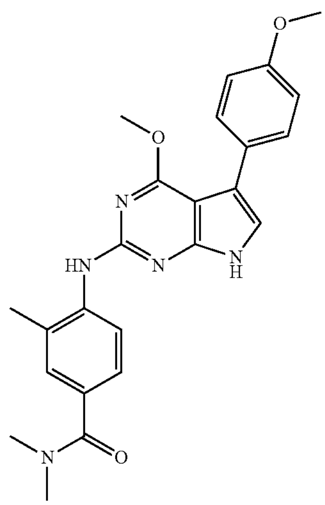 | 4-(4-methoxy-5-(4-methoxyphenyl)-7H-pyrrolo[2,3-d]pyrimidin-2-ylamino)-N,N,3-trimethylbenzamide |
| 392 | 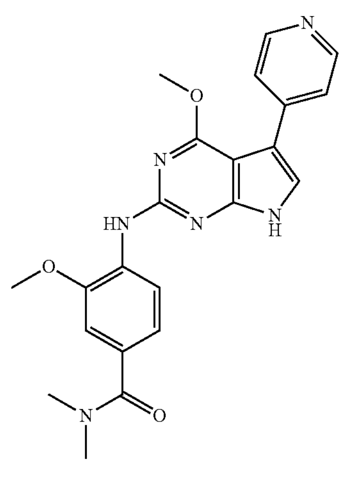 [SMILES: COc1cc(C(=O)N(C)C)ccc1Nc1nc(OC)c2c(-c3ccncc3)c[nH]c2n1] | 3-methoxy-4-(4-methoxy-5-(pyridin-4-yl)-7H-pyrrolo[2,3-d]pyrimidin-2-ylamino)-N,N-dimethylbenzamide |

TABLE A-continued

| Cmpd No. | Structure | Name |
|---|---|---|
| 393 | 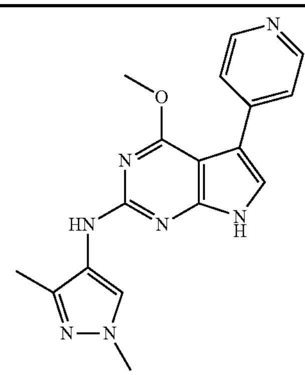 | N-(1,3-dimethyl-1H-pyrazol-4-yl)-4-methoxy-5-(pyridin-4-yl)-7H-pyrrolo[2,3-d]pyrimidin-2-amine |
| 394 | 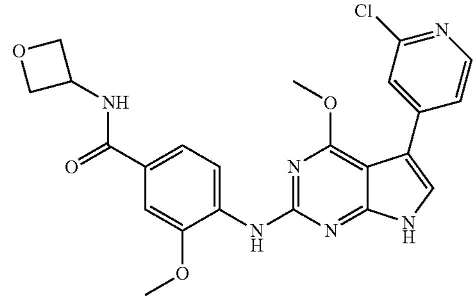 | 4-(5-(2-chloropyridin-4-yl)-4-methoxy-7H-pyrrolo[2,3-d]pyrimidin-2-ylamino)-3-methoxy-N-(oxetan-3-yl)benzamide |
| 395 | 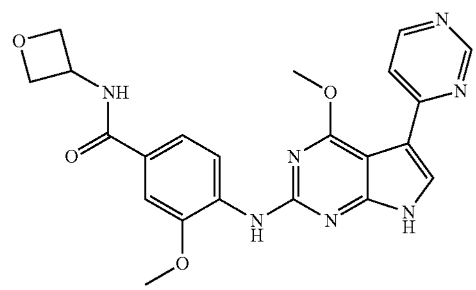 [SMILES: COc1cc(C(=O)NC2COC2)ccc1Nc1nc(OC)c2c(-c3ccncn3)c[nH]c2n1] | 3-methoxy-4-(4-methoxy-5-(pyrimidin-4-yl)-7H-pyrrolo[2,3-d]pyrimidin-2-ylamino)-N-(oxetan-3-yl)benzamide |
| 396 | 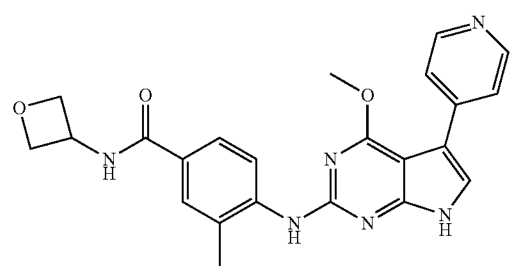 [SMILES: COc1nc(Nc2ccc(C(=O)NC3COC3)cc2C)nc2[nH]cc(-c3ccncc3)c12] | 4-(4-methoxy-5-(pyridin-4-yl)-7H-pyrrolo[2,3-d]pyrimidin-2-ylamino)-3-methyl-N-(oxetan-3-yl)benzamide |
| 397 | 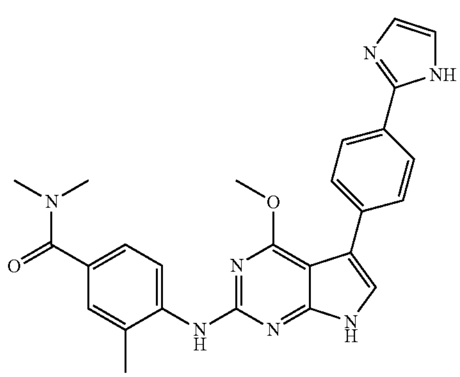 [SMILES: COc1nc(Nc2ccc(C(=O)N(C)C)cc2C)nc2[nH]cc(-c3ccc(-c4ncc[nH]4)cc3)c12] | 4-(5-(4-(1H-imidazol-2-yl)phenyl)-4-methoxy-7H-pyrrolo[2,3-d]pyrimidin-2-ylamino)-N,N,3-trimethylbenzamide |

| Cmpd No. | Structure | Name |
|---|---|---|
| 398 | 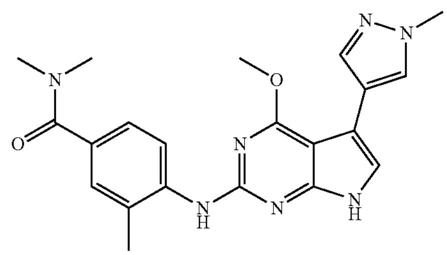 [SMILES: COc1nc(Nc2ccc(C(=O)N(C)C)cc2C)nc2[nH]cc(-c3cnn(C)c3)c12] | 4-(4-methoxy-5-(1-methyl-1H-pyrazol-4-yl)-7H-pyrrolo[2,3-d]pyrimidin-2-ylamino)-N,N,3-trimethylbenzamide |
| 399 | 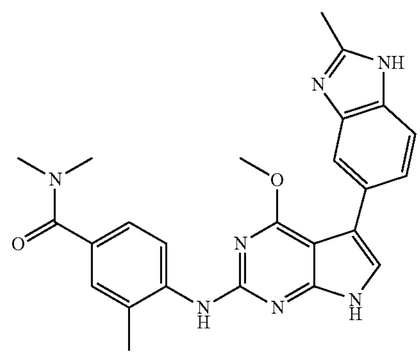 [SMILES: COc1nc(Nc2ccc(C(=O)N(C)C)cc2C)nc2[nH]cc(-c3ccc4[nH]c(C)nc4c3)c12] | 4-(4-methoxy-5-(2-methyl-1H-benzo[d]imidazol-5-yl)-7H-pyrrolo[2,3-d]pyrimidin-2-ylamino)-N,N,3-trimethylbenzamide |
| 400 | 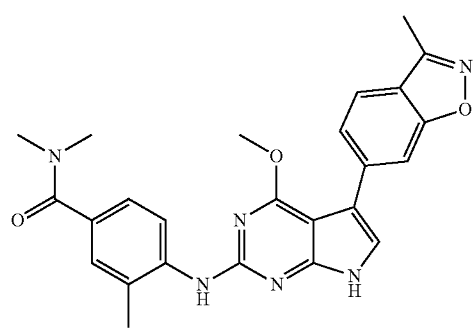 [SMILES: COc1nc(Nc2ccc(C(=O)N(C)C)cc2C)nc2[nH]cc(-c3ccc4c(C)noc4c3)c12] | 4-(4-methoxy-5-(3-methylbenzo[d]isoxazol-6-yl)-7H-pyrrolo[2,3-d]pyrimidin-2-ylamino)-N,N,3-trimethylbenzamide |
| 401 | 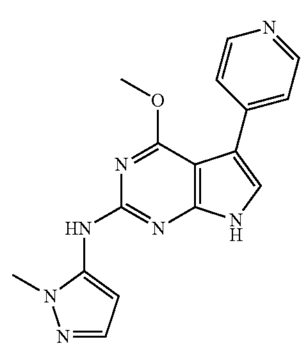 [SMILES: COc1nc(Nc2ccnn2C)nc2[nH]cc(-c3ccncc3)c12] | 4-methoxy-N-(1-methyl-1H-pyrazol-5-yl)-5-(pyridin-4-yl)-7H-pyrrolo[2,3-d]pyrimidin-2-amine |

TABLE A-continued

| Cmpd No. | Structure | Name |
|---|---|---|
| 402 | 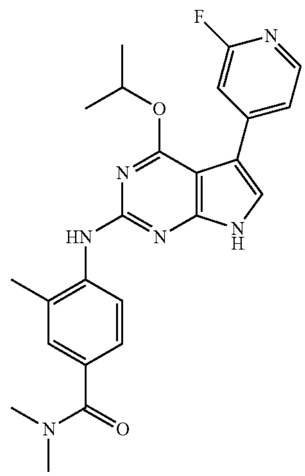 [SMILES: Cc1cc(C(=O)N(C)C)ccc1Nc1nc(OC(C)C)c2c(-c3ccnc(F)c3)c[nH]c2n1] | 4-(5-(2-fluoropyridin-4-yl)-4-isopropoxy-7H-pyrrolo[2,3-d]pyrimidin-2-ylamino)-N,N,3-trimethylbenzamide |
| 403 | 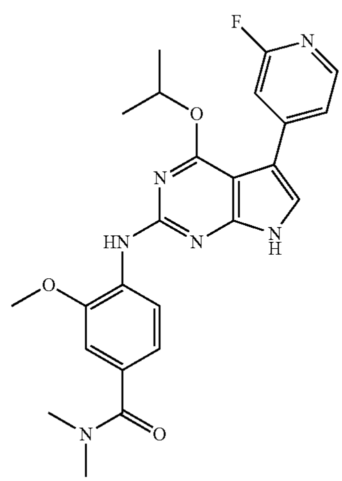 [SMILES: COc1cc(C(=O)N(C)C)ccc1Nc1nc(OC(C)C)c2c(-c3ccnc(F)c3)c[nH]c2n1] | 4-(5-(2-fluoropyridin-4-yl)-4-isopropoxy-7H-pyrrolo[2,3-d]pyrimidin-2-ylamino)-3-methoxy-N,N-dimethylbenzamide |
| 404 | 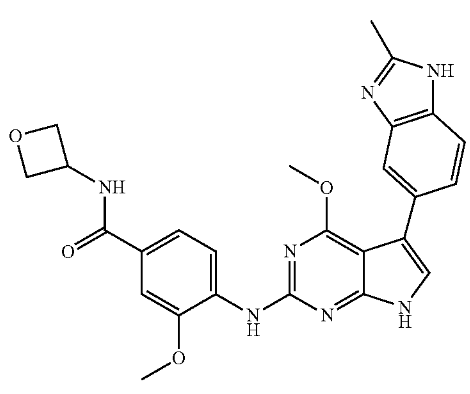 [SMILES: COc1cc(C(=O)NC2COC2)ccc1Nc1nc(OC)c2c(-c3ccc4[nH]c(C)nc4c3)c[nH]c2n1] | 3-methoxy-4-(4-methoxy-5-(2-methyl-1H-benzo[d]imidazol-5-yl)-7H-pyrrolo[2,3-d]pyrimidin-2-ylamino)-N-(oxetan-3-yl)benzamide |

TABLE A-continued

| Cmpd No. | Structure | Name |
|---|---|---|
| 405 | 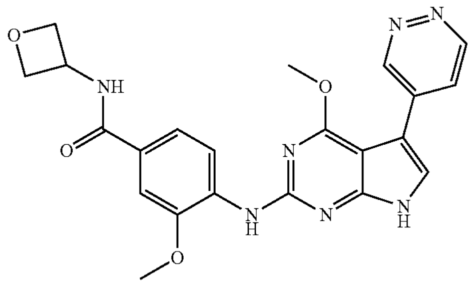 [SMILES: COc1cc(C(=O)NC2COC2)ccc1Nc1nc(OC)c2c(-c3ccnnc3)c[nH]c2n1] | 3-methoxy-4-(4-methoxy-5-(pyridazin-4-yl)-7H-pyrrolo[2,3-d]pyrimidin-2-ylamino)-N-(oxetan-3-yl)benzamide |
| 406 | 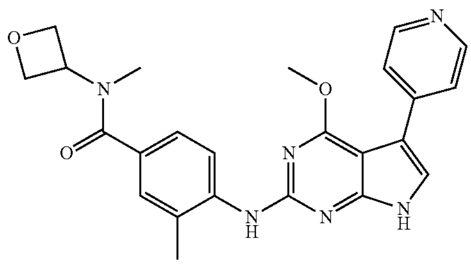 [SMILES: COc1nc(Nc2ccc(C(=O)N(C)C3COC3)cc2C)nc2[nH]cc(-c3ccncc3)c12] | 4-(4-methoxy-5-(pyridin-4-yl)-7H-pyrrolo[2,3-d]pyrimidin-2-ylamino)-N,3-dimethyl-N-(oxetan-3-yl)benzamide |
| 407 | 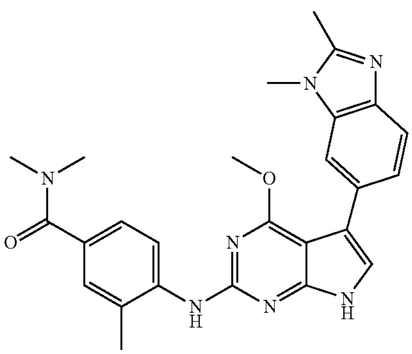 [SMILES: COc1nc(Nc2ccc(C(=O)N(C)C)cc2C)nc2[nH]cc(-c3ccc4nc(C)n(C)c4c3)c12] | 4-(5-(1,2-dimethyl-1H-benzo[d]imidazol-6-yl)-4-methoxy-7H-pyrrolo[2,3-d]pyrimidin-2-ylamino)-N,N,3-trimethylbenzamide |
| 408 | 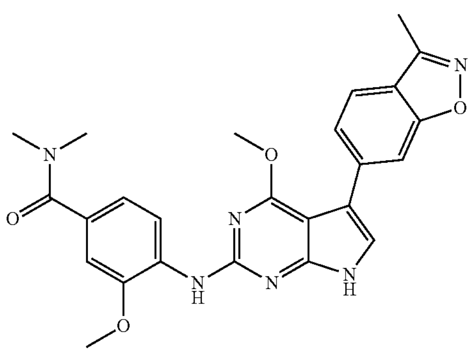 [SMILES: COc1cc(C(=O)N(C)C)ccc1Nc1nc(OC)c2c(-c3ccc4c(C)noc4c3)c[nH]c2n1] | 3-methoxy-4-(4-methoxy-5-(3-methylbenzo[d]isoxazol-6-yl)-7H-pyrrolo[2,3-d]pyrimidin-2-ylamino)-N,N-dimethylbenzamide |
| 409 | 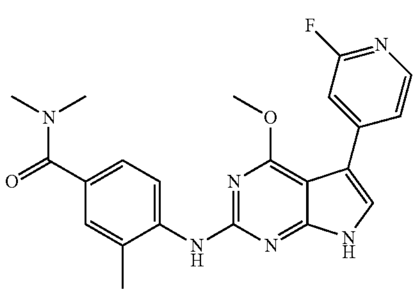 [SMILES: COc1nc(Nc2ccc(C(=O)N(C)C)cc2C)nc2[nH]cc(-c3ccnc(F)c3)c12] | 4-(5-(2-fluoropyridin-4-yl)-4-methoxy-7H-pyrrolo[2,3-d]pyrimidin-2-ylamino)-N,N,3-trimethylbenzamide |

TABLE A-continued

| Cmpd No. | Structure | Name |
|---|---|---|
| 410 | 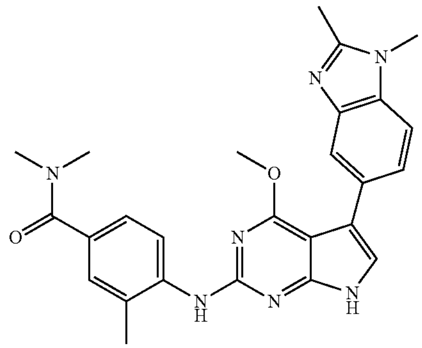 [SMILES: COc1nc(Nc2ccc(C(=O)N(C)C)cc2C)nc2[nH]cc(-c3ccc4c(c3)nc(C)n4C)c12] | 4-(5-(1,2-dimethyl-1H-benzo[d]imidazol-5-yl)-4-methoxy-7H-pyrrolo[2,3-d]pyrimidin-2-ylamino)-N,N,3-trimethylbenzamide |
| 411 | 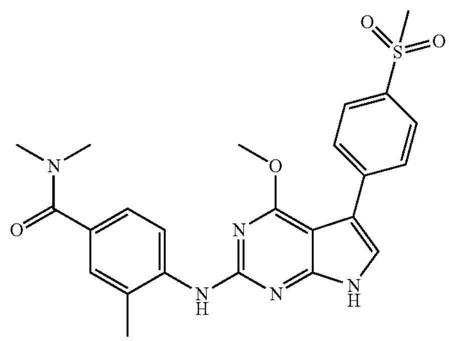 [SMILES: COc1nc(Nc2ccc(C(=O)N(C)C)cc2C)nc2[nH]cc(-c3ccc(S(C)(=O)=O)cc3)c12] | 4-(4-methoxy-5-(4-(methylsulfonyl)phenyl)-7H-pyrrolo[2,3-d]pyrimidin-2-ylamino)-N,N,3-trimethylbenzamide |
| 412 | 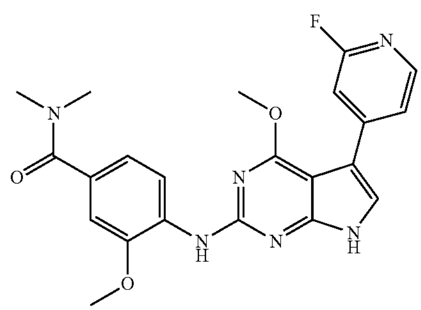 [SMILES: COc1cc(C(=O)N(C)C)ccc1Nc1nc(OC)c2c(-c3ccnc(F)c3)c[nH]c2n1] | 4-(5-(2-fluoropyridin-4-yl)-4-methoxy-7H-pyrrolo[2,3-d]pyrimidin-2-ylamino)-3-methoxy-N,N-dimethylbenzamide |
| 413 | 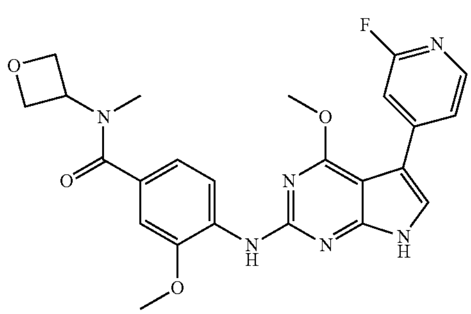 [SMILES: COc1cc(C(=O)N(C)C2COC2)ccc1Nc1nc(OC)c2c(-c3ccnc(F)c3)c[nH]c2n1] | 4-(5-(2-fluoropyridin-4-yl)-4-methoxy-7H-pyrrolo[2,3-d]pyrimidin-2-ylamino)-3-methoxy-N-methyl-N-(oxetan-3-yl)benzamide |
| 414 | 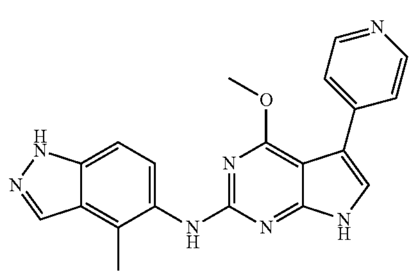 [SMILES: COc1nc(Nc2ccc3[nH]ncc3c2C)nc2[nH]cc(-c3ccncc3)c12] | 4-methoxy-N-(4-methyl-1H-indazol-5-yl)-5-(pyridin-4-yl)-7H-pyrrolo[2,3-d]pyrimidin-2-amine |

TABLE A-continued

| Cmpd No. | Structure | Name |
|---|---|---|
| 415 | 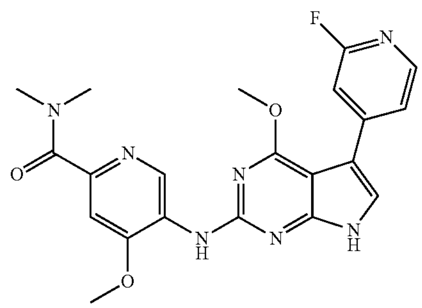 [SMILES: COc1cc(C(=O)N(C)C)ncc1Nc1nc(OC)c2c(-c3ccnc(F)c3)c[nH]c2n1] | 5-(5-(2-fluoropyridin-4-yl)-4-methoxy-7H-pyrrolo[2,3-d]pyrimidin-2-ylamino)-4-methoxy-N,N-dimethylpicolinamide |
| 416 | 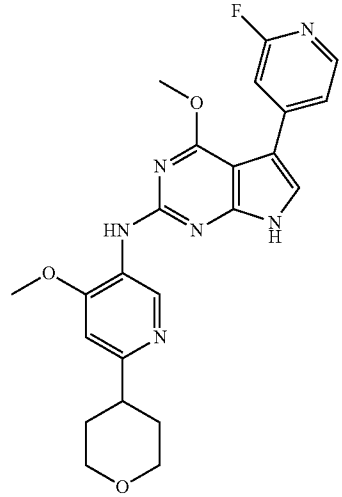 [SMILES: COc1cc(C2CCOCC2)ncc1Nc1nc(OC)c2c(-c3ccnc(F)c3)c[nH]c2n1] | 5-(2-fluoropyridin-4-yl)-4-methoxy-N-(4-methoxy-6-(tetrahydro-2H-pyran-4-yl)pyridin-3-yl)-7H-pyrrolo[2,3-d]pyrimidin-2-amine |
| 417 | 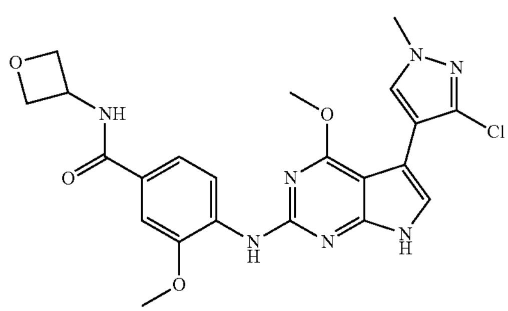 [SMILES: COc1cc(C(=O)NC2COC2)ccc1Nc1nc(OC)c2c(-c3cn(C)nc3Cl)c[nH]c2n1] | 4-(5-(3-chloro-1-methyl-1H-pyrazol-4-yl)-4-methoxy-7H-pyrrolo[2,3-d]pyrimidin-2-ylamino)-3-methoxy-N-(oxetan-3-yl)benzamide |
| 418 | 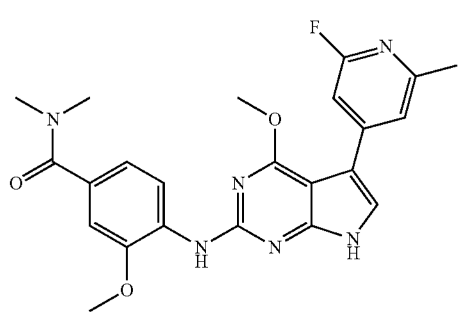 [SMILES: COc1cc(C(=O)N(C)C)ccc1Nc1nc(OC)c2c(-c3cc(C)nc(F)c3)c[nH]c2n1] | 4-(5-(2-fluoro-6-methylpyridin-4-yl)-4-methoxy-7H-pyrrolo[2,3-d]pyrimidin-2-ylamino)-3-methoxy-N,N-dimethylbenzamide |

TABLE A-continued

| Cmpd No. | Structure | Name |
|---|---|---|
| 419 | 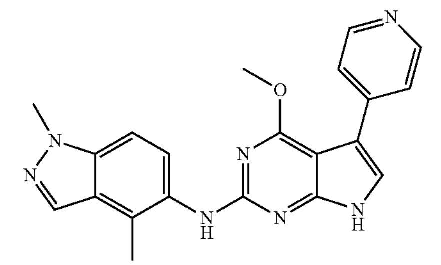 [SMILES: COc1nc(Nc2ccc3c(cnn3C)c2C)nc2[nH]cc(-c3ccncc3)c12] | N-(1,4-dimethyl-1H-indazol-5-yl)-4-methoxy-5-(pyridin-4-yl)-7H-pyrrolo[2,3-d]pyrimidin-2-amine |
| 420 | 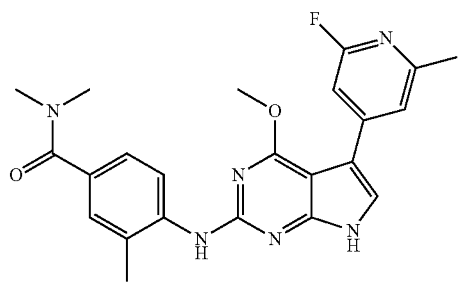 [SMILES: COc1nc(Nc2ccc(C(=O)N(C)C)cc2C)nc2[nH]cc(-c3cc(C)nc(F)c3)c12] | 4-(5-(2-fluoro-6-methylpyridin-4-yl)-4-methoxy-7H-pyrrolo[2,3-d]pyrimidin-2-ylamino)-N,N,3-trimethylbenzamide |
| 421 | 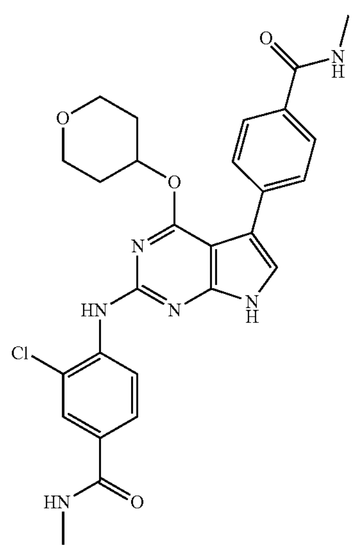 [SMILES: CNC(=O)c1ccc(-c2c[nH]c3nc(Nc4ccc(C(=O)NC)cc4Cl)nc(OC4CCOCC4)c23)cc1] | 3-chloro-N-methyl-4-(5-(4-(methylcarbamoyl)phenyl)-4-(tetrahydro-2H-pyran-4-yloxy)-7H-pyrrolo[2,3-d]pyrimidin-2-ylamino)benzamide |

| Cmpd No. | Structure | Name |
|---|---|---|
| 422 | 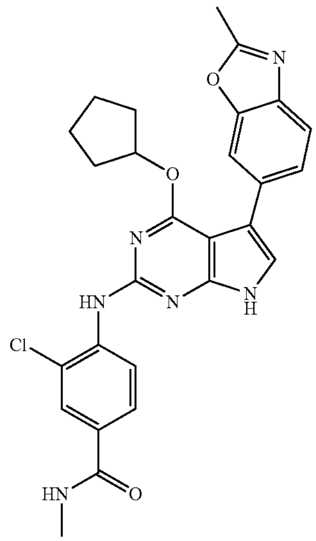 [SMILES: CNC(=O)c1ccc(Nc2nc(OC3CCCC3)c3c(-c4ccc5nc(C)oc5c4)c[nH]c3n2)c(Cl)c1] | 3-chloro-4-(4-(cyclopentyloxy)-5-(2-methylbenzo[d]oxazol-6-yl)-7H-pyrrolo[2,3-d]pyrimidin-2-ylamino)-N-methylbenzamide |
| 423 | 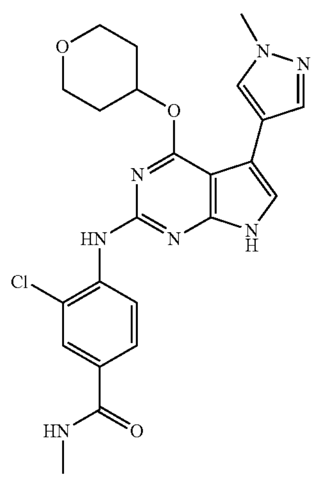 [SMILES: CNC(=O)c1ccc(Nc2nc(OC3CCOCC3)c3c(-c4cnn(C)c4)c[nH]c3n2)c(Cl)c1] | 3-chloro-N-methyl-4-(5-(1-methyl-1H-pyrazol-4-yl)-4-(tetrahydro-2H-pyran-4-yloxy)-7H-pyrrolo[2,3-d]pyrimidin-2-ylamino)benzamide |
| 424 | 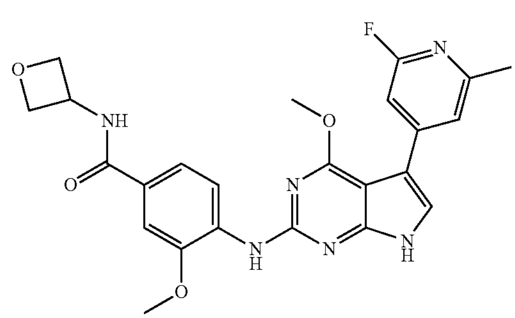 [SMILES: COc1cc(C(=O)NC2COC2)ccc1Nc1nc(OC)c2c(-c3cc(C)nc(F)c3)c[nH]c2n1] | 4-(5-(2-fluoro-6-methylpyridin-4-yl)-4-methoxy-7H-pyrrolo[2,3-d]pyrimidin-2-ylamino)-3-methoxy-N-(oxetan-3-yl)benzamide |

| Cmpd No. | Structure | Name |
|---|---|---|
| 425 | 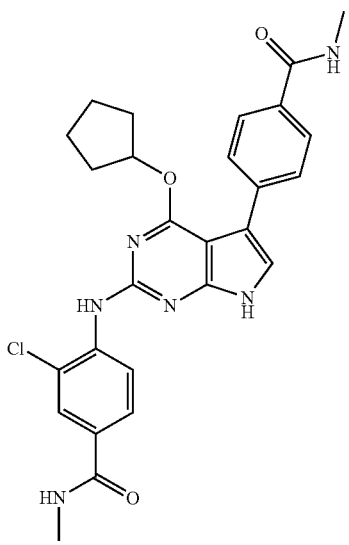 [SMILES: CNC(=O)c1ccc(-c2c[nH]c3nc(Nc4ccc(C(=O)NC)cc4Cl)nc(OC4CCCC4)c23)cc1] | 3-chloro-4-(4-(cyclopentyloxy)-5-(4-(methylcarbamoyl)phenyl)-7H-pyrrolo[2,3-d]pyrimidin-2-ylamino)-N-methylbenzamide |
| 426 | 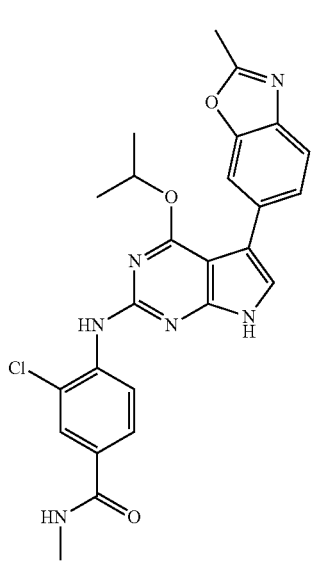 [SMILES: CNC(=O)c1ccc(Nc2nc(OC(C)C)c3c(-c4ccc5nc(C)oc5c4)c[nH]c3n2)c(Cl)c1] | 3-chloro-4-(4-isopropoxy-5-(2-methylbenzo[d]oxazol-6-yl)-7H-pyrrolo[2,3-d]pyrimidin-2-ylamino)-N-methylbenzamide |

| Cmpd No. | Structure | Name |
|---|---|---|
| 427 | 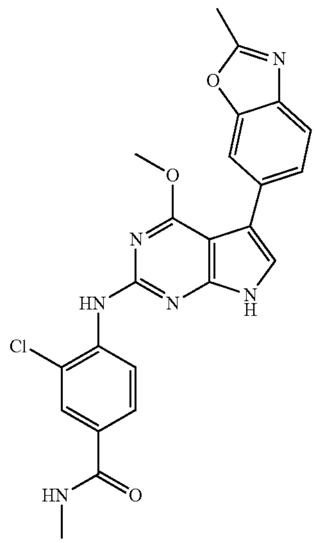 [SMILES: CNC(=O)c1ccc(Nc2nc(OC)c3c(-c4ccc5nc(C)oc5c4)c[nH]c3n2)c(Cl)c1] | 3-chloro-4-(4-methoxy-5-(2-methylbenzo[d]oxazol-6-yl)-7H-pyrrolo[2,3-d]pyrimidin-2-ylamino)-N-methylbenzamide |
| 428 | 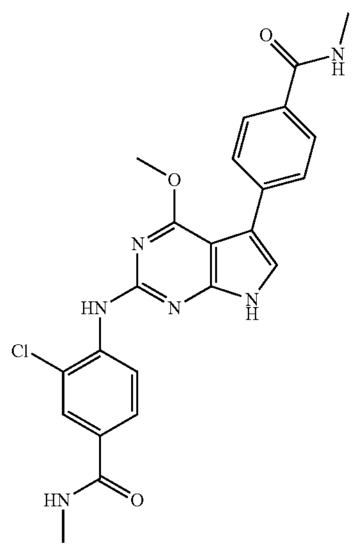 [SMILES: CNC(=O)c1ccc(-c2c[nH]c3nc(Nc4ccc(C(=O)NC)cc4Cl)nc(OC)c23)cc1] | 3-chloro-4-(4-methoxy-5-(4-(methylcarbamoyl)phenyl)-7H-pyrrolo[2,3-d]pyrimidin-2-ylamino)-N-methylbenzamide |
| 429 | 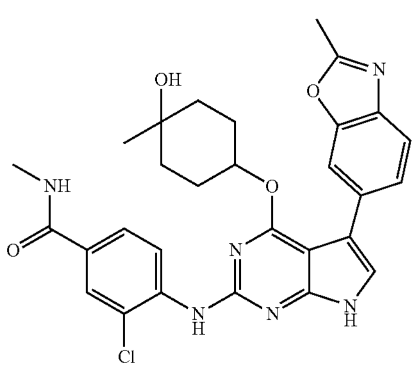 [SMILES: CNC(=O)c1ccc(Nc2nc(OC3CCC(C)(O)CC3)c3c(-c4ccc5nc(C)oc5c4)c[nH]c3n2)c(Cl)c1] | 3-chloro-4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-N-methylbenzamide |

TABLE A-continued
| Cmpd No. | Structure | Name |
|---|---|---|
| 430 | 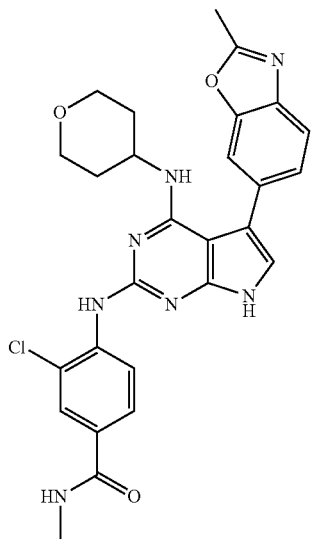 [SMILES: CNC(=O)c1ccc(Nc2nc(NC3CCOCC3)c3c(-c4ccc5nc(C)oc5c4)c[nH]c3n2)c(Cl)c1] | 3-chloro-N-methyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide |
| 431 | 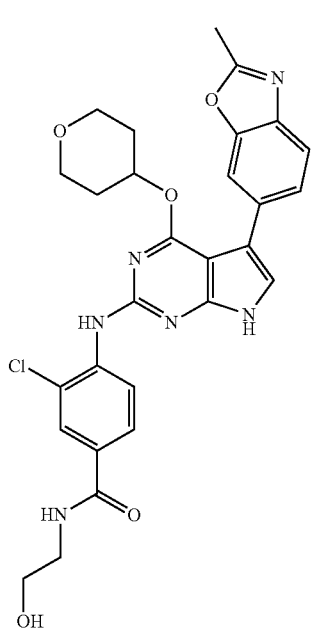 [SMILES: Cc1nc2ccc(-c3c[nH]c4nc(Nc5ccc(C(=O)NCCO)cc5Cl)nc(OC5CCOCC5)c34)cc2o1] | 3-chloro-N-(2-hydroxyethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide |

TABLE A-continued
| Cmpd No. | Structure | Name |
|---|---|---|
| 432 | 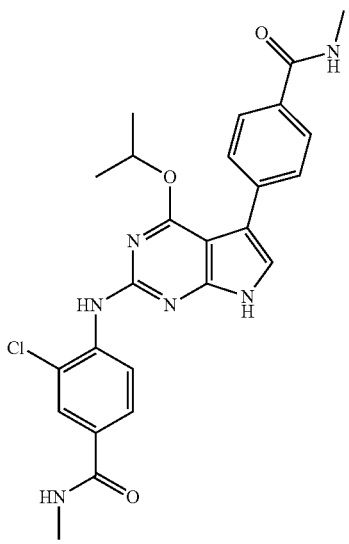 [SMILES: CNC(=O)c1ccc(-c2c[nH]c3nc(Nc4ccc(C(=O)NC)cc4Cl)nc(OC(C)C)c23)cc1] | 3-chloro-4-(4-isopropoxy-5-(4-(methylcarbamoyl)phenyl)-7H-pyrrolo[2,3-d]pyrimidin-2-ylamino)-N-methylbenzamide |
| 433 | 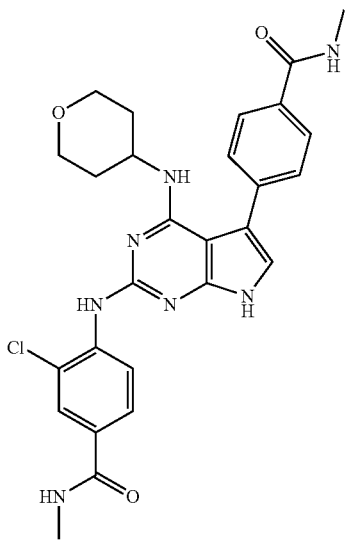 [SMILES: CNC(=O)c1ccc(-c2c[nH]c3nc(Nc4ccc(C(=O)NC)cc4Cl)nc(NC4CCOCC4)c23)cc1] | 3-chloro-N-methyl-4-(5-(4-(methylcarbamoyl)phenyl)-4-(tetrahydro-2H-pyran-4-ylamino)-7H-pyrrolo[2,3-d]pyrimidin-2-ylamino)benzamide |

| Cmpd No. | Structure | Name |
|---|---|---|
| 434 | 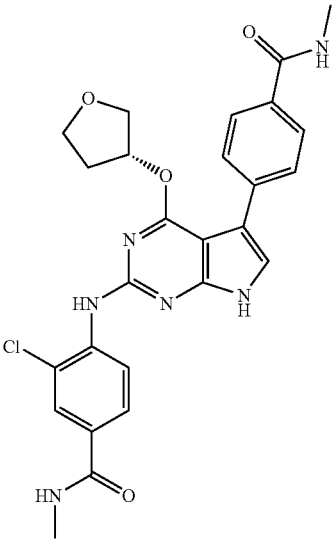 [SMILES: CNC(=O)c1ccc(-c2c[nH]c3nc(Nc4ccc(C(=O)NC)cc4Cl)nc(O[C@@H]4CCOC4)c23)cc1] | (R)-3-chloro-N-methyl-4-(5-(4-(methylcarbamoyl)phenyl)-4-(tetrahydrofuran-3-yloxy)-7H-pyrrolo[2,3-d]pyrimidin-2-ylamino)benzamide |
| 435 | 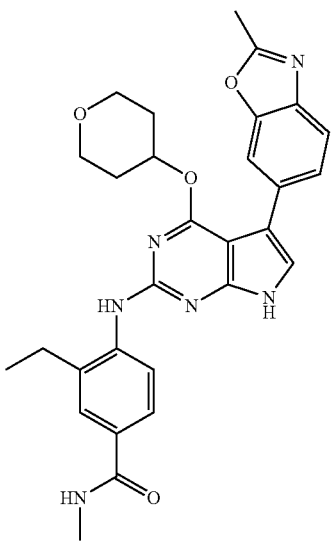 | 3-ethyl-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide |

TABLE A-continued

| Cmpd No. | Structure | Name |
|---|---|---|
| 436 | 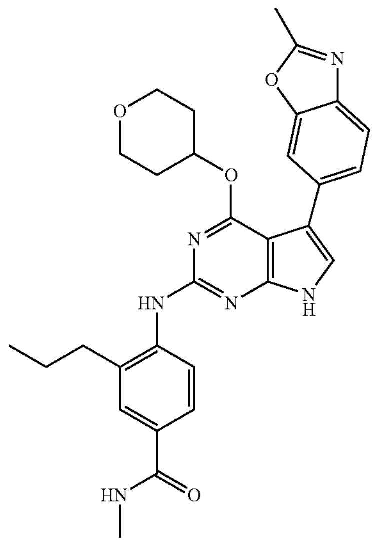 [SMILES: CCCc1cc(C(=O)NC)ccc1Nc1nc(OC2CCOCC2)c2c(-c3ccc4nc(C)oc4c3)c[nH]c2n1] | N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-propylbenzamide |
| 437 | 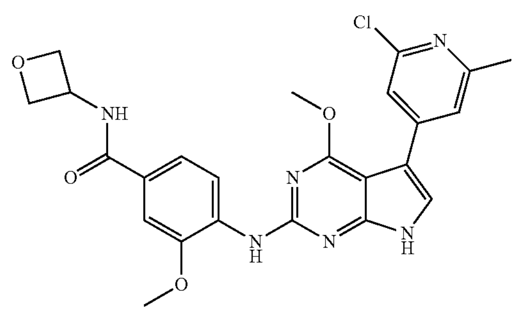 | 4-(5-(2-chloro-6-methylpyridin-4-yl)-4-methoxy-7H-pyrrolo[2,3-d]pyrimidin-2-ylamino)-3-methoxy-N-(oxetan-3-yl)benzamide |
| 438 | 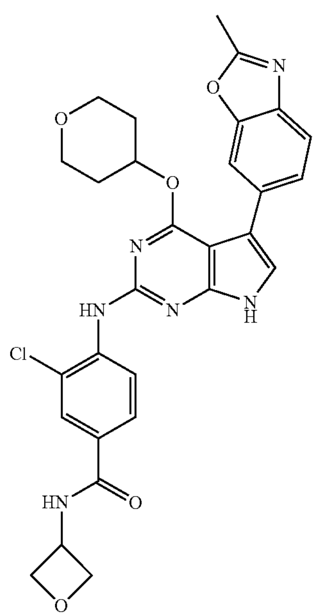 [SMILES: Cc1nc2ccc(-c3c[nH]c4nc(Nc5ccc(C(=O)NC6COC6)cc5Cl)nc(OC5CCOCC5)c34)cc2o1] | 3-chloro-4-(5-(2-methylbenzo[d]oxazol-6-yl)-4-(tetrahydro-2H-pyran-4-yloxy)-7H-pyrrolo[2,3-d]pyrimidin-2-ylamino)-N-(oxetan-3-yl)benzamide |

Methods for Making Pyrrolopyrimidine Compounds

The Pyrrolopyrimidine Compounds described herein can be obtained using conventional organic syntheses and commercially available starting materials.

Starting materials useful for preparing compounds of formula (I) and intermediates therefore, are commercially available or can be prepared from commercially available materials using known synthetic methods and reagents.

Particular methods for preparing compounds of formula (I) are disclosed in U.S. patent application Ser. No. 14/155,485, filed Jan. 15, 2014, and U.S. patent application Ser. No. 14/155,498, filed Jan. 15, 2014, each incorporated by reference herein in their entirety.

Methods of Use

The Pyrrolopyrimidine Compounds have utility as pharmaceuticals to treat, prevent or improve cancer in animals or humans. Accordingly, the Pyrrolopyrimidine Compounds provided herein can be used in all the methods as provided herein. Particularly, the Pyrrolopyrimidine Compounds provided herein can be used in the treatment, prevention or improvement of all diseases disorders, or conditions provided herein. Accordingly, provided herein are uses of the Pyrrolopyrimidine Compounds, including the treatment or prevention of those cancers set forth below. The methods provided herein comprise the administration of an effective amount of one or more Pyrrolopyrimidine Compound(s) to a subject in need thereof.

In another aspect, provided herein are methods for treating or preventing a cancer, comprising administering to a subject in need thereof an effective amount of a Pyrrolopyrimidine Compound, as described herein. In some embodiments, the cancer is a solid tumor or a hematological tumor. In some embodiments, the cancer is not triple negative breast cancer (TNBC).

In some embodiments, the solid tumor is bladder cancer (including superficial bladder cancer), breast cancer (including luminal B type, ER+, PR+ and Her2+ breast cancer), central nervous system cancer (including glioblastoma multiforme (GBM), glioma, medulloblastoma, and astrocytoma), colorectal cancer, gastrointestinal cancer (including stomach cancer, oesophagus cancer, and rectum cancer), endocrine cancer (including thyroid cancer, and adrenal gland cancer), eye cancer (including retinoblastoma), female genitourinary cancer (including cancer of the placenta, uterus, vulva, ovary, cervix), head and neck cancer (including cancer of the pharynx, oesophagus, and tongue), liver cancer, lung cancer (including non-small cell lung cancer (NSCLC), small cell lung cancer (SCLC), mucoepidermoid, bronchogenic, squamous cell carcinoma (SQCC), and anaplastic/NSCLC), skin cancer (including melanoma, and SQCC), soft tissue cancer (including sarcoma, Ewing's sarcoma, and rhabdomyosarcoma), bone cancer (including sarcoma, Ewing's sarcoma, and osteosarcoma), squamous cell cancer (including lung, esophageal, cervical, and head and neck cancer), pancreas cancer, kidney cancer (including renal Wilm's tumor and renal cell carcinoma), or prostate cancer. In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

In some embodiments, the hematological cancer is leukemia (including acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), and large cell immunoblastic lymphoma), or multiple myeloma.

In some embodiments, provided herein are methods for preventing cancer metastasis, comprising administering to a subject in need thereof an effective amount of a Pyrrolopyrimidine Compound, as described herein. In some embodiments, the cancer is a metastatic cancer, in particular, a metastatic solid tumor or metastatic hematologic cancer, wherein the solid tumor and hematologic cancer is as described herein. In other embodiments, provided herein are methods of preventing cancer metastasis, comprising administering to a subject in need thereof an effective amount of a Pyrrolopyrimidine Compound, as described herein. In yet another aspect, provided herein are methods of eradicating cancer stem cells in a subject, comprising administering to a subject in need thereof an effective amount of a Pyrrolopyrimidine Compound, as described herein. In other embodiments, provided herein are methods of inducing differentiation in cancer stem cells in a subject, comprising administering to a subject in need thereof an effective amount of a Pyrrolopyrimidine Compound, as described herein. In other embodiments, provided herein are methods of inducing cancer stem cell death in a subject, comprising administering to a subject in need thereof an effective amount of a Pyrrolopyrimidine Compound, as described herein. In some such embodiments, the cancer is a solid tumor, for example a CNS cancer (e.g. GBM) or breast cancer, or a hematological cancer, such as leukemia.

In another aspect, provided herein are methods for treating or preventing a cancer, in particular a solid tumor or a hematological tumor as described herein, comprising administering to a subject in need thereof an effective amount of a compound that inhibits TTK, CLK1, and CLK2 kinase activity, and optionally CAMKK2 kinase activity. In some embodiments, provided are methods for treating or preventing a cancer, in particular a solid tumor or a hematological tumor as described herein, comprising administering to a subject in need thereof an effective amount of a compound that inhibits TTK, CLK1, and CLK2 kinase activity. In some embodiments, the TTK, CLK1, and CLK2 kinase activity is inhibited in a cell. In some embodiments, the TTK, CLK1, and CLK2 kinase activity is inhibited in vivo. In some embodiments, the compound that inhibits TTK, CLK1, and CLK2 kinase activity is a Pyrrolopyrimidine Compound as described herein. In another aspect, provided herein are methods for treating or preventing a cancer associated with the pathways involving TTK, CLK1, and CLK2, and optionally CAMKK2, and mutants or isoforms thereof, comprising administering to a subject in need thereof an effective amount of a compound that inhibits TTK, CLK1, and CLK2 kinase activity, and optionally CAMKK2 kinase activity. In some embodiments, the cancer associated with the TTK, CLK1, and CLK2, and optionally CAMKK2, pathways include a solid tumor or a hematological tumor as described herein. In some embodiments, the TTK, CLK1, and CLK2, and optionally CAMKK2, pathway is inhibited in a cell. In some embodiments, the TTK, CLK1, and CLK2, and optionally CAMKK2, pathway is inhibited in vivo. In some embodiments, the compound that inhibits TTK, CLK1, and CLK2, and optionally CAMKK2, pathway is a Pyrrolopyrimidine Compound as described herein.

In certain embodiments, provided herein are methods for measuring inhibition of TTK, CLK1, and CLK2 kinase activity, and optionally CAMKK2 kinase activity, in a patient having a cancer, for example a solid tumor or a hematological tumor as described herein, comprising administering an effective amount of a Pyrrolopyrimidine Compound to said patient, measuring the amount of TTK, CLK1, and CLK2 kinase activity in said patient, and comparing said amount of TTK, CLK1, and CLK2 kinase activity to that of said patient prior to administration of an effective amount of a Pyrrolopyrimidine Compound. In certain embodiments, less TTK, CLK1, and CLK2 kinase activity, and optionally CAMKK2 kinase activity, in said biological sample obtained after administration of said Pyrrolopyrimidine Compound relative to the amount of TTK, CLK1, and CLK2 kinase activity, and optionally CAMKK2 kinase activity, in said biological sample obtained prior to administration of said Pyrrolopyrimidine Compound indicates inhibition.

In one embodiment, the kinase activity is measured using a radioactivity based kinase assay, which measures the incorporation of a radioactively labeled phosphate moiety (for example, $^{33}P$ labeled phosphate) into a substrate, for example, a peptide substrate. Reduced levels of radioactively labeled phosphate incorporation into the substrate indicates inhibition of kinase activity. In another embodiment, the kinase activity is measured using a time-resolved-fluorescence resonance energy transfer (TR-FRET) based kinase assay, which measures loss of fluorescence as a result of substrate phosphorylation, for example, a peptide substrate (see for example Invitrogen Z'-Lyte Assay®). Increased levels of fluorescence indicates inhibition of kinase activity. In another embodiment, the kinase activity is measured using a competitive tracer binding assay (for example, Invitrogen Lanthascreen® Eu binding assay), which measures fluorescence as a result of tracer binding (for example ATP site binding). Reduced fluorescence indicates displacement of tracer binding, which indicates inhibition of kinase activity. In yet another embodiment, the kinase activity is measured using a cellular biomarker assay, which measures the phosphorylation of a substrate, for example a downstream substrate, using Western Blot, ELISA or Mesoscale. Reduced phosphorylation of the substrate indicates inhibition of kinase activity.

In some embodiments, the inhibition of TTK, CLK1, and CLK2 kinase activity, and optionally CAMKK2 kinase activity, is assessed in a biological sample of the patient, such as in circulating blood cells, or tumor or skin biopsies. In such embodiments, the amount of inhibition of kinase activity is assessed by comparison of the amount of phosphorylated substrate (for example for TTK: phospho-TTK, such as p-TTK T686, or phosphorylated borealin, BubR1, Chk2, c-Abl, p53, Mip1 or TACC2; and for CLK2 (phospho-SRp75, or phosphorylated PP2A regulatory subunit B56β (PPP2R5B, B'β) or PGC-1α) before and after administration of the Pyrrolopyrimidine Compound to the patient. In some such embodiments, less phosphorylated TTK substrate and less phosphorylated CLK2 substrate, in said biological sample, obtained after administration of said Pyrrolopyrimidine Compound relative to the amount of phosphorylated TTK substrate and phosphorylated CLK2 substrate, in said biological sample obtained prior to administration of said Pyrrolopyrimidine Compound indicates inhibition. In some such embodiments, less phospho-TTK (for example p-TTK T686) and phospho-SRp75, in said biological sample obtained after administration of said Pyrrolopyrimidine Compound relative to the amount of phospho-TTK (for example p-TTK T686) and phospho-SRp75, in said biological sample obtained prior to administration of said Pyrrolopyrimidine Compound indicates inhibition.

In certain embodiments, provided herein are methods for inhibiting TTK, CLK1, and CLK2 kinase activity, and optionally CAMKK2 kinase activity, in a patient having a cancer, in particular a solid tumor or a hematological tumor as described herein, comprising administering an effective amount of a Pyrrolopyrimidine Compound to said patient. In some embodiments, the methods additionally comprise comparing the amount of TTK, CLK1, and CLK2 kinase activity, and optionally CAMKK2 activity, in a biological sample of a patient obtained prior to and after administration of said Pyrrolopyrimidine Compound, wherein less TTK, CLK1, and CLK2 kinase activity, and optionally CAMKK2 kinase activity, in said biological sample obtained after administration of said Pyrrolopyrimidine Compound relative to the amount of TTK, CLK1, and CLK2 kinase activity, and optionally CAMKK2 kinase activity, in said biological sample obtained prior to administration of said Pyrrolopyrimidine Compound indicates inhibition.

In some embodiments, the methods additionally comprise comparing the amount of phosphorylated substrate (for example for TTK: phospho-TTK, such as p-TTK T686, or phosphorylated borealin, BubR1, Chk2, c-Abl, p53, Mip1 or TACC2; and for CLK2 (phospho-SRp75, or phosphorylated PP2A regulatory subunit B56β (PPP2R5B, B'β) or PGC-1α) in a biological sample of a patient obtained prior to and after administration of said Pyrrolopyrimidine Compound, wherein less phosphorylated substrate in said biological sample obtained after administration of said Pyrrolopyrimidine Compound relative to the amount of phosphorylated substrate in said biological sample obtained prior to administration of said Pyrrolopyrimidine Compound indicates inhibition. In other embodiments, the methods additionally comprise comparing the amount of phospho-TTK (for example p-TTK T686) and phospho-SRp75, in a biological sample of a patient obtained prior to and after administration of said Pyrrolopyrimidine Compound, wherein less phospho-TTK (for example p-TTK T686) and phospho-SRp75, in said biological sample obtained after administration of said Pyrrolopyrimidine Compound relative to the amount of phospho-TTK (for example p-TTK T686) and phospho-SRp75, in said biological sample obtained prior to administration of said Pyrrolopyrimidine Compound indicates inhibition.

In some embodiments, the TTK kinase activity is inhibited with an $IC_{50}$ no greater than about 20 nM. In another, the TTK kinase activity is inhibited with an $IC_{50}$ between about 0.01 nM and about 20 nM. In others, the TTK kinase activity is inhibited with an $IC_{50}$ between about 0.01 nM and about 100 nM. In still others, the TTK kinase activity is inhibited with an $IC_{50}$ between about 0.01 nM and about 200 nM. In yet others, the TTK kinase activity is inhibited with an $IC_{50}$ between about 0.1 nM and about 500 nM. In some embodiments, the CLK1 kinase activity is inhibited with an $IC_{50}$ no greater than about 300 nM. In some embodiments, the CLK1 kinase activity is inhibited with an $IC_{50}$ between about 1 nM and about 100 nM. In others, the CLK1 kinase activity is inhibited with an $IC_{50}$ between about 1 nM and about 500 nM. In yet others, the CLK1 kinase activity is inhibited with an $IC_{50}$ between about 1 nM and about 1000 nM. In some embodiments, the CLK2 kinase activity is inhibited with an $IC_{50}$ no greater than about 10 nM. In another, the CLK2 kinase activity is inhibited with an $IC_{50}$ between about 0.01 nM and about 20 nM. In others, the CLK2 kinase activity is inhibited with an $IC_{50}$ between about 0.01 nM and about 100 nM. In still others, the CLK2 kinase activity is inhibited with an $IC_{50}$ between about 0.01 nM and about 200 nM. In yet others, the CLK2 kinase activity is inhibited with an $IC_{50}$ between about 0.1 nM and about 500 nM. In some embodiments, the CAMKK2 kinase activity is inhibited with an $IC_{50}$ no greater than about 1000 nM. In another, the CAMKK2 kinase activity is inhibited with an $IC_{50}$ between about 1 nM and about 500 nM. In others, the CAMKK2 kinase activity is inhibited with an $IC_{50}$ between about 1 nM and about 1000 nM. In still others, the CAMKK2 kinase activity is inhibited with an $IC_{50}$ between about 1 nM and about 2000 nM. In yet others, the CAMKK2 kinase activity is inhibited with an $IC_{50}$ between about 1 nM and about 5000 nM.

In one embodiment, provided herein are methods for achieving a Response Evaluation Criteria in Solid Tumors (RECIST 1.1) of complete response, partial response or stable disease in a patient comprising administering an effective amount of a Pyrrolopyrimidine Compound to a patient having a cancer, in particular a solid tumor as described herein. In another embodiment, provided herein are methods to increase Progression Free Survival rates, as determined by Kaplan-Meier estimates.

In one embodiment, provided herein are methods for preventing or delaying a Response Evaluation Criteria in Solid Tumors (RECIST 1.1) of progressive disease in a patient, comprising administering an effective amount of a Pyrrolopyrimidine Compound to a patient having a solid tumor as described herein. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain.

In certain embodiments, provided herein are methods for decreasing the size of target lesions in a patient compared to pre-treatment, comprising administering an effective amount of a Pyrrolopyrimidine Compound to a patient having a cancer, in particular a solid tumor as described herein.

In certain embodiments, provided herein are methods for decreasing the size of a non-target lesion in a patient compared to pre-treatment, comprising administering an effective amount of a Pyrrolopyrimidine Compound to a patient having a cancer, in particular a solid tumor as described herein.

In certain embodiments, provided herein are methods for achieving a reduction in the number of target lesions in a patient compared to pre-treatment, comprising administering an effective amount of a Pyrrolopyrimidine Compound to a patient having a cancer, in particular a solid tumor as described herein.

In certain embodiments, provided herein are methods for achieving a reduction in the number of non-target lesions in a patient compared to pre-treatment, comprising administering an effective amount a Pyrrolopyrimidine Compound to a patient having a cancer, in particular a solid tumor as described herein.

In certain embodiments, provided herein are methods for achieving an absence of all target lesions in a patient, comprising administering an effective amount of a Pyrrolopyrimidine Compound to a patient having a cancer, in particular a solid tumor as described herein.

In certain embodiments, provided herein are methods for achieving an absence of all non-target lesions in a patient, comprising administering an effective amount of a Pyrrolopyrimidine Compound to a patient having a cancer, in particular a solid tumor as described herein.

In certain embodiments, provided herein are methods for treating a cancer, in particular a solid tumor as described herein, the methods comprising administering an effective amount of a Pyrrolopyrimidine Compound to a patient having a cancer, in particular a solid tumor, wherein the treatment results in a complete response, partial response or stable disease, as determined by Response Evaluation Criteria in Solid Tumors (RECIST 1.1).

In certain embodiments, provided herein are methods for treating a cancer, in particular a solid tumor as described herein, the methods comprising administering an effective amount of a Pyrrolopyrimidine Compound to a patient having a cancer, in particular a solid tumor as described herein, wherein the treatment results in a reduction in target lesion size, a reduction in non-target lesion size and/or the absence of new target and/or non-target lesions, compared to pre-treatment.

In certain embodiments, provided herein are methods for treating a cancer, in particular a solid tumor as described herein, the methods comprising administering an effective amount a Pyrrolopyrimidine Compound to a patient having a cancer, in particular a solid tumor as described herein, wherein the treatment results in prevention or retarding of clinical progression, such as cancer-related cachexia or increased pain.

In another embodiment, provided herein are methods for inducing a therapeutic response characterized with the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586) of a patient, comprising administering an effective amount a Pyrrolopyrimidine Compound to a patient having a cancer, in particular hematological cancers such as lymphoma, as described herein. In another embodiment, provided herein are methods for achieving complete remission, partial remission or stable disease, as determined by the International Workshop Criteria (IWC) for NHL in a patient, comprising administering an effective amount of a Pyrrolopyrimidine Compound to a patient having a cancer, in particular hematological cancers such as lymphoma, as described herein. In another embodiment, provided herein are methods for achieving an increase in overall survival, progression-free survival, event-free survival, time to progression, disease-free survival or lymphoma-free survival as determined by the International Workshop Criteria (IWC)

for NHL in a patient, comprising administering an effective amount of a Pyrrolopyrimidine Compound to a patient having a cancer, in particular hematological cancers such as lymphoma, as described herein.

In another embodiment, provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a patient, comprising administering an effective amount of a Pyrrolopyrimidine Compound to a patient having a cancer, in particular multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a Pyrrolopyrimidine Compound to a patient having a cancer, in particular multiple myeloma. In another embodiment, provided herein are methods for achieving an increase in overall survival, progression-free survival, event-free survival, time to progression, or disease-free survival in a patient, comprising administering an effective amount of a Pyrrolopyrimidine Compound to a patient having a cancer, in particular multiple myeloma.

In another embodiment, provided herein are methods for inducing a therapeutic response assessed with the Response Assessment for Neuro-Oncology (RANO) Working Group for GBM (see Wen P., Macdonald, D R., Reardon, D A., et al. Updated response assessment criteria for highgrade gliomas: Response assessment in neuro-oncology working group. J. Clin. Oncol. 2010; 28: 1963-1972) of a patient, comprising administering an effective amount of a Pyrrolopyrimidine Compound to a patient having a cancer, in particular glioblastoma multiforme (GBM). In one embodiment, RANO will be used to establish the proportion of subjects progression-free at 6 months from Day 1 relative to efficacy evaluable subjects in the GBM type.

In another embodiment, provided herein are methods for improving the Eastern Cooperative Oncology Group Performance Status (ECOG) of a patient, comprising administering an effective amount a Pyrrolopyrimidine Compound to a patient having a cancer, in particular a solid tumor or hematological cancer as described herein.

In another embodiment, provided herein are methods for inducing a therapeutic response assessed by Positron Emission Tomography (PET) outcome of a patient, comprising administering an effective amount of a Pyrrolopyrimidine Compound to a patient having a cancer, in particular a solid tumor or hematological cancer as described herein. In certain embodiments, provided herein are methods for treating a cancer, in particular a solid tumor or hematological cancer as described herein, the methods comprising administering an effective amount of a Pyrrolopyrimidine Compound to a patient having a cancer, in particular a solid tumor or hematological cancer as described herein, wherein the treatment results in a reduction in tumor metabolic activity, for example, as measured by PET imaging.

In some embodiments of the methods described herein, the Pyrrolopyrimidine Compound is a compound as described herein. In one embodiment, the Pyrrolopyrimidine Compound is a compound of formula (I). In another embodiment, the Pyrrolopyrimidine Compound is a compound from Table A. In one embodiment, the Pyrrolopyrimidine Compound is a Pyrrolopyrimidine Compound set forth herein having molecular formula $C_{26}H_{24}N_6O_4$. In another, the Pyrrolopyrimidine Compound is a Pyrrolopyrimidine Compound set forth herein having molecular formula $C_{26}H_{26}N_6O_4$. In yet another, the Pyrrolopyrimidine Compound is a Pyrrolopyrimidine Compound set forth herein having molecular formula $C_{26}H_{27}N_5O_4$. In yet another, the Pyrrolopyrimidine Compound is a Pyrrolopyrimidine Compound set forth herein having molecular formula $C_{28}H_{28}N_6O_4$. In still another, the Pyrrolopyrimidine Compound is a Pyrrolopyrimidine Compound set forth herein having molecular formula $C_{28}H_{30}N_6O_4$. In another embodiment, the Pyrrolopyrimidine Compound is a Pyrrolopyrimidine Compound set forth herein having molecular formula $C_{29}H_{30}N_6O_5$. In one embodiment, the Pyrrolopyrimidine Compound is 4-((4-(cyclopentyloxy)-5-(4-hydroxyphenyl)-7H-pyrrolo[2,3-d]pyrimidin-2-yl)amino)-3-methoxy-N-methylbenzamide (Compound 3). In another, the Pyrrolopyrimidine Compound is 4-((4-cyclopropoxy-5-(2-methylbenzo[d]oxazol-6-yl)-7H-pyrrolo[2,3-d]pyrimidin-2-yl)amino)-3-methoxy-N-methylbenzamide (Compound 152). In yet another, the Pyrolopyrimidine is 4-((4-isopropoxy-5-(2-methylbenzo[d]oxazol-6-yl)-7H-pyrrolo[2,3-d]pyrimidin-2-yl)amino)-3-methoxy-N-methylbenzamide (Compound 125). In still another, the Pyrolopyrimidine is 4-((4-(cyclopentyloxy)-5-(2-methylbenzo[d]oxazol-6-yl)-7H-pyrrolo[2,3-d]pyrimidin-2-yl)amino)-3-methoxy-N-methylbenzamide (Compound 38). In another embodiment, the Pyrolopyrimidine is 4-((4-(cyclopentyloxy)-5-(4-(methylcarbamoyl)phenyl)-7H-pyrrolo[2,3-d]pyrimidin-2-yl)amino)-3-methoxy-N-methylbenzamide (Compound 79). In yet another embodiment, the Pyrolopyrimidine is 4-((4-(cyclopentyloxy)-5-(2-methylbenzo[d]oxazol-6-yl)-7H-pyrrolo[2,3-d]pyrimidin-2-yl)amino)-N-(2-hydroxyethyl)-3-methoxybenzamide (Compound 101).

Further provided herein are methods for treating patients who have been previously treated for a cancer, in particular a solid tumor or a hematological cancer as described herein, as well as those who have not previously been treated. Because patients with a cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

Pharmaceutical Compositions and Routes of Administration

The Pyrrolopyrimidine Compounds can be administered to a subject parenterally in the conventional form of preparations, such as injections, suspensions, solutions and emulsions. Suitable vehicles that can be used to provide intravenous formulations of a Pyrrolopyrimidine Compound are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. An intravenous formulation can be prepared by reconstituting a Pyrrolopyrimidine Compound with such a suitable liquid vehicle. A desired concentration of the intravenous formulation can be obtained by reconstituting an appropriate amount of a Pyrrolopyrimidine Compound with an appropriate volume of liquid vehicle. A desired concentration of the intravenous formulation provides a therapeutically effective amount of a Pyrrolopyrimidine Compound to the patient in need of the intravenous formulation and maintains a therapeutically effective level of a Pyrrolopyrimidine Compound in the patient. The dose which is therapeutically effective will depend on the rate at which the intravenous formulation is delivered to the patient and the concentration of the intravenous formulation.

The effective amount of the Pyrrolopyrimidine Compound in the pharmaceutical composition may be at a level that will exercise the desired effect; for example, about 0.005 mg/kg of a subject's body weight to about 100 mg/kg of a subject's body weight in unit dosage for parenteral administration.

The dose of a Pyrrolopyrimidine Compound to be administered to a subject is rather widely variable and can be subject to the judgment of a health-care practitioner. In general, the Pyrrolopyrimidine Compounds can be administered one to seven times a week, once every two weeks, once every three weeks or once every four weeks in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per week. In others, one dose is given two, three or four times per week. In still others, one dose is given per two weeks, per three weeks or per four weeks. In any given case, the amount of the Pyrrolopyrimidine Compound administered will depend on such factors as the solubility of the active component, the formulation used and the route of administration.

In another embodiment, provided herein are methods for the treatment or prevention of a disease or disorder comprising the administration of about 0.375 mg/dose to about 750 mg/dose, about 0.75 mg/dose to about 375 mg/dose, about 3.75 mg/dose to about 75 mg/dose, about 7.5 mg/dose to about 55 mg/dose or about 18 mg/dose to about 37 mg/dose of a Pyrrolopyrimidine Compound to a subject in need thereof.

In another embodiment, provided herein are methods for the treatment or prevention of a disease or disorder comprising the administration of about 1 mg/dose to about 1200 mg/dose, about 10 mg/dose to about 1200 mg/dose, about 100 mg/dose to about 1200 mg/dose, about 400 mg/dose to about 1200 mg/dose, about 600 mg/dose to about 1200 mg/dose, about 400 mg/dose to about 800 mg/dose or about 600 mg/dose to about 800 mg/dose of a Pyrrolopyrimidine Compound to a subject in need thereof. In a particular embodiment, the methods disclosed herein comprise the administration of 400 mg/dose, 600 mg/dose or 800 mg/dose of a Pyrrolopyrimidine Compound to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Pyrrolopyrimidine Compound.

In a particular embodiment, provided herein are unit dosage formulations comprising about 100 mg or 400 mg of a Pyrrolopyrimidine Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Pyrrolopyrimidine Compound.

A Pyrrolopyrimidine Compound can be administered once, twice, three, four or more times daily. In a particular embodiment, doses of 600 mg or less are administered as a once daily dose and doses of more than 600 mg are administered twice daily in an amount equal to one half of the total daily dose.

In another embodiment, provided herein are compositions comprising an effective amount of a Pyrrolopyrimidine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of solutions, parenteral solutions, and suspensions and the like. Compositions can be formulated to contain a single dose, or a convenient fraction of a single dose, in a dosage unit, which may be a single vial or convenient volume of a liquid. In one embodiment, the solutions are prepared from water-soluble salts, such as the hydrochloride salt. In general, all of the compositions are prepared according to known methods in pharmaceutical chemistry.

The effect of the Pyrrolopyrimidine Compound can be delayed or prolonged by proper formulation. The parenteral preparations can be made long-acting, by dissolving or suspending the Pyrrolopyrimidine Compound in oily or emulsified vehicles that allow it to disperse slowly in the serum.

EXAMPLES

The following Examples are presented by way of illustration, not limitation.

ENZYME ASSAYS

CLK1 Kinase Assay.

A fluorescence resonance energy transfer-based Z'-LYTE® kinase assay kit-Ser/Thr 09 (Invitrogen, Carlsbad, Calif., cat.# PV3324) was used to determine the $IC_{50}$ values for inhibition of CLK1 kinase activity. The reactions were performed in a 384-well plate with a 10 µl reaction volume per well containing CLK1 enzyme (16.2-128 ng), 25 µM adenosine triphosphate (ATP), 2 µM Z'-Lyte® Ser/Thr 9 peptide substrate in 50 mM 4-(2-hydroxyethyl)-1-piperazineethanesulfonic acid (HEPES), pH 7.5, 0.01% Brij-35, 10 mM magnesium chloride ($MgCl_2$), 1 mM ethylene glycol tetraacetic acid (EGTA) buffer with a serial 3-fold dilution of the test compounds. After a 1 hour incubation, 5 µL of Development Reagent A (1:256 dilution) was added, and the fluorescence ratio was calculated. The dose-response curves were fitted to a sigmoidal dose-response model using XLfit from IDBS. The $IC_{50}$ values were determined as the concentration of compound resulting in 50% of remaining enzyme activity. Results for certain Pyrrolopyrimidine Compounds are shown in Tables B and C.

CLK2 Kinase Assay.

A fluorescence resonance energy transfer-based Z'-LYTE® kinase assay kit-Ser/Thr 6 peptide (Invitrogen, Carlsbad, Calif., cat.# PV3179) was used to determine the $IC_{50}$ values for inhibition of CLK2 kinase activity. The reactions were performed in a 384-well plate with a 10 µl reaction volume per well containing CLK2 enzyme (ranging from 0.97-11.5 ng), 25 µM ATP, 2 µM Z'-Lyte® Ser/Thr 6 peptide substrate in 50 mM HEPES, pH 7.5, 0.01% Brij-35, 10 mM $MgCl_2$, 1 mM EGTA buffer with a serial 3-fold dilution of the test compounds. After a 1 hour incubation, 5 µL of Development Reagent A (1:2048 dilution) was added, and the fluorescence ratio was calculated. A dose-response curves were fitted to a sigmoidal dose-response model using XLfit from IDBS. The $IC_{50}$ values were determined as the concentration of compound resulting in 50% of remaining enzyme activity. Results for certain Pyrrolopyrimidine Compounds are shown in Tables B and C.

TTK Kinase Assay.

The LanthaScreen® Eu Kinase Binding Assay (Invitrogen, Carlsbad, Calif. cat.#) was used to determine the $IC_{50}$ values for inhibition of TTK kinase activity. The reaction was performed in a 384-well plate with a 16 µL reaction volume per well containing 5 nM TTK enzyme, 30 nM of Tracer 236 (Invitrogen PV5592), and 2 nM LanthaScreen® Eu-anti-GST antibody in 50 mM HEPES pH 7.5, 0.01% BRIJ-35, 10 mM $MgCl_2$, 1 mM EGTA buffer with a serial 3-fold dilution of test compound. The reaction was incubated for 1 hour at room temperature and then read on a fluorescence plate reader (Excitation 340 nm, Kinase Tracer 236 Emission: 665 nm, LanthaScreen™ Eu-anti-Tag Antibody: Emission 615 nm). The TR-FRET ratio was calculated as the intensity of the acceptor signal (665 nm) divided by the intensity of the donor signal (615 nm). The dose-response curves were fitted to a sigmoidal dose-response model using XLfit from IDBS. The $IC_{50}$ values were determined as the concentration of compound resulting in 50% of displaced Tracer 236 (ATP competitive inhibitor). Results for certain Pyrrolopyrimidine Compounds are shown in Tables B and C.

CAMKK2 Kinase Assay.

The LanthaScreen® Eu Kinase Binding Assay (Invitrogen, Carlsbad, Calif.) was used to determine the $IC_{50}$ values for inhibition of CAMKK2 kinase activity. The reaction was performed in a 384-well plate with a 16 µL reaction volume per well containing 5 nM CAMKK2 enzyme, 10 nM of Kinase Tracer 236, and 2 nM LanthaScreen® Eu-anti-GST antibody in 50 mM HEPES pH 7.5, 0.01% BRIJ-35, 10 mM MgCl2, 1 mM EGTA buffer with a serial 3-fold dilution of test compound. The reaction was incubated for 1 hour at room temperature and then read on a fluorescence plate reader (Excitation 340 nm, Kinase Tracer 236 Emission: 665 nm, and LanthaScreen™ Eu-anti-Tag Antibody: Emission 615 nm). The TR-FRET ratio was calculated as the intensity of the acceptor signal (665 nm) divided by the intensity of the donor signal (615 nm). The dose-response curves were fitted to a sigmoidal dose-response model using XLfit from IDBS. The $IC_{50}$ values were determined as the concentration of compound resulting in 50% of displaced Tracer 236 (ATP competitive inhibitor).

Alternative CAMKK2 Kinase Assay.

CAMKK2 enzyme was mixed with 1 µM of $Ca^{2+}$-Calmodulin and 10 µM of the Myelin Basic Protein (MBP) substrate in reaction buffer; 20 mM 4-(2-hydroxyethyl)-1-piperazineethane sulfonic acid (HEPES), 10 mM magnesium chloride ($MgCl_2$), 1 mM ethyleneglycoltetraacetic acid (EGTA), 0.02% Brij35, 0.02 mg/ml bovine serum albumin (BSA), 0.1 mM sodium orthovanadate, 2 mM dithiothreitol (DTT), 1% dimethyl sulfoxide (DMSO) at pH 7.5. Compounds were delivered into the reaction, followed 20 min later by addition of a mixture of ATP (Sigma) and $^{33}P$ ATP (PerkinElmer) to a final concentration of 10 µM. Reactions were carried out at 25° C. for 120 min, followed by spotting of the reactions onto P81 ion exchange filter paper (Whatman). Unbound phosphate was removed by extensive washing of filters in 0.75% phosphoric acid. After subtraction of background derived from control reactions containing inactive enzyme, kinase activity data were expressed as the percent remaining kinase activity in test samples compared to the DMSO vehicle reactions. $IC_{50}$ values and curve fits were obtained using Prism (GraphPad Software). Results for certain Pyrrolopyrimidine Compounds are shown in Tables C.

TABLE B

Inhibition by Pyrrolopyrimidine Compounds of TTK, CLK1, and CLK2 kinase activity (% inhibition at 3 µM).

| Cmpd No. | TTK (% Inh.) | CLK1 (% Inh.) | CLK2 (% Inh.) |
| --- | --- | --- | --- |
| 3 |  | 91 | 104 |
| 11 |  | 95 | 94 |
| 16 |  | 92 | 90 |
| 17 |  | 97 | 98 |
| 38 |  | 99 | 98 |
| 58 |  | 96 | 103 |
| 64 |  | 68 | 99 |
| 79 |  | 97 | 97 |
| 89 |  | 101 | 100 |
| 90 |  | 101 | 101 |
| 98 |  | 103 | 104 |
| 101 |  | 95 | 98 |
| 118 | 102 | 98 | 98 |
| 132 |  | 92 | 98 |
| 133 |  | 104 | 101 |
| 134 |  | 101 | 100 |
| 139 |  | 104 | 99 |
| 140 |  | 97 | 103 |
| 145 |  | 96 | 97 |
| 146 |  | 103 | 100 |
| 148 |  | 99 | 106 |
| 150 |  | 99 | 111 |
| 152 |  | 99 | 100 |
| 157 |  | 95 | 105 |
| 160 |  | 98 | 108 |
| 162 |  | 100 | 106 |
| 163 |  | 100 | 102 |
| 169 |  | 100 | 105 |
| 171 |  | 97 | 102 |
| 184 |  | 101 | 98 |
| 185 |  | 98 | 106 |
| 191 |  | 100 | 99 |
| 192 | 102 | 101 | 103 |
| 193 |  | 100 | 99 |
| 197 |  | 100 | 103 |
| 198 |  | 93 | 100 |
| 201 |  | 100 | 103 |
| 202 |  | 99 | 99 |
| 203 |  | 98 | 99 |
| 204 |  | 98 | 99 |
| 205 |  | 99 | 103 |
| 206 |  | 92 | 97 |
| 207 |  | 99 | 99 |
| 213 |  | 99 | 100 |
| 214 |  | 97 | 100 |
| 216 |  | 99 | 99 |
| 237 |  | 93 | 100 |
| 296 |  | 101 | 104 |
| 300 |  | 100 | 100 |
| 304 |  | 53 | 101 |
| 307 |  | 99 | 103 |
| 334 |  | 95 | 104 |
| 339 | 100 | 63 | 98 |
| 340 | 105 | 100 | 99 |

TABLE B-continued

Inhibition by Pyrrolopyrimidine Compounds of TTK, CLK1, and CLK2 kinase activity (% inhibition at 3 µM.

| Cmpd No. | TTK (% Inh.) | CLK1 (% Inh.) | CLK2 (% Inh.) |
|---|---|---|---|
| 349 | 95 | 101 | 102 |
| 371 |  | 100 | 100 |
| 377 |  | 99 | 100 |
| 384 | 102 | 57 | 88 |
| 392 | 99 | 106 | 99 |
| 421 |  | 99 | 101 |
| 422 |  | 94 | 99 |
| 423 |  | 99 | 100 |
| 426 | 98 | 101 | 101 |
| 429 | 101 | 96 | 101 |
| 435 | 100 | 100 | 101 |

TABLE C

Inhibition by Pyrrolopyrimidine Compounds of TTK, CLK1, CLK2 and CAMKK2 kinase activity.

| Cmpd No. | TTK ($IC_{50}$, µM) | CLK1 ($IC_{50}$, µM) | CLK2 ($IC_{50}$, µM) | CAMKK2 ($IC_{50}$, µM) |
|---|---|---|---|---|
| 3 |  | 1.435624 | 0.05389 |  |
| 11 |  | 0.298738 | 0.034896 |  |
| 16 |  | 0.225404 | 0.025999 |  |
| 17 |  | 0.082369 | 0.00433 |  |
| 38 | 0.014 | 0.267 | 0.008168 | 0.728 |
| 55 | 0.013312 |  |  |  |
| 67 | 0.016027 |  |  |  |
| 79 | 0.002379 | 0.058587 | 0.001911 | 0.034 |
| 89 | <1.5e−003 | 0.041473 | 0.004557 |  |
| 90 | 0.001675 | 0.12394 | 0.003497 |  |
| 101 | 0.002128 | 0.099779 | 0.003377 | 0.501 |
| 118 | 0.005136 |  | 0.002294 |  |
| 132 | 0.004116 | 0.225986 | 0.029057 |  |
| 134 | 0.001678 | 0.130033 | 0.00227 |  |
| 145 | 0.002451 | 0.219809 | 0.040123 |  |
| 146 | 0.002121 |  |  |  |
| 152 | 0.00296 |  |  |  |
| 171 | 0.001471 | 0.082812 | 0.002317 |  |
| 191 | 0.003653 | 0.172406 | 0.009409 |  |
| 237 | 0.008062 | 0.237221 | 0.010372 |  |
| 300 | 0.004536 |  |  |  |
| 304 | 0.00235 |  |  |  |
| 334 | 0.001418 |  |  |  |
| 339 | 0.007004 | 0.526142 | 0.005915 |  |
| 349 | 0.001145 | 0.059278 | 0.001429 |  |
| 421 |  | 0.084639 | 0.002095 |  |
| 422 | 0.011578 | 0.504877 | 0.012494 |  |
| 423 | 0.001904 | 0.097765 | 0.003294 |  |

Conclusion.

Tables B and C show that Pyrrolopyrimidine Compounds, as described herein, inhibit the kinase activity of TTK, CLK1, and CLK2. In some embodiments, the Pyrrolopyrimidine Compounds also inhibit the kinase activity of CAMKK2.

CELL ASSAYS

Breast Cancer Cell Line Growth Inhibition.

The 49 breast cancer cell lines used in the study are shown in Table 1. The luminal and basal subtype classification was based upon public information that was verified internally. The estrogen receptor (ER), progesterone receptor (PR), and human epidermal growth factor receptor 2 (HER2) status of each cell line was based upon public information that was verified internally.

TABLE 1

Breast Cancer Cell Lines

| Cell Line | Subtype1 | Subtype2 | Vendor | Media |
|---|---|---|---|---|
| AU565 | Luminal | Her2+ | ATCC | RPMI + 10% FBS |
| BT-20 | Basal | TN | ATCC | DMEM + 10% FBS |
| BT-474 | Luminal | Her2+ | ATCC | RPMI + 10% FBS |
| BT-483 | Luminal | ER+/PR+ | ATCC | RPMI + 10% FBS |
| BT-549 | Basal | TN | ATCC | RPMI + 10% FBS |
| CAL-120 | Basal | TN | DSMZ | DMEM + 10% FBS |
| CAL-148 | Luminal | TN | DSMZ | DMEM + 10% FBS |
| CAL-51 | Basal | TN | DSMZ | DMEM + 10% FBS |
| CAL-85-1 | Basal | TN | DSMZ | DMEM + 10% FBS |
| CAMA-1 | Luminal | ER+/PR+ | ATCC | DMEM + 10% FBS |
| DU4475 | Basal | TN | ATCC | RPMI + 10% FBS |
| EFM-19 | Luminal | ER+/PR+ | DSMZ | RPMI + 10% FBS |
| EFM-192A | Luminal | Her2+ | DSMZ | RPMI + 10% FBS |
| EVSA-T | Luminal | ER+/PR+ | DSMZ | DMEM + 10% FBS |
| HCC1143 | Basal | TN | ATCC | RPMI + 10% FBS |
| HCC1187 | Basal | TN | ATCC | RPMI + 10% FBS |
| HCC1419 | Luminal | Her2+ | ATCC | RPMI + 10% FBS |
| HCC1428 | Luminal | ER+/PR+ | ATCC | RPMI + 10% FBS |
| HCC1500 | Luminal | ER+/PR+ | ATCC | RPMI + 10% FBS |
| HCC1569 | Basal | Her2+ | ATCC | RPMI + 10% FBS |
| HCC1806 | Basal | TN | ATCC | RPMI + 10% FBS |
| HCC1937 | Basal | TN | ATCC | RPMI + 10% FBS |
| HCC1954 | Basal | Her2+ | ATCC | RPMI + 10% FBS |
| HCC202 | Luminal | Her2+ | ATCC | RPMI + 10% FBS |
| HCC38 | Basal | TN | ATCC | RPMI + 10% FBS |
| HCC70 | Basal | TN | ATCC | RPMI + 10% FBS |
| HCC2157 | Basal | TN | ATCC | RPMI + 10% FBS |
| HDQ-P1 | Basal | TN | DSMZ | DMEM + 10% FBS |
| HS578T | Basal | TN | ATCC | RPMI + 10% FBS |
| JIMT-1 | Basal | Her2+ | DSMZ | DMEM + 10% FBS |
| KPL-1 | Luminal | ER+/PR+ | DSMZ | DMEM + 10% FBS |
| MB157 | Basal | TN | ATCC | DMEM + 10% FBS |
| MCF7 | Luminal | ER+/PR+ | NCI | RPMI + 10% FBS |
| MCF10A | Basal | TN | ATCC | RPMI + 10% FBS |
| MCF12A | Basal | TN | ATCC | DMEM + 10% FBS |
| MDA-MB-134-VI | Luminal | ER+/PR+ | ATCC | DMEM + 10% FBS |
| MDA-MB-157 | Basal | TN | ATCC | DMEM + 10% FBS |
| MDA-MB-175-VII | Luminal | ER+/PR+ | ATCC | DMEM + 10% FBS |
| MDA-MB-231 | Basal | TN | ATCC | RPMI + 10% FBS |
| MDA-MB-361 | Luminal | Her2+ | ATCC | DMEM + 10% FBS |
| MDA-MB-415 | Luminal | ER+/PR+ | ATCC | DMEM + 10% FBS |
| MDA-MB-436 | Basal | TN | ATCC | DMEM + 10% FBS |
| MDA-MB-453 | Luminal | Her2+ | ATCC | DMEM + 10% FBS |
| MDA-MB-468 | Basal | TN | ATCC | DMEM + 10% FBS |
| MFM-223 | Luminal | ER+/PR+ | DSMZ | DMEM + 10% FBS |
| MT-3 | Basal | TN | DSMZ | RPMI + 10% FBS |
| SK-BR-3 | Luminal | Her2+ | ATCC | RPMI + 10% FBS |
| T47D | Luminal | ER+/PR+ | ATCC | RPMI + 10% FBS |
| UACC-812 | Luminal | Her2+ | ATCC | DMEM + 10% FBS |
| UACC-893 | Luminal | Her2+ | ATCC | DMEM + 10% FBS |
| ZR-75-1 | Luminal | ER+/PR+ | ATCC | RPMI + 10% FBS |
| ZR-75-30 | Luminal | Her2+ | ATCC | RPMI + 10% FBS |

ATCC = American Type Culture Collection;
DMEM = Dulbecco's Modified Eagle's Medium;
DSMZ = Deutsche Sammlung von. Mikroorganismen and Zellkulturen;
ER = estrogen receptor;
FBS = fetal bovine serum;
HER2 = human epidermal growth factor receptor 2;
NCI = National Cancer Institute;
PR = progesterone receptor;
TN = triple negative breast cancer: ER−, PR−, and HER2−.

Experimental Procedures.

All breast cancer cell lines were maintained and tested in the culture media indicated in Table 1. The seeding density for each cell line was optimized to ensure assay linearity in 384-well plates. Increasing concentrations of compound were spotted via an acoustic dispenser (EDC ATS-100) into an empty 384-well plate. Compound was spotted in a 10-point serial dilution fashion (3-fold dilution) in duplicate within the plate. The dimethyl sulfoxide (DMSO) concentration was kept constant for a final assay concentration of 0.1% DMSO. Plates were replicated for use against different cell lines and testing periods. After compound plate replication, all plates were sealed (Agilent ThermoLoc) and stored at −20° C. for up to 1 month. When ready for testing, plates were removed from the freezer, thawed, and unsealed just prior to the addition of the test cell. Prior to testing, cells were grown and expanded in culture flasks to provide sufficient amounts of starting material. Cells were then diluted to their desired densities and added directly to the compound-spotted 384-well plates. Cells were allowed to grow for 96 hours at 37° C./5% $CO_2$. At the time of setup ($t_0$), initial cell number was assessed via a viability assay (Cell Titer-Glo) and read for luminescence. After 96 hours, viability of compound-treated cells was assessed via Cell Titer-Glo and read for luminescence.

Cell lines were assayed for growth inhibition by the Pyrrolopyrimidine Compounds for at least two independent tests. To ensure a comparable compound response throughout the assay period to complete all 49 cell lines, a control cell line (A549) was included in each of the assays. All data was normalized and represented as a percentage of the DMSO-treated control cells. Results were then expressed as an $IC_{50}$ (Table 2). In addition, $GI_{50}$ was calculated (Table 3).

All statistical analyses were implemented using R software (R Development Core Team, 2009).

Determination of Inhibitory Concentration and Growth Inhibition ($IC_{50}$ and $GI_{50}$).

$IC_{50}$ is the concentration of the compound when Y=50% of DMSO control. $GI_{50}$ is the concentration of the compound when Y=(YMax+$Yt_0$)/2. All growth inhibition curves were processed and evaluated using Activity Base XE (IDBS).

TABLE 2

Growth Inhibition $IC_{50}$ (µM)

| Cell Line | Cmpd 79 | Cmpd 101 | Cmpd 125 | Cmpd 38 | Cmpd 152 | Cmpd 3 |
|---|---|---|---|---|---|---|
| AU565 | 0.019 | 0.213 | 0.021 | 0.038 | 0.047 | 1.099 |
| BT-20 | 0.053 | 0.897 | 0.044 | 0.049 | 0.094 | 0.608 |
| BT-474 | 0.358 | 10.000 | 0.595 | 10.000 | 5.423 | 16.345 |
| BT-483 | 10.000 | 10.000 | 3.402 | 10.000 | 10.000 | 10.000 |
| BT-549 | 0.013 | 0.292 | 0.066 | 0.051 | 0.079 | 0.180 |
| CAL-120 | 0.592 | 10.000 | 0.272 | 10.000 | 4.638 | 10.000 |
| CAL-148 | 0.003 | 0.074 | 0.168 | 0.065 | 0.069 | |
| CAL-51 | 0.001 | 0.069 | 0.010 | 0.010 | 0.018 | 0.009 |
| CAL-85-1 | 0.029 | 0.423 | 0.093 | 0.052 | 0.087 | 0.076 |
| CAMA-1 | 10.000 | 10.000 | 0.763 | 10.000 | 10.000 | 10.706 |
| DU4475 | 0.087 | 0.248 | 0.246 | 2.253 | 0.244 | 0.560 |
| EFM-19 | 0.083 | 0.263 | 0.181 | 0.196 | 0.221 | 0.730 |
| EFM-192A | 2.085 | 10.000 | 1.279 | 10.000 | 5.042 | 10.000 |
| EVSA-T | 0.311 | 9.438 | 0.206 | 10.000 | 1.720 | |
| HCC1143 | 0.308 | 0.685 | 0.481 | 0.579 | 0.711 | 17.483 |
| HCC1187 | 0.002 | 0.119 | 0.031 | 0.042 | 0.066 | 0.881 |
| HCC1419 | 10.000 | 10.000 | 2.511 | 10.000 | 10.000 | |
| HCC1428 | 0.523 | 8.149 | 0.472 | 10.000 | 0.945 | 4.967 |
| HCC1500 | 10.000 | 10.000 | 2.279 | 10.000 | 10.000 | 13.857 |
| HCC1569 | 0.170 | 0.327 | 0.408 | 0.288 | 1.037 | 5.434 |
| HCC1806 | 0.001 | 0.062 | 0.011 | 0.009 | 0.022 | |
| HCC1937 | 0.695 | 10.000 | 0.311 | 10.000 | 5.646 | 10.000 |
| HCC1954 | 0.016 | 0.258 | 0.068 | 0.039 | 0.102 | 0.482 |
| HCC202 | 0.216 | 2.104 | 0.190 | 3.072 | 0.462 | 15.961 |
| HCC2157 | | | | | | 0.120 |
| HCC38 | 0.001 | 0.052 | 0.012 | 0.011 | 0.021 | 0.047 |
| HCC70 | 0.047 | 6.705 | 0.268 | 1.300 | 1.023 | 1.950 |
| HDQ-P1 | 0.128 | 1.775 | 0.083 | 0.326 | 0.204 | |
| HS578T | 0.012 | 0.221 | 0.041 | 0.052 | 0.059 | 0.183 |
| JIMT-1 | 5.336 | 9.074 | 0.165 | 0.111 | 0.215 | |
| KPL-1 | 0.429 | 6.464 | 0.064 | 5.202 | 0.318 | 0.693 |
| MB157 | 0.351 | 9.404 | 0.419 | 10.000 | 5.318 | |
| MCF10A | | | | | | 17.449 |
| MCF12A | | | | | | 3.151 |
| MCF7 | 0.002 | 0.079 | 0.012 | 0.012 | 0.025 | 0.170 |
| MDA-MB-134-VI | 10.000 | 10.000 | 3.168 | 10.000 | 10.000 | 1.386 |
| MDA-MB-157 | 1.636 | 10.000 | 0.631 | 6.290 | 10.000 | 0.695 |
| MDA-MB-175-VII | 10.000 | 10.000 | 2.843 | 10.000 | 10.000 | 8.497 |
| MDA-MB-231 | 0.004 | 0.135 | 0.031 | 0.024 | 0.054 | 0.038 |
| MDA-MB-361 | 2.830 | 10.000 | 1.472 | 10.000 | 10.000 | 18.751 |
| MDA-MB-415 | 10.000 | 10.000 | 5.512 | 10.000 | 10.000 | 13.454 |
| MDA-MB-436 | 1.108 | 4.194 | 0.510 | 7.821 | 0.718 | 2.100 |
| MDA-MB-453 | 0.316 | 10.000 | 0.668 | 10.000 | 0.443 | 2.788 |
| MDA-MB-468 | 0.001 | 0.096 | 0.024 | 0.027 | 0.057 | 0.032 |
| MFM-223 | 0.355 | 0.984 | 0.172 | 1.879 | 0.429 | |
| MT-3 | 10.000 | 10.000 | 8.500 | 10.000 | 10.000 | |
| SK-BR-3 | 0.323 | 0.570 | 0.272 | 0.578 | 0.417 | 3.688 |
| T47D | 0.419 | 10.000 | 0.336 | 1.651 | 0.715 | 0.418 |
| UACC-812 | 4.375 | 8.030 | 0.296 | 10.000 | 0.888 | 1.794 |
| UACC-893 | 10.000 | 10.000 | 0.787 | 10.000 | 1.833 | |
| ZR-75-1 | 10.000 | 10.000 | 3.314 | 10.000 | 10.000 | 6.386 |
| ZR-75-30 | 1.268 | 3.413 | 0.715 | 10.000 | 1.576 | 30.000 |

TABLE 3

Growth inhibition $GI_{50}$ (µM)

| Cell Line | Cmpd 79 | Cmpd 101 | Cmpd 125 | Cmpd 38 | Cmpd 152 | Cmpd 3 |
|---|---|---|---|---|---|---|
| AU565 | 0.005 | 0.100 | 0.016 | 0.011 | 0.024 | 0.426 |
| BT-20 | 0.019 | 0.553 | 0.028 | 0.028 | 0.057 | 0.289 |
| BT-474 | 0.106 | 7.373 | 10.000 | 0.202 | 0.645 | 6.016 |
| BT-483 | n/a | n/a | n/a | n/a | n/a | 0.704 |
| BT-549 | 0.006 | 0.166 | 0.034 | 0.043 | 0.055 | 0.085 |
| CAL-120 | 0.521 | 10.000 | 10.000 | 0.245 | 3.462 | 10.000 |
| CAL-148 | 0.002 | 0.048 | 0.047 | 0.060 | 0.052 | |
| CAL-51 | 0.001 | 0.059 | 0.009 | 0.009 | 0.016 | 0.008 |
| CAL-85-1 | 0.014 | 0.218 | 0.029 | 0.061 | 0.055 | 0.025 |
| CAMA-1 | 1.066 | 0.628 | 0.590 | 0.261 | 0.308 | 4.895 |
| DU4475 | 0.004 | 0.046 | 0.038 | 0.058 | 0.059 | 0.082 |
| EFM-19 | 0.006 | 0.051 | 0.035 | 0.047 | 0.065 | 0.067 |
| EFM-192A | 0.309 | 0.451 | 0.294 | 0.424 | 0.411 | 10.000 |
| EVSA-T | 0.121 | 6.665 | 6.000 | 0.130 | 0.557 | |
| HCC1143 | 0.093 | 0.325 | 0.215 | 0.275 | 0.374 | 0.286 |
| HCC1187 | 0.002 | 0.083 | 0.027 | 0.021 | 0.044 | 0.470 |
| HCC1419 | 1.684 | 6.162 | 10.000 | 1.008 | 1.491 | |
| HCC1428 | 0.215 | 0.516 | 0.326 | 0.206 | 0.288 | 1.086 |
| HCC1500 | 0.058 | 0.090 | 0.103 | 0.112 | 0.103 | 0.053 |
| HCC1569 | 0.036 | 0.116 | 0.088 | 0.140 | 0.102 | 0.073 |
| HCC1806 | 0.001 | 0.057 | 0.008 | 0.010 | 0.020 | |
| HCC1937 | 0.245 | 8.128 | 6.376 | 0.161 | 0.426 | 7.460 |
| HCC1954 | 0.007 | 0.159 | 0.027 | 0.041 | 0.061 | 0.131 |
| HCC202 | 0.009 | 0.052 | 0.028 | 0.018 | 0.044 | 15.026 |
| HCC2157 | | | | | | 0.024 |
| HCC38 | 0.001 | 0.040 | 0.009 | 0.010 | 0.017 | 0.017 |
| HCC70 | 0.005 | 0.128 | 0.047 | 0.080 | 0.086 | 0.442 |
| HDQ-P1 | 0.037 | 0.890 | 0.106 | 0.046 | 0.108 | |
| HS578T | 0.010 | 0.203 | 0.047 | 0.038 | 0.055 | 0.104 |
| JIMT-1 | 2.098 | 2.498 | 0.061 | 0.116 | 0.154 | |
| KPL-1 | 0.136 | 2.884 | 0.126 | 0.034 | 0.108 | 0.245 |
| MCF10A | | | | | | 0.426 |
| MCF12A | | | | | | 0.486 |
| MB157 | 0.026 | 0.425 | 0.116 | 0.067 | 0.123 | |
| MCF7 | 0.001 | 0.070 | 0.011 | 0.010 | 0.021 | 0.124 |
| MDA-MB-134-VI | n/a | n/a | n/a | n/a | n/a | 0.874 |
| MDA-MB-157 | 0.018 | 5.117 | 0.114 | 0.176 | 0.110 | 0.225 |

TABLE 3-continued

Growth inhibition GI$_{50}$ (μM)

| Cell Line | Cmpd 79 | Cmpd 101 | Cmpd 125 | Cmpd 38 | Cmpd 152 | Cmpd 3 |
|---|---|---|---|---|---|---|
| MDA-MB-175-VII | 0.700 | 0.534 | 5.285 | 0.523 | 1.087 | 0.400 |
| MDA-MB-231 | 0.003 | 0.104 | 0.019 | 0.022 | 0.041 | 0.022 |
| MDA-MB-361 | 0.043 | 0.110 | 0.091 | 0.231 | 0.143 | 5.481 |
| MDA-MB-415 | 10.000 | 9.995 | 10.000 | 0.441 | 10.000 | 11.707 |
| MDA-MB-436 | 0.433 | 1.020 | 0.999 | 0.289 | 0.327 | 1.382 |
| MDA-MB-453 | 0.212 | 5.387 | 10.000 | 0.475 | 0.390 | 0.799 |
| MDA-MB-468 | 0.001 | 0.083 | 0.023 | 0.020 | 0.049 | 0.027 |
| MFM-223 | 0.009 | 0.050 | 0.043 | 0.035 | 0.058 | |
| MT-3 | 1.093 | 1.117 | 5.757 | 1.659 | 10.000 | |
| SK-BR-3 | 0.051 | 0.102 | 0.081 | 0.082 | 0.124 | 1.181 |
| T47D | 0.040 | 0.386 | 0.081 | 0.106 | 0.140 | 0.162 |
| UACC-812 | 0.369 | 0.748 | 0.319 | 0.110 | 0.201 | 0.842 |
| UACC-893 | n/a | n/a | n/a | n/a | n/a | |
| ZR-75-1 | 0.002 | 0.039 | 0.032 | 0.050 | 0.062 | 1.136 |
| ZR-75-30 | n/a | n/a | n/a | n/a | n/a | 11.619 | n/a: not applicable

Conclusions.

As can be seen from Tables 2 and 3, Pyrrolopyrimidine Compounds inhibited breast cancer cell line growth, as measured by IC$_{50}$ and GI$_{50}$. Cell proliferation inhibition was shown in TNBC, as well as ER+/PR+ and Her2+, to varying degrees.

Non-Small Cell Lung Cancer Cell Line Growth Inhibition.

Sixteen non small cell lung cancer (NSCLC) cell lines were purchased from the American Tissue Culture Collection and maintained in growth media consisting of 90% RPMI1640 (Invitrogen) and 10% fetal bovine serum (Hyclone). All cells were cultured at 37° C. in 95% air and 5% CO$_2$. Cells were plated at optimal density for each cell line (see Table 5) per well in a 96-well plate in 100 μL of growth media. After overnight culture, compound stock solutions (30 mM) were diluted serially in DMSO, further diluted in growth media, and was added to each well as a 10× concentrated solution in a volume of 11 μL, mixed, and allowed to incubate with cells. The compound vehicle (DMSO) was maintained at a final concentration of 0.2% in all wells. After 72 hrs, 100 μL of Cell Titer Glo solution (Promega) were added to each well of the 96-well plate. The plate was placed on a shaker for 2 minutes. After 10 minutes incubation, luminescence signal was detected with Envision microplate reader (Perkin Elmer). The IC$_{50}$ values were calculated as the concentration of compound at which the level of luminescence signal was reduced to 50% of the signal window. Table 4 shows the results for Compound 3. Compounds show or will show an IC$_{50}$ value ranging from 0.01-30 μM in this assay.

TABLE 4

Growth Inhibition IC$_{50}$ Values and Growth Conditions

| Cell Line | Plating Density | Average IC$_{50}$ (μM) | SD |
|---|---|---|---|
| H1734 | 16000 | 0.91 | 0.59 |
| H1838 | 12000 | 16.11 | 19.65 |
| H2228 | 20000 | 1.58 | 0.41 |
| H441 | 16000 | 2.10 | 0.32 |
| H1437 | 12000 | 0.39 | 0.33 |
| Hop62 | 2800 | 0.05 | N/A |
| H1650 | 8000 | 0.62 | 0.02 |
| HOP92 | 6000 | 1.27 | 0.62 |
| H520 | 32000 | 1.45 | 0.18 |
| H1299 | 2800 | 0.36 | 0.34 |
| H2291 | 16000 | 16.29 | 19.39 |
| H1563 | 6000 | 1.77 | 0.09 |
| SK-LU-1 | 5000 | 0.83 | 0.10 |
| SW1573 | 5000 | 0.96 | 0.23 |
| A549 | 2500 | 0.05 | 0.04 |
| H460 | 1500 | 0.04 | 0.01 |

Conclusion.

Pyrrolopyrimidine Compounds demonstrated potent growth inhibition over a panel of non small cell lung cancer cell (NSCLC) lines profiled, as shown in Table 4. The majority of NSCLC lines (14 out of 16) are sensitive to growth inhibition by Pyrrolopyrimidine Compounds (for example, Compound 3) with a IC$_{50}$ values ≤2 μM.

Multiplexed Cytotoxicity Assay.

Cells were grown in RPMI1640, 10% FBS, 2 mM L-alanyl-L-Glutamine, 1 mM Na pyruvate or a special medium in a humidified atmosphere of 5% CO$_2$ at 37° C. Cells were seeded into 384-well plates and incubated in a humidified atmosphere of 5% CO$_2$ at 37° C. Compounds were added 24 hours post cell seeding. At the same time, a time zero untreated cell plate was generated. After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody. Compounds were serially diluted 3.16-fold and assayed over 10 concentrations in a final assay concentration of 0.1% DMSO from the highest test concentration of 10 μM. Automated fluorescence microscopy was carried out using a GE Healthcare IN Cell Analyzer 1000, and images were collected with a 4× objective.

Data Analysis.

Twelve bit tiff images were acquired using the InCell Analyzer 1000 3.2 and analyzed with Developer Toolbox 1.6 software. Cell proliferation was measured by the signal intensity of the incorporated nuclear dye. Results for Compound 38 are shown in Table 6. The cell proliferation assay output is referred to as the relative cell count. To determine the cell proliferation end point, the cell proliferation data output is transformed to percentage of control (POC) using the following formula:

POC=relative cell count(compound wells)/relative cell count(vehicle wells)×100

Relative cell count IC$_{50}$ is the test compound concentration at 50% of maximal possible response relative to the DMSO control. GI$_{50}$ is the concentration needed to reduce the observed growth by half. This is the concentration that inhibits the growth to the level midway between growth in untreated cells and the number of cells seeded in the well (Time zero value). The IC$_{50}$ values were calculated using nonlinear regression to fit data to a sigmoidal 4 point, 4 parameter One-Site dose response model, where:

$$y(\text{fit}) = A + [(B-A)/(1+((C/x)^D))].$$

The activated caspase-3 marker labels cells from early to late stage apoptosis. The output is shown as a fold increase of apoptotic cells over vehicle background normalized to the relative cell count in each well. Concentrations of test compound that cause a 5-fold induction in the caspase-3 signal (Cal_X5) indicate significant apoptosis induction. The maximal induction of caspase 3 by compound in comparison with DMSO control is reported as Max_Fold_Change.

TABLE 5

| Cell lines | | | |
|---|---|---|---|
| Cell line | Tumor Type | Subtype | Classification |
| 5637 | Bladder | | |
| 639-V | Bladder | | |
| 647-V | Bladder | | |
| BFTC-905 | Bladder | | |
| HT1197 | Bladder | | |
| HT1376 | Bladder | | |
| J82 | Bladder | | |
| SCaBER | Bladder | | |
| T24 | Bladder | | |
| TCCSUP | Bladder | | |
| UM-UC-3 | Bladder | | |
| AU565 | Breast | Luminal | Luminal |
| BT-20 | Breast | Basal | Basal |
| BT-474 | Breast | Luminal | Luminal |
| BT-549 | Breast | Basal | Basal |
| CAMA-1 | Breast | Luminal | Luminal |
| EFM-19 | Breast | Luminal | Luminal |
| HS578T | Breast | Basal | Basal |
| KPL-1 | Breast | Luminal | Luminal |
| MCF7 | Breast | Luminal | Luminal |
| MDA-MB-231 | Breast | Basal | Basal |
| MDA-MB-436 | Breast | Basal | Basal |
| MDA-MB-453 | Breast | Luminal | Luminal |
| MDA-MB-468 | Breast | Basal | Basal |
| MT-3 | Breast | Basal | Basal |
| SK-BR-3 | Breast | Luminal | Luminal |
| T47D | Breast | Luminal | Luminal |
| A172 | CNS | Glioblastoma | Glioblastoma |
| BE(2)C | CNS | | |
| CCF-STTG1 | CNS | Astrocytoma | Astrocytoma |
| CHP-212 | CNS | | |
| D-283MED | CNS | | |
| Daoy | CNS | Medulloblastoma | Medulloblastoma |
| DBTRG-05MG | CNS | Glioblastoma | Glioblastoma |
| DK-MG | CNS | Glioblastoma | Glioblastoma |
| H4 | CNS | Neuroglioma | Neuroglioma |
| MC-IXC | CNS | | |
| SK-N-AS | CNS | | |
| SK-N-DZ | CNS | | |
| SK-N-FI | CNS | | |
| SNB-19 | CNS | Glioblastoma | Glioblastoma |
| SW1088 | CNS | Astrocytoma | Astrocytoma |
| SW1783 | CNS | Astrocytoma | Astrocytoma |
| T98G | CNS | Glioblastoma | Glioblastoma |
| U-138MG | CNS | Glioblastoma | Glioblastoma |
| U-87-MG | CNS | Astrocytoma | Astrocytoma |
| COLO-201 | Colon | Large Intestine | |
| COLO-205 | Colon | Large Intestine | |
| COLO-320DM | Colon | Large Intestine | |
| COLO-320-HSR | Colon | Large Intestine | |
| DLD-1 | Colon | Large Intestine | |
| HCT-116 | Colon | Large Intestine | |
| HCT-15 | Colon | Large Intestine | |
| HCT-8 | Colon | Large Intestine | |
| HT29 | Colon | Large Intestine | |
| LS-1034 | Colon | Large Intestine | |
| LS-174T | Colon | Large Intestine | |
| NCI-H508 | Colon | Large Intestine | |
| NCI-H747 | Colon | Large Intestine | |
| RKO | Colon | Large Intestine | |
| RKO-AS45-1 | Colon | Large Intestine | |
| RKO-E6 | Colon | Large Intestine | |
| SW1417 | Colon | Large Intestine | |

TABLE 5-continued

| Cell lines | | | |
|---|---|---|---|
| Cell line | Tumor Type | Subtype | Classification |
| SW403 | Colon | Large Intestine | |
| SW48 | Colon | Large Intestine | |
| SW480 | Colon | Large Intestine | |
| SW620 | Colon | Large Intestine | |
| SW837 | Colon | Large Intestine | |
| SW948 | Colon | Large Intestine | |
| WiDr | Colon | Large Intestine | |
| AGS | Colon/GI | Stomach | |
| HS746T | Colon/GI | Stomach | |
| KATOIII | Colon/GI | Stomach | |
| OE19 | Colon/GI | Oesophagus | |
| SNU-1 | Colon/GI | Stomach | |
| SNU-16 | Colon/GI | Stomach | |
| SNU-5 | Colon/GI | Stomach | |
| SW1463 | Colon | Rectum | |
| BHT-101 | Endocrine | Thyroid | |
| CAL-62 | Endocrine | Thyroid | |
| CGTH-W-1 | Endocrine | Thyroid | |
| NCI-H295 | Endocrine | Adrenal cortex | |
| SW13 | Endocrine | Adrenal gland | |
| SW579 | Endocrine | Thyroid | |
| Y79 | Eye | Retinoblastoma | |
| AN3 CA | Female GU | Uterus | |
| BeWo | Female GU | Placenta | |
| C-33-A | Female GU | Cervix | |
| C4-1 | Female GU | Cervix | |
| C4-2 | Female GU | Cervix | |
| Caov-3 | Female GU | Ovary | |
| DoTc2-4510 | Female GU | Cervix | |
| ES-2 | Female GU | Ovary | |
| HEC-1-A | Female GU | Uterus | |
| HeLa | Female GU | Cervix | |
| HT3 | Female GU | Cervix | |
| JAR | Female GU | Placenta | |
| JEG-3 | Female GU | Placenta | |
| KLE | Female GU | Uterus | |
| Ovcar-3 | Female GU | Ovary | |
| RL95-2 | Female GU | Uterus | |
| SiHa | Female GU | Cervix | |
| SK-OV-3 | Female GU | Ovary | |
| SW954 | Female GU | Vulva | |
| SW962 | Female GU | Vulva | |
| CAL-27 | Head and Neck | Tongue | |
| Detroit562 | Head and Neck | Pharynx | |
| FADU | Head and Neck | Pharynx | |
| OE21 | Head and Neck | | |
| OE33 | Head and Neck | Oesophagus | |
| SCC-25 | Head and Neck | Tongue | |
| SCC-4 | Head and Neck | Tongue | |
| SCC-9 | Head and Neck | Tongue | |
| L428 | Hodgkin's lymphoma | | |
| RPMI-6666 | Hodgkin's lymphoma | | |
| 769-P | Kidney | | |
| 786-0 | Kidney | | |
| A498 | Kidney | | |
| ACHN | Kidney | | |
| CAKI-1 | Kidney | | |
| CAKI-2 | Kidney | | |
| G-401 | kidney | | |
| G-402 | Kidney | | |
| SK-NEP-1 | Kidney | | |
| ARH-77 | Myeloma | Plasma cell | |
| BV-173 | Leukemia | CML | |
| CCRF-CEM | Leukemia | myelomonoblastic | T-ALL |
| CEM-C1 | Leukemia | ALL | |
| CML-T1 | Leukemia | CML | |
| EM-2 | Leukemia | CML | |
| HEL-92-1-7 | Leukemia | Erythroleukemia | |
| J-RT3-T3-5 | Leukemia | Acute T cell | |
| Jurkat | Leukemia | Acute T cell | |

TABLE 5-continued

| Cell line | Tumor Type | Subtype | Classification |
|---|---|---|---|
| K-562 | Leukemia | CML | CML |
| MEG-01 | Leukemia | CML | |
| MOLT-16 | Leukemia | ALL | |
| MOLT-3 | Leukemia | ALL | |
| MV-4-11 | Leukemia | B myelo-monocytic | |
| MX1 | Leukemia | APML | |
| NALM-6 | Leukemia | B cell precursor | |
| THP-1 | Leukemia | AML | AML |
| HepG2 | Liver | | |
| HLE | Liver | | |
| HLF | Liver | | |
| HuCCT1 | Liver | | |
| HUH-6-clone5 | Liver | | |
| OCUG-1 | Liver | | |
| SNU-423 | Liver | | |
| A427 | Lung | | |
| A549 | Lung | | NSCLC |
| Calu-1 | Lung | SQCC | NSCLC |
| Calu-6 | Lung | Anaplastic | NSCLC |
| ChaGo-K-1 | Lung | Broncho-genic | |
| COR-L105 | Lung | | |
| COR-L23 | Lung | | NSCLC |
| DMS-114 | Lung | SCLC | SCLC |
| DMS-273 | Lung | | SCLC |
| DMS-53 | Lung | SCLC | SCLC |
| NCI-H292 | Lung | | Mucoepidermoid |
| NCI-H441 | Lung | NSCLC | NSCLC |
| NCI-H446 | Lung | | SCLC |
| NCI-H460 | Lung | | NSCLC |
| NCI-H520 | Lung | NSCLC | NSCLC |
| NCI-H596 | Lung | NSCLC | NSCLC |
| NCI-H661 | Lung | | NSCLC |
| NCI-H69 | Lung | | SCLC |
| SHP-77 | Lung | | SCLC |
| SK-MES-1 | Lung | SQCC | SQCC |
| SW900 | Lung | SQCC | NSCLC |
| Wi38 | Lung | Normal fibroblasts | Normal Fibroblasts |
| BC-1 | Lymphoma | | |
| CRO-AP2 | Lymphoma | B cell | |
| Daudi | Lymphoma | BL | BL |
| DB | Lymphoma | Large cell | DLBCL |
| DOHH-2 | Lymphoma | B cell | FL |
| EB-3 | Lymphoma | BL | |
| HT | Lymphoma | Diffuse mixed | DLBCL |
| MHH-PREB-1 | Lymphoma | B cell | Lymphoblastic |
| Raji | Lymphoma | BL | BL |
| Ramos RA1 | Lymphoma | BL | BL |
| SKO-007 | Lymphoma | B lymphocyte | |
| SR | Lymphoma | Large cell immuno-blastic | Large |
| ST486 | Lymphoma | BL | |
| RPMI-8226 | Myeloma | Plasma-cytoma; myeloma | B-cell |
| U266B1 | Myeloma | Myeloma | B-cell |
| AsPC-1 | Pancreas | | |
| BxPC-3 | Pancreas | | |
| CAPAN-1 | Pancreas | | |
| CAPAN-2 | Pancreas | | |
| CFPAC-1 | Pancreas | | |
| HPAF-II | Pancreas | | |
| HS766T | Pancreas | | |
| HuP-T4 | Pancreas | | |
| MIA-PaCa-2 | Pancreas | | |
| PANC-1 | Pancreas | | |
| SU.86.86 | Pancreas | | |
| YAPC | Pancreas | | |
| 22RV1 | Prostate | | |
| BM-1604 | Prostate | | |
| BPH-1 | Prostate | | |
| BPH-1 | Prostate | | |
| BPH-1 | Prostate | | |
| DU-145 | Prostate | | |
| LNCaP | Prostate | | |
| PC-3 | Prostate | | |
| A101D | Skin | Melanoma | |
| A375 | Skin | Melanoma | |
| A431 | Skin | SQCC | |
| A7 | Skin | Melanoma | |
| C32 | Skin | Melanoma | |
| C32TG | Skin | Melanoma | |
| CHL-1 | Skin | Melanoma | |
| COLO-829 | Skin | Melanoma | |
| HMCB | Skin | Melanoma | |
| HS294T | Skin | Melanoma | |
| HS695T | Skin | Melanoma | |
| MALME-3M | Skin | Melanoma | |
| Mewo | Skin | Melanoma | |
| RPMI-7951 | Skin | Melanoma | |
| SH-4 | Skin | Melanoma | |
| SK-MEL-1 | Skin | Melanoma | |
| SK-MEL-28 | Skin | Melanoma | |
| SK-MEL-3 | Skin | Melanoma | |
| A204 | Soft Tissue | Rhabdomyo-sarcoma | |
| A673 | Soft Tissue | Sarcoma | |
| HOS | Bone | Sarcoma | |
| HT1080 | Soft Tissue | Sarcoma | |
| KHOS-240S | Bone | Osteo-sarcoma | |
| MES-SA | Soft Tissue | Sarcoma | |
| MG-63 | Bone | Sarcoma | |
| RD | Soft Tissue | Sarcoma | |
| Saos-2 | Bone | Sarcoma | |
| SJRH30 | Soft Tissue | Rhabdomyo-sarcoma | |
| SJSA-1 | Bone | Osteo-sarcoma | |
| SK-LMS-1 | Soft Tissue | Sarcoma | |
| SK-UT-1 | Soft Tissue | Sarcoma | |
| SW1353 | Bone | Sarcoma | |
| SW684 | Soft Tissue | Sarcoma | |
| SW872 | Soft Tissue | Sarcoma | |
| SW982 | Soft Tissue | Sarcoma | |
| TE 381.T | Soft Tissue | Rhabdomyo-sarcoma | |
| U-2-OS | Bone | Sarcoma | |

TABLE 6

Cell line screening results

| Cell Line | $GI_{50}$ (µM) | $IC_{50}$ (µM) | Max. Fold. Change | Cal_X |
|---|---|---|---|---|
| 5637 | 0.0905 | 0.0946 | 51.0 | 0.1026 |
| 639-V | 0.0855 | 0.0904 | 13.5 | 0.0540 |
| 647-V | 0.1022 | 0.1177 | 12.4 | 0.0757 |
| BFTC-905 | 0.0626 | 0.0649 | 22.1 | 0.0428 |
| HT1197 | 1.7581 | 5.7255 | 5.5 | 8.8398 |
| HT1376 | 0.9204 | 1.9883 | 5.3 | 9.1659 |
| J82 | 1.0029 | 10.0000 | 4.9 | 10.0000 |
| SCaBER | 0.0894 | 0.0927 | 16.3 | 0.0581 |
| T24 | 0.0941 | 0.0960 | 68.3 | 0.0008 |
| TCCSUP | 0.0657 | 0.0958 | 5.2 | 0.0974 |
| UM-UC-3 | 0.1021 | 0.1314 | 70.6 | 0.0372 |
| AU565 | 0.4598 | 1.2290 | 33.8 | 0.2656 |
| BT-20 | 0.4591 | 1.2935 | 4.4 | 10.0000 |
| BT-474 | 0.0837 | 4.3719 | 20.0 | 1.1580 |
| BT-549 | 1.7310 | 4.8054 | 5.6 | 0.2720 |
| CAMA-1 | 0.4279 | 1.1890 | 7.5 | 5.2170 |

TABLE 6-continued

Cell line screening results

| Cell Line | GI$_{50}$ (μM) | IC$_{50}$ (μM) | Max. Fold. Change | Cal_X |
|---|---|---|---|---|
| EFM-19 | 0.0618 | 0.1036 | 32.5 | 0.0686 |
| HS578T | 10.0000 | 10.0000 | 3.8 | 10.0000 |
| KPL-1 | 0.8217 | 2.4194 | 67.2 | 0.0888 |
| MCF7 | 0.1287 | 0.8192 | 26.2 | 0.0625 |
| MDA-MB-231 | 0.3690 | 0.7750 | 5.6 | 0.2184 |
| MDA-MB-436 | 0.8881 | 1.8798 | 1.8 | 10.0000 |
| MDA-MB-453 | 0.0810 | 0.1111 | 9.7 | 0.1290 |
| MDA-MB-468 | 0.0928 | 0.1017 | 14.1 | 0.1679 |
| MT-3 | 0.0395 | 0.0478 | 7.3 | 0.0696 |
| SK-BR-3 | 0.2868 | 1.3152 | 4.4 | 10.0000 |
| T47D | 0.2919 | 1.1604 | 10.4 | 4.9403 |
| A172 | 0.0457 | 10.0000 | 11.9 | 0.0521 |
| BE(2)C | 0.0796 | 0.0893 | 29.6 | 0.0468 |
| CCF-STTG1 | 4.4267 | 5.6280 | 5.0 | 10.0000 |
| CHP-212 | 0.0278 | 0.0364 | 11.4 | 0.0458 |
| D-283MED | 0.0584 | 0.0654 | 26.0 | 0.0580 |
| Daoy | 0.0887 | 0.1043 | 13.1 | 0.0849 |
| DBTRG-05MG | 4.2986 | 10.0000 | 4.4 | 10.0000 |
| DK-MG | 10.0000 | 10.0000 | 9.2 | 5.4460 |
| H4 | 0.0718 | 0.0736 | 44.9 | 0.0422 |
| MC-IXC | 0.0471 | 0.0539 | 51.6 | 0.0439 |
| SK-N-AS | 0.4244 | 1.5168 | 14.5 | 0.0515 |
| SK-N-DZ | 0.1618 | 0.2077 | 34.8 | 0.2178 |
| SK-N-FI | 2.2181 | 9.5496 | 3.2 | 10.0000 |
| SNB-19 | 10.0000 | 10.0000 | 1.6 | 10.0000 |
| SW1088 | 0.0469 | 10.0000 | 13.1 | 0.0560 |
| SW1783 | 10.0000 | 10.0000 | 3.1 | 10.0000 |
| T98G | 2.6239 | 10.0000 | 61.2 | 0.0426 |
| U-138MG | 10.0000 | 10.0000 | 4.8 | 10.0000 |
| U-87-MG | 0.1044 | 10.0000 | 11.2 | 0.0659 |
| COLO-201 | 0.1052 | 0.1272 | 8.2 | 0.3152 |
| COLO-205 | 0.0824 | 0.0838 | 182.5 | 0.0440 |
| COLO-320DM | 0.0927 | 0.1254 | 75.6 | 0.0723 |
| COLO-320-HSR | 0.1034 | 0.1261 | 37.3 | 0.0717 |
| DLD-1 | 0.0473 | 0.0496 | 45.1 | 0.0338 |
| HCT-116 | 0.0479 | 0.0488 | 37.9 | 0.0385 |
| HCT-15 | 0.0531 | 0.0559 | 58.9 | 0.0377 |
| HCT-8 | 0.0298 | 0.0312 | 282.4 | 0.0138 |
| HT29 | 0.1156 | 0.1265 | 35.8 | 0.0632 |
| LS-1034 | 0.1033 | 0.1061 | 6.7 | 0.2283 |
| LS-174T | 0.0665 | 0.0914 | 16.1 | 0.0479 |
| NCI-H508 | 0.2291 | 0.5928 | 30.5 | 0.0649 |
| NCI-H747 | 0.3733 | 1.6297 | 3.3 | 10.0000 |
| RKO | 0.0504 | 0.0526 | 35.1 | 0.0394 |
| RKO-AS45-1 | 0.0415 | 0.0445 | 24.5 | 0.0371 |
| RKO-E6 | 0.0513 | 0.0527 | 14.4 | 0.0490 |
| SW1417 | 4.5665 | 10.0000 | 6.5 | 6.7147 |
| SW403 | 0.2573 | 0.2969 | 12.2 | 0.4506 |
| SW48 | 0.0459 | 0.0497 | 12.0 | 0.0623 |
| SW480 | 1.0169 | 2.1065 | 25.3 | 3.9577 |
| SW620 | 0.0572 | 0.0636 | 20.3 | 0.0559 |
| SW837 | 0.3301 | 0.8362 | 34.9 | 0.0815 |
| SW948 | 0.2469 | 0.2875 | 26.6 | 0.2257 |
| WiDr | 0.3583 | 0.6266 | 22.3 | 0.1700 |
| AGS | 0.0308 | 0.0328 | 12.1 | 0.0312 |
| HS746T | 10.0000 | 10.0000 | 2.6 | 10.0000 |
| KATOIII | 1.0051 | 1.9453 | 31.3 | 0.0715 |
| OE19 | 0.0575 | 0.0636 | 33.6 | 0.0524 |
| SNU-1 | 0.2788 | 0.4798 | 12.6 | 0.0473 |
| SNU-16 | 0.1487 | 0.2269 | 3.9 | 10.0000 |
| SNU-5 | 5.9807 | 10.0000 | 2.3 | 10.0000 |
| SW1463 | 5.0067 | 10.0000 | 4.3 | 10.0000 |
| BHT-101 | 0.3120 | 0.4093 | 64.6 | 0.1877 |
| CAL-62 | 0.0972 | 0.0987 | 35.2 | 0.0450 |
| CGTH-W-1 | 0.1027 | 0.1096 | 32.2 | 0.0429 |
| NCI-H295 | 10.0000 | 10.0000 | 3.1 | 10.0000 |
| SW13 | 0.1621 | 0.2426 | 19.3 | 0.0657 |
| SW579 | 2.6704 | 10.0000 | 6.6 | 0.0772 |
| Y79 | 0.1843 | 0.2576 | 6.4 | 1.6819 |
| AN3 CA | 0.5117 | 1.1664 | 14.1 | 3.7957 |
| BeWo | 0.5064 | 0.7466 | 5.2 | 9.4738 |
| C-33-A | 0.0745 | 0.1220 | 33.7 | 0.3941 |
| C4-1 | 0.0804 | 0.1144 | 20.8 | 0.0827 |
| C4-2 | 0.2487 | 0.4270 | 16.3 | 1.1314 |
| Caov-3 | 0.0666 | 0.1061 | 4.0 | 10.0000 |
| DoTc2-4510 | 0.3552 | 0.7875 | 12.9 | 0.7698 |
| ES-2 | 0.0915 | 0.0936 | 33.3 | 0.0487 |
| HEC-1-A | 0.1656 | 0.4534 | 4.3 | 10.0000 |
| HeLa | 0.3882 | 0.6010 | 6.5 | 0.8340 |
| HT3 | 1.3798 | 2.5017 | 6.2 | 7.0920 |
| JAR | 0.0495 | 0.0519 | 24.8 | 0.0576 |
| JEG-3 | 0.0859 | 0.0954 | 15.8 | 0.0726 |
| KLE | 2.3130 | 6.4698 | 15.4 | 4.5020 |
| Ovcar-3 | 0.4434 | 0.8643 | 135.6 | 0.7343 |
| RL95-2 | 0.0455 | 0.0649 | 4.0 | 10.0000 |
| SiHa | 10.0000 | 10.0000 | 6.0 | 8.3919 |
| SK-OV-3 | 10.0000 | 10.0000 | 8.0 | 1.8718 |
| SW954 | 0.0866 | 0.0887 | 11.0 | 0.1179 |
| SW962 | 10.0000 | 10.0000 | 3.6 | 10.0000 |
| CAL-27 | 0.0538 | 0.0567 | 15.5 | 0.0493 |
| Detroit562 | 0.0471 | 0.0537 | 22.6 | 0.0553 |
| FADU | 0.1223 | 0.1661 | 8.0 | 0.0792 |
| OE21 | 0.0651 | 0.0682 | 12.3 | 0.0738 |
| OE33 | 0.1965 | 0.3052 | 8.8 | 0.2006 |
| SCC-25 | 0.0673 | 0.0731 | 19.5 | 0.0894 |
| SCC-4 | 8.3155 | 10.0000 | 3.0 | 10.0000 |
| SCC-9 | 0.2650 | 0.5288 | 17.0 | 0.2767 |
| L428 | 3.2804 | 4.5993 | 4.8 | 10.0000 |
| RPMI-6666 | 0.1481 | 0.1535 | 7.8 | 0.2252 |
| 769-P | 0.2663 | 0.3597 | 4.9 | 10.0000 |
| 786-0 | 0.1115 | 0.1199 | 22.1 | 0.0690 |
| A498 | 0.4915 | 1.3982 | 7.3 | 0.0728 |
| ACHN | 0.3960 | 0.8495 | 60.4 | 0.0460 |
| CAKI-1 | 0.1284 | 10.0000 | 3.9 | 10.0000 |
| CAKI-2 | 10.0000 | 10.0000 | 3.0 | 10.0000 |
| G-401 | 0.0794 | 0.0817 | 12.7 | 0.7392 |
| G-402 | 0.0378 | 0.0431 | 16.3 | 0.0566 |
| SK-NEP-1 | 0.1270 | 0.1681 | 17.4 | 0.3116 |
| ARH-77 | 0.0594 | 0.0618 | 26.4 | 0.0525 |
| BV-173 | 0.0444 | 0.0454 | 29.4 | 0.0427 |
| CCRF-CEM | 0.0813 | 0.0819 | 16.6 | 0.0617 |
| CEM-C1 | 0.4524 | 0.4805 | 18.3 | 0.0529 |
| CML-T1 | 0.0689 | 0.0716 | 29.8 | 0.0430 |
| EM-2 | 0.0903 | 0.0988 | 13.5 | 0.0766 |
| HEL-92-1-7 | 0.5351 | 0.6301 | 20.7 | 1.1545 |
| J-RT3-T3-5 | 0.0463 | 0.0534 | 13.4 | 0.0286 |
| Jurkat | 0.0501 | 0.0551 | 19.0 | 0.0460 |
| K-562 | 2.6980 | 4.7723 | 13.7 | 0.6802 |
| MEG-01 | 2.1931 | 3.8366 | 3.1 | 10.0000 |
| MOLT-16 | 0.0383 | 0.0388 | 12.0 | 0.0798 |
| MOLT-3 | 0.1187 | 0.4689 | 4.5 | 10.0000 |
| MV-4-11 | 0.0906 | 0.0940 | 14.8 | 0.3032 |
| MX1 | 0.0576 | 0.0589 | 44.7 | 0.0394 |
| NALM-6 | 0.0547 | 0.0560 | 72.7 | 0.0359 |
| THP-1 | 10.0000 | 10.0000 | 4.8 | 10.0000 |
| HepG2 | 0.1366 | 0.2124 | 18.1 | 0.0853 |
| HLE | 0.1020 | 0.1067 | 4.5 | 10.0000 |
| HLF | 0.1232 | 0.1817 | 29.3 | 0.0430 |
| HuCCT1 | 1.4582 | 2.6967 | 13.2 | 0.0503 |
| HUH-6-clone5 | 0.1433 | 0.1756 | 31.2 | 0.1025 |
| OCUG-1 | 1.2036 | 3.9346 | 11.5 | 0.2126 |
| SNU-423 | 10.0000 | 10.0000 | 3.2 | 10.0000 |
| A427 | 0.0794 | 0.1168 | 15.7 | 0.0238 |
| A549 | 0.0528 | 0.0602 | 61.6 | 0.0287 |
| Calu-1 | 2.9029 | 9.0678 | 11.7 | 0.1295 |
| Calu-6 | 4.6564 | 8.1661 | 5.2 | 8.9974 |
| ChaGo-K-1 | 0.1465 | 0.3720 | 4.4 | 10.0000 |
| COR-L105 | 0.1447 | 0.5875 | 4.7 | 10.0000 |
| COR-L23 | 0.1414 | 0.1531 | 7.2 | 0.1411 |
| DMS-114 | 1.3925 | 4.6519 | 4.0 | 10.0000 |
| DMS-273 | 0.0674 | 0.0690 | 15.9 | 0.0568 |
| DMS-53 | 1.7366 | 6.6828 | 48.7 | 0.2879 |
| NCI-H292 | 0.0817 | 0.0921 | 30.5 | 0.0722 |
| NCI-H441 | 0.8207 | 3.0855 | 4.2 | 10.0000 |
| NCI-H446 | 0.3539 | 0.4244 | 6.5 | 1.9460 |
| NCI-H460 | 0.0870 | 0.0877 | 98.0 | 0.0407 |
| NCI-H520 | 0.3189 | 0.4497 | 7.9 | 1.2581 |
| NCI-H596 | 0.2824 | 10.0000 | 2.2 | 10.0000 |
| NCI-H661 | 1.7213 | 4.2789 | 10.7 | 0.0680 |
| NCI-H69 | NaN | NaN | 3.0 | 10.0000 |

TABLE 6-continued

Cell line screening results

| Cell Line | GI$_{50}$ (μM) | IC$_{50}$ (μM) | Max. Fold. Change | Cal_X |
|---|---|---|---|---|
| SHP-77 | 0.1818 | 0.2783 | 6.9 | 1.9384 |
| SK-MES-1 | 0.4135 | 0.9021 | 18.5 | 0.1941 |
| SW900 | 10.0000 | 10.0000 | 2.1 | 10.0000 |
| Wi38 | 0.6851 | 1.8760 | 6.8 | 0.0772 |
| BC-1 | 0.0621 | 0.0655 | 60.2 | 0.0548 |
| CRO-AP2 | 0.0458 | 0.0494 | 87.5 | 0.0602 |
| Daudi | 0.0953 | 0.0974 | 14.8 | 0.0573 |
| DB | 0.0758 | 0.0833 | 40.8 | 0.0742 |
| DOHH-2 | 0.0677 | 0.0714 | 17.5 | 0.0971 |
| EB-3 | 0.2738 | 0.4248 | 8.4 | 0.2986 |
| HT | 0.1784 | 0.2437 | 3.1 | 10.0000 |
| MHH-PREB-1 | 0.0637 | 0.0653 | 44.2 | 0.0422 |
| Raji | 0.0511 | 0.0544 | 21.3 | 0.0504 |
| RamosRA1 | 0.0871 | 0.0881 | 50.0 | 0.0617 |
| SKO-007 | 0.9528 | 1.2076 | 10.7 | 2.0090 |
| SR | 0.0855 | 0.0867 | 33.0 | 0.0603 |
| ST486 | 0.0361 | 0.0401 | 27.5 | 0.0584 |
| RPMI-8226 | 0.1150 | 0.1836 | 13.8 | 0.5722 |
| U266B1 | 0.1590 | 0.3756 | 7.6 | 4.1758 |
| AsPC-1 | 1.5312 | 10.0000 | 6.9 | 5.2046 |
| BxPC-3 | 0.0814 | 0.1361 | 8.8 | 0.0630 |
| CAPAN-1 | 0.9358 | 2.4121 | 3.1 | 10.0000 |
| CAPAN-2 | 0.2937 | 10.0000 | 28.8 | 0.0583 |
| CFPAC-1 | 10.0000 | 10.0000 | 15.2 | 0.0568 |
| HPAF-II | 0.2492 | 0.3684 | 11.5 | 0.2588 |
| HS766T | 10.0000 | 10.0000 | 5.7 | 0.7781 |
| HuP-T4 | 0.1092 | 0.1366 | 12.6 | 0.2143 |
| MIA-PaCa-2 | 0.3260 | 0.5436 | 15.6 | 0.0639 |
| PANC-1 | 3.3504 | 9.5585 | 3.4 | 10.0000 |
| SU.86.86 | 0.8641 | 1.9177 | 17.9 | 0.0704 |
| YAPC | 0.8691 | 3.1871 | 51.2 | 0.0322 |
| 22RV1 | 0.1405 | 0.2485 | 39.2 | 0.0361 |
| BM-1604 | 1.1194 | 2.0149 | 20.8 | 0.2011 |
| BPH-1 | 0.1498 | 0.1669 | 7.5 | 0.2422 |
| DU-145 | 0.0958 | 0.0991 | 394.0 | 0.0382 |
| LNCaP | 9.6042 | 10.0000 | 2.9 | 10.0000 |
| PC-3 | 1.2048 | 2.3542 | 14.1 | 1.2528 |
| A101D | 0.3510 | 0.8607 | 18.1 | 0.1754 |
| A375 | 0.0460 | 0.0475 | 38.5 | 0.0356 |
| A431 | 0.0924 | 0.0986 | 13.5 | 0.1298 |
| A7 | 0.1262 | 0.2490 | 9.0 | 0.0468 |
| C32 | 1.1087 | 10.0000 | 13.0 | 1.9676 |
| C32TG | 0.8305 | 2.0288 | 15.1 | 0.2294 |
| CHL-1 | 0.0972 | 0.1044 | 41.1 | 0.0180 |
| COLO-829 | 2.0590 | 8.5007 | 6.8 | 0.7345 |
| HMCB | 0.0964 | 0.0988 | 20.4 | 0.0619 |
| HS294T | 0.0970 | 0.1178 | 16.5 | 0.0567 |
| HS695T | 0.7708 | 3.0838 | 18.4 | 3.0148 |
| MALME-3M | 1.6636 | 10.0000 | 1.8 | 10.0000 |
| Mewo | 10.0000 | 10.0000 | 4.5 | 10.0000 |
| RPMI-7951 | 0.0999 | 0.1052 | 5.1 | 0.2834 |
| SH-4 | 0.0565 | 0.3220 | 9.9 | 0.0396 |
| SK-MEL-1 | 10.0000 | 10.0000 | 1.9 | 10.0000 |
| SK-MEL-28 | 10.0000 | 10.0000 | 6.6 | 0.2632 |
| SK-MEL-3 | 2.5742 | 10.0000 | 4.1 | 10.0000 |
| A204 | 0.0579 | 0.1457 | 9.2 | 0.0629 |
| A673 | 0.0560 | 0.0735 | 4.3 | 10.0000 |
| HOS | 0.0737 | 0.0756 | 85.6 | 0.0362 |
| HT1080 | 0.0855 | 0.0899 | 17.5 | 0.0672 |
| KHOS-240S | 0.0991 | 0.1100 | 16.3 | 0.0789 |
| MES-SA | 0.0354 | 0.0379 | 47.3 | 0.0241 |
| MG-63 | 2.0387 | 4.6830 | 7.5 | 0.4768 |
| RD | 0.4567 | 0.7541 | 26.7 | 0.1603 |
| Saos-2 | 1.8273 | 4.5508 | 3.6 | 10.0000 |
| SJRH30 | 0.5334 | 1.3424 | 6.9 | 0.0992 |
| SJSA-1 | 10.0000 | 10.0000 | 89.2 | 0.0538 |
| SK-LMS-1 | 4.4020 | 10.0000 | 4.5 | 10.0000 |
| SK-UT-1 | 0.2891 | 0.9592 | 10.1 | 0.3581 |
| SW1353 | 10.0000 | 10.0000 | 8.3 | 0.2769 |
| SW684 | 10.0000 | 10.0000 | 3.0 | 10.0000 |
| SW872 | 0.1001 | 0.1204 | 53.3 | 0.0551 |
| SW982 | 3.6570 | 10.0000 | 2.7 | 10.0000 |
| TE 381.T | 4.8712 | 10.0000 | 6.8 | 0.2981 |
| U-2-OS | 0.0821 | 0.0887 | 35.6 | 0.0438 |

Note: NaN: variable data

Conclusion.

Figure 2:
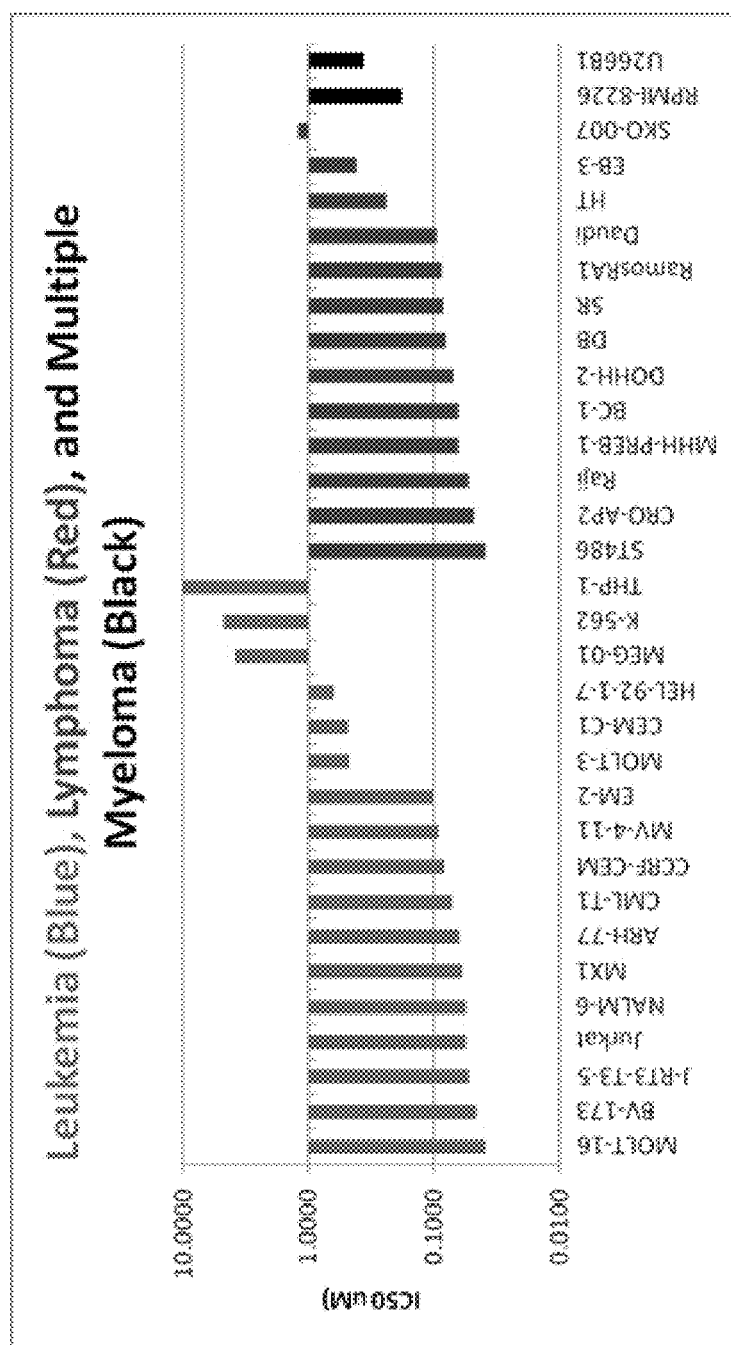
FIG. 2: Pyrrolopyrimidine Compounds showed anti-proliferative activity in a variety of hematological cancers, namely, a variety of lymphomas (ST486, CRO-AP2, Faji, MHH-PREB-1, BC-1, DOHH-2, DB, SR, RamosRA1, Daudi, HT, EB-3, SKO-007) and leukemias MOLT-16, BV-173, J-RT3-T3-5, Jurkat, NALM-6, MX1, ARH-77, CML-T1, CCRF-CEM, MV-4-11, EM-2, MOLT-3, CEM-C1, HEL-92-1-7, MEG-01, K-562, THP-1)/myeloma (RPMI-8226, U266B1) (exemplified by Cmpd. 38 in FIG. 2).

As shown in Table 6 and FIGS. 1 and 2, Pyrrolopyrimidine Compounds (exemplified by Compound 38) showed anti-proliferative activity in a variety of cancers, comprising solid tumors (FIG. 1), for example, cancers of the bladder, breast, CNS, colon, endocrine, female GU, head and neck, kidney, liver, lung, pancreas, prostate, skin, bone and soft-tissue, and hematological cancers (FIG. 2), for example, lymphomas, leukemias and multiple myeloma.

GBM Cancer Stem Cell Viability Assay.

Five high grade glioblastoma-derived tumor cultures in defined serum-free medium that enriches the GBM-CSC tumor subfraction were established, as described previously [Mao P, et al. Proc Nat Acad Sci 2013; 110(21): 8644-9]. Clinical diagnoses and stem cell marker analyses were performed. The cancer stem cells (CSCs) (8311, 81611, 32612, 1912, and 52810), were plated in a 20 μL/well volume of serum-free growth medium at a density of 800 cells/well in a 384-well format. GBM CSCs were mechanically-dissociated by trituration prior to counting and plating. As a normal cell control, 1200 HUVECs were plated in 20 μL per well of a 384-well plate in Endothelial Growth Media Microvascular-2. After 1 day of cultivation, 20 μL/well of respective fresh medium for each cell type was added and the cells were treated with Pyrrolopyrimidine Compounds at multiple concentrations or 0.04 μL DMSO for 3 days under 5% $CO_2$/37° C. culture conditions. After 3 days of compound treatment, cells were lysed through the addition of 30 μL of CellTiter-Glo (CTG) reagent to evaluate relative cell density. The plate was placed at room temperature for 30 minutes after which luminescent signal was monitored.

Results.

Figure 3:
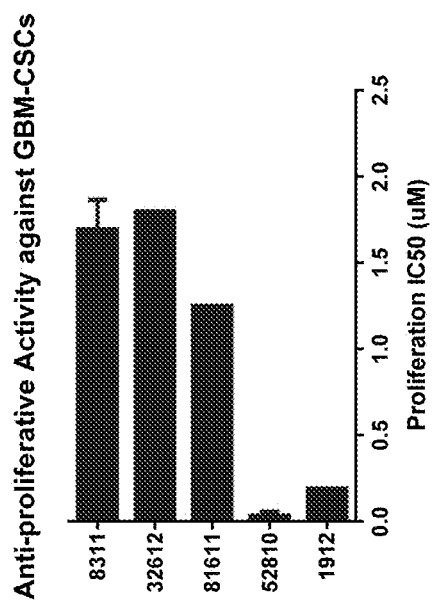
FIG. 3: Pyrrolopyrimidine Compounds demonstrated potency against several mesenchymal GBM CSCs (8311, 32612, 81611) with $IC_{50}$s in the range of 1-2 µM. The data indicated that Pyrrolopyrimidine Compounds, exemplified by Cmpd. 38, are particularly potent against two GBM CSC sphere models derived from proneural subtype GBM patients (52810 and 1912) with $IC_{50}$ in the range of 50-190 nM.

Table 7 summarizes the GBM subtype affiliation of each GBM-CSC model utilized. The impact of Pyrrolopyrimidine Compounds on the growth of GBM-CSCs was tested under defined serum-free culture conditions by CTG. The concentration of compound that inhibited the cell growth by 50% was determined in those five models (data for Compound 38 is summarized in FIG. 3). Pyrrolopyrimidine Compounds (exemplified by Compound 38) demonstrated potency against mesenchymal GBM CSCs with IC$_{50}$s in the range of 1-2 μM. This data also indicated that Pyrrolopyrimdine Compounds (as shown for Compound 38) were particularly potent against two GBM CSC sphere models derived from proneural subtype GBM patients with IC$_{50}$ in the range of 50-190 nM.

TABLE 7

Characteristics of GBM-Cancer Stem Cells

| Patient CSCs | Clinical Diagnosis | Subtype |
|---|---|---|
| 8311 | GBM | Mesenchymal (Mes) |
| 52810 | GBM | Proneural (PN) |
| 81611 | GBM | PN/Relapse |

TABLE 7-continued

Characteristics of GBM-Cancer Stem Cells

| Patient CSCs | Clinical Diagnosis | Subtype |
|---|---|---|
| 32612 | GBM | Mesenchymal (Mes) |
| 1912 | GBM | Proneural (PN) |

Stem Cell Marker Oct-4 Assay.

Figure 4:
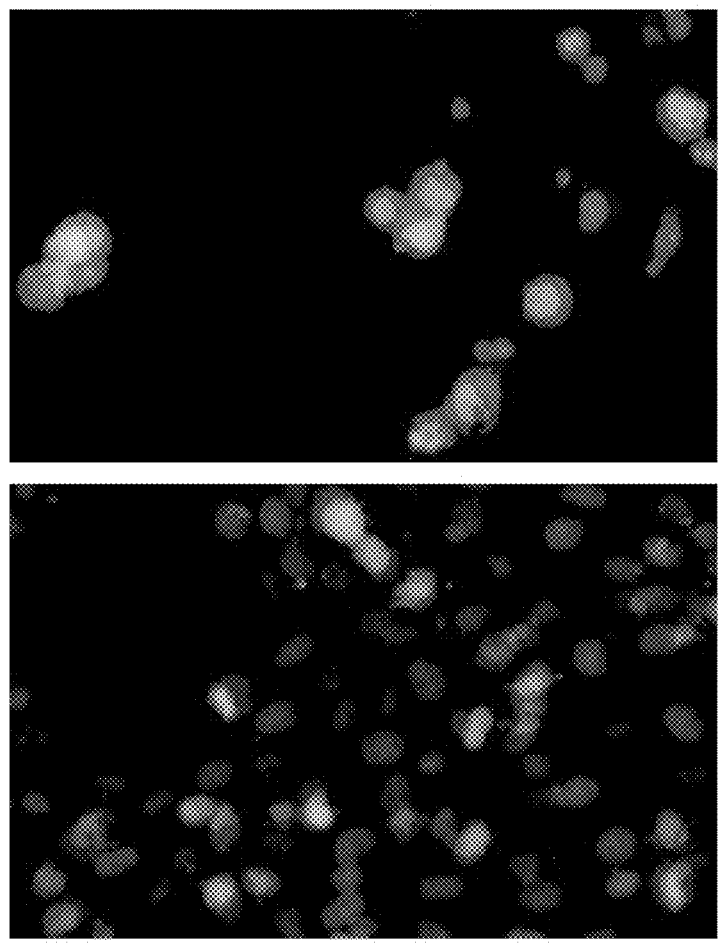
FIG. 4: Induction of GBM-CSC differentiation by Pyrrolopyrimidine Compounds (for example, Cmpd. 38) is shown in FIG. 4 (left panel: DMSO, right panel: Cmpd. 38). Abbreviations: DMSO=dimethyl sulfoxide; Oct4=octamer-binding transcription factor 4; Tuj1=tubulinβ3; DAPI=4',6-diamidino-2-phenylindole. The 8311 GBM CSCs and HUAEC cells were allowed to co-culture for 1 day prior to compound administration. After 3 days of compound or mock/DMSO-treatment, cells were fixed and monitored for expression of Oct4 and Tuj1 by indirect immunofluorescence. Pyrrolopyrimidine Compounds (exemplified by Cmpd. 38) induced differentiation of GBM CSCs in the context of a HUAEC co-culture model.

1200 HUAECs were plated per well of a 384-well plate. After 1 day 8311 GBM CSCs were mechanically-dissociated by trituration and added at a density of 600 cells per well. The cells were allowed to co-culture for 1 day and then treated with various concentrations of Pyrrolopyrimidine Compound or DMSO for 3 days in 5% $CO_2$ at 37° C. After incubation with compound, 40 µL of 4% paraformaldehyde was added. Cell fixation was allowed to proceed at room temperature for 1 hour and each well was washed 5 times with a 50 µL volume of PBS. Each well was treated overnight at 4° C. with a 50 µL volume of PBS supplemented with 3% goat serum and 0.25% triton X-100. Cells were the incubated overnight at 4° C. with anti Oct4 and anti Tuj1 antibodies diluted 1:100 and 1:1000 respectively in PBS/3% goat serum/0.25% triton. Cells were washed 5 times with PBS/0.25% triton and incubated with AlexaFluor-labeled secondary antibodies for 3 hours at room temperature after which the wells were washed 5 times with PBS/0.25% Triton. Images of 4 randomly chosen fields were acquired using an EVOS Cell Imaging System at 10× magnification. Adobe Photoshop (Adobe Systems Incorporated) was used to process raw images, assign and merge channels. Representative images are shown in FIG. 4.

Results.

A defining property of stem cells is their capacity to generate differentiated progeny. GBM CSCs demonstrated the ability to undergo neuronal and astrocytic differentiation upon growth factor withdrawal or following exposure to BMP-4 [Pollard et at *Cell Stem Cell* 2009; 4(6):568-80]. We evaluated the impact of Pyrrolopyrimidine Compounds on 8311 glioma stem cells in a pathologically relevant GBM-CSC/HUAEC co-culture model. Endothelial cells are known to interact closely with self-renewal GBM-CSC and secret factors maintaining these cells in stem-cell like state [Calabrese et al. *Cancer cell* 2007; 11(1):69-82]. In this assay, Oct 4 was used as stem cell marker and Tuj-1 was used as neuronal marker for GBM-CSC and differentiated neuronal cell populations, respectively. As shown in FIG. 4, upon Pyrrolopyrimidine Compound treatment (as shown for Compound 38), the Oct4 positive GBM CSC population was decreased while the proportion of Tuj-1 positive neuronal cells was increased. This data indicates that Pyrrolopyrimidine Compounds can eliminate the Oct-4 positive cancer stem cell population and induce neuronal differentiation in the 8311/HUAEC co-culture model.

Conclusions.

Pyrrolopyrimidine Compounds were shown to impair the proliferation of GBM CSC models. Five models isolated from primary GBM patient specimens, representative of mesenchymal and proneural GBM subclasses, were utilized to test Pyrrolopyrimidine Compound activity upon GBM CSCs. Pyrrolopyrimidine Compounds (as exemplified by Compound 38) potently inhibited proliferation of proneural 52810 and 1912 cells with $IC_{50}$ values of 0.048 and 0.19 µM, respectively. Pyrrolopyrimidine Compounds (exemplified by Compound 38) had less potency in the inhibition of mesenchymal models 8311 and 32612 cells with $IC_{50}$ values of 1.6 and 1.8 µM, respectively. Furthermore, Pyrrolopyrimidine Compounds (exemplified by Compound 38) induced differentiation of GBM CSCs in the context of a HUAEC co-culture model. Hence, our data indicates that Pyrrolopyrimidine Compounds can both inhibit proliferation and induce neuronal differentiation of GBM CSCs.

ANIMAL MODELS

Cancer Xenograft Model.

For xenograft model studies human cancer cell lines were injected into SCID (severe combined immunodeficiency) mice. Cancer cell lines were propagated in culture in vitro. Tumor bearing animals were generated by injecting precisely determined numbers of cells into mice. Following inoculation of animals, the tumors were allowed to grow to a certain size prior to randomization. The mice bearing xenograft tumors, typically ranging between 100 and 400 $mm^3$, were pooled together and randomized into various treatment groups. Primary tumorgrafts were propagated in vivo. Tumor fragments from donor mice were implanted into small numbers of mice for maintenance, or larger numbers of mice for study initiation. A typical efficacy study design involved administering one or more compounds at various dose levels to tumor-bearing mice. Additionally, reference chemotherapeutic agents (positive control) and negative controls were similarly administered and maintained. Routes of administration can include subcutaneous (SC), intraperitoneal (IP), intravenous (IV), intramuscular (IM) and oral (PO). Tumor measurements and body weights were taken over the course of the study and morbidity and mortality were recorded. Necropsy, histopathology, and PCR can also be performed to enhance understanding of disease and drug action.

Some of the typical human bladder cancer cell lines, for example transitional cell carcinoma, that were or can be used in the above xenograft models are: HT-1376, HT-1197, UMUC-3, KU-7, and KU-19-19 cell lines.

Some of the typical human breast cancer cell lines that were or can be used in the above xenograft models are: luminal-B type cell lines, for example BT-474, or ZR-75, and basal type cell lines, for example, MDA-MB-231, T47D, and Cal-51 cell lines.

Some of the typical human lung squamous cell carcinoma cell lines, that were or can be used in the above xenograft models are: SK-MES-1, NCI-H1703, HCC-15, and Calu-1 cell line.

Some of the typical human esophageal squamous carcinoma cell lines that were or can be used in the above xenograft models are: Kyse-140 and KYSE-510 cell lines.

Some of the typical human squamous cervical cancer cell lines that were or can be used in the above xenograft models are: A-431 and SiHa cell lines.

Some of the typical human squamous head and neck cancer cell lines that were or can be used in the above xenograft models are: FaDu and SCC-15 cell lines.

Some of the typical human leukemia cell lines that were or can be used in the above xenograft models are: CCRF-CEM and MOLT-4.

Some of the typical human lymphoma cell lines that were or can be used in the above xenograft models are: WSU-DLCL2 and OCI-Ly10.

Some of the typical human colorectal cancer (CRC) cell lines that were or can be used in the above xenograft models are: HCT-116, HT-29, and LOVO.

Some of the typical human thyroid cancer cell lines that were or can be used in the above xenograft models are: TT and 8305C.

Some of the typical human central nervous system (CNS) cancer cell lines that were or can be used in the above xenograft models are: U87MG and U-118.

Some of the typical human pancreas cancer cell lines that were or can be used in the above xenograft models are: PANC-1 and BxPC3.

For a typical xenograft study, SCID mice bearing tumors were randomized and dosed with compounds ranging from, for example, 100 mg/kg to 0.1 mg/kg with different dose scheduling. The mice were dosed for 2-4 weeks. Tumors were measured twice a week using calipers and tumor volumes were calculated using the formula of $W^2 \times L/2$.

In thesexenograft cancer models, Pyrrolopyrimidine Compounds have, or are expected to have, an $ED_{50}$ value of <100 mg/kg, with some compounds having an $ED_{50}$ of <10 mg/kg and others an $ED_{50}$ of <1 mg/kg.

A number of references have been cited, the disclosures of which are incorporated herein by reference in their entirety.

What is claimed is:

1. A method for treating glioblastoma multiforme, comprising administering to a subject having glioblastoma multiforme an effective amount of Pyrrolopyrimidine Compound, wherein the Pyrrolopyrimidine Compound is a compound of formula (I):

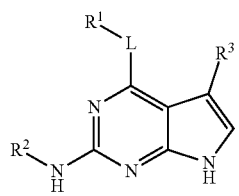

(I)

and pharmaceutically acceptable salts, tautomers, stereoisomers, enantiomers, and isotopologues thereof,
wherein:
$R^1$ is substituted or unsubstituted $C_{1-8}$ alkyl, substituted or unsubstituted $C_{3-8}$ cycloalkyl, or substituted or unsubstituted non-aromatic heterocyclyl;
$R^2$ is substituted or unsubstituted aryl, or substituted or unsubstituted heteroaryl;
$R^3$ is substituted or unsubstituted heterocyclyl or substituted or unsubstituted aryl, and
L is NH or O;
provided
$R^3$ is not pyridyl when L is NH or when $R^2$ is pyrazolyl; and
the compound is not
N-methyl-N-[trans-3-[[5-(1-methyl-1H-pyrazol-4-yl)-2-[(1-methyl-1H-pyrazol-4-yl)amino]-7H-pyrrolo[2,3-d]pyrimidin-4-yl]oxy]cyclobutyl]-2-propenamide; or
N-methyl-N-[trans-3-[[5-(1-methyl-1H-pyrazol-3-yl)-2-[(1-methyl-1H-pyrazol-4-yl)amino]-7H-pyrrolo[2,3-d]pyrimidin-4-yl]oxy]cyclobutyl]-2-propenamide.

2. The method of claim 1, wherein L is O.
3. The method of claim 1, wherein $R^1$ is substituted or unsubstituted $C_{3-8}$ cycloalkyl.
4. The method of claim 1, wherein $R^1$ is substituted or unsubstituted cyclopropyl, cyclobutyl, cyclopentyl, cyclohexyl, or cycloheptyl.

5. The method of claim 3, wherein the cycloalkyl is substituted with one or more —CN, halogen, —OR or a substituted or unsubstituted $C_{1-3}$ alkyl, wherein each R is independently —H or substituted or unsubstituted $(C_{1-4})$ alkyl.

6. The method of claim 1, wherein $R^1$ is substituted or unsubstituted $C_{1-8}$ alkyl,

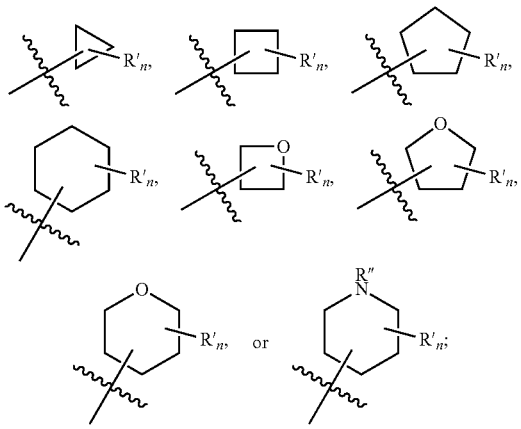

wherein
each R' is independently —CN, halogen, —OR or $C_{1-3}$ alkyl;
R" is —H or $C_{1-3}$ alkyl;
each R is independently H or substituted or unsubstituted $(C_{1-4})$alkyl; and
n is 0-2.

7. The method of claim 1, wherein $R^2$ is substituted phenyl.

8. The method of claim 7, wherein $R^2$ is phenyl, substituted with one or more substituted or unsubstituted $C_{1-6}$ alkyl, halogen, —CN, —$OR^5$, —C(=O)$NR^5_2$, —C(=O) (substituted or unsubstituted heterocyclyl), —C(=O) (substituted or unsubstituted alkylheterocyclyl), —NHC(=O)$R^5$, —$SO_2NR^5_2$, or substituted or unsubstituted heteroaryl, wherein each $R^5$ is independently —H, substituted or unsubstituted alkyl, substituted or unsubstituted cycloalkyl, substituted or unsubstituted heterocyclyl, or substituted or unsubstituted alkylheterocyclyl.

9. The method of claim 7, wherein $R^2$ is phenyl, substituted with one or more —($C_{1-3}$ alkyl), —($C_{1-3}$ alkyl)$NR_2$, —$CF_3$, —Cl, —F, —CN, —$OCH_3$, —$OCF_3$, —C(=O)$NR_2$, —C(=O)NR (substituted or unsubstituted cycloalkyl), —C(=O)NR$(CH_2)_{0-2}CR_2(CH_2)_{0-2}$OR, —C(=O)NR$(CH_2)_{0-2}CR_2(CH_2)_{0-2}NR_2$, —C(=O)NR$(CH_2)_{0-2}CR_2(CH_2)_{0-2}$C(=O)$NR_2$, —C(=O)N (substituted or unsubstituted cycloalkyl)$(CH_2)_{0-2}$OR, —C(=O)NR$(CH_2)_{0-3}$ (substituted or unsubstituted heterocyclyl), —C(=O)$(CH_2)_{0-3}$ (substituted or unsubstituted heterocyclyl), —C(=NR)$NR_2$, —NRC(=O)R, —$SO_2NR_2$, —$SO_2R$, or substituted or unsubstituted heterocyclyl, wherein each R is independently —H or substituted or unsubstituted $(C_{1-4})$alkyl.

10. The method of claim 9, wherein each R is independently —H or —$CH_3$.

11. The method of claim 7, wherein $R^2$ is phenyl, substituted with one or more —$CH_3$, —$CH_2CH_3$, —$CH_2CH_2CH_3$, —$CH(CH_3)_2$, —$CH_2NH_2$, —$CF_3$, —Cl, —F, —CN, —$OCH_3$, —$OCF_3$, —C(=O)$NH_2$, —C(=O)$NHCH_3$, —C(=O)$N(CH_3)_2$, —C(=O)$NC(CH_3)_3$, —C(=O)

NHCH₂CH₂F, —C(=O)NHCH₂CHF₂, —C(=O)NHCH₂CF₃, —C(=O)NHCH₂CF₂CH₃, —C(=O)NHCH₂CN, —C(=O)N(CH₃)CH₂CN, —C(=O)NHCH₂CH₂CN, —C(=O)N(CH₃)CH₂CH₂CN, —C(=O)NH-cyclobutyl, —C(=O)NH-(hydroxy-cyclobutyl), —C(=O)NH-cyclopentyl, —C(=O)NH-(hydroxy-cyclopentyl), —C(=O)NHCH₂CH₂OH, —C(=O)NHCH₂CH₂OCH₃, —C(=O)N(CH₃)CH₂CH₂OH, —C(=O)N(CH₃)CH₂CH₂OCH₃, —C(=O)NHCH₂CH₂CH₂OH, —C(=O)N(CH₃)CH₂CH₂CH₂OH, —C(=O)N(CH₃)CH₂CH₂CH₂OCH₃, —C(=O)NHCH₂CH(CH₃)OH, —C(=O)NHCH₂C(CH₃)₂OH, —C(=O)NHCH(CH₃)CH₂OH, —C(=O)NHC(CH₃)₂CH₂OH, —C(=O)NHCH₂CH₂NH₂, —C(=O)NHCH₂CH₂NH(CH₃), —C(=O)NHCH₂CH₂N(CH₃)₂, —C(=O)NHCH₂C(=O)NH₂, —C(=O)N(CH₃)CH₂C(=O)NH₂, —C(=O)NHCH₂CH₂C(=O)NH₂, —C(=O)N(CH₃)CH₂CH₂C(=O)NH₂, —C(=O)N(cyclopropyl)CH₂CH₂OH, —C(=O)NH-oxetanyl, —C(=O)N(CH₃)-oxetanyl, —C(=O)NH-(methyl-oxetanyl), —C(=O)NH-azetidinyl, —C(=O)NH-(methylazetidinyl), —C(=O)NH-(1-acetylazetidinyl), —C(=O)NH-pyrrolidyl, —C(=O)NH-piperidyl, —C(=O)NH-tetrahydrofuranyl, —C(=O)N(CH₃)-tetrahydrofuranyl, —C(=O)NH-tetrahydropyranyl, —C(=O)N(CH₃)-tetrahydropyranyl, —C(=O)NHCH₂-oxetanyl, —C(=O)N(CH₃)CH₂-oxetanyl, —C(=O)NHCH₂-(methyl-oxetanyl), —C(=O)N(CH₃)CH₂-(methyl-oxetanyl), —C(=O)NHCH₂-tetrahydrofuranyl, —C(=O)NHCH₂-tetrahydropyranyl, —C(=O)NHCH₂-dioxanyl, —C(=O)aziridinyl, —C(=O)(methyl-aziridinyl), —C(=O)(dimethyl-aziridinyl), —C(=O)(hydroxymethyl-aziridinyl), —C(=O)azetidinyl, —C(=O)pyrrolidinyl, —C(=O)(hydroxyl-pyrrolidinyl), —C(=O)(hydroxyl, methoxypyrrolidinyl), —C(=O)(dimethoxypyrrolidinyl), —C(=O)morpholinyl, —C(=O)piperazinyl, —C(=O)(methylpiperazinyl), —C(=O)(hydroxy-piperidyl), —C(=O)(fluoropiperidinyl), —(C=O)(methoxy-piperidyl), —C(=NH)NH₂, —NHC(=O)CH₃, —SO₂NHCH₃, —SO₂CH₃, or substituted or unsubstituted pyrazolyl.

12. The method of claim 7, wherein R² is phenyl, substituted with one or more —CH₃, —CH₂CH₃, —CH₂CH₂CH₃, —CH(CH₃)₂, —CH₂NH₂, —CF₃, —F, —CN, —OCH₃, —OCF₃, —C(=O)NH₂, —C(=O)NHCH₃, —C(=O)N(CH₃)₂, —C(=O)NC(CH₃)₃, —C(=O)NHCH₂CH₂F, —C(=O)NHCH₂CF₃, —C(=O)N(CH₃)CH₂CN, —C(=O)N(CH₃)CH₂CH₂CN, —C(=O)NH-(3-hydroxy-cyclobutyl), —C(=O)NH-cyclopentyl, —C(=O)NH-(2-hydroxycyclopentyl), —C(=O)NHCH₂CH₂OH, —C(=O)NHCH₂CH₂OCH₃, —C(=O)N(CH₃)CH₂CH₂OH, —C(=O)N(CH₃)CH₂CH₂OCH₃, —C(=O)NHCH₂CH₂CH₂OH, —C(=O)N(CH₃)CH₂CH₂CH₂OH, —C(=O)NHCH₂CH(CH₃)OH, —C(=O)NHCH₂C(CH₃)₂OH, —C(=O)NHCH(CH₃)CH₂OH, —C(=O)NHC(CH₃)₂CH₂OH, —C(=O)NHCH₂CH₂NH₂, —C(=O)NHCH₂CH₂NH(CH₃), —C(=O)NHCH₂CH₂N(CH₃)₂, —C(=O)N(CH₃)CH₂C(=O)NH₂, —C(=O)N(CH₃)CH₂CH₂C(=O)NH₂, —C(=O)N(cyclopropyl)CH₂CH₂OH, —C(=O)NH-oxetanyl, —C(=O)N(CH₃)-oxetanyl, —C(=O)NH-(3-methyl-oxetanyl), —C(=O)NH-(1-methylazetidinyl), —C(=O)NH-(1-acetylazetidinyl), —C(=O)NH-piperidyl, —C(=O)NH-tetrahydrofuranyl, —C(=O)NH-tetrahydropyranyl, —C(=O)N(CH₃)-tetrahydropyranyl, —C(=O)NHCH₂-oxetanyl, —C(=O)N(CH₃)CH₂-(3-methyl-oxetanyl), —C(=O)NHCH₂-tetrahydrofuranyl, —C(=O)NHCH₂-tetrahydropyranyl, —C(=O)NHCH₂-dioxanyl, —C(=O)aziridinyl, —C(=O)(2-methyl-aziridinyl), —C(=O)(2,2-dimethyl-aziridinyl), —C(=O)(2-(hydroxymethyl)aziridinyl), —C(=O)azetidinyl, —C(=O)pyrrolidinyl, —C(=O)(3-hydroxy-4-methoxypyrrolidinyl), —C(=O)(3,4-dimethoxypyrrolidinyl), —C(=O)morpholinyl, —C(=O)piperazinyl, —C(=O)(4-methylpiperazinyl), —C(=O)(4-hydroxy-piperidyl), —C(=O)(4,4-difluoropiperidinyl), —(C=O)(4-methoxy-piperidyl), —C(=NH)NH₂, —NHC(=O)CH₃, —SO₂NHCH₃, —SO₂CH₃, or substituted or unsubstituted pyrazolyl.

13. The method of claim 1, wherein R³ is substituted or unsubstituted heterocyclyl.

14. The method of claim 13, wherein the heterocyclyl is substituted or unsubstituted pyrazolyl, oxazolyl, isoxazolyl, oxadiazolyl, pyridyl, pyridazinyl, pyrimidyl, pyrazinyl, benztriazolyl, indazolyl, indolyl, benzoxazolyl, benzisoxazolyl, benzthiazolyl, benzoxazolonyl, benzoxadiazolyl, benzimidazolyl, or quinolyl.

15. The method of claim 13, wherein the heterocyclyl is substituted with one or more substituents selected from substituted or unsubstituted $(C_{1-4})$alkyl, halogen, —OR, —CN, —NR₂, —C(=O)NR₂, —NRC(=O)R, or substituted or unsubstituted triazolyl, wherein each R is independently H or substituted or unsubstituted $(C_{1-4})$alkyl.

16. The method of claim 13, wherein the heterocyclyl is substituted with one or more substituents selected from —CH₃, —CH(CH₃)₂, —F, —Cl, —OH, —OCH₃, —OCH₂CH₃, —CN, —NH₂, —NHCH₃, —N(CH₃)₂, —C(=O)NH(CH₃), —NHC(=O)CH₃, or substituted or unsubstituted triazolyl.

17. The method of claim 1, wherein R³ is substituted or unsubstituted aryl.

18. The method of claim 1, wherein the compound is selected from 4-(4-(cyclopentyloxy)-5-(4-hydroxyphenyl)-7H-pyrrolo[2,3-d]pyrimidin-2-ylamino)-N-methylbenzamide, 4-(4-(cyclopentyloxy)-5-(3-hydroxyphenyl)-7H-pyrrolo[2,3-d]pyrimidin-2-ylamino)-N-methylbenzamide, 4-(4-(cyclopentyloxy)-5-(4-hydroxyphenyl)-7H-pyrrolo[2,3-d]pyrimidin-2-ylamino)-3-methoxy-N-methylbenzamide, 4-(5-(4-hydroxyphenyl)-4-methoxy-7H-pyrrolo[2,3-d]pyrimidin-2-ylamino)-N-methylbenzamide, 4-(2-(1H-indazol-5-ylamino)-4-(cyclohexyloxy)-7H-pyrrolo[2,3-d]pyrimidin-5-yl)phenol, 4-(2-(4-(1H-pyrazol-4-yl)phenylamino)-4-(cyclohexyloxy)-7H-pyrrolo[2,3-d]pyrimidin-5-yl)phenol, 4-(5-(2-chloro-4-hydroxyphenyl)-4-(cyclohexyloxy)-7H-pyrrolo[2,3-d]pyrimidin-2-ylamino)-N-methylbenzamide, 4-(2-(3-(1H-pyrazol-4-yl)phenylamino)-4-(cyclohexyloxy)-7H-pyrrolo[2,3-d]pyrimidin-5-yl)phenol, 4-(4-(cyclopentyloxy)-5-(4-hydroxyphenyl)-7H-pyrrolo[2,3-d]pyrimidin-2-ylamino)-N,3-dimethylbenzamide, 4-(4-(cyclopentyloxy)-5-(4-hydroxyphenyl)-7H-pyrrolo[2,3-d]pyrimidin-2-ylamino)-3-ethyl-N-methylbenzamide, 4-(4-(cyclopentyloxy)-5-(4-hydroxyphenyl)-7H-pyrrolo[2,3-d]pyrimidin-2-ylamino)-3-isopropyl-N-methylbenzamide, 4-(4-(cyclopentyloxy)-5-(4-fluorophenyl)-7H-pyrrolo[2,3-d]pyrimidin-2-ylamino)-3-methoxy-N-methylbenzamide, 4-(4-(cyclopentyloxy)-5-phenyl-7H-pyrrolo[2,3-d]pyrimidin-2-ylamino)-3-methoxy-N-methylbenzamide, 3-chloro-4-(4-(cyclopentyloxy)-5-(4-hydroxyphenyl)-7H-pyrrolo[2,3-d]pyrimidin-2-ylamino)-N-methylbenzamide, 4-(4-(cyclopentyloxy)-5-(4-hydroxyphenyl)-7H-pyrrolo[2,3-d]pyrimidin-2-ylamino)-3-fluoro-N-methylbenzamide,
4-(4-(cyclopentylamino)-5-(4-hydroxyphenyl)-7H-pyrrolo[2,3-d]pyrimidin-2-ylamino)-3-methoxy-N-methylbenzamide,
4-(5-(4-hydroxyphenyl)-4-(tetrahydro-2H-pyran-4-yloxy)-7H-pyrrolo[2,3-d]pyrimidin-2-ylamino)-3-methoxy-N-methylbenzamide,
4-(5-(4-hydroxyphenyl)-4-(neopentyloxy)-7H-pyrrolo[2,3-d]pyrimidin-2-ylamino)-3-methoxy-N-methylbenzamide,
4-(5-(4-hydroxyphenyl)-4-methoxy-7H-pyrrolo[2,3-d]pyrimidin-2-ylamino)-3-methoxy-N-methylbenzamide,
4-(4-(cyclopentyloxy)-2-(1-methyl-1H-indazol-5-ylamino)-7H-pyrrolo[2,3-d]pyrimidin-5-yl)phenol,
4-(4-(cyclopentyloxy)-2-(6-methyl-1H-indazol-5-ylamino)-7H-pyrrolo[2,3-d]pyrimidin-5-yl)phenol,
4-(4-(cyclopentyloxy)-2-(4-methyl-1H-indazol-5-ylamino)-7H-pyrrolo[2,3-d]pyrimidin-5-yl)phenol,
4-(4-(cyclopentyloxy)-5-(4-(hydroxymethyl)phenyl)-7H-pyrrolo[2,3-d]pyrimidin-2-ylamino)-3-methoxy-N-methylbenzamide,
4-(5-(3-chloro-4-hydroxyphenyl)-4-(cyclopentyloxy)-7H-pyrrolo[2,3-d]pyrimidin-2-ylamino)-3-methoxy-N-methylbenzamide,
4-(4-(cyclopentyloxy)-5-(1H-indazol-6-yl)-7H-pyrrolo[2,3-d]pyrimidin-2-ylamino)-3-methoxy-N-methylbenzamide,
4-(4-(cyclopentyloxy)-5-(3-(hydroxymethyl)phenyl)-7H-pyrrolo[2,3-d]pyrimidin-2-ylamino)-3-methoxy-N-methylbenzamide,
4-(5-(1H-benzo[d][1,2,3]triazol-6-yl)-4-(cyclopentyloxy)-7H-pyrrolo[2,3-d]pyrimidin-2-ylamino)-3-methoxy-N-methylbenzamide,
4-(5-(4-(4H-1,2,4-triazol-3-yl)phenyl)-4-(cyclopentyloxy)-7H-pyrrolo[2,3-d]pyrimidin-2-ylamino)-3-methoxy-N-methylbenzamide,
3-chloro-4-(5-(4-hydroxyphenyl)-4-(tetrahydro-2H-pyran-4-yloxy)-7H-pyrrolo[2,3-d]pyrimidin-2-ylamino)-N-methylbenzamide,
4-(5-(1H-benzo[d]imidazol-6-yl)-4-(cyclopentyloxy)-7H-pyrrolo[2,3-d]pyrimidin-2-ylamino)-3-methoxy-N-methylbenzamide,
4-(4-(cyclopentyloxy)-5-(4-hydroxyphenyl)-7H-pyrrolo[2,3-d]pyrimidin-2-ylamino)-3-methoxy-N,N-dimethylbenzamide,
4-(4-(cyclopentyloxy)-5-(4-(methylsulfonamido)phenyl)-7H-pyrrolo[2,3-d]pyrimidin-2-ylamino)-3-methoxy-N-methylbenzamide,
4-(5-(3-cyano-4-hydroxyphenyl)-4-(cyclopentyloxy)-7H-pyrrolo[2,3-d]pyrimidin-2-ylamino)-3-methoxy-N-methylbenzamide,
3-chloro-4-(4-(cyclopentyloxy)-5-(5-methoxypyridin-3-yl)-7H-pyrrolo[2,3-d]pyrimidin-2-ylamino)-N-methylbenzamide,
4-(4-(cyclopentyloxy)-5-(2-methylbenzo[d]oxazol-5-yl)-7H-pyrrolo[2,3-d]pyrimidin-2-ylamino)-3-methoxy-N-methylbenzamide,
4-(4-(cyclohexylamino)-5-(4-hydroxyphenyl)-7H-pyrrolo[2,3-d]pyrimidin-2-ylamino)-3-methoxy-N-methylbenzamide,
4-(5-(4-aminophenyl)-4-(cyclopentyloxy)-7H-pyrrolo[2,3-d]pyrimidin-2-ylamino)-3-methoxy-N-methylbenzamide,
4-(4-(cyclopentyloxy)-5-(2-methylbenzo[d]oxazol-6-yl)-7H-pyrrolo[2,3-d]pyrimidin-2-ylamino)-3-methoxy-N-methylbenzamide,
4-(4-(cyclopentyloxy)-5-(4-ureidophenyl)-7H-pyrrolo[2,3-d]pyrimidin-2-ylamino)-3-methoxy-N-methylbenzamide,
4-(5-(4-hydroxyphenyl)-4-(tetrahydro-2H-pyran-4-ylamino)-7H-pyrrolo[2,3-d]pyrimidin-2-ylamino)-3-methoxy-N-methylbenzamide,
4-(5-(4-(1H-pyrazol-5-yl)phenyl)-4-(cyclopentyloxy)-7H-pyrrolo[2,3-d]pyrimidin-2-ylamino)-3-methoxy-N-methylbenzamide,
4-(4-(cyclopentyloxy)-5-(3-fluoro-4-hydroxyphenyl)-7H-pyrrolo[2,3-d]pyrimidin-2-ylamino)-3-methoxy-N-methylbenzamide,
4-(4-(cyclopentyloxy)-5-(4-hydroxy-3-methylphenyl)-7H-pyrrolo[2,3-d]pyrimidin-2-ylamino)-3-methoxy-N-methylbenzamide,
4-(4-(cyclopentyloxy)-5-(4-hydroxyphenyl)-7H-pyrrolo[2,3-d]pyrimidin-2-ylamino)-3-methoxybenzamide,
4-(4-((1r,4r)-4-hydroxycyclohexyloxy)-5-(4-hydroxyphenyl)-7H-pyrrolo[2,3-d]pyrimidin-2-ylamino)-3-methoxy-N-methylbenzamide,
4-(4-((1s,4s)-4-hydroxycyclohexyloxy)-5-(4-hydroxyphenyl)-7H-pyrrolo[2,3-d]pyrimidin-2-ylamino)-3-methoxy-N-methylbenzamide,
4-(4-(cyclopentyloxy)-5-(3-(2-hydroxypropan-2-yl)phenyl)-7H-pyrrolo[2,3-d]pyrimidin-2-ylamino)-3-methoxy-N-methylbenzamide,
4-(5-(4-(1H-imidazol-2-yl)phenyl)-4-(cyclopentyloxy)-7H-pyrrolo[2,3-d]pyrimidin-2-ylamino)-3-methoxy-N-methylbenzamide,
4-(4-(cyclopentyloxy)-5-(4-(2-hydroxypropan-2-yl)phenyl)-7H-pyrrolo[2,3-d]pyrimidin-2-ylamino)-3-methoxy-N-methylbenzamide,
4-(4-(cyclopentyloxy)-2-(2-methoxy-4-(1H-pyrazol-4-yl)phenylamino)-7H-pyrrolo[2,3-d]pyrimidin-5-yl)phenol,
4-(4-(cyclopentyloxy)-5-(5-hydroxypyridin-3-yl)-7H-pyrrolo[2,3-d]pyrimidin-2-ylamino)-3-methoxy-N-methylbenzamide,
4-(2-(4-(aminomethyl)-2-methoxyphenylamino)-4-(cyclopentyloxy)-7H-pyrrolo[2,3-d]pyrimidin-5-yl)phenol,
4-(5-(4-(4H-1,2,4-triazol-3-yl)phenyl)-4-methoxy-7H-pyrrolo[2,3-d]pyrimidin-2-ylamino)-3-chloro-N,N-dimethylbenzamide,
4-(4-(cyclopentyloxy)-5-(3-fluoro-4-methoxyphenyl)-7H-pyrrolo[2,3-d]pyrimidin-2-ylamino)-3-methoxy-N-methylbenzamide,
4-(4-(cyclopentyloxy)-5-(6-methoxypyridin-3-yl)-7H-pyrrolo[2,3-d]pyrimidin-2-ylamino)-3-methoxy-N-methylbenzamide,
4-(5-(3-acetamidophenyl)-4-(cyclopentyloxy)-7H-pyrrolo[2,3-d]pyrimidin-2-ylamino)-3-methoxy-N-methylbenzamide,
4-(4-(cyclopentyloxy)-5-(3-(methylsulfonamido)phenyl)-7H-pyrrolo[2,3-d]pyrimidin-2-ylamino)-3-methoxy-N-methylbenzamide,
4-(4-(cyclopentyloxy)-5-(pyridin-3-yl)-7H-pyrrolo[2,3-d]pyrimidin-2-ylamino)-3-methoxy-N-methylbenzamide,
4-(4-(cyclopentyloxy)-5-(3-(methylcarbamoyl)phenyl)-7H-pyrrolo[2,3-d]pyrimidin-2-ylamino)-3-methoxy-N-methylbenzamide, 4-(4-(cyclopentyloxy)-5-(3-methoxyphenyl)-7H-pyrrolo[2,3-d]pyrimidin-2-ylamino)-3-methoxy-N-methylbenzamide, 4-(4-(cyclopentyloxy)-5-(4-(methylsulfonyl)phenyl)-7H-pyrrolo[2,3-d]pyrimidin-2-ylamino)-3-methoxy-N-methylbenzamide, 4-(5-(4-acetamidophenyl)-4-(cyclopentyloxy)-7H-pyrrolo[2,3-d]pyrimidin-2-ylamino)-3-methoxy-N-methylbenzamide, 4-(4-(cyclopentyloxy)-5-(3-(methylsulfonyl)phenyl)-7H-pyrrolo[2,3-d]pyrimidin-2-ylamino)-3-methoxy-N-methylbenzamide, 4-(4-(cyclopentyloxy)-5-(3,4-dimethoxyphenyl)-7H-pyrrolo[2,3-d]pyrimidin-2-ylamino)-3-methoxy-N-methylbenzamide, 4-(5-(3-aminophenyl)-4-(cyclopentyloxy)-7H-pyrrolo[2,3-d]pyrimidin-2-ylamino)-3-methoxy-N-methylbenzamide, 4-(4-(cyclopentyloxy)-5-(pyridin-4-yl)-7H-pyrrolo[2,3-d]pyrimidin-2-ylamino)-3-methoxy-N-methylbenzamide, 4-(4-(cyclopentyloxy)-5-(6-ethoxypyridin-3-yl)-7H-pyrrolo[2,3-d]pyrimidin-2-ylamino)-3-methoxy-N-methylbenzamide, (4-(5-(4-(4H-1,2,4-triazol-3-yl)phenyl)-4-methoxy-7H-pyrrolo[2,3-d]pyrimidin-2-ylamino)-3-chlorophenyl)(morpholino)-methanone, N,N,3-trimethyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide, N,N,3-trimethyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide, 4-(5-(2-amino-1H-benzo[d]imidazol-5-yl)-4-methoxy-7H-pyrrolo[2,3-d]pyrimidin-2-ylamino)-3-chloro-N,N-dimethylbenzamide, 4-(5-(4-(4H-1,2,4-triazol-3-yl)phenyl)-4-(methylamino)-7H-pyrrolo[2,3-d]pyrimidin-2-ylamino)-3-chloro-N,N-dimethylbenzamide, 4-(4-methoxy-5-(2-methylbenzo[d]oxazol-6-yl)-7H-pyrrolo[2,3-d]pyrimidin-2-ylamino)-N,N,3-trimethylbenzamide, (3-methyl-4-(5-(2-methylbenzo[d]oxazol-6-yl)-4-(tetrahydro-2H-pyran-4-ylamino)-7H-pyrrolo[2,3-d]pyrimidin-2-ylamino)phenyl)(piperazin-1-yl)methanone, 4-(4-(cyclopentyloxy)-5-(4-(dimethylamino)phenyl)-7H-pyrrolo[2,3-d]pyrimidin-2-ylamino)-3-methoxy-N-methylbenzamide, 4-(4-(cyclopentyloxy)-5-(4-methoxyphenyl)-7H-pyrrolo[2,3-d]pyrimidin-2-ylamino)-3-methoxy-N-methylbenzamide, 4-(5-(4-cyanophenyl)-4-(cyclopentyloxy)-7H-pyrrolo[2,3-d]pyrimidin-2-ylamino)-3-methoxy-N-methylbenzamide, 4-(4-(cyclopentyloxy)-5-(1-methyl-1H-indol-5-yl)-7H-pyrrolo[2,3-d]pyrimidin-2-ylamino)-3-methoxy-N-methylbenzamide, 4-(4-(cyclopentyloxy)-5-(4-(methylcarbamoyl)phenyl)-7H-pyrrolo[2,3-d]pyrimidin-2-ylamino)-3-methoxy-N-methylbenzamide, 4-(4-(cyclopentyloxy)-5-(1H-pyrazol-3-yl)-7H-pyrrolo[2,3-d]pyrimidin-2-ylamino)-3-methoxy-N-methylbenzamide, 4-(4-(cyclopentyloxy)-5-(1H-indol-5-yl)-7H-pyrrolo[2,3-d]pyrimidin-2-ylamino)-3-methoxy-N-methylbenzamide, 4-(4-(cyclopentyloxy)-5-(1H-pyrazol-4-yl)-7H-pyrrolo[2,3-d]pyrimidin-2-ylamino)-3-methoxy-N-methylbenzamide, 3-chloro-4-(4-methoxy-5-(2-methyl-1H-benzo[d]imidazol-5-yl)-7H-pyrrolo[2,3-d]pyrimidin-2-ylamino)-N,N-dimethylbenzamide, (R)-3-chloro-4-(5-(3-(1-hydroxyethyl)phenyl)-4-(tetrahydro-2H-pyran-4-ylamino)-7H-pyrrolo[2,3-d]pyrimidin-2-ylamino)-N,N-dimethylbenzamide, (S)-3-chloro-4-(5-(3-(1-hydroxyethyl)phenyl)-4-(tetrahydro-2H-pyran-4-ylamino)-7H-pyrrolo[2,3-d]pyrimidin-2-ylamino)-N,N-dimethylbenzamide, (4-(4-(cyclopentyloxy)-5-(2-methylbenzo[d]oxazol-6-yl)-7H-pyrrolo[2,3-d]pyrimidin-2-ylamino)-3-methylphenyl)(morpholino)methanone, N-(1H-indazol-5-yl)-4-methoxy-5-(2-methylbenzo[d]oxazol-6-yl)-7H-pyrrolo[2,3-d]pyrimidin-2-amine, N-(4-(1H-pyrazol-4-yl)phenyl)-4-methoxy-5-(2-methylbenzo[d]oxazol-6-yl)-7H-pyrrolo[2,3-d]pyrimidin-2-amine, 4-(4-methoxy-5-(pyridin-4-yl)-7H-pyrrolo[2,3-d]pyrimidin-2-ylamino)-N,N,3-trimethylbenzamide, 3-methoxy-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide, 4-(4-(cyclopentyloxy)-5-(2-methylbenzo[d]oxazol-6-yl)-7H-pyrrolo[2,3-d]pyrimidin-2-ylamino)-3-methoxy-N,N-dimethylbenzamide, 4-(4-((1r,4r)-4-hydroxycyclohexyloxy)-5-(2-methylbenzo[d]oxazol-6-yl)-7H-pyrrolo[2,3-d]pyrimidin-2-ylamino)-N,N,3-trimethylbenzamide, N,N,3-trimethyl-4-(5-(pyridin-4-yl)-4-(tetrahydro-2H-pyran-4-yloxy)-7H-pyrrolo[2,3-d]pyrimidin-2-ylamino)benzamide, 4-(4-(cyclopentyloxy)-5-(2-methylbenzo[d]oxazol-6-yl)-7H-pyrrolo[2,3-d]pyrimidin-2-ylamino)-N,3-dimethylbenzamide, N,N,3-trimethyl-4-(5-(2-methylbenzo[d]oxazol-6-yl)-4-(1-methylpiperidin-4-yloxy)-7H-pyrrolo[2,3-d]pyrimidin-2-ylamino)benzamide, (4-(4-(cyclopentyloxy)-5-(2-methylbenzo[d]oxazol-6-yl)-7H-pyrrolo[2,3-d]pyrimidin-2-ylamino)-3-methoxyphenyl)(morpholino)methanone, N,N,3-trimethyl-4-(5-(2-methylbenzo[d]oxazol-6-yl)-4-(piperidin-4-yloxy)-7H-pyrrolo[2,3-d]pyrimidin-2-ylamino)benzamide, (S)-N,N,3-trimethyl-4-(5-(2-methylbenzo[d]oxazol-6-yl)-4-(tetrahydrofuran-3-yloxy)-7H-pyrrolo[2,3-d]pyrimidin-2-ylamino)benzamide, (R)-N,N,3-trimethyl-4-(5-(2-methylbenzo[d]oxazol-6-yl)-4-(tetrahydrofuran-3-yloxy)-7H-pyrrolo[2,3-d]pyrimidin-2-ylamino)benzamide, N-(2-aminoethyl)-4-(4-(cyclopentyloxy)-5-(2-methylbenzo[d]oxazol-6-yl)-7H-pyrrolo[2,3-d]pyrimidin-2-ylamino)-3-methoxybenzamide, 4-(4-(cyclopentyloxy)-5-(2-methylbenzo[d]oxazol-6-yl)-7H-pyrrolo[2,3-d]pyrimidin-2-ylamino)-N-(2-hydroxyethyl)-3-methoxybenzamide, 4-(5-(6-ethoxypyridin-3-yl)-4-(tetrahydro-2H-pyran-4-yloxy)-7H-pyrrolo[2,3-d]pyrimidin-2-ylamino)-3-methoxy-N-methylbenzamide, 4-(cyclopentyloxy)-N-(2-methoxyphenyl)-5-(2-methylbenzo[d]oxazol-6-yl)-7H-pyrrolo[2,3-d]pyrimidin-2-amine, (S)-N,N,3-trimethyl-4-(5-(2-methylbenzo[d]oxazol-6-yl)-4-(tetrahydro-2H-pyran-3-yloxy)-7H-pyrrolo[2,3-d]pyrimidin-2-ylamino)benzamide, N,N,3-trimethyl-4-(5-(3-(methyl sulfonyl)phenyl)-4-(tetrahydro-2H-pyran-4-yloxy)-7H-pyrrolo[2,3-d]pyrimidin-2-ylamino)benzamide,
3-methoxy-N-methyl-4-(5-(3-(methylsulfonyl)phenyl)-4-(tetrahydro-2H-pyran-4-yloxy)-7H-pyrrolo[2,3-d]pyrimidin-2-ylamino)benzamide,
N,N,3-trimethyl-4-(5-(pyrimidin-5-yl)-4-(tetrahydro-2H-pyran-4-yloxy)-7H-pyrrolo[2,3-d]pyrimidin-2-ylamino)benzamide,
3-methoxy-N-methyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide,
4-(5-(6-ethoxypyridin-3-yl)-4-(tetrahydro-2H-pyran-4-yloxy)-7H-pyrrolo[2,3-d]pyrimidin-2-ylamino)-N,N,3-trimethylbenzamide,
4-(5-(2-amino-1H-benzo[d]imidazol-6-yl)-4-(cyclopentyloxy)-7H-pyrrolo[2,3-d]pyrimidin-2-ylamino)-3-methoxy-N-methylbenzamide,
4-(5-(1,3,4-oxadiazol-2-yl)-4-(tetrahydro-2H-pyran-4-yloxy)-7H-pyrrolo[2,3-d]pyrimidin-2-ylamino)-N,N,3-trimethylbenzamide,
N,N,3-trimethyl-4-(5-(1-methyl-1H-pyrazol-4-yl)-4-(tetrahydro-2H-pyran-4-yloxy)-7H-pyrrolo[2,3-d]pyrimidin-2-ylamino)benzamide,
N,N,3-trimethyl-4-(5-(1-methyl-1H-pyrazol-3-yl)-4-(tetrahydro-2H-pyran-4-yloxy)-7H-pyrrolo[2,3-d]pyrimidin-2-ylamino)benzamide,
3-methoxy-N-methyl-4-(5-(pyridin-4-yl)-4-(tetrahydro-2H-pyran-4-yloxy)-7H-pyrrolo[2,3-d]pyrimidin-2-ylamino)benzamide,
N,N,3-trimethyl-4-(5-(oxazol-2-yl)-4-(tetrahydro-2H-pyran-4-yloxy)-7H-pyrrolo[2,3-d]pyrimidin-2-ylamino)benzamide,
4-(5-(2-amino-1H-benzo[d]imidazol-6-yl)-4-(tetrahydro-2H-pyran-4-yloxy)-7H-pyrrolo[2,3-d]pyrimidin-2-ylamino)-N,N,3-trimethylbenzamide,
N,N,3-trimethyl-4-(5-(2-methylpyridin-4-yl)-4-(tetrahydro-2H-pyran-4-yloxy)-7H-pyrrolo[2,3-d]pyrimidin-2-ylamino)benzamide,
3-methoxy-4-(4-methoxy-5-(6-methoxypyridin-3-yl)-7H-pyrrolo[2,3-d]pyrimidin-2-ylamino)-N-methylbenzamide,
3-methoxy-4-(5-(6-methoxypyridin-3-yl)-4-(tetrahydro-2H-pyran-4-yloxy)-7H-pyrrolo[2,3-d]pyrimidin-2-ylamino)-N-methylbenzamide,
3-methoxy-N-(2-methoxyethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
(R)-N,N,3-trimethyl-4-(5-(2-methylbenzo[d]oxazol-6-yl)-4-(tetrahydro-2H-pyran-3-yloxy)-7H-pyrrolo[2,3-d]pyrimidin-2-ylamino)benzamide,
4-(5-(1H-pyrazol-4-yl)-4-(tetrahydro-2H-pyran-4-yloxy)-7H-pyrrolo[2,3-d]pyrimidin-2-ylamino)-3-methoxy-N-methylbenzamide,
3-methoxy-N-methyl-4-(5-(4-(methylcarbamoyl)phenyl)-4-(tetrahydro-2H-pyran-4-yloxy)-7H-pyrrolo[2,3-d]pyrimidin-2-ylamino)benzamide,
3-methoxy-4-(4-methoxy-5-(4-(methylcarbamoyl)phenyl)-7H-pyrrolo[2,3-d]pyrimidin-2-ylamino)-N-methylbenzamide,
4-(4-isopropoxy-5-(2-methylbenzo[d]oxazol-6-yl)-7H-pyrrolo[2,3-d]pyrimidin-2-ylamino)-3-methoxy-N-methylbenzamide,
4-(5-(6-(dimethylamino)pyridin-3-yl)-4-(tetrahydro-2H-pyran-4-yloxy)-7H-pyrrolo[2,3-d]pyrimidin-2-ylamino)-3-methoxy-N-methylbenzamide,
N-(2-(dimethylamino)ethyl)-3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
N,N,3-trimethyl-4-(5-(2-methyl-1H-benzo[d]imidazol-6-yl)-4-(tetrahydro-2H-pyran-4-yloxy)-7H-pyrrolo[2,3-d]pyrimidin-2-ylamino)benzamide,
3-methoxy-4-(4-methoxy-5-(1H-pyrazol-4-yl)-7H-pyrrolo[2,3-d]pyrimidin-2-ylamino)-N-methylbenzamide,
3-methoxy-N-(2-(methylamino)ethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
4-(5-(2-(dimethylamino)pyridin-4-yl)-4-(tetrahydro-2H-pyran-4-yloxy)-7H-pyrrolo[2,3-d]pyrimidin-2-ylamino)-3-methoxy-N-methylbenzamide,
3-chloro-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
(S)-N,3-dimethyl-4-(5-(2-methylbenzo[d]oxazol-6-yl)-4-(tetrahydrofuran-3-yloxy)-7H-pyrrolo[2,3-d]pyrimidin-2-ylamino)benzamide,
(S)-3-chloro-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide,
4-(5-(2,7-dimethylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide,
4-(5-(2,5-dimethylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide,
4-(4-((1r,4r-4-hydroxycyclohexyloxy)-5-(2-methylbenzo[d]oxazol-6-yl)-7H-pyrrolo[2,3-d]pyrimidin-2-ylamino)-3-methoxy-N-methylbenzamide,
3-methoxy-N-methyl-4-(4-(2-(methylamino)ethoxy)-5-(2-methylbenzo[d]oxazol-6-yl)-7H-pyrrolo[2,3-d]pyrimidin-2-ylamino)benzamide,
3-methoxy-4-(4-(2-methoxyethoxy)-5-(2-methylbenzo[d]oxazol-6-yl)-7H-pyrrolo[2,3-d]pyrimidin-2-ylamino)-N-methylbenzamide,
4-(5-(2-cyanopyridin-4-yl)-4-(tetrahydro-2H-pyran-4-yloxy)-7H-pyrrolo[2,3-d]pyrimidin-2-ylamino)-N,N,3-trimethylbenzamide,
4-(5-(4-(1H-imidazol-2-yl)phenyl)-4-methoxy-7H-pyrrolo[2,3-d]pyrimidin-2-ylamino)-3-methoxy-N-methylbenzamide,
4-(5-(2-aminopyridin-4-yl)-4-(tetrahydro-2H-pyran-4-yloxy)-7H-pyrrolo[2,3-d]pyrimidin-2-ylamino)-3-methoxy-N-methylbenzamide,
3-methoxy-4-(5-(2-methoxypyridin-4-yl)-4-(tetrahydro-2H-pyran-4-yloxy)-7H-pyrrolo[2,3-d]pyrimidin-2-ylamino)-N-methylbenzamide,
N,3-dimethyl-4-(5-(3-(methylcarbamoyl)phenyl)-4-(tetrahydro-2H-pyran-4-yloxy)-7H-pyrrolo[2,3-d]pyrimidin-2-ylamino)benzamide,
N,3-dimethyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
4-(5-(4-(1H-imidazol-2-yl)phenyl)-4-(tetrahydro-2H-pyran-4-yloxy)-7H-pyrrolo[2,3-d]pyrimidin-2-ylamino)-3-methoxy-N-methylbenzamide,
4-(5-(2-hydroxypyridin-4-yl)-4-(tetrahydro-2H-pyran-4-yloxy)-7H-pyrrolo[2,3-d]pyrimidin-2-ylamino)-3-methoxy-N-methylbenzamide,
4-(5-(1,2-dimethyl-1H-benzo[d]imidazol-6-yl)-4-(tetrahydro-2H-pyran-4-yloxy)-7H-pyrrolo[2,3-d]pyrimidin-2-ylamino)-3-methoxy-N-methylbenzamide, 4-(4-methoxy-5-(3-(methylcarbamoyl)phenyl)-7H-pyrrolo[2,3-d]pyrimidin-2-ylamino)-N,3-dimethylbenzamide,
4-(4-((1r,4r-4-hydroxy-4-methylcyclohexyloxy)-5-(2-methylbenzo[d]oxazol-6-yl)-7H-pyrrolo[2,3-d]pyrimidin-2-ylamino)-N,3-dimethylbenzamide,
4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-N,3-dimethylbenzamide,
4-(4-cyclopropoxy-5-(2-methylbenzo[d]oxazol-6-yl)-7H-pyrrolo[2,3-d]pyrimidin-2-ylamino)-3-methoxy-N-methylbenzamide,
(S)-N,3-dimethyl-4-(5-(4-(methylcarbamoyl)phenyl)-4-(tetrahydrofuran-3-yloxy)-7H-pyrrolo[2,3-d]pyrimidin-2-ylamino)benzamide,
3-methoxy-N-methyl-4-(5-(pyrimidin-5-yl)-4-(tetrahydro-2H-pyran-4-yloxy)-7H-pyrrolo[2,3-d]pyrimidin-2-ylamino)benzamide,
3-methoxy-N-methyl-4-(5-(2-(methylamino)pyridin-4-yl)-4-(tetrahydro-2H-pyran-4-yloxy)-7H-pyrrolo[2,3-d]pyrimidin-2-ylamino)benzamide,
4-(4-methoxy-5-(pyridin-4-yl)-7H-pyrrolo[2,3-d]pyrimidin-2-ylamino)-N,3-dimethylbenzamide,
3-chloro-4-(4-methoxy-5-(pyridin-4-yl)-7H-pyrrolo[2,3-d]pyrimidin-2-ylamino)-N,N-dimethylbenzamide,
N,3-dimethyl-4-(5-(4-(methyl sulfonyl)phenyl)-4-(tetrahydro-2H-pyran-4-yloxy)-7H-pyrrolo[2,3-d]pyrimidin-2-ylamino)benzamide,
5-(2-(4-(dimethylcarbamoyl)-2-methylphenylamino)-4-(tetrahydro-2H-pyran-4-yloxy)-7H-pyrrolo[2,3-d]pyrimidin-5-yl)-N-methylpicolinamide,
N-(2-hydroxyethyl)-4-(4-isopropoxy-5-(2-methylbenzo[d]oxazol-6-yl)-7H-pyrrolo[2,3-d]pyrimidin-2-ylamino)-3-methoxybenzamide,
(S)-4-(5-(6-ethoxypyridin-3-yl)-4-(tetrahydrofuran-3-yloxy)-7H-pyrrolo[2,3-d]pyrimidin-2-ylamino)-3-methoxy-N-methylbenzamide,
(S)-4-(5-(6-ethoxypyridin-3-yl)-4-(tetrahydrofuran-3-yloxy)-7H-pyrrolo[2,3-d]pyrimidin-2-ylamino)-N,3-dimethylbenzamide,
3-methoxy-N-methyl-4-(5-(1-methyl-1H-pyrazol-3-yl)-4-(tetrahydro-2H-pyran-4-yloxy)-7H-pyrrolo[2,3-d]pyrimidin-2-ylamino)benzamide,
(S)-N,N,3-trimethyl-4-(5-(1-methyl-1H-pyrazol-4-yl)-4-(tetrahydrofuran-3-yloxy)-7H-pyrrolo[2,3-d]pyrimidin-2-ylamino)benzamide,
(S)-N,3-dimethyl-4-(5-(1-methyl-1H-pyrazol-4-yl)-4-(tetrahydrofuran-3-yloxy)-7H-pyrrolo[2,3-d]pyrimidin-2-ylamino)benzamide,
3-methoxy-4-(4-methoxy-5-(2-methylpyridin-4-yl)-7H-pyrrolo[2,3-d]pyrimidin-2-ylamino)-N-methylbenzamide,
3-methoxy-N-methyl-4-(5-(2-methylpyridin-4-yl)-4-(tetrahydro-2H-pyran-4-yloxy)-7H-pyrrolo[2,3-d]pyrimidin-2-ylamino)benzamide,
4-(4-(2-hydroxyethoxy)-5-(2-methylbenzo[d]oxazol-6-yl)-7H-pyrrolo[2,3-d]pyrimidin-2-ylamino)-3-methoxy-N-methylbenzamide,
(S)-3-methoxy-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide,
4-(5-(2-isopropylbenzo[d]oxazol-6-yl)-4-(tetrahydro-2H-pyran-4-yloxy)-7H-pyrrolo[2,3-d]pyrimidin-2-ylamino)-3-methoxy-N-methylbenzamide,
3-cyano-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
3-methoxy-N-methyl-4-(5-(1-methyl-1H-imidazol-2-yl)-4-(tetrahydro-2H-pyran-4-yloxy)-7H-pyrrolo[2,3-d]pyrimidin-2-ylamino)benzamide,
3-methoxy-N-methyl-4-(5-(oxazol-2-yl)-4-(tetrahydro-2H-pyran-4-yloxy)-7H-pyrrolo[2,3-d]pyrimidin-2-ylamino)benzamide,
4-(5-(1,3,4-oxadiazol-2-yl)-4-(tetrahydro-2H-pyran-4-yloxy)-7H-pyrrolo[2,3-d]pyrimidin-2-ylamino)-3-methoxy-N-methylbenzamide,
(S)-4-(5-(3-(1-hydroxyethyl)phenyl)-4-(tetrahydro-2H-pyran-4-yloxy)-7H-pyrrolo[2,3-d]pyrimidin-2-ylamino)-3-methoxy-N-methylbenzamide,
(S)-N,N,3-trimethyl-4-(5-(pyridin-4-yl)-4-(tetrahydrofuran-3-yloxy)-7H-pyrrolo[2,3-d]pyrimidin-2-ylamino)benzamide,
3-methoxy-4-(4-methoxy-5-(1-methyl-1H-pyrazol-4-yl)-7H-pyrrolo[2,3-d]pyrimidin-2-ylamino)-N-methylbenzamide,
(S)-3-methoxy-N-methyl-4-(5-(2-methylpyridin-4-yl)-4-(tetrahydrofuran-3-yloxy)-7H-pyrrolo[2,3-d]pyrimidin-2-ylamino)benzamide,
3-methoxy-N-methyl-4-(5-(2-methylbenzo[d]oxazol-6-yl)-4-(oxetan-3-yloxy)-7H-pyrrolo[2,3-d]pyrimidin-2-ylamino)benzamide,
3-(4-isopropoxy-5-(2-methylbenzo[d]oxazol-6-yl)-7H-pyrrolo[2,3-d]pyrimidin-2-ylamino)-4-methoxy-N-methylbenzamide,
4-methoxy-N-methyl-3-(5-(2-methylbenzo[d]oxazol-6-yl)-4-(tetrahydro-2H-pyran-4-yloxy)-7H-pyrrolo[2,3-d]pyrimidin-2-ylamino)benzamide,
(S)-3-methoxy-N-methyl-4-(5-(4-(methylcarbamoyl)phenyl)-4-(tetrahydrofuran-3-yloxy)-7H-pyrrolo[2,3-d]pyrimidin-2-ylamino)benzamide,
6-methoxy-N-methyl-5-(5-(2-methylbenzo[d]oxazol-6-yl)-4-(tetrahydro-2H-pyran-4-yloxy)-7H-pyrrolo[2,3-d]pyrimidin-2-ylamino)picolinamide,
3-methoxy-N-methyl-4-(5-(1-methyl-1H-pyrazol-4-yl)-4-(tetrahydro-2H-pyran-4-yloxy)-7H-pyrrolo[2,3-d]pyrimidin-2-ylamino)benzamide,
4-(4-isopropoxy-5-(2-methoxypyridin-4-yl)-7H-pyrrolo[2,3-d]pyrimidin-2-ylamino)-3-methoxy-N-methylbenzamide,
3-methoxy-N-methyl-4-(5-(pyrazin-2-yl)-4-(tetrahydro-2H-pyran-4-yloxy)-7H-pyrrolo[2,3-d]pyrimidin-2-ylamino)benzamide,
4-(4-isopropoxy-5-(3-(methylsulfonyl)phenyl)-7H-pyrrolo[2,3-d]pyrimidin-2-ylamino)-3-methoxy-N-methylbenzamide,
4-(4-isopropoxy-5-(4-(methylcarbamoyl)phenyl)-7H-pyrrolo[2,3-d]pyrimidin-2-ylamino)-3-methoxy-N-methylbenzamide,
4-(4-isopropoxy-5-(1-methyl-1H-pyrazol-4-yl)-7H-pyrrolo[2,3-d]pyrimidin-2-ylamino)-3-methoxy-N-methylbenzamide,
3-methoxy-4-(4-methoxy-5-(pyridin-4-yl)-7H-pyrrolo[2,3-d]pyrimidin-2-ylamino)-N-methylbenzamide,
N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-(trifluoromethyl)benzamide,
N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-(trifluoromethoxy)benzamide,
4-(5-(4-(1H-imidazol-2-yl)phenyl)-4-isopropoxy-7H-pyrrolo[2,3-d]pyrimidin-2-ylamino)-3-methoxy-N-methylbenzamide, 4-(5-(2-aminopyridin-4-yl)-4-isopropoxy-7H-pyrrolo[2,3-d]pyrimidin-2-ylamino)-3-methoxy-N-methylbenzamide,
3-methoxy-N-methyl-4-(5-(4-(1-methyl-1H-imidazol-2-yl)phenyl)-4-(tetrahydro-2H-pyran-4-yloxy)-7H-pyrrolo[2,3-d]pyrimidin-2-ylamino)benzamide,
4-(5-(6-ethoxypyridin-3-yl)-4-isopropoxy-7H-pyrrolo[2,3-d]pyrimidin-2-ylamino)-3-methoxy-N-methylbenzamide,
4-(5-(4-(4, 5-dimethyl-1H-imidazol-2-yl)phenyl)-4-(tetrahydro-2H-pyran-4-yloxy)-7H-pyrrolo[2,3-d]pyrimidin-2-ylamino)-3-methoxy-N-methylbenzamide,
4-(4-cyclobutoxy-5-(2-methylbenzo[d]oxazol-6-yl)-7H-pyrrolo[2,3-d]pyrimidin-2-ylamino)-3-methoxy-N-methylbenzamide,
4-(4-isopropoxy-5-(2-(methylamino)pyridin-4-yl)-7H-pyrrolo[2,3-d]pyrimidin-2-ylamino)-3-methoxy-N-methylbenzamide,
3-isopropyl-N-methyl-4-(5-(pyridin-4-yl)-4-(tetrahydro-2H-pyran-4-yloxy)-7H-pyrrolo[2,3-d]pyrimidin-2-ylamino)benzamide,
4-(4-isopropoxy-5-(2-methylpyridin-4-yl)-7H-pyrrolo[2,3-d]pyrimidin-2-ylamino)-3-methoxy-N-methylbenzamide,
4-(4-(isopropylamino)-5-(2-methylbenzo[d]oxazol-6-yl)-7H-pyrrolo[2,3-d]pyrimidin-2-ylamino)-3-methoxy-N-methylbenzamide,
(R)-4-(4-sec-butoxy-5-(2-methylbenzo[d]oxazol-6-yl)-7H-pyrrolo[2,3-d]pyrimidin-2-ylamino)-3-methoxy-N-methylbenzamide,
(S)-4-(4-sec-butoxy-5-(2-methylbenzo[d]oxazol-6-yl)-7H-pyrrolo[2,3-d]pyrimidin-2-ylamino)-3-methoxy-N-methylbenzamide,
4-(4-((1r,4r-4-hydroxy-4-methylcyclohexyloxy)-5-(2-methylbenzo[d]oxazol-6-yl)-7H-pyrrolo[2,3-d]pyrimidin-2-ylamino)-3-methoxy-N-methylbenzamide,
4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-methylbenzamide,
3-methoxy-N-methyl-4-(5-(4-(4-methyl-1H-imidazol-2-yl)phenyl)-4-(tetrahydro-2H-pyran-4-yloxy)-7H-pyrrolo[2,3-d]pyrimidin-2-ylamino)benzamide,
(S)-3-isopropyl-N-methyl-4-(5-(1-methyl-1H-pyrazol-4-yl)-4-(tetrahydrofuran-3-yloxy)-7H-pyrrolo[2,3-d]pyrimidin-2-ylamino)benzamide,
(S)-3-isopropyl-N-methyl-4-(5-(2-methylbenzo[d]oxazol-6-yl)-4-(tetrahydrofuran-3-yloxy)-7H-pyrrolo[2,3-d]pyrimidin-2-ylamino)benzamide,
3-methoxy-N-methyl-4-(5-(1-methyl-1H-pyrazol-4-yl)-4-(tetrahydro-2H-pyran-4-ylamino)-7H-pyrrolo[2,3-d]pyrimidin-2-ylamino)benzamide,
4-(4-(cyclopropylamino)-5-(1-methyl-1H-pyrazol-4-yl)-7H-pyrrolo[2,3-d]pyrimidin-2-ylamino)-3-methoxy-N-methylbenzamide,
4-(4-(cyclopropylamino)-5-(2-methylbenzo[d]oxazol-6-yl)-7H-pyrrolo[2,3-d]pyrimidin-2-ylamino)-3-methoxy-N-methylbenzamide,
N-(2-hydroxyethyl)-3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)benzamide,
(R)-4-(4-(cyclopentyloxy)-5-(2-methylbenzo[d]oxazol-6-yl)-7H-pyrrolo[2,3-d]pyrimidin-2-ylamino)-N-(1-hydroxypropan-2-yl)-3-methoxybenzamide,
(S)-4-(4-(cyclopentyloxy)-5-(2-methylbenzo[d]oxazol-6-yl)-7H-pyrrolo[2,3-d]pyrimidin-2-ylamino)-N-(1-hydroxypropan-2-yl)-3-methoxybenzamide,
4-(4-cyclopropoxy-5-(2-methylbenzo[d]oxazol-6-yl)-7H-pyrrolo[2,3-d]pyrimidin-2-ylamino)-N-(2-hydroxyethyl)-3-methoxybenzamide,
4-(4-cyclopropoxy-5-(1-methyl-1H-pyrazol-4-yl)-7H-pyrrolo[2,3-d]pyrimidin-2-ylamino)-N-(2-hydroxyethyl)-3-methoxybenzamide,
4-(4-cyclopropoxy-5-(1-methyl-1H-pyrazol-3-yl)-7H-pyrrolo[2,3-d]pyrimidin-2-ylamino)-3-methoxy-N-methylbenzamide,
3-methoxy-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzenesulfonamide,
4-(4-isopropoxy-5-(1-methyl-1H-pyrazol-3-yl)-7H-pyrrolo[2,3-d]pyrimidin-2-ylamino)-3-methoxy-N-methylbenzamide,
3-methoxy-4-(4-(2-methoxyethoxy)-5-(1-methyl-1H-pyrazol-4-yl)-7H-pyrrolo[2,3-d]pyrimidin-2-ylamino)-N,N-dimethylbenzamide,
(R)-3-methoxy-N,N-dimethyl-4-(5-(2-methylbenzo[d]oxazol-6-yl)-4-(tetrahydrofuran-3-yloxy)-7H-pyrrolo[2,3-d]pyrimidin-2-ylamino)benzamide,
3-methoxy-N-methyl-4-(5-(2-methylbenzo[d]thiazol-6-yl)-4-(tetrahydro-2H-pyran-4-yloxy)-7H-pyrrolo[2,3-d]pyrimidin-2-ylamino)benzamide,
N-tert-butyl-4-(4-(cyclopentyloxy)-5-(2-methylbenzo[d]oxazol-6-yl)-7H-pyrrolo[2,3-d]pyrimidin-2-ylamino)-3-methoxybenzamide,
(S)-3-isopropyl-N-methyl-4-(5-(1-methyl-1H-pyrazol-5-yl)-4-(tetrahydrofuran-3-yloxy)-7H-pyrrolo[2,3-d]pyrimidin-2-ylamino)benzamide,
4-(4-isopropoxy-5-(1-methyl-1H-pyrazol-5-yl)-7H-pyrrolo[2,3-d]pyrimidin-2-ylamino)-3-methoxy-N-methylbenzamide,
4-(cyclopentyloxy)-N-(2-methoxy-4-(1-methyl-1H-pyrazol-4-yl)phenyl)-5-(2-methylbenzo[d]oxazol-6-yl)-7H-pyrrolo[2,3-d]pyrimidin-2-amine,
4-(cyclopentyloxy)-N-(2-methoxy-4-(1H-pyrazol-1-yl)phenyl)-5-(2-methylbenzo[d]oxazol-6-yl)-7H-pyrrolo[2,3-d]pyrimidin-2-amine,
N-cyclopentyl-4-(4-(cyclopentyloxy)-5-(2-methylbenzo[d]oxazol-6-yl)-7H-pyrrolo[2,3-d]pyrimidin-2-ylamino)-3-methoxybenzamide,
(R)-4-(4-(cyclopentyloxy)-5-(2-methylbenzo[d]oxazol-6-yl)-7H-pyrrolo[2,3-d]pyrimidin-2-ylamino)-N-(2-hydroxypropyl)-3-methoxybenzamide,
(4-(4-(cyclopentyloxy)-5-(2-methylbenzo[d]oxazol-6-yl)-7H-pyrrolo[2,3-d]pyrimidin-2-ylamino)-3-methoxyphenyl)(4-hydroxypiperidin-1-yl)methanone,
4-(4-(cyclopentyloxy)-5-(2-methylbenzo[d]oxazol-6-yl)-7H-pyrrolo[2,3-d]pyrimidin-2-ylamino)-N-(3-hydroxypropyl)-3-methoxybenzamide,
4-(4-(cyclopentyloxy)-5-(2-methylbenzo[d]oxazol-6-yl)-7H-pyrrolo[2,3-d]pyrimidin-2-ylamino)-N-(2-hydroxyethyl)-3-methoxy-N-methylbenzamide,
4-(4-(cyclopentyloxy)-5-(2-methylbenzo[d]oxazol-6-yl)-7H-pyrrolo[2,3-d]pyrimidin-2-ylamino)-N-(1-hydroxy-2-methylpropan-2-yl)-3-methoxybenzamide,
5-(4-(cyclopentyloxy)-5-(2-methylbenzo[d]oxazol-6-yl)-7H-pyrrolo[2,3-d]pyrimidin-2-ylamino)isoindolin-1-one,
4-(5-(2-acetamidopyridin-4-yl)-4-(tetrahydro-2H-pyran-4-yloxy)-7H-pyrrolo[2,3-d]pyrimidin-2-ylamino)-3-methoxy-N-methylbenzamide,
4-(cyclopentyloxy)-5-(2-methylbenzo[d]oxazol-6-yl)-7H-pyrrolo[2,3-d]pyrimidin-2-ylamino)-2-fluoro-5-methoxy-N-methylbenzamide, 4-(4-(cyclopentyloxy)-5-(2-methylbenzo[d]oxazol-6-yl)-7H-pyrrolo[2,3-d]pyrimidin-2-ylamino)-N-((1s,3s)-3-hydroxycyclobutyl)-3-methoxybenzamide, 4-(4-(cyclopentyloxy)-5-(2-methylbenzo[d]oxazol-6-yl)-7H-pyrrolo[2,3-d]pyrimidin-2-ylamino)-N-((1r,3r)-3-hydroxycyclobutyl)-3-methoxybenzamide, (S)-4-(4-(cyclopentyloxy)-5-(2-methylbenzo[d]oxazol-6-yl)-7H-pyrrolo[2,3-d]pyrimidin-2-ylamino)-N-(2-hydroxypropyl)-3-methoxybenzamide, azetidin-1-yl(4-(4-(cyclopentyloxy)-5-(2-methylbenzo[d]oxazol-6-yl)-7H-pyrrolo[2,3-d]pyrimidin-2-ylamino)-3-methoxyphenyl)methanone, (R)-4-(4-(cyclopentyloxy)-5-(2-methylbenzo[d]oxazol-6-yl)-7H-pyrrolo[2,3-d]pyrimidin-2-ylamino)-3-methoxy-N-((tetrahydrofuran-2-yl)methyl)benzamide, 4-(4-(cyclopentyloxy)-5-(2-methylbenzo[d]oxazol-6-yl)-7H-pyrrolo[2,3-d]pyrimidin-2-ylamino)-3-methoxy-N-((tetrahydro-2H-pyran-4-yl)methyl)benzamide, 5-(4-(cyclopentyloxy)-5-(2-methylbenzo[d]oxazol-6-yl)-7H-pyrrolo[2,3-d]pyrimidin-2-ylamino)-2-methylisoindolin-1-one, 4-(5-(4-carbamimidoylphenyl)-4-(cyclopentyloxy)-7H-pyrrolo[2,3-d]pyrimidin-2-ylamino)-3-methoxy-N-methylbenzamide, 4-(4-tert-butoxy-5-(2-methylbenzo[d]oxazol-6-yl)-7H-pyrrolo[2,3-d]pyrimidin-2-ylamino)-3-methoxy-N-methylbenzamide, N-(4-(4-(cyclopentyloxy)-5-(2-methylbenzo[d]oxazol-6-yl)-7H-pyrrolo[2,3-d]pyrimidin-2-ylamino)-3-methoxyphenyl)acetamide, N-(2-cyanoethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide, (4-(4-(cyclopentyloxy)-5-(2-methylbenzo[d]oxazol-6-yl)-7H-pyrrolo[2,3-d]pyrimidin-2-ylamino)-3-methoxyphenyl)(pyrrolidin-1-yl)methanone, 4-(4-(cyclopentyloxy)-5-(2-methylbenzo[d]oxazol-6-yl)-7H-pyrrolo[2,3-d]pyrimidin-2-ylamino)-3-methoxy-N-methyl-N-(tetrahydro-2H-pyran-4-yl)benzamide, 4-(4-(cyclopentyloxy)-5-(2-methylbenzo[d]oxazol-6-yl)-7H-pyrrolo[2,3-d]pyrimidin-2-ylamino)-N-cyclopropyl-N-(2-hydroxyethyl)-3-methoxybenzamide, 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-4-yl)benzamide, 4-(4-(cyclopentyloxy)-5-(2-methylbenzo[d]oxazol-6-yl)-7H-pyrrolo[2,3-d]pyrimidin-2-ylamino)-N-((1R,2S)-2-hydroxycyclopentyl)-3-methoxybenzamide, (S)-4-(4-(cyclopentyloxy)-5-(2-methylbenzo[d]oxazol-6-yl)-7H-pyrrolo[2,3-d]pyrimidin-2-ylamino)-3-methoxy-N-((tetrahydrofuran-2-yl)methyl)benzamide, 4-(4-(cyclopentyloxy)-5-(2-methylbenzo[d]oxazol-6-yl)-7H-pyrrolo[2,3-d]pyrimidin-2-ylamino)-3-methoxy-N-(oxetan-3-yl)benzamide, 4-(4-(cyclopentyloxy)-5-(2-methylbenzo[d]oxazol-6-yl)-7H-pyrrolo[2,3-d]pyrimidin-2-ylamino)-N-(2-fluoroethyl)-3-methoxybenzamide, N-(3-amino-3-oxopropyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide, 4-(4-(cyclopentyloxy)-5-(4-(methylcarbamoyl)phenyl)-7H-pyrrolo[2,3-d]pyrimidin-2-ylamino)-N-(2-hydroxyethyl)-3-methoxybenzamide, (4-(4-(cyclopentyloxy)-5-(2-methylbenzo[d]oxazol-6-yl)-7H-pyrrolo[2,3-d]pyrimidin-2-ylamino)-3-methoxyphenyl)(4-methylpiperazin-1-yl)methanone, 4-(5-(benzo[c][1,2,5]oxadiazol-5-yl)-4-(cyclopentyloxy)-7H-pyrrolo[2,3-d]pyrimidin-2-ylamino)-3-methoxy-N-methylbenzamide, 4-(cyclopentyloxy)-N-(5-fluoro-2-methoxy-4-(methylsulfonyl)phenyl)-5-(2-methylbenzo[d]oxazol-6-yl)-7H-pyrrolo[2,3-d]pyrimidin-2-amine, aziridin-1-yl(4-(4-(cyclopentyloxy)-5-(2-methylbenzo[d]oxazol-6-yl)-7H-pyrrolo[2,3-d]pyrimidin-2-ylamino)-3-methoxyphenyl)methanone, N-(cyanomethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide, 4-(4-(cyclopentyloxy)-5-(2-methylbenzo[d]oxazol-6-yl)-7H-pyrrolo[2,3-d]pyrimidin-2-ylamino)-N-((1S,2R)-2-hydroxycyclopentyl)-3-methoxybenzamide, 4-(4-(cyclopentyloxy)-5-(2-methylbenzo[d]oxazol-6-yl)-7H-pyrrolo[2,3-d]pyrimidin-2-ylamino)-N-((1S,2S)-2-hydroxycyclopentyl)-3-methoxybenzamide, 4-(4-(cyclopentyloxy)-5-(2-methylbenzo[d]oxazol-6-yl)-7H-pyrrolo[2,3-d]pyrimidin-2-ylamino)-N-((1R,2R)-2-hydroxycyclopentyl)-3-methoxybenzamide, (S)-4-(4-(cyclopentyloxy)-5-(2-methylbenzo[d]oxazol-6-yl)-7H-pyrrolo[2,3-d]pyrimidin-2-ylamino)-3-methoxy-N-(tetrahydrofuran-3-yl)benzamide, N-(2-amino-2-oxoethyl)-4-(4-(cyclopentyloxy)-5-(2-methylbenzo[d]oxazol-6-yl)-7H-pyrrolo[2,3-d]pyrimidin-2-ylamino)-3-methoxy-N-methylbenzamide, 3-methoxy-N-methyl-4-(5-(pyridazin-4-yl)-4-(tetrahydro-2H-pyran-4-yloxy)-7H-pyrrolo[2,3-d]pyrimidin-2-ylamino)benzamide, 3-methoxy-N-methyl-4-(5-(pyrimidin-4-yl)-4-(tetrahydro-2H-pyran-4-yloxy)-7H-pyrrolo[2,3-d]pyrimidin-2-ylamino)benzamide, 4-(4-(cyclopentyloxy)-5-(2-methylbenzo[d]oxazol-6-yl)-7H-pyrrolo[2,3-d]pyrimidin-2-ylamino)-3-methoxy-N-methyl-N-((3-methyloxetan-3-yl)methyl)benzamide, 4-(4-(cyclopentyloxy)-5-(2-methylbenzo[d]oxazol-6-yl)-7H-pyrrolo[2,3-d]pyrimidin-2-ylamino)-3-methoxy-N-methyl-N-(oxetan-3-yl)benzamide, 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-3-yl)benzamide, 4-(4-(cyclopentyloxy)-5-(2-methylbenzo[d]oxazol-6-yl)-7H-pyrrolo[2,3-d]pyrimidin-2-ylamino)-3-methoxy-N-(tetrahydro-2H-pyran-3-yl)benzamide, (4-(4-(cyclopentyloxy)-5-(2-methylbenzo[d]oxazol-6-yl)-7H-pyrrolo[2,3-d]pyrimidin-2-ylamino)-3-methoxyphenyl)(4-methoxypiperidin-1-yl)methanone, (S)-4-(4-sec-butoxy-5-(1-methyl-1H-pyrazol-4-yl)-7H-pyrrolo[2,3-d]pyrimidin-2-ylamino)-3-methoxy-N-methylbenzamide, 4-(4-(cyclopentyloxy)-5-(2-methylbenzo[d]oxazol-6-yl)-7H-pyrrolo[2,3-d]pyrimidin-2-ylamino)-3-methoxybenzonitrile, 4-(4-(cyclopentyloxy)-5-(1-methyl-1H-indazol-6-yl)-7H-pyrrolo[2,3-d]pyrimidin-2-ylamino)-3-methoxy-N-methylbenzamide, 4-(4-(cyclopentyloxy)-5-(3-methylbenzo[d]isoxazol-6-yl)-7H-pyrrolo[2,3-d]pyrimidin-2-ylamino)-3-methoxy-N-methylbenzamide, 5-(4-(cyclopentyloxy)-5-(2-methylbenzo[d]oxazol-6-yl)-7H-pyrrolo[2,3-d]pyrimidin-2-ylamino)-4-methoxy-N-methylpicolinamide, N-((1,4-dioxan-2-yl)methyl)-4-(4-(cyclopentyloxy)-5-(2-methylbenzo[d]oxazol-6-yl)-7H-pyrrolo[2,3-d]pyrimidin-2-ylamino)-3-methoxybenzamide,

- 4-(4-(cyclopentyloxy)-5-(2-methylbenzo[d]oxazol-6-yl)-7H-pyrrolo[2,3-d]pyrimidin-2-ylamino)-3-methoxy-N-(oxetan-3-ylmethyl)benzamide,
- 4-(4-(cyclopentyloxy)-5-(2-methylbenzo[d]oxazol-6-yl)-7H-pyrrolo[2,3-d]pyrimidin-2-ylamino)-N-(3-hydroxypropyl)-3-methoxy-N-methylbenzamide,
- 4-(4-(cyclopentyloxy)-5-(2-methylbenzo[d]oxazol-6-yl)-7H-pyrrolo[2,3-d]pyrimidin-2-ylamino)-3-methoxy-N-(2-methoxyethyl)-N-methylbenzamide,
- 4-(4-(cyclopentyloxy)-5-(2-methylbenzo[d]oxazol-6-yl)-7H-pyrrolo[2,3-d]pyrimidin-2-ylamino)-N-(2-hydroxy-2-methylpropyl)-3-methoxybenzamide,
- (S)-4-(4-sec-butoxy-5-(1-methyl-1H-pyrazol-4-yl)-7H-pyrrolo[2,3-d]pyrimidin-2-ylamino)-N-(2-hydroxyethyl)-3-methoxybenzamide,
- 4-(4-(cyclopentyloxy)-5-(2-methylbenzo[d]oxazol-6-yl)-7H-pyrrolo[2,3-d]pyrimidin-2-ylamino)-3-methoxybenzimidamide,
- 4-(2-(2-methoxy-4-(methylcarbamoyl)phenylamino)-4-(tetrahydro-2H-pyran-4-yloxy)-7H-pyrrolo[2,3-d]pyrimidin-5-yl)-N-methylpicolinamide,
- (4-(4-(cyclopentyloxy)-5-(2-methylbenzo[d]oxazol-6-yl)-7H-pyrrolo[2,3-d]pyrimidin-2-ylamino)-3-methoxyphenyl)(4,4-difluoropiperidin-1-yl)methanone,
- 4-(5-(4-acetamido-3-hydroxyphenyl)-4-(cyclopentyloxy)-7H-pyrrolo[2,3-d]pyrimidin-2-ylamino)-3-methoxy-N-methylbenzamide,
- (4-(4-(cyclopentyloxy)-5-(2-methylbenzo[d]oxazol-6-yl)-7H-pyrrolo[2,3-d]pyrimidin-2-ylamino)-3-methoxyphenyl)((3R,4R)-3-hydroxy-4-methoxypyrrolidin-1-yl)methanone,
- 4-(4-(cyclopentyloxy)-5-(2-methylbenzo[d]oxazol-6-yl)-7H-pyrrolo[2,3-d]pyrimidin-2-ylamino)-3-methoxy-N-(piperidin-1-yl)benzamide,
- 4-(4-(cyclopentyloxy)-5-(2-ethoxybenzo[d]oxazol-6-yl)-7H-pyrrolo[2,3-d]pyrimidin-2-ylamino)-3-methoxy-N-methylbenzamide,
- 4-(5-(4-amino-3-hydroxyphenyl)-4-(cyclopentyloxy)-7H-pyrrolo[2,3-d]pyrimidin-2-ylamino)-3-methoxy-N-methylbenzamide,
- 4-(cyclopentyloxy)-N-(1-methyl-1H-pyrazol-5-yl)-5-(2-methylbenzo[d]oxazol-6-yl)-7H-pyrrolo[2,3-d]pyrimidin-2-amine,
- 4-(cyclopentyloxy)-N-(1,5-dimethyl-1H-pyrazol-4-yl)-5-(2-methylbenzo[d]oxazol-6-yl)-7H-pyrrolo[2,3-d]pyrimidin-2-amine,
- 4-(cyclopentyloxy)-N-(1,4-dimethyl-1H-pyrazol-3-yl)-5-(2-methylbenzo[d]oxazol-6-yl)-7H-pyrrolo[2,3-d]pyrimidin-2-amine,
- 4-(4-(cyclopentyloxy)-5-(2-methylbenzo[d]oxazol-6-yl)-7H-pyrrolo[2,3-d]pyrimidin-2-ylamino)-3-methoxy-N,5-dimethylbenzamide,
- 4-(4-(cyclopentyloxy)-5-(2-oxo-2,3-dihydrobenzo[d]oxazol-6-yl)-7H-pyrrolo[2,3-d]pyrimidin-2-ylamino)-3-methoxy-N-methylbenzamide,
- 4-(4-(cyclopentyloxy)-5-(2-methylbenzo[d]oxazol-6-yl)-7H-pyrrolo[2,3-d]pyrimidin-2-ylamino)-3-methoxy-N-(1-methylazetidin-3-yl)benzamide,
- 4-(4-(cyclopentyloxy)-5-(2-methylbenzo[d]oxazol-6-yl)-7H-pyrrolo[2,3-d]pyrimidin-2-ylamino)-3-methoxy-N-(3-methyloxetan-3-yl)benzamide,
- 4-(4-cyclobutoxy-5-(1-methyl-1H-pyrazol-4-yl)-7H-pyrrolo[2,3-d]pyrimidin-2-ylamino)-3-methoxy-N-(oxetan-3-yl)benzamide,
- 4-(4-(cyclopentyloxy)-5-(1-methyl-1H-pyrazol-4-yl)-7H-pyrrolo[2,3-d]pyrimidin-2-ylamino)-3-methoxy-N-(oxetan-3-yl)benzamide,
- 4-(4-cyclobutoxy-5-(4-(methylcarbamoyl)phenyl)-7H-pyrrolo[2,3-d]pyrimidin-2-ylamino)-3-methoxy-N-(oxetan-3-yl)benzamide,
- 4-(4-(cyclopentyloxy)-5-(4-(methylcarbamoyl)phenyl)-7H-pyrrolo[2,3-d]pyrimidin-2-ylamino)-3-methoxy-N-(oxetan-3-yl)benzamide,
- 4-(4-(cyclopentyloxy)-5-(quinolin-6-yl)-7H-pyrrolo[2,3-d]pyrimidin-2-ylamino)-3-methoxy-N-methylbenzamide,
- 4-(cyclopentyloxy)-N-(1,3-dimethyl-1H-pyrazol-4-yl)-5-(2-methylbenzo[d]oxazol-6-yl)-7H-pyrrolo[2,3-d]pyrimidin-2-amine,
- N-(1-acetylazetidin-3-yl)-4-(4-(cyclopentyloxy)-5-(2-methylbenzo[d]oxazol-6-yl)-7H-pyrrolo[2,3-d]pyrimidin-2-ylamino)-3-methoxybenzamide,
- 4-(4-(cyclopentyloxy)-5-(2-methylbenzo[d]oxazol-6-yl)-7H-pyrrolo[2,3-d]pyrimidin-2-ylamino)-N-(2,2-difluoropropyl)-3-methoxybenzamide,
- 3-methoxy-4-(5-(4-(methylcarbamoyl)phenyl)-4-(tetrahydro-2H-pyran-4-yloxy)-7H-pyrrolo[2,3-d]pyrimidin-2-ylamino)-N-(oxetan-3-yl)benzamide,
- (4-(4-(cyclopentyloxy)-5-(2-methylbenzo[d]oxazol-6-yl)-7H-pyrrolo[2,3-d]pyrimidin-2-ylamino)-3-methoxyphenyl)((3R,4R)-3,4-dimethoxypyrrolidin-1-yl)methanone,
- (4-(4-(cyclopentyloxy)-5-(2-methylbenzo[d]oxazol-6-yl)-7H-pyrrolo[2,3-d]pyrimidin-2-ylamino)-3-methoxyphenyl)(2,2-dimethylaziridin-1-yl)methanone,
- (S)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone,
- 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-(oxetan-3-yl)benzamide,
- aziridin-1-yl(4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxyphenyl)methanone,
- 4-(4-(cyclopentyloxy)-2-(1-methyl-1H-pyrazol-5-ylamino)-7H-pyrrolo[2,3-d]pyrimidin-5-yl)-N-methylbenzamide,
- N-methyl-4-(2-(1-methyl-1H-pyrazol-5-ylamino)-4-(tetrahydro-2H-pyran-4-yloxy)-7H-pyrrolo[2,3-d]pyrimidin-5-yl)benzamide,
- methyl 4-(4-(cyclopentyloxy)-2-(2-methoxy-4-(methylcarbamoyl)phenylamino)-7H-pyrrolo[2,3-d]pyrimidin-5-yl)benzoate,
- 4-(4-(cyclopentyloxy)-5-(4-fluoro-2-methylphenyl)-7H-pyrrolo[2,3-d]pyrimidin-2-ylamino)-3-methoxy-N-methylbenzamide,
- 4-(4-(cyclopentyloxy)-5-(2,4-dimethoxyphenyl)-7H-pyrrolo[2,3-d]pyrimidin-2-ylamino)-3-methoxy-N-methylbenzamide,
- 4-(4-(cyclopentyloxy)-5-(3,5-dimethylisoxazol-4-yl)-7H-pyrrolo[2,3-d]pyrimidin-2-ylamino)-3-methoxy-N-methylbenzamide,
- 4-(4-(cyclopentyloxy)-5-(3-(dimethylamino)phenyl)-7H-pyrrolo[2,3-d]pyrimidin-2-ylamino)-3-methoxy-N-methylbenzamide,
- 4-(4-(cyclopentyloxy)-5-(3-hydroxyphenyl)-7H-pyrrolo[2,3-d]pyrimidin-2-ylamino)-3-methoxy-N-methylbenzamide, 4-(5-(3-cyanophenyl)-4-(cyclopentyloxy)-7H-pyrrolo[2,3-d]pyrimidin-2-ylamino)-3-methoxy-N-methylbenzamide, 3-methoxy-4-(5-(5-methoxypyridin-3-yl)-4-(tetrahydro-2H-pyran-4-yloxy)-7H-pyrrolo[2,3-d]pyrimidin-2-ylamino)-N-methylbenzamide, 3-methoxy-4-(4-(2-methoxyethoxy)-5-(1-methyl-1H-pyrazol-4-yl)-7H-pyrrolo[2,3-d]pyrimidin-2-ylamino)-N-methylbenzamide, N-(2-hydroxyethyl)-3-methoxy-4-(5-(1-methyl-1H-pyrazol-4-yl)-4-(tetrahydro-2H-pyran-4-yloxy)-7H-pyrrolo[2,3-d]pyrimidin-2-ylamino)benzamide, (S)-3-methoxy-N-methyl-4-(5-(1-methyl-1H-pyrazol-4-yl)-4-(tetrahydrofuran-3-yloxy)-7H-pyrrolo[2,3-d]pyrimidin-2-ylamino)benzamide, N-methyl-4-(2-(1-methyl-1H-pyrazol-5-ylamino)-4-(tetrahydro-2H-pyran-4-yloxy)-7H-pyrrolo[2,3-d]pyrimidin-5-yl)benzamide, 4-(4-(cyclopentyloxy)-5-(4-fluoro-2-methylbenzo[d]oxazol-6-yl)-7H-pyrrolo[2,3-d]pyrimidin-2-ylamino)-3-methoxy-N-methylbenzamide, 4-(4-cyclobutoxy-5-(4-(methylcarbamoyl)phenyl)-7H-pyrrolo[2,3-d]pyrimidin-2-ylamino)-N-(2-hydroxyethyl)-3-methoxybenzamide, 4-(4-cyclobutoxy-5-(4-(methylcarbamoyl)phenyl)-7H-pyrrolo[2,3-d]pyrimidin-2-ylamino)-3-methyl-N-(oxetan-3-yl)benzamide, 3-chloro-4-(4-cyclobutoxy-5-(4-(methylcarbamoyl)phenyl)-7H-pyrrolo[2,3-d]pyrimidin-2-ylamino)-N-(oxetan-3-yl)benzamide, 4-(4-isopropoxy-5-(4-(methylcarbamoyl)phenyl)-7H-pyrrolo[2,3-d]pyrimidin-2-ylamino)-3-methoxy-N-(oxetan-3-yl)benzamide, (R)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-methylaziridin-1-yl)methanone, 4-(2-(4-(aziridine-1-carbonyl)-2-methoxyphenylamino)-4-((1s,4s)-4-hydroxy-4-methylcyclohexyloxy)-7H-pyrrolo[2,3-d]pyrimidin-5-yl)-N-methylbenzamide, 4-(4-((1s,4s)-4-hydroxy-4-methylcyclohexyloxy)-5-(4-(methylcarbamoyl)phenyl)-7H-pyrrolo[2,3-d]pyrimidin-2-ylamino)-3-methoxy-N-(oxetan-3-yl)benzamide, aziridin-1-yl(3-methoxy-4-(4-methoxy-5-(pyridin-4-yl)-7H-pyrrolo[2,3-d]pyrimidin-2-ylamino)phenyl)methanone, 4-(4-cyclobutoxy-5-(2-methylbenzo[d]oxazol-6-yl)-7H-pyrrolo[2,3-d]pyrimidin-2-ylamino)-3-methoxy-N-(oxetan-3-yl)benzamide, 4-(4-cyclobutoxy-2-(1,3-dimethyl-1H-pyrazol-4-ylamino)-7H-pyrrolo[2,3-d]pyrimidin-5-yl)-N-methylbenzamide, 4-(4-(3-cyanocyclobutoxy)-5-(4-(methylcarbamoyl)phenyl)-7H-pyrrolo[2,3-d]pyrimidin-2-ylamino)-3-methoxy-N-(oxetan-3-yl)benzamide, 4-(2-(5-chloro-1-methyl-1H-pyrazol-4-ylamino)-4-cyclobutoxy-7H-pyrrolo[2,3-d]pyrimidin-5-yl)-N-methylbenzamide, (S)-3-methoxy-4-(5-(2-methylbenzo[d]oxazol-6-yl)-4-(tetrahydrofuran-3-yloxy)-7H-pyrrolo[2,3-d]pyrimidin-2-ylamino)-N-(oxetan-3-yl)benzamide, 4-(4-cyclopropoxy-5-(4-(methylcarbamoyl)phenyl)-7H-pyrrolo[2,3-d]pyrimidin-2-ylamino)-3-methoxy-N-(oxetan-3-yl)benzamide, 4-(4-(3,3-difluorocyclobutoxy)-5-(4-(methylcarbamoyl)phenyl)-7H-pyrrolo[2,3-d]pyrimidin-2-ylamino)-3-methoxy-N-(oxetan-3-yl)benzamide, (R)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-(hydroxymethyl)aziridin-1-yl)methanone, 3-methoxy-4-(4-methoxy-5-(pyridin-4-yl)-7H-pyrrolo[2,3-d]pyrimidin-2-ylamino)-N-(oxetan-3-yl)benzamide, 4-(4-cyclobutoxy-5-(4-(methylcarbamoyl)phenyl)-7H-pyrrolo[2,3-d]pyrimidin-2-ylamino)-3-methoxy-N-(1-methylazetidin-3-yl)benzamide, 4-(4-((1s,4s)-4-hydroxy-4-methylcyclohexyloxy)-5-(4-(methylcarbamoyl)phenyl)-7H-pyrrolo[2,3-d]pyrimidin-2-ylamino)-3-methoxy-N-(1-methylazetidin-3-yl)benzamide, (S)-(4-(4-(cyclopentyloxy)-5-(2-methylbenzo[d]oxazol-6-yl)-7H-pyrrolo[2,3-d]pyrimidin-2-ylamino)-3-methoxyphenyl)(2-(hydroxymethyl)aziridin-1-yl)methanone, N-(5-chloro-1-isopropyl-1H-pyrazol-4-yl)-4-(cyclopentyloxy)-5-(2-methylbenzo[d]oxazol-6-yl)-7H-pyrrolo[2,3-d]pyrimidin-2-amine, 5-(4-cyclobutoxy-2-(2-methoxy-4-(oxetan-3-ylcarbamoyl)phenylamino)-7H-pyrrolo[2,3-d]pyrimidin-5-yl)-N-methylpicolinamide, 4-(4-cyclobutoxy-2-(2-methoxy-4-(oxetan-3-ylcarbamoyl)phenylamino)-7H-pyrrolo[2,3-d]pyrimidin-5-yl)-2-fluoro-N-methylbenzamide, 4-(4-tert-butoxy-5-(2-methylbenzo[d]oxazol-6-yl)-7H-pyrrolo[2,3-d]pyrimidin-2-ylamino)-3-methoxy-N-(1-methylazetidin-3-yl)benzamide, 4-(4-tert-butoxy-5-(4-(methylcarbamoyl)phenyl)-7H-pyrrolo[2,3-d]pyrimidin-2-ylamino)-3-methoxy-N-(1-methylazetidin-3-yl)benzamide, 4-(4-isopropoxy-5-(2-methylbenzo[d]oxazol-6-yl)-7H-pyrrolo[2,3-d]pyrimidin-2-ylamino)-3-methoxy-N-(1-methylazetidin-3-yl)benzamide, 4-(4-isopropoxy-5-(4-(methylcarbamoyl)phenyl)-7H-pyrrolo[2,3-d]pyrimidin-2-ylamino)-3-methoxy-N-(1-methylazetidin-3-yl)benzamide, 4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-3-methoxy-N-(1-methylazetidin-3-yl)benzamide, 3-methoxy-4-(5-(4-(methylcarbamoyl)phenyl)-4-(oxetan-3-yloxy)-7H-pyrrolo[2,3-d]pyrimidin-2-ylamino)-N-(oxetan-3-yl)benzamide, 4-(5-(4-(1H-imidazol-2-yl)phenyl)-4-cyclobutoxy-7H-pyrrolo[2,3-d]pyrimidin-2-ylamino)-3-methoxy-N-(oxetan-3-yl)benzamide, 4-(5-(4-(1H-imidazol-2-yl)phenyl)-4-(cyclopentyloxy)-7H-pyrrolo[2,3-d]pyrimidin-2-ylamino)-3-methoxy-N-(1-methylazetidin-3-yl)benzamide, 4-(4-isopropoxy-5-(2-methylbenzo[d]oxazol-6-yl)-7H-pyrrolo[2,3-d]pyrimidin-2-ylamino)-3-methoxy-N-(oxetan-3-yl)benzamide, 4-(4-cyclopropoxy-5-(2-methylbenzo[d]oxazol-6-yl)-7H-pyrrolo[2,3-d]pyrimidin-2-ylamino)-3-methoxy-N-(1-methylazetidin-3-yl)benzamide, 4-(4-cyclopropoxy-5-(4-(methylcarbamoyl)phenyl)-7H-pyrrolo[2,3-d]pyrimidin-2-ylamino)-3-methoxy-N-(1-methylazetidin-3-yl)benzamide, 3-methoxy-4-(4-(2-methoxyethoxy)-5-(2-methylbenzo[d]oxazol-6-yl)-7H-pyrrolo[2,3-d]pyrimidin-2-ylamino)-N-(oxetan-3-yl)benzamide, 3-methoxy-N-(1-methylazetidin-3-yl)-4-(5-(4-(methylcarbamoyl)phenyl)-4-(tetrahydro-2H-pyran-4-yloxy)-7H-pyrrolo[2,3-d]pyrimidin-2-ylamino)benzamide, 3-methoxy-N-(1-methylazetidin-3-yl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide, 3-methoxy-4-(5-(2-methylbenzo[d]oxazol-6-yl)-4-(tetrahydro-2H-pyran-4-yloxy)-7H-pyrrolo[2,3-d]pyrimidin-2-ylamino)-N-(oxetan-3-yl)benzamide,
4-(4-cyclopropoxy-5-(2-methylbenzo[d]oxazol-6-yl)-7H-pyrrolo[2,3-d]pyrimidin-2-ylamino)-3-methoxy-N-(oxetan-3-yl)benzamide,
4-(4-tert-butoxy-5-(2-methylbenzo[d]oxazol-6-yl)-7H-pyrrolo[2,3-d]pyrimidin-2-ylamino)-3-methoxy-N-(oxetan-3-yl)benzamide,
1-(5-chloro-4-(4-(cyclopentyloxy)-5-(2-methylbenzo[d]oxazol-6-yl)-7H-pyrrolo[2,3-d]pyrimidin-2-ylamino)-1H-pyrazol-1-yl)-2-methylpropan-2-ol,
4-(2-(5-chloro-1-(2-hydroxy-2-methylpropyl)-1H-pyrazol-4-ylamino)-4-cyclobutoxy-7H-pyrrolo[2,3-d]pyrimidin-5-yl)-N-methylbenzamide,
3-methoxy-4-(4-(2-methoxyethoxy)-5-(4-(methylcarbamoyl)phenyl)-7H-pyrrolo[2,3-d]pyrimidin-2-ylamino)-N-(oxetan-3-yl)benzamide,
(S)-3-methoxy-N-(1-methylazetidin-3-yl)-4-(5-(2-methylbenzo[d]oxazol-6-yl)-4-(tetrahydrofuran-3-yloxy)-7H-pyrrolo[2,3-d]pyrimidin-2-ylamino)benzamide,
(S)-3-methoxy-N-(1-methylazetidin-3-yl)-4-(5-(4-(methylcarbamoyl)phenyl)-4-(tetrahydrofuran-3-yloxy)-7H-pyrrolo[2,3-d]pyrimidin-2-ylamino)benzamide,
(S)-3-methoxy-4-(5-(4-(methylcarbamoyl)phenyl)-4-(tetrahydrofuran-3-yloxy)-7H-pyrrolo[2,3-d]pyrimidin-2-ylamino)-N-(oxetan-3-yl)benzamide,
N-(5-chloro-1-(tetrahydro-2H-pyran-4-yl)-1H-pyrazol-4-yl)-4-(cyclopentyloxy)-5-(2-methylbenzo[d]oxazol-6-yl)-7H-pyrrolo[2,3-d]pyrimidin-2-amine,
N-(5-chloro-1-(2-methoxyethyl)-1H-pyrazol-4-yl)-4-(cyclopentyloxy)-5-(2-methylbenzo[d]oxazol-6-yl)-7H-pyrrolo[2,3-d]pyrimidin-2-amine,
3-methoxy-4-(5-(2-methylbenzo[d]oxazol-6-yl)-4-(1-methylcyclobutoxy)-7H-pyrrolo[2,3-d]pyrimidin-2-ylamino)-N-(oxetan-3-yl)benzamide,
3-methoxy-4-(4-methoxy-5-(3-methylbenzo[d]isoxazol-6-yl)-7H-pyrrolo[2,3-d]pyrimidin-2-ylamino)-N-(oxetan-3-yl)benzamide,
4-(5-(2-fluoropyridin-4-yl)-4-methoxy-7H-pyrrolo[2,3-d]pyrimidin-2-ylamino)-3-methoxy-N-(oxetan-3-yl)benzamide,
3-methoxy-4-(4-methoxy-5-(1-methyl-1H-pyrazol-4-yl)-7H-pyrrolo[2,3-d]pyrimidin-2-ylamino)-N-(oxetan-3-yl)benzamide,
3-methoxy-4-(4-methoxy-5-(2-methylpyridin-4-yl)-7H-pyrrolo[2,3-d]pyrimidin-2-ylamino)-N-(oxetan-3-yl)benzamide,
4-(5-(2,6-dimethylpyridin-4-yl)-4-methoxy-7H-pyrrolo[2,3-d]pyrimidin-2-ylamino)-3-methoxy-N-(oxetan-3-yl)benzamide,
N-(5-chloro-1-ethyl-1H-pyrazol-4-yl)-4-(cyclopentyloxy)-5-(2-methylbenzo[d]oxazol-6-yl)-7H-pyrrolo[2,3-d]pyrimidin-2-amine,
3-methoxy-4-(4-(2-methoxyethoxy)-5-(2-methylbenzo[d]oxazol-6-yl)-7H-pyrrolo[2,3-d]pyrimidin-2-ylamino)-N-(1-methylazetidin-3-yl)benzamide,
4-(5-(1,3-dimethyl-1H-pyrazol-4-yl)-4-methoxy-7H-pyrrolo[2,3-d]pyrimidin-2-ylamino)-3-methoxy-N-(oxetan-3-yl)benzamide,
3-methoxy-4-(4-methoxy-5-(3-methylbenzo[d]isoxazol-6-yl)-7H-pyrrolo[2,3-d]pyrimidin-2-ylamino)-N-methylbenzamide,
3-methoxy-4-(4-methoxy-5-(2-methoxypyridin-4-yl)-7H-pyrrolo[2,3-d]pyrimidin-2-ylamino)-N-(oxetan-3-yl)benzamide,
4-(5-(4-fluorophenyl)-4-methoxy-7H-pyrrolo[2,3-d]pyrimidin-2-ylamino)-N,N,3-trimethylbenzamide,
4-(4-methoxy-5-(4-methoxyphenyl)-7H-pyrrolo[2,3-d]pyrimidin-2-ylamino)-N,N,3-trimethylbenzamide,
3-methoxy-4-(4-methoxy-5-(pyridin-4-yl)-7H-pyrrolo[2,3-d]pyrimidin-2-ylamino)-N,N-dimethylbenzamide,
N-(1,3-dimethyl-1H-pyrazol-4-yl)-4-methoxy-5-(pyridin-4-yl)-7H-pyrrolo[2,3-d]pyrimidin-2-amine,
4-(5-(2-chloropyridin-4-yl)-4-methoxy-7H-pyrrolo[2,3-d]pyrimidin-2-ylamino)-3-methoxy-N-(oxetan-3-yl)benzamide,
3-methoxy-4-(4-methoxy-5-(pyrimidin-4-yl)-7H-pyrrolo[2,3-d]pyrimidin-2-ylamino)-N-(oxetan-3-yl)benzamide,
4-(4-methoxy-5-(pyridin-4-yl)-7H-pyrrolo[2,3-d]pyrimidin-2-ylamino)-3-methyl-N-(oxetan-3-yl)benzamide,
4-(5-(4-(1H-imidazol-2-yl)phenyl)-4-methoxy-7H-pyrrolo[2,3-d]pyrimidin-2-ylamino)-N,N,3-trimethylbenzamide,
4-(4-methoxy-5-(1-methyl-1H-pyrazol-4-yl)-7H-pyrrolo[2,3-d]pyrimidin-2-ylamino)-N,N,3-trimethylbenzamide,
4-(4-methoxy-5-(2-methyl-1H-benzo[d]imidazol-5-yl)-7H-pyrrolo[2,3-d]pyrimidin-2-ylamino)-N,N,3-trimethylbenzamide,
4-(4-methoxy-5-(3-methylbenzo[d]isoxazol-6-yl)-7H-pyrrolo[2,3-d]pyrimidin-2-ylamino)-N,N,3-trimethylbenzamide,
4-methoxy-N-(1-methyl-1H-pyrazol-5-yl)-5-(pyridin-4-yl)-7H-pyrrolo[2,3-d]pyrimidin-2-amine,
4-(5-(2-fluoropyridin-4-yl)-4-isopropoxy-7H-pyrrolo[2,3-d]pyrimidin-2-ylamino)-N,N,3-trimethylbenzamide,
4-(5-(2-fluoropyridin-4-yl)-4-isopropoxy-7H-pyrrolo[2,3-d]pyrimidin-2-ylamino)-3-methoxy-N,N-dimethylbenzamide,
3-methoxy-4-(4-methoxy-5-(2-methyl-1H-benzo[d]imidazol-5-yl)-7H-pyrrolo[2,3-d]pyrimidin-2-ylamino)-N-(oxetan-3-yl)benzamide,
3-methoxy-4-(4-methoxy-5-(pyridazin-4-yl)-7H-pyrrolo[2,3-d]pyrimidin-2-ylamino)-N-(oxetan-3-yl)benzamide,
4-(4-methoxy-5-(pyridin-4-yl)-7H-pyrrolo[2,3-d]pyrimidin-2-ylamino)-N,3-dimethyl-N-(oxetan-3-yl)benzamide,
4-(5-(1,2-dimethyl-1H-benzo[d]imidazol-6-yl)-4-methoxy-7H-pyrrolo[2,3-d]pyrimidin-2-ylamino)-N,N,3-trimethylbenzamide,
3-methoxy-4-(4-methoxy-5-(3-methylbenzo[d]isoxazol-6-yl)-7H-pyrrolo[2,3-d]pyrimidin-2-ylamino)-N,N-dimethylbenzamide,
4-(5-(2-fluoropyridin-4-yl)-4-methoxy-7H-pyrrolo[2,3-d]pyrimidin-2-ylamino)-N,N,3-trimethylbenzamide,
4-(5-(1,2-dimethyl-1H-benzo[d]imidazol-5-yl)-4-methoxy-7H-pyrrolo[2,3-d]pyrimidin-2-ylamino)-N,N,3-trimethylbenzamide,
4-(4-methoxy-5-(4-(methylsulfonyl)phenyl)-7H-pyrrolo[2,3-d]pyrimidin-2-ylamino)-N,N,3-trimethylbenzamide,
4-(5-(2-fluoropyridin-4-yl)-4-methoxy-7H-pyrrolo[2,3-d]pyrimidin-2-ylamino)-3-methoxy-N,N-dimethylbenzamide,
4-(5-(2-fluoropyridin-4-yl)-4-methoxy-7H-pyrrolo[2,3-d]pyrimidin-2-ylamino)-3-methoxy-N-methyl-N-(oxetan-3-yl)benzamide,
4-methoxy-N-(4-methyl-1H-indazol-5-yl)-5-(pyridin-4-yl)-7H-pyrrolo[2,3-d]pyrimidin-2-amine, 5-(5-(2-fluoropyridin-4-yl)-4-methoxy-7H-pyrrolo[2,3-d]pyrimidin-2-ylamino)-4-methoxy-N,N-dimethylpicolinamide, 5-(2-fluoropyridin-4-yl)-4-methoxy-N-(4-methoxy-6-(tetrahydro-2H-pyran-4-yl)pyridin-3-yl)-7H-pyrrolo[2,3-d]pyrimidin-2-amine, 4-(5-(3-chloro-1-methyl-1H-pyrazol-4-yl)-4-methoxy-7H-pyrrolo[2,3-d]pyrimidin-2-ylamino)-3-methoxy-N-(oxetan-3-yl)benzamide, 4-(5-(2-fluoro-6-methylpyridin-4-yl)-4-methoxy-7H-pyrrolo[2,3-d]pyrimidin-2-ylamino)-3-methoxy-N,N-dimethylbenzamide, N-(1,4-dimethyl-1H-indazol-5-yl)-4-methoxy-5-(pyridin-4-yl)-7H-pyrrolo[2,3-d]pyrimidin-2-amine 4-(5-(2-fluoro-6-methylpyridin-4-yl)-4-methoxy-7H-pyrrolo[2,3-d]pyrimidin-2-ylamino)-N,N,3-trimethylbenzamide, 3-chloro-N-methyl-4-(5-(4-(methylcarbamoyl)phenyl)-4-(tetrahydro-2H-pyran-4-yloxy)-7H-pyrrolo[2,3-d]pyrimidin-2-ylamino)benzamide, 3-chloro-4-(4-(cyclopentyloxy)-5-(2-methylbenzo[d]oxazol-6-yl)-7H-pyrrolo[2,3-d]pyrimidin-2-ylamino)-N-methylbenzamide, 3-chloro-N-methyl-4-(5-(1-methyl-1H-pyrazol-4-yl)-4-(tetrahydro-2H-pyran-4-yloxy)-7H-pyrrolo[2,3-d]pyrimidin-2-ylamino)benzamide, 4-(5-(2-fluoro-6-methylpyridin-4-yl)-4-methoxy-7H-pyrrolo[2,3-d]pyrimidin-2-ylamino)-3-methoxy-N-(oxetan-3-yl)benzamide, 3-chloro-4-(4-(cyclopentyloxy)-5-(4-(methylcarbamoyl)phenyl)-7H-pyrrolo[2,3-d]pyrimidin-2-ylamino)-N-methylbenzamide, 3-chloro-4-(4-isopropoxy-5-(2-methylbenzo[d]oxazol-6-yl)-7H-pyrrolo[2,3-d]pyrimidin-2-ylamino)-N-methylbenzamide, 3-chloro-4-(4-methoxy-5-(2-methylbenzo[d]oxazol-6-yl)-7H-pyrrolo[2,3-d]pyrimidin-2-ylamino)-N-methylbenzamide, 3-chloro-4-(4-methoxy-5-(4-(methylcarbamoyl)phenyl)-7H-pyrrolo[2,3-d]pyrimidin-2-ylamino)-N-methylbenzamide, 3-chloro-4-(4-((1s,4s)-4-hydroxy-4-methylcyclohexyloxy)-5-(2-methylbenzo[d]oxazol-6-yl)-7H-pyrrolo[2,3-d]pyrimidin-2-ylamino)-N-methylbenzamide, 3-chloro-N-methyl-4-(5-(2-methylbenzo[d]oxazol-6-yl)-4-(tetrahydro-2H-pyran-4-ylamino)-7H-pyrrolo[2,3-d]pyrimidin-2-ylamino)benzamide, 3-chloro-N-(2-hydroxyethyl)-4-(5-(2-methylbenzo[d]oxazol-6-yl)-4-(tetrahydro-2H-pyran-4-yloxy)-7H-pyrrolo[2,3-d]pyrimidin-2-ylamino)benzamide, 3-chloro-4-(4-isopropoxy-5-(4-(methylcarbamoyl)phenyl)-7H-pyrrolo[2,3-d]pyrimidin-2-ylamino)-N-methylbenzamide, 3-chloro-N-methyl-4-(5-(4-(methylcarbamoyl)phenyl)-4-(tetrahydro-2H-pyran-4-ylamino)-7H-pyrrolo[2,3-d]pyrimidin-2-ylamino)benzamide, (R)-3-chloro-N-methyl-4-(5-(4-(methylcarbamoyl)phenyl)-4-(tetrahydrofuran-3-yloxy)-7H-pyrrolo[2,3-d]pyrimidin-2-ylamino)benzamide, 3-ethyl-N-methyl-4-(5-(2-methylbenzo[d]oxazol-6-yl)-4-(tetrahydro-2H-pyran-4-yloxy)-7H-pyrrolo[2,3-d]pyrimidin-2-ylamino)benzamide, N-methyl-4-(5-(2-methylbenzo[d]oxazol-6-yl)-4-(tetrahydro-2H-pyran-4-yloxy)-7H-pyrrolo[2,3-d]pyrimidin-2-ylamino)-3-propylbenzamide, 4-(5-(2-chloro-6-methylpyridin-4-yl)-4-methoxy-7H-pyrrolo[2,3-d]pyrimidin-2-ylamino)-3-methoxy-N-(oxetan-3-yl)benzamide, 3-chloro-4-(5-(2-methylbenzo[d]oxazol-6-yl)-4-(tetrahydro-2H-pyran-4-yloxy)-7H-pyrrolo[2,3-d]pyrimidin-2-ylamino)-N-(oxetan-3-yl)benzamide, or a pharmaceutically acceptable salt, tautomer, stereoisomer, enantiomer, or isotopologue thereof.

* * * * *